United States Patent
Shelton, IV et al.

(10) Patent No.: US 12,096,910 B2
(45) Date of Patent: Sep. 24, 2024

(54) SURGICAL HUB FOR USE WITH A SURGICAL SYSTEM IN A SURGICAL PROCEDURE

(71) Applicant: Cilag GmbH International, Zug (CH)

(72) Inventors: Frederick E. Shelton, IV, Hillsboro, OH (US); Andrew C. Deck, Cincinnati, OH (US); Jason L. Harris, Lebanon, OH (US); Chad E. Eckert, Terrace Park, OH (US); Daniel J. Mumaw, Liberty Township, OH (US); Kevin M. Fiebig, Cincinnati, OH (US); Sarah A. Worthington, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/348,315

(22) Filed: Jun. 15, 2021

(65) Prior Publication Data

US 2021/0307866 A1 Oct. 7, 2021

Related U.S. Application Data

(63) Continuation of application No. 16/729,807, filed on Dec. 30, 2019, now Pat. No. 11,284,963.

(51) Int. Cl.
*A61B 1/00* (2006.01)
*A61B 1/005* (2006.01)
(Continued)

(52) U.S. Cl.
CPC .... *A61B 1/000094* (2022.02); *A61B 1/00194* (2022.02); *A61B 1/009* (2022.02);
(Continued)

(58) Field of Classification Search
CPC ......... A61B 90/37; A61B 34/25; G06T 7/521; G06T 19/00; G06T 2200/24
See application file for complete search history.

(56) References Cited

U.S. PATENT DOCUMENTS 3,901,602 A 8/1975 Gravatt, Jr.
4,753,641 A 6/1988 Vaslow
(Continued)

FOREIGN PATENT DOCUMENTS

CN 109011149 A 12/2018
DE 102015115903 A1 3/2017
(Continued)

OTHER PUBLICATIONS

Kurata et al. "Time-of-flight Near-infrared Spectroscopy for Non-destructive Measurement of Internal Quality in Grapefruit," J. Amer. Soc. Hort. Sci. 138(3): 225-228, 2013.
(Continued)

*Primary Examiner* — Yingchun He

(57) ABSTRACT

A method for generating and updating a three-dimensional representation of a surgical site based on imaging data from an imaging system is disclosed. The method comprises the steps of generating a first image of the surgical site based on structured electromagnetic radiation emitted from the imaging system, receiving a second image of the surgical site, aligning the first image and the second image, generating a three-dimensional representation of the surgical site based on the first image and the second image as aligned, displaying the three-dimensional representation on a display screen, receiving a user selection to manipulate the three-dimensional representation, and updating the three-dimensional representation as displayed on the display screen from a first state to a second state according to the received user selection.

20 Claims, 90 Drawing Sheets

(51) Int. Cl.

| | | |
|---|---|---|
| *A61B 1/04* | (2006.01) | |
| *A61B 1/06* | (2006.01) | |
| *A61B 17/064* | (2006.01) | |
| *A61B 34/00* | (2016.01) | |
| *A61B 34/30* | (2016.01) | |
| *A61B 90/00* | (2016.01) | |
| *G06T 7/30* | (2017.01) | |
| *G06T 7/521* | (2017.01) | |
| *G06T 19/00* | (2011.01) | |

(52) U.S. Cl.
CPC .......... *A61B 1/046* (2022.02); *A61B 1/0605* (2022.02); *A61B 90/361* (2016.02); *A61B 90/37* (2016.02); *G06T 7/30* (2017.01); *G06T 7/521* (2017.01); *G06T 19/00* (2013.01); *A61B 17/064* (2013.01); *A61B 34/25* (2016.02); *A61B 34/30* (2016.02); *A61B 2090/064* (2016.02); *A61B 2090/367* (2016.02); *A61B 2090/3735* (2016.02); *G06T 2200/24* (2013.01); *G06T 2207/10081* (2013.01); *G06T 2207/10088* (2013.01); *G06T 2207/20221* (2013.01); *G06T 2207/30092* (2013.01); *G06T 2210/41* (2013.01); *G06T 2219/004* (2013.01)

(56) References Cited

U.S. PATENT DOCUMENTS

| | | | |
|---|---|---|---|
| 4,785,180 | A | 11/1988 | Dietrich et al. |
| 4,986,262 | A | 1/1991 | Saito |
| 5,434,667 | A | 7/1995 | Hutchins et al. |
| 5,460,182 | A | 10/1995 | Goodman et al. |
| 5,609,562 | A | 3/1997 | Kaali |
| 6,350,233 | B1 | 2/2002 | Lubowski |
| 6,386,758 | B2 | 5/2002 | Loser |
| 6,614,453 | B1 * | 9/2003 | Suri ................ G16H 30/20 715/848 |
| 6,632,183 | B2 | 10/2003 | Bowman et al. |
| 6,804,012 | B2 | 10/2004 | Gombert |
| 6,869,430 | B2 | 3/2005 | Balbierz et al. |
| 6,951,535 | B2 | 10/2005 | Ghodoussi et al. |
| 7,137,980 | B2 | 11/2006 | Buysse et al. |
| 7,314,048 | B2 | 1/2008 | Couture et al. |
| 7,477,931 | B2 | 1/2009 | Hoyt |
| 7,516,675 | B2 | 4/2009 | Kurtz et al. |
| 7,726,171 | B2 | 6/2010 | Langlotz et al. |
| 7,740,623 | B2 | 6/2010 | Nayak et al. |
| 7,766,210 | B2 | 8/2010 | Shelton, IV et al. |
| 7,770,775 | B2 | 8/2010 | Shelton, IV et al. |
| 7,798,385 | B2 | 9/2010 | Boyden et al. |
| 7,810,691 | B2 | 10/2010 | Boyden et al. |
| 7,901,353 | B2 | 3/2011 | Vayser et al. |
| 7,905,840 | B2 | 3/2011 | Pimenta et al. |
| 7,975,894 | B2 | 7/2011 | Boyden et al. |
| 8,041,089 | B2 | 10/2011 | Drumm et al. |
| 8,063,883 | B2 | 11/2011 | Senft et al. |
| 8,073,528 | B2 | 12/2011 | Zhao et al. |
| 8,079,950 | B2 | 12/2011 | Stern et al. |
| 8,142,450 | B2 | 3/2012 | Harris et al. |
| 8,161,977 | B2 | 4/2012 | Shelton, IV et al. |
| 8,224,484 | B2 | 7/2012 | Swarup et al. |
| 8,231,639 | B2 | 7/2012 | Bolduc et al. |
| 8,523,043 | B2 | 9/2013 | Ullrich et al. |
| 8,632,468 | B2 | 1/2014 | Glossop et al. |
| 8,652,148 | B2 | 2/2014 | Zuhars |
| 8,706,211 | B2 | 4/2014 | Dacey, Jr. et al. |
| 8,755,576 | B2 | 6/2014 | Taerum |
| 8,763,879 | B2 | 7/2014 | Shelton, IV et al. |
| 8,820,603 | B2 | 9/2014 | Shelton, IV et al. |
| 8,840,616 | B2 | 9/2014 | Wilkinson et al. |
| 8,932,208 | B2 | 1/2015 | Kendale et al. |
| 8,934,003 | B2 | 1/2015 | Popovic et al. |
| 8,989,528 | B2 | 3/2015 | Udd |
| 8,992,558 | B2 | 3/2015 | Stone et al. |
| 9,005,118 | B2 | 4/2015 | Selover et al. |
| 9,044,230 | B2 | 6/2015 | Morgan et al. |
| 9,064,173 | B2 | 6/2015 | Redden |
| 9,072,501 | B2 | 7/2015 | Menchaca et al. |
| 9,072,535 | B2 | 7/2015 | Shelton, IV et al. |
| 9,119,670 | B2 | 9/2015 | Yang et al. |
| 9,141,868 | B2 | 9/2015 | Xu et al. |
| 9,161,817 | B2 | 10/2015 | Olson et al. |
| 9,161,820 | B2 | 10/2015 | Mark et al. |
| 9,179,822 | B2 | 11/2015 | Kitamura et al. |
| 9,179,890 | B2 * | 11/2015 | Ionasec ................ A61B 8/0883 |
| 9,241,693 | B2 | 1/2016 | Taylor et al. |
| 9,254,103 | B2 | 2/2016 | Krishnaswamy et al. |
| 9,259,290 | B2 | 2/2016 | Jenkins et al. |
| 9,265,587 | B2 | 2/2016 | Vancamberg et al. |
| 9,274,047 | B2 | 3/2016 | Velten et al. |
| 9,282,878 | B2 | 3/2016 | Grey et al. |
| 9,295,773 | B2 | 3/2016 | Prosl et al. |
| 9,326,770 | B2 | 5/2016 | Shelton, IV et al. |
| 9,345,389 | B2 | 5/2016 | Nie et al. |
| 9,402,726 | B2 | 8/2016 | Linderman et al. |
| 9,480,534 | B2 | 11/2016 | Bowling et al. |
| 9,547,940 | B1 | 1/2017 | Sun et al. |
| 9,561,019 | B2 | 2/2017 | Mihailescu et al. |
| 9,561,082 | B2 | 2/2017 | Yen et al. |
| 9,597,054 | B2 | 3/2017 | Kudavelly et al. |
| 9,649,109 | B2 | 5/2017 | Ranucci et al. |
| 9,720,076 | B2 | 8/2017 | Guo et al. |
| 9,730,690 | B2 | 8/2017 | Shanley et al. |
| 9,760,989 | B2 | 9/2017 | Yin et al. |
| 9,775,497 | B2 | 10/2017 | Igarashi et al. |
| 9,788,851 | B2 | 10/2017 | Dannaher et al. |
| 9,801,685 | B2 | 10/2017 | Nguyen et al. |
| 9,855,317 | B2 | 1/2018 | Bright |
| 9,857,167 | B2 | 1/2018 | Jovanovski et al. |
| 9,883,857 | B2 | 2/2018 | Shluzas et al. |
| 9,901,409 | B2 | 2/2018 | Yang et al. |
| 9,911,187 | B2 | 3/2018 | Steinle et al. |
| 9,918,640 | B2 | 3/2018 | Ntziachristos et al. |
| 9,987,019 | B2 | 6/2018 | Sato |
| 10,010,326 | B2 | 7/2018 | Sato |
| 10,022,199 | B2 | 7/2018 | Gassner et al. |
| 10,042,150 | B2 | 8/2018 | Brown |
| 10,045,763 | B2 | 8/2018 | Sato |
| 10,068,173 | B2 | 9/2018 | Vayser et al. |
| 10,070,929 | B2 | 9/2018 | Tanji |
| 10,085,611 | B2 | 10/2018 | Yabe et al. |
| 10,105,470 | B2 | 10/2018 | Reasoner et al. |
| 10,123,706 | B2 | 11/2018 | Elbaz et al. |
| 10,136,959 | B2 | 11/2018 | Mintz et al. |
| 10,143,470 | B2 | 12/2018 | Sato |
| 10,170,205 | B2 | 1/2019 | Curd et al. |
| 10,194,981 | B2 | 2/2019 | Margallo Balbas et al. |
| 10,194,990 | B2 | 2/2019 | Amanatullah et al. |
| 10,219,738 | B2 | 3/2019 | Monty et al. |
| 10,226,299 | B2 | 3/2019 | Raffy et al. |
| 10,238,356 | B2 * | 3/2019 | Suzuki ................ A61B 6/488 |
| 10,255,679 | B2 | 4/2019 | Yin et al. |
| 10,255,723 | B2 | 4/2019 | Thomas et al. |
| 10,314,463 | B2 | 6/2019 | Agrawal et al. |
| 10,357,253 | B2 | 7/2019 | Sato |
| 10,357,317 | B2 | 7/2019 | Dupont et al. |
| 10,390,835 | B2 | 8/2019 | Williams |
| 10,433,911 | B2 | 10/2019 | Wang et al. |
| 10,467,752 | B2 | 11/2019 | Tanji |
| 10,470,687 | B2 | 11/2019 | Garbey et al. |
| 10,470,763 | B2 | 11/2019 | Yates et al. |
| 10,506,991 | B2 | 12/2019 | Govari |
| 10,510,149 | B2 | 12/2019 | Cutu et al. |
| 10,512,518 | B2 | 12/2019 | Vayser et al. |
| 10,531,074 | B2 | 1/2020 | Wilson et al. |
| 10,546,423 | B2 | 1/2020 | Jones et al. |
| 10,548,679 | B2 | 2/2020 | Carlson et al. |
| 10,561,465 | B2 | 2/2020 | Scholl et al. |
| 10,576,246 | B2 | 3/2020 | Fischell et al. |
| 10,587,659 | B2 | 3/2020 | Miller |
| 10,588,699 | B2 | 3/2020 | Richmond et al. |
| 10,607,738 | B2 | 3/2020 | Davidson et al. |
| 10,643,371 | B2 | 5/2020 | Bharadwaj et al. |

(56) References Cited

U.S. PATENT DOCUMENTS

| | | |
|---|---|---|
| 10,666,928 B2 | 5/2020 | Liu |
| 10,687,797 B2 | 6/2020 | Stone et al. |
| 10,695,166 B2 | 6/2020 | Willis et al. |
| 10,702,186 B2 | 7/2020 | Amies et al. |
| 10,704,093 B2 | 7/2020 | Deng et al. |
| 10,743,868 B2 | 8/2020 | Shelton, IV et al. |
| 10,768,402 B2 | 9/2020 | Brown |
| 10,792,034 B2 | 10/2020 | Scheib et al. |
| 10,806,518 B2 | 10/2020 | Amanatullah |
| 10,813,700 B2 | 10/2020 | Amanatullah |
| 10,861,197 B2 | 12/2020 | Kobayashi |
| 10,866,783 B2 | 12/2020 | Atarot et al. |
| 10,881,458 B2 | 1/2021 | Fischell et al. |
| 10,898,064 B2 | 1/2021 | Atarot et al. |
| 10,925,465 B2 | 2/2021 | Tully et al. |
| 10,925,598 B2 | 2/2021 | Scheib et al. |
| 10,945,787 B2 | 3/2021 | Fischell et al. |
| 10,945,796 B2 | 3/2021 | Popovic et al. |
| 10,973,519 B2 | 4/2021 | Weir et al. |
| 10,980,420 B2 | 4/2021 | Fengler et al. |
| 10,986,999 B2 | 4/2021 | Frangioni et al. |
| 10,987,176 B2 | 4/2021 | Poltaretskyi et al. |
| 11,000,270 B2 | 5/2021 | Scheib et al. |
| 11,006,100 B1 | 5/2021 | Douglas |
| 11,013,563 B2 | 5/2021 | Shelton, IV et al. |
| 11,020,016 B2 | 6/2021 | Wallace et al. |
| 11,058,501 B2 | 7/2021 | Tokarchuk et al. |
| 11,100,631 B2 | 8/2021 | Yates et al. |
| 11,109,866 B2 | 9/2021 | Shelton, IV et al. |
| 11,122,987 B2 | 9/2021 | Barash et al. |
| 11,183,141 B2 | 11/2021 | Yamada |
| 11,213,361 B2 | 1/2022 | Denlinger et al. |
| 11,219,501 B2 | 1/2022 | Shelton, IV et al. |
| 11,257,589 B2 | 2/2022 | Shelton, IV et al. |
| 11,259,793 B2 | 3/2022 | Scheib et al. |
| 11,269,173 B2 | 3/2022 | Komp et al. |
| 11,276,175 B2 | 3/2022 | Witte |
| 11,284,957 B2 | 3/2022 | Denlinger et al. |
| 11,284,963 B2 | 3/2022 | Shelton, IV et al. |
| 11,298,128 B2 | 4/2022 | Messerly et al. |
| 11,304,692 B2 | 4/2022 | Scheib |
| 11,304,699 B2 | 4/2022 | Shelton, IV et al. |
| 11,315,438 B1 | 4/2022 | Hannaford et al. |
| 11,369,366 B2 | 6/2022 | Scheib et al. |
| 11,389,164 B2 | 7/2022 | Yates et al. |
| 11,410,259 B2 | 8/2022 | Harris et al. |
| 11,419,604 B2 | 8/2022 | Scheib et al. |
| 11,424,027 B2 | 8/2022 | Shelton, IV |
| 11,432,885 B2 | 9/2022 | Shelton, IV et al. |
| 11,471,151 B2 | 10/2022 | Scheib et al. |
| 11,471,229 B2 | 10/2022 | Denlinger et al. |
| 11,490,981 B2 | 11/2022 | Denlinger et al. |
| 11,559,298 B2 | 1/2023 | Scheib et al. |
| 11,559,307 B2 | 1/2023 | Shelton, IV et al. |
| 11,559,308 B2 | 1/2023 | Yates et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,583,349 B2 | 2/2023 | Azizian et al. |
| 11,583,350 B2 | 2/2023 | Denlinger et al. |
| 11,589,731 B2 | 2/2023 | Shelton, IV et al. |
| 11,589,888 B2 | 2/2023 | Shelton, IV et al. |
| 11,607,239 B2 | 3/2023 | Swensgard et al. |
| 11,771,487 B2 | 10/2023 | Shelton, IV et al. |
| 2001/0012327 A1 | 8/2001 | Loser |
| 2003/0069591 A1 | 4/2003 | Carson et al. |
| 2004/0082842 A1 | 4/2004 | Lumba et al. |
| 2004/0106916 A1 | 6/2004 | Quaid et al. |
| 2004/0147926 A1 | 7/2004 | Iversen |
| 2004/0176751 A1 | 9/2004 | Weitzner et al. |
| 2004/0230199 A1 | 11/2004 | Jansen et al. |
| 2005/0113846 A1 | 5/2005 | Carson |
| 2005/0124975 A1 | 6/2005 | Law |
| 2005/0167621 A1 | 8/2005 | Zeng et al. |
| 2005/0177181 A1 | 8/2005 | Kagan et al. |
| 2005/0279354 A1 | 12/2005 | Deutsch et al. |
| 2006/0013454 A1 | 1/2006 | Flewelling et al. |
| 2006/0079841 A1 | 4/2006 | Duff et al. |
| 2006/0206007 A1 | 9/2006 | Bala |
| 2006/0224045 A1 | 10/2006 | Whipple et al. |
| 2006/0227324 A1 | 10/2006 | Bloom et al. |
| 2006/0282096 A1 | 12/2006 | Papa et al. |
| 2006/0293557 A1 | 12/2006 | Chuanggui et al. |
| 2007/0014784 A1 | 1/2007 | Nayak et al. |
| 2007/0019781 A1 | 1/2007 | Haras |
| 2007/0040906 A1 | 2/2007 | Iketani |
| 2007/0066970 A1 | 3/2007 | Ineson |
| 2007/0093748 A1 | 4/2007 | Nayak et al. |
| 2007/0100210 A1 | 5/2007 | Selover et al. |
| 2007/0123912 A1 | 5/2007 | Carson |
| 2007/0156021 A1 | 7/2007 | Morse et al. |
| 2007/0172472 A1 | 7/2007 | Nayak |
| 2007/0175955 A1 | 8/2007 | Shelton et al. |
| 2007/0239149 A1 | 10/2007 | Lieponis |
| 2007/0265495 A1 | 11/2007 | Vayser |
| 2008/0001919 A1 | 1/2008 | Pascucci |
| 2008/0004633 A1 | 1/2008 | Arata et al. |
| 2008/0015664 A1 | 1/2008 | Podhajsky |
| 2008/0069433 A1 | 3/2008 | Corcoran et al. |
| 2008/0077158 A1 | 3/2008 | Haider et al. |
| 2008/0144906 A1 | 6/2008 | Allred et al. |
| 2008/0151233 A1 | 6/2008 | Blanke et al. |
| 2008/0194930 A1 | 8/2008 | Harris et al. |
| 2008/0205588 A1 | 8/2008 | Kim |
| 2008/0228104 A1 | 9/2008 | Uber et al. |
| 2008/0234866 A1 | 9/2008 | Kishi et al. |
| 2008/0269596 A1 | 10/2008 | Revie et al. |
| 2008/0297360 A1 | 12/2008 | Knox et al. |
| 2008/0319491 A1 | 12/2008 | Schoenefeld |
| 2009/0000627 A1 | 1/2009 | Quaid et al. |
| 2009/0012533 A1 | 1/2009 | Barbagli et al. |
| 2009/0057559 A1 | 3/2009 | Koyama |
| 2009/0234223 A1 | 9/2009 | Onoda et al. |
| 2009/0322864 A1 | 12/2009 | Karasawa et al. |
| 2009/0326336 A1 | 12/2009 | Lemke et al. |
| 2010/0030231 A1 | 2/2010 | Revie et al. |
| 2010/0036374 A1 | 2/2010 | Ward |
| 2010/0081875 A1 | 4/2010 | Fowler et al. |
| 2010/0087755 A1 | 4/2010 | Boezaart |
| 2010/0137882 A1 | 6/2010 | Quaid, III |
| 2010/0152539 A1 | 6/2010 | Ghabrial et al. |
| 2010/0194574 A1 | 8/2010 | Monk et al. |
| 2010/0217278 A1* | 8/2010 | Tripathi .................. A61F 2/16 606/130 |
| 2010/0280493 A1 | 11/2010 | Nayak |
| 2011/0014181 A1 | 1/2011 | Thornton |
| 2011/0046476 A1 | 2/2011 | Cinquin et al. |
| 2011/0071531 A1 | 3/2011 | Carson |
| 2011/0082369 A1 | 4/2011 | Mohr et al. |
| 2011/0201881 A1 | 8/2011 | Emch |
| 2011/0257611 A1 | 10/2011 | Locke et al. |
| 2011/0257661 A1 | 10/2011 | Choi et al. |
| 2011/0306873 A1 | 12/2011 | Shenai et al. |
| 2011/0306985 A1 | 12/2011 | Inoue et al. |
| 2012/0004894 A1 | 1/2012 | Butler et al. |
| 2012/0046668 A1 | 2/2012 | Gantes |
| 2012/0143341 A1 | 6/2012 | Zipnick |
| 2012/0165837 A1 | 6/2012 | Belman et al. |
| 2012/0179189 A1* | 7/2012 | Zingaretti ............ G06T 7/0004 606/187 |
| 2012/0265022 A1 | 10/2012 | Menn |
| 2012/0300051 A1 | 11/2012 | Daigo et al. |
| 2013/0035583 A1 | 2/2013 | Park et al. |
| 2013/0053679 A1 | 2/2013 | Owen |
| 2013/0090554 A1* | 4/2013 | Zvuloni .................. A61B 5/061 600/424 |
| 2013/0100250 A1 | 4/2013 | Raskar et al. |
| 2013/0172902 A1 | 7/2013 | Lightcap et al. |
| 2013/0211244 A1 | 8/2013 | Nathaniel |
| 2013/0274596 A1 | 10/2013 | Azizian et al. |
| 2013/0274673 A1 | 10/2013 | Fischell et al. |
| 2013/0274674 A1 | 10/2013 | Fischell et al. |
| 2013/0296712 A1 | 11/2013 | Durvasula |
| 2014/0005685 A1 | 1/2014 | Modrow et al. |

(56) References Cited

U.S. PATENT DOCUMENTS

| | | |
|---|---|---|
| 2014/0018788 A1* | 1/2014 | Engelman .......... A61B 18/1492 606/33 |
| 2014/0024945 A1 | 1/2014 | Mung et al. |
| 2014/0035762 A1 | 2/2014 | Shelton, IV et al. |
| 2014/0039520 A1 | 2/2014 | Haider et al. |
| 2014/0114180 A1 | 4/2014 | Jain |
| 2014/0148679 A1 | 5/2014 | Eary et al. |
| 2014/0163359 A1 | 6/2014 | Sholev et al. |
| 2014/0163664 A1 | 6/2014 | Goldsmith |
| 2014/0171793 A1 | 6/2014 | Lin et al. |
| 2014/0175150 A1 | 6/2014 | Shelton, IV et al. |
| 2014/0179997 A1 | 6/2014 | von Grunberg et al. |
| 2014/0267549 A1 | 9/2014 | Pinter et al. |
| 2014/0320684 A1 | 10/2014 | Chatenever et al. |
| 2014/0336461 A1 | 11/2014 | Reiter et al. |
| 2014/0358162 A1 | 12/2014 | Valdastri et al. |
| 2014/0378843 A1 | 12/2014 | Valdes et al. |
| 2015/0009473 A1 | 1/2015 | Su |
| 2015/0018999 A1 | 1/2015 | Lee et al. |
| 2015/0025548 A1 | 1/2015 | Franklin et al. |
| 2015/0032140 A1 | 1/2015 | Khouri |
| 2015/0051460 A1 | 2/2015 | Saxena et al. |
| 2015/0066107 A1 | 3/2015 | Richter et al. |
| 2015/0133909 A1 | 5/2015 | van der Weide et al. |
| 2015/0145966 A1 | 5/2015 | Krieger et al. |
| 2015/0202005 A1 | 7/2015 | Fuflyigin et al. |
| 2015/0209035 A1 | 7/2015 | Zemlok |
| 2015/0223903 A1 | 8/2015 | Bell et al. |
| 2015/0238071 A1 | 8/2015 | Hua et al. |
| 2015/0238276 A1 | 8/2015 | Atarot et al. |
| 2015/0243056 A1* | 8/2015 | Lee .................. G06T 11/005 382/131 |
| 2015/0245878 A1 | 9/2015 | Jaramaz et al. |
| 2015/0272557 A1 | 10/2015 | Overmyer et al. |
| 2015/0297177 A1 | 10/2015 | Boctor et al. |
| 2015/0305650 A1 | 10/2015 | Hunter et al. |
| 2015/0366628 A1 | 12/2015 | Ingmanson |
| 2015/0374435 A1* | 12/2015 | Cao .................. A61B 18/1492 29/601 |
| 2016/0000516 A1 | 1/2016 | Cheng et al. |
| 2016/0007827 A1 | 1/2016 | Frimer et al. |
| 2016/0014328 A1 | 1/2016 | Rokutanda |
| 2016/0022146 A1 | 1/2016 | Piron et al. |
| 2016/0038004 A1 | 2/2016 | Tanaka |
| 2016/0070436 A1 | 3/2016 | Thomas et al. |
| 2016/0086380 A1 | 3/2016 | Vayser et al. |
| 2016/0135909 A1 | 5/2016 | Ogawa et al. |
| 2016/0183841 A1 | 6/2016 | Duindam et al. |
| 2016/0206204 A1 | 7/2016 | Matsuda et al. |
| 2016/0228090 A1 | 8/2016 | Boctor et al. |
| 2016/0235304 A1 | 8/2016 | Tzoumas et al. |
| 2016/0256101 A1 | 9/2016 | Aharoni et al. |
| 2016/0270861 A1 | 9/2016 | Guru et al. |
| 2016/0331467 A1 | 11/2016 | Slamin et al. |
| 2016/0338795 A1 | 11/2016 | Vayser et al. |
| 2016/0346034 A1 | 12/2016 | Arya et al. |
| 2017/0007350 A1 | 1/2017 | Popovic et al. |
| 2017/0020460 A1 | 1/2017 | Leblond et al. |
| 2017/0020613 A1 | 1/2017 | Kang et al. |
| 2017/0055819 A1 | 3/2017 | Hansen et al. |
| 2017/0059408 A1 | 3/2017 | Korner et al. |
| 2017/0071475 A1 | 3/2017 | Irisawa |
| 2017/0071688 A1 | 3/2017 | Cohen et al. |
| 2017/0079530 A1 | 3/2017 | DiMaio et al. |
| 2017/0099479 A1 | 4/2017 | Browd et al. |
| 2017/0143428 A1* | 5/2017 | Raffy .................. G16H 40/63 |
| 2017/0165008 A1 | 6/2017 | Finley |
| 2017/0172382 A1 | 6/2017 | Nir et al. |
| 2017/0172662 A1 | 6/2017 | Panescu et al. |
| 2017/0180704 A1 | 6/2017 | Panescu et al. |
| 2017/0181808 A1 | 6/2017 | Panescu et al. |
| 2017/0181809 A1 | 6/2017 | Panescu et al. |
| 2017/0189006 A1 | 7/2017 | Shluzas et al. |
| 2017/0197028 A1 | 7/2017 | Goldsmith |
| 2017/0202624 A1 | 7/2017 | Atarot et al. |
| 2017/0238962 A1 | 8/2017 | Hansen et al. |
| 2017/0251900 A1 | 9/2017 | Hansen et al. |
| 2017/0258526 A1 | 9/2017 | Lang |
| 2017/0265943 A1 | 9/2017 | Sela et al. |
| 2017/0265947 A1 | 9/2017 | Dyer et al. |
| 2017/0304007 A1 | 10/2017 | Piron et al. |
| 2017/0312032 A1 | 11/2017 | Amanatullah et al. |
| 2017/0319057 A1 | 11/2017 | Inglese et al. |
| 2017/0366773 A1 | 12/2017 | Kiraly et al. |
| 2017/0367580 A1 | 12/2017 | DiMaio et al. |
| 2018/0000533 A1 | 1/2018 | Boll et al. |
| 2018/0014777 A1 | 1/2018 | Amir et al. |
| 2018/0014851 A1 | 1/2018 | Hansen et al. |
| 2018/0064498 A1 | 3/2018 | Kapadia et al. |
| 2018/0082480 A1 | 3/2018 | White et al. |
| 2018/0168741 A1 | 6/2018 | Swayze et al. |
| 2018/0214016 A1 | 8/2018 | Thommen et al. |
| 2018/0228555 A1 | 8/2018 | Charron et al. |
| 2018/0228559 A1 | 8/2018 | Brierton et al. |
| 2018/0235715 A1 | 8/2018 | Amiot et al. |
| 2018/0242967 A1 | 8/2018 | Meade |
| 2018/0247128 A1 | 8/2018 | Alvi et al. |
| 2018/0247153 A1 | 8/2018 | Ganapati et al. |
| 2018/0250086 A1 | 9/2018 | Grubbs |
| 2018/0271603 A1 | 9/2018 | Nir et al. |
| 2018/0271615 A1 | 9/2018 | Mahadik et al. |
| 2018/0333210 A1 | 11/2018 | Nijkamp et al. |
| 2018/0338806 A1 | 11/2018 | Grubbs |
| 2018/0343381 A1 | 11/2018 | Kobayashi et al. |
| 2018/0344140 A1 | 12/2018 | Aizenfeld |
| 2018/0368883 A1 | 12/2018 | Rossa et al. |
| 2019/0008579 A1 | 1/2019 | Begg et al. |
| 2019/0022418 A1 | 1/2019 | Fishman |
| 2019/0046276 A1 | 2/2019 | Inglese et al. |
| 2019/0053691 A1 | 2/2019 | Hansen et al. |
| 2019/0053872 A1 | 2/2019 | Meglan |
| 2019/0059736 A1 | 2/2019 | Maier-Hein et al. |
| 2019/0069824 A1 | 3/2019 | Darty et al. |
| 2019/0076186 A1 | 3/2019 | Fischell et al. |
| 2019/0099070 A1 | 4/2019 | Mark et al. |
| 2019/0099226 A1 | 4/2019 | Hallen |
| 2019/0104919 A1 | 4/2019 | Shelton, IV et al. |
| 2019/0110924 A1 | 4/2019 | Moreno et al. |
| 2019/0117319 A1 | 4/2019 | Cima et al. |
| 2019/0125361 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125459 A1 | 5/2019 | Shelton, IV et al. |
| 2019/0142524 A1 | 5/2019 | Hladio et al. |
| 2019/0159848 A1 | 5/2019 | Quaid et al. |
| 2019/0172371 A1 | 6/2019 | Eckert et al. |
| 2019/0175272 A1 | 6/2019 | Khan et al. |
| 2019/0180865 A1 | 6/2019 | Kashima et al. |
| 2019/0192145 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201045 A1 | 7/2019 | Yates et al. |
| 2019/0201102 A1 | 7/2019 | Shelton, IV et al. |
| 2019/0201116 A1 | 7/2019 | Shelton, IV et al. |
| 2019/0201136 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205567 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0223961 A1 | 7/2019 | Barral et al. |
| 2019/0247050 A1 | 8/2019 | Goldsmith |
| 2019/0269476 A1 | 9/2019 | Bowling et al. |
| 2019/0279524 A1 | 9/2019 | Stoyanov et al. |
| 2019/0290524 A1 | 9/2019 | Augustine et al. |
| 2019/0293554 A1 | 9/2019 | Nakao et al. |
| 2019/0307524 A1 | 10/2019 | Popovic |

(56) References Cited

U.S. PATENT DOCUMENTS

| | | |
|---|---|---|
| 2019/0311542 A1 | 10/2019 | Douglas et al. |
| 2019/0320117 A1 | 10/2019 | Wu et al. |
| 2019/0320878 A1 | 10/2019 | Duindam et al. |
| 2019/0321118 A1 | 10/2019 | Genova et al. |
| 2019/0374140 A1 | 12/2019 | Tucker et al. |
| 2019/0388157 A1 | 12/2019 | Shameli et al. |
| 2020/0008879 A1 | 1/2020 | Popovic et al. |
| 2020/0015899 A1 | 1/2020 | Scheib et al. |
| 2020/0015900 A1 | 1/2020 | Scheib et al. |
| 2020/0015904 A1 | 1/2020 | Scheib et al. |
| 2020/0015907 A1 | 1/2020 | Scheib |
| 2020/0015924 A1 | 1/2020 | Scheib et al. |
| 2020/0015925 A1 | 1/2020 | Scheib |
| 2020/0018844 A1 | 1/2020 | Fridman et al. |
| 2020/0030036 A1 | 1/2020 | Forstein |
| 2020/0035348 A1* | 1/2020 | Sartor ............... A61B 90/361 |
| 2020/0037858 A1 | 2/2020 | Pedreira de Cerqueira Filho |
| 2020/0038112 A1 | 2/2020 | Amanatullah et al. |
| 2020/0060725 A1 | 2/2020 | Sato |
| 2020/0078120 A1 | 3/2020 | Aldridge et al. |
| 2020/0121245 A1 | 4/2020 | Barclay et al. |
| 2020/0188032 A1 | 6/2020 | Komp et al. |
| 2020/0222146 A1 | 7/2020 | Komp |
| 2020/0246073 A1 | 8/2020 | Rossetto et al. |
| 2020/0253669 A1 | 8/2020 | Diolaiti et al. |
| 2020/0271565 A1 | 8/2020 | Gütle et al. |
| 2020/0273577 A1 | 8/2020 | Wolf et al. |
| 2020/0281662 A1 | 9/2020 | Cong et al. |
| 2020/0289205 A1 | 9/2020 | Scheib et al. |
| 2020/0289216 A1 | 9/2020 | Denlinger et al. |
| 2020/0289219 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0291476 A1 | 9/2020 | Deng et al. |
| 2020/0315721 A1 | 10/2020 | Rabindran et al. |
| 2020/0330166 A1 | 10/2020 | Meglan et al. |
| 2020/0345451 A1 | 11/2020 | Peine et al. |
| 2020/0367972 A1 | 11/2020 | Zhang et al. |
| 2020/0397266 A1 | 12/2020 | Hufford |
| 2020/0405395 A1 | 12/2020 | Gullotti et al. |
| 2021/0045838 A1 | 2/2021 | Bradbury et al. |
| 2021/0068908 A1 | 3/2021 | Thienphrapa et al. |
| 2021/0121251 A1* | 4/2021 | Aljuri ............... G16H 50/20 |
| 2021/0137634 A1 | 5/2021 | Lang |
| 2021/0153943 A1 | 5/2021 | Piron et al. |
| 2021/0196098 A1 | 7/2021 | Shelton, IV et al. |
| 2021/0196108 A1 | 7/2021 | Shelton, IV |
| 2021/0196109 A1 | 7/2021 | Shelton, IV et al. |
| 2021/0196381 A1 | 7/2021 | Eckert et al. |
| 2021/0196382 A1 | 7/2021 | Mumaw et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0199557 A1 | 7/2021 | Shelton, IV et al. |
| 2021/0205019 A1 | 7/2021 | Shelton, IV et al. |
| 2021/0212792 A1 | 7/2021 | Shelton, IV et al. |
| 2021/0259660 A1 | 8/2021 | Bharat et al. |
| 2021/0259789 A1 | 8/2021 | Wright et al. |
| 2021/0275251 A1 | 9/2021 | Shelton, IV et al. |
| 2021/0275252 A1 | 9/2021 | Shelton, IV et al. |
| 2021/0282861 A1 | 9/2021 | Eckert et al. |
| 2021/0307835 A1 | 10/2021 | Shelton, IV et al. |
| 2021/0307865 A1 | 10/2021 | Shelton, IV et al. |
| 2021/0307867 A1 | 10/2021 | Shelton, IV et al. |
| 2021/0307868 A1 | 10/2021 | Shelton, IV et al. |
| 2021/0307869 A1 | 10/2021 | Shelton, IV et al. |
| 2021/0307870 A1 | 10/2021 | Shelton, IV et al. |
| 2021/0315645 A1 | 10/2021 | Hares et al. |
| 2022/0000559 A1 | 1/2022 | Leonard et al. |
| 2022/0000565 A1 | 1/2022 | Gururaj et al. |
| 2022/0047259 A1 | 2/2022 | Prior et al. |
| 2022/0079675 A1 | 3/2022 | Lang |
| 2022/0133412 A1 | 5/2022 | Tolkowsky et al. |
| 2022/0273288 A1 | 9/2022 | Scheib et al. |
| 2022/0323066 A1 | 10/2022 | Scheib et al. |
| 2023/0046220 A1 | 2/2023 | Scheib et al. |
| 2023/0074951 A1 | 3/2023 | Scheib et al. |

FOREIGN PATENT DOCUMENTS

| | | |
|---|---|---|
| EP | 2700365 A1 | 2/2014 |
| EP | 2754383 A2 | 7/2014 |
| EP | 3367387 A1 | 8/2018 |
| JP | 2006280591 A | 10/2006 |
| JP | 4106991 B2 | 6/2008 |
| KR | 20120068597 A | 6/2012 |
| WO | WO-2008033133 A2 | 3/2008 |
| WO | WO-2013093391 A1 | 6/2013 |
| WO | WO-2013163391 A1 | 10/2013 |
| WO | WO-2015135058 A1 | 9/2015 |
| WO | WO-2017042171 A1 | 3/2017 |
| WO | WO-2018171851 A1 | 9/2018 |
| WO | WO-2018200767 A1 | 11/2018 |
| WO | WO-2019130085 A1 | 7/2019 |
| WO | WO-2020116991 A1 | 6/2020 |

OTHER PUBLICATIONS

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

Elhajj, et al., "Sleeve Gastrectomy Surgical Assistive Instrument for Accurate Remnant Stomach Volume," ASME, J. Med. Devices, vol. 4, pp. 1-10, Jun. 2010.

Brecht, Hans-Peter et al., "Whole-body three-dimensional optoacoustic tomography system for small animals," Journal of Biomedical Optics, vol. 14, No. 6, 064007-1-064007-7 (2009).

Ge, Jiawei et al., "Landmark-Guided Deformable Image Registration for Supervised Autonomous Robotic Tumor Resection," Advances in Intelligent Data Analysis XIX, LNCS, Springer International Publishing, pp. 320-328, Oct. 10, 2019.

Ueda et al., "Quantitative computed tomography for the prediction of pulmonary function after lung cancer surgery: a simple method using simulation software," European Journal of Cardio-thoracic Surgery, 35 (2009) 414-418.

Fuchs et al., "Three-dimensional visualization and virtual simulation of resections in pediatric solid tumors," Journal of Pediatric Surgery (2005) 40, 364-370.

Brainlab Ag: "iPLAN CRANIAL—Software user guide", Jan. 1, 2014, Retrieved from the internet: URL: https://userguides.brainlab.com/wp-content/uploads/2019/12/iPlan-Cranial-3.0-Software-User-Guide-English-60914-63EN-Rev.1.4.pdf, pp. 1-268 (Jan. 1, 2014).

* cited by examiner

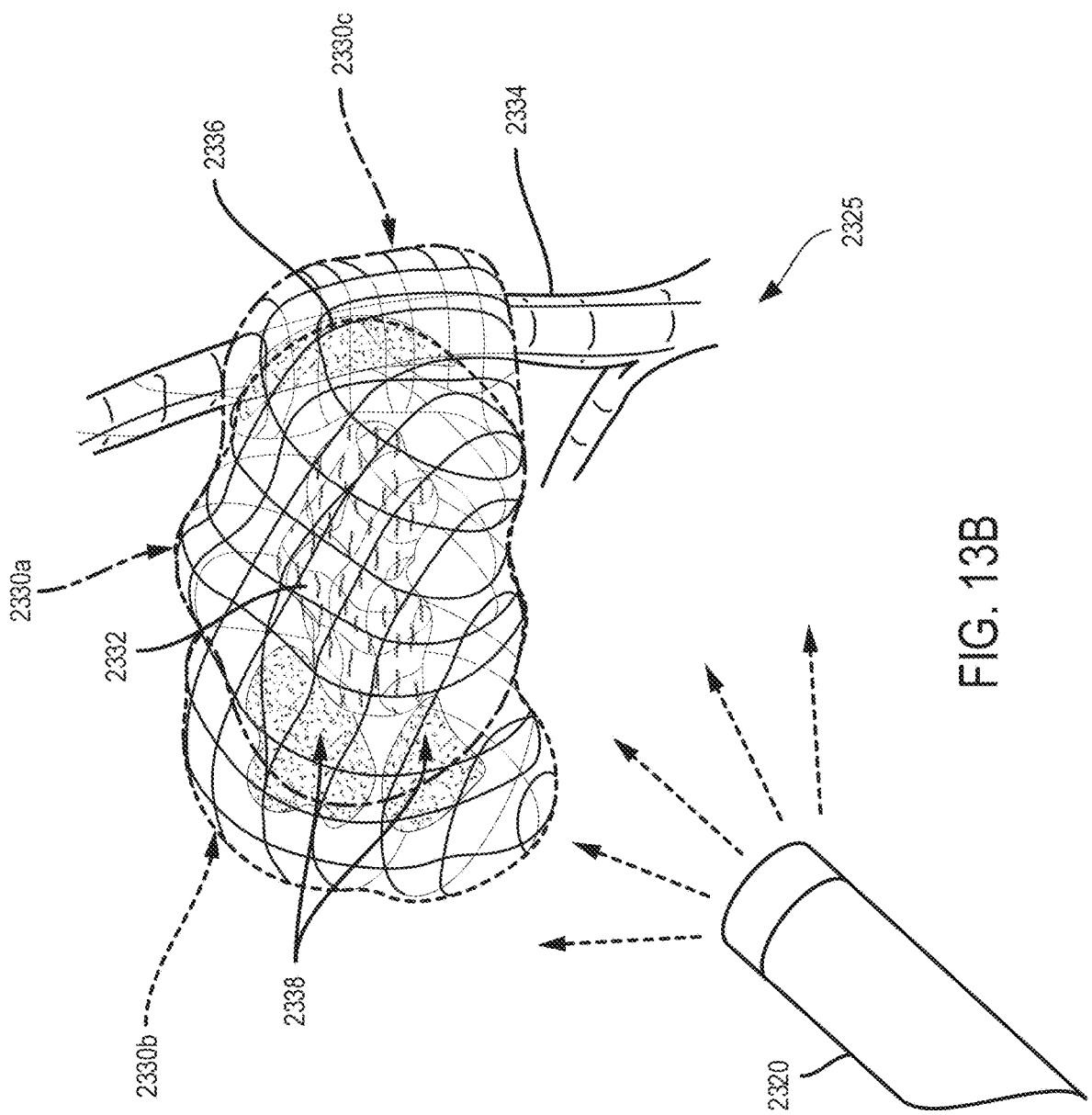

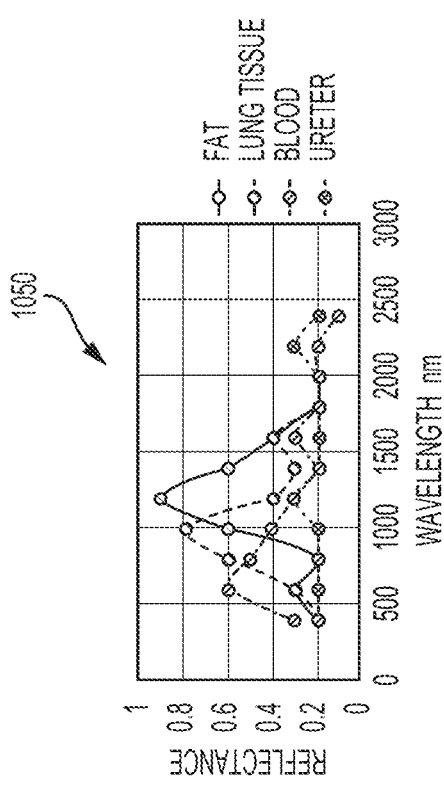
FIG. 13C
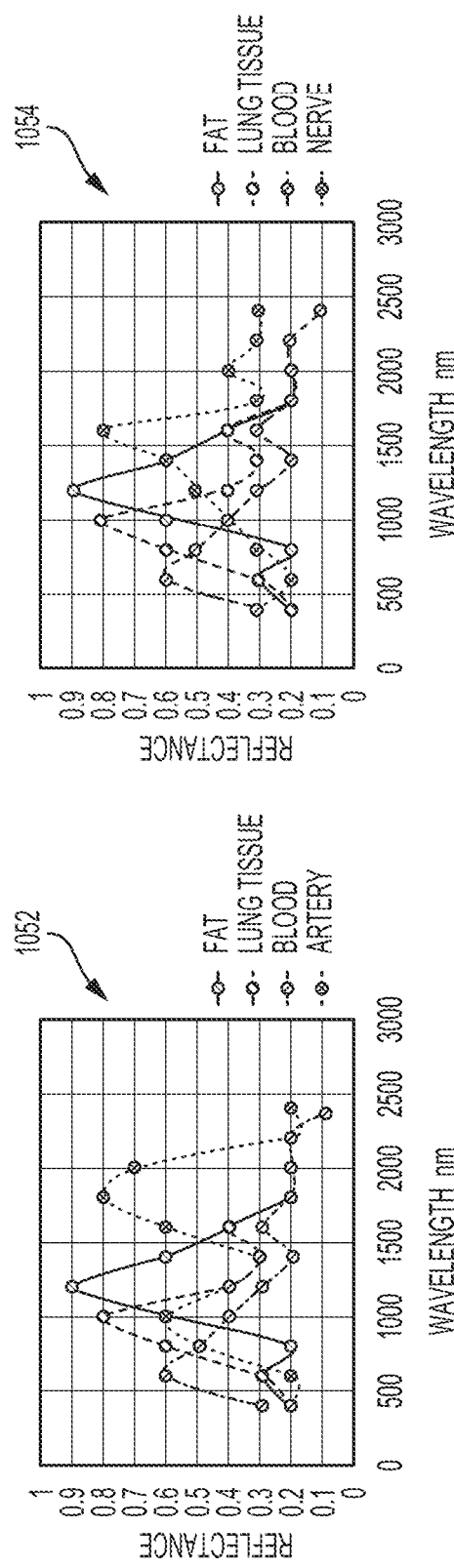
FIG. 13E
FIG. 13D

| THORACIC PROCEDURE | NOT A WEDGE PROCEDURE | CONFIRM PATIENT | VATS | CONFIRM PATIENT IS IN O.R. | PATIENT UNDER | PROCEDURE BEGINS | CONFIRM LOBECTOMY vs. SEGMENTECTOMY LAP PORTION STARTS |
|---|---|---|---|---|---|---|---|
| SELECT PATIENT DATA 2502 | SCAN PRODUCTS 2504 | UNIQUE ID 2506 | SMOKE EVAC. DATA INSUFFLATION DATA SCOPE DATA | EKG DATA | EKG, BP AND VENTILATOR DATA | VENTILATOR DATA | SCOPE DATA 2516 |
| PULL ELECTRONIC MEDICAL RECORDS | SCAN INCOMING SUPPLIES | SCAN PATIENT BAND | 2508 TURN ON HUB AUXILIARY EQUIPMENT | 2510 ATTACH EKG | 2512 INDUCE ANESTHESIA | 2514 COLLAPSE LUNG | SCOPE IMAGE |
| WHAT THE HUB KNOWS | TYPE OF DATA | | | | | PROCEDURE STEP | |

| DISSECT TO MOBILIZE LUNG | LIGATE ARTERY & VEIN | TRANSECT PARENCHYMA | DISSECT NODES | PATIENT EMERGENCE | PATIENT TRANSFER TO RECOVERY ROOM |
|---|---|---|---|---|---|
| GENERATOR DATA 2518 | STAPLER DATA 2520 | STAPLER & CARTRIDGE DATA 2522 | LEAK TEST GENERATOR DATA 2524 | VENTILATOR DATA 2526 | LOSS OF EKG DATA LOSS OF BP DATA 2528 |
| DISSECTION | LIGATION | SEGMENTECTOMY | NODE DISSECTION | REVERSE ANESTHESIA | REMOVE MONITORS |
| WHAT THE HUB KNOWS | TYPE OF DATA | | | | PROCEDURE STEP |

FIG. 21

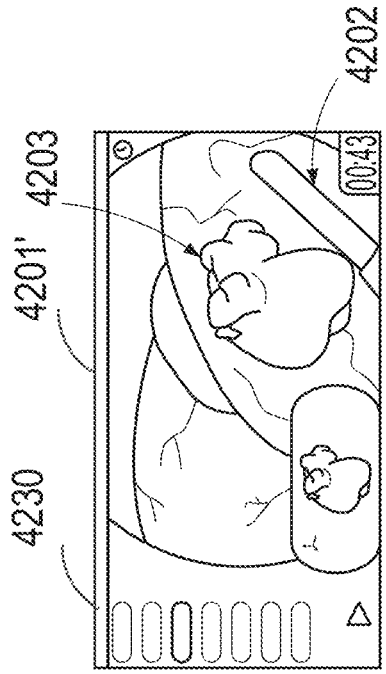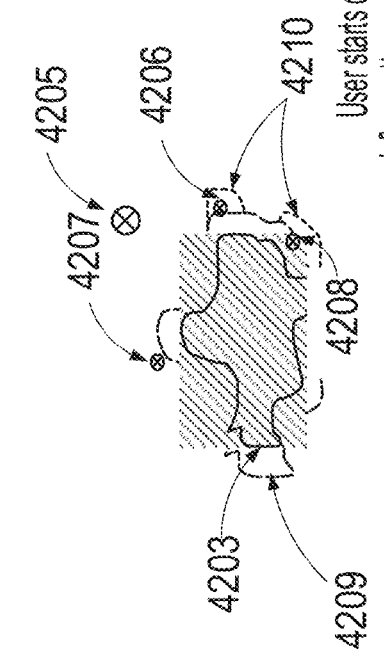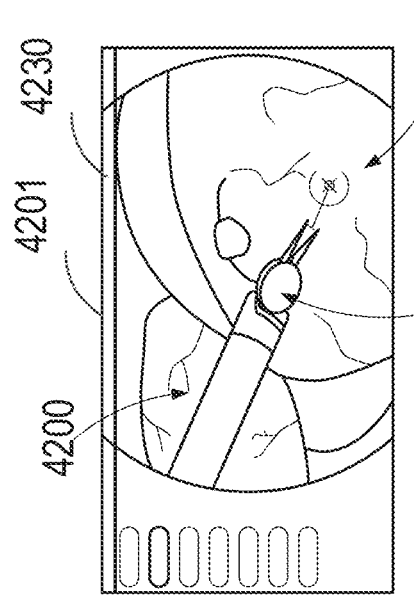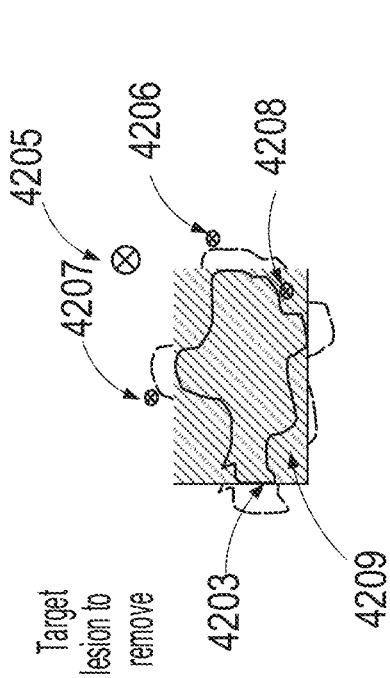
FIG. 32A
FIG. 32C
FIG. 32B
FIG. 32D

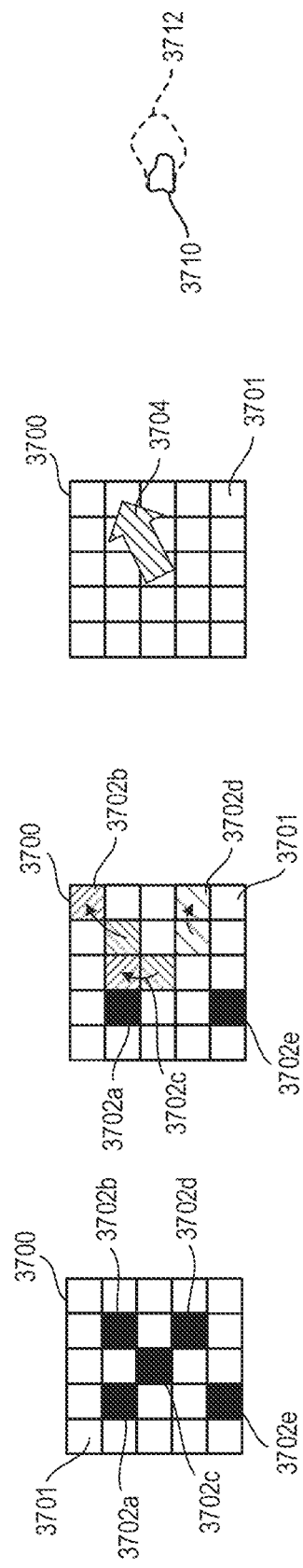

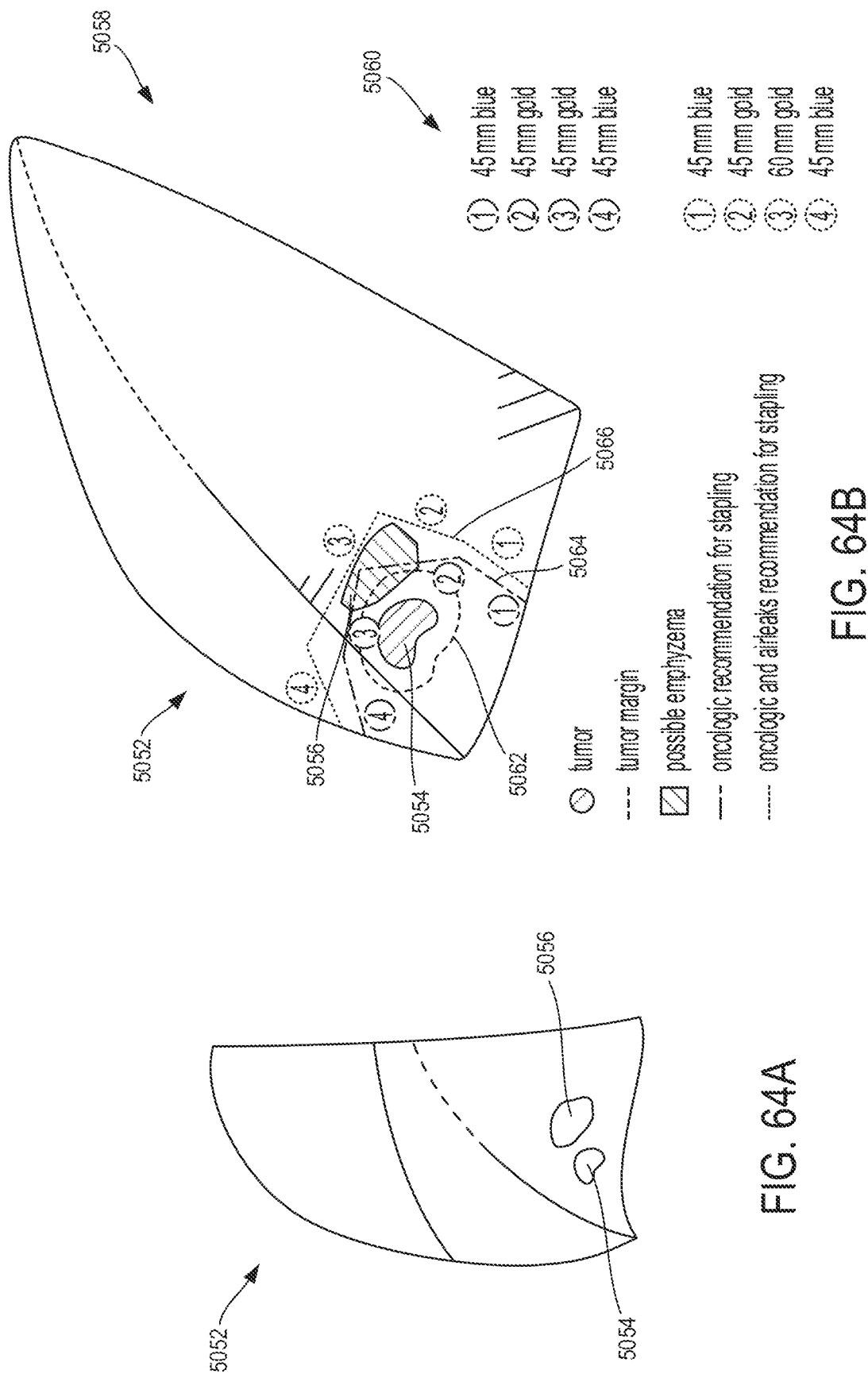

SURGICAL HUB FOR USE WITH A SURGICAL SYSTEM IN A SURGICAL PROCEDURE

CROSS-REFERENCE TO RELATED APPLICATION

This application is a continuation application claiming priority under 35 U.S.C. § 120 to U.S. patent application Ser. No. 16/729,807, entitled METHOD OF USING IMAGING DEVICES IN SURGERY, filed Dec. 30, 2019, which issued on Mar. 29, 2022 as U.S. Pat. No. 11,284,963, the entire disclosure of which is hereby incorporated by reference herein.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In various embodiments, a method for generating and updating a three-dimensional representation of a surgical site based on imaging data from an imaging system is disclosed. The method comprises the steps of generating a first image of the surgical site based on structured electromagnetic radiation (EMR) emitted from the imaging system, receiving a second image of the surgical site, aligning the first image and the second image, generating a three-dimensional representation of the surgical site based on the first image and the second image as aligned, displaying the three-dimensional representation on a display screen, receiving a user selection to manipulate the three-dimensional representation, and updating the three-dimensional representation as displayed on the display screen from a first state to a second state according to the received user selection.

In various embodiments, a method for generating a three-dimensional representation of a surgical site is disclosed. The method comprises the steps of detecting a first pattern of structured light on an anatomical surface contour of the surgical site via an image sensor, detecting a second pattern of structured light on a subsurface contour of the surgical site via the image sensor, transmitting first imaging data indicative of the first pattern of structured light to a control circuit, transmitting second imaging data indicative of the second pattern of structured light to the control circuit, processing the first imaging data and the second imaging data via the control circuit, generating a three-dimensional digital representation of an anatomical structure including the anatomical surface contour and the subsurface contour, and transmitting the three-dimensional digital representation of the anatomical structure to a display.

In various embodiments, a method for determining a surgical scenario based on input signals from multiple surgical devices is disclosed. The method comprises detecting imaging data from a plurality of light sources via an image sensor. The plurality of light sources are configured to emit a pattern of structured light onto an anatomical structure. The method further comprises receiving the imaging data from the image sensor, generating a three-dimensional digital representation of the anatomical structure from the pattern of structured light detected by the imaging data, obtaining metadata from the imaging data, overlaying the metadata on the three-dimensional digital representation, receiving updated imaging data from the image sensor, generating an updated three-dimensional digital representation of the anatomical structure based on the updated imaging data, and updating the overlaid metadata on the updated three-dimensional digital representation of the anatomical structure in response to a surgical scenario determined by a situational awareness module.

In various aspects, a surgical hub for use with a surgical system in a surgical procedure performed in an operating room is disclosed. The surgical hub comprising a control circuit configured to receive real-time visualization data from a camera, and determine an estimated parameter change based on the visualization data and surgical procedure. The control circuit is configured to receive pre-operative non-visualization data. The pre-operative non-visualization data is received before the surgical procedure is performed. The control circuit is configured to determine a tissue parameter based on the real-time visualization data. The control circuit is configured to adjust an operational parameter of a surgical device used to perform the surgical procedure based on the tissue parameter. The surgical device is communicably coupled to the surgical hub. The control circuit is configured to receive post-operative non-visualization data. The post-operative non-visualization data is received after the surgical procedure is performed. The control circuit is configured to determine a difference between the pre-operative non-visualization data and the post-operative non-visualization data. The control circuit is configured to assess an output of the surgical procedure based on a comparison of the difference and the estimated parameter change. The pre-operative non-visualization data comprises pre-operative partial pressure of carbon dioxide of a patient, and the post-operative non-visualization data comprises post-operative partial pressure of carbon dioxide of the patient. The difference comprises a difference between the pre-operative partial pressure of carbon dioxide and the post-operative partial pressure of carbon dioxide. Assessing the output of the surgical procedure based on the comparison of the difference and the estimated parameter change comprises comparing the comparison of the difference between the pre-operative partial pressure of carbon dioxide and the post-operative partial pressure of carbon dioxide with the estimated parameter change.

In various aspects, a surgical hub for use with a surgical system in a surgical procedure performed in an operating room is disclosed. The surgical hub comprising a control circuit configured to receive real-time visualization data from a camera. The control circuit is configured to determine an estimated parameter change based on the visualization data and surgical procedure. The control circuit is configured to receive pre-operative data. The pre-operative data is received before the surgical procedure is performed. The control circuit is configured to determine a tissue parameter based on the real-time visualization data. The control circuit is configured to adjust an operational parameter of a surgical device used to perform the surgical procedure based on the tissue parameter. The surgical device is communicably coupled to the surgical hub. The control circuit is configured to receive post-operative data. The post-operative data is received after the surgical procedure is performed. The control circuit is configured to determine a difference between the pre-operative data and post-operative data. The control circuit is configured to assess an output of the surgical procedure based on the difference and the estimated parameter change. The pre-operative data comprises pre-operative partial pressure of carbon dioxide of a patient, and the post-operative data comprises post-operative partial pressure of carbon dioxide of the patient. The difference comprises a difference between the pre-operative partial pressure of carbon dioxide and the post-operative partial pressure of carbon dioxide. Assessing the output of the surgical procedure based on the difference and the estimated parameter change comprises comparing the difference between the pre-operative partial pressure of carbon dioxide and the post-operative partial pressure of carbon dioxide with the estimated parameter change.

In various aspects, a surgical hub for use with a surgical system in a surgical procedure performed in an operating room is disclosed. The surgical hub comprising a control circuit configured to receive real-time visualization data from a camera. The control circuit is configured to determine an estimated parameter change based on the visualization data and surgical procedure. The control circuit is configured to receive pre-operative non-visualization data from a surgical device. The pre-operative non-visualization data is received before the surgical procedure is performed. The control circuit is configured to determine a first value of a non-visualization parameter based on the pre-operative non-visualization data. The control circuit is configured to determine a tissue parameter based on the real-time visualization data. The control circuit is configured to adjust an operational parameter of a surgical device used to perform the surgical procedure based on the tissue parameter. The surgical device is communicably coupled to the surgical hub. The control circuit is configured to receive post-operative non-visualization data from the surgical device. The post-operative non-visualization data is received after the surgical procedure is performed. The control circuit is configured to determine a second value of the non-visualization parameter based on the post-operative non-visualization data. The control circuit is configured to assess an output of the surgical procedure based on at least the estimated parameter change, the first value, and the second value. The first value of the non-visualization parameter comprises a pre-operative partial pressure value of carbon dioxide of a patient, and the second value of the non-visualization parameter comprises a post-operative partial pressure value of carbon dioxide of the patient. Assessing the output of the surgical procedure based on at least the estimated parameter change, the first value, and the second value comprises comparing a difference between the pre-operative partial pressure value of carbon dioxide and the post-operative partial pressure value of carbon dioxide with the estimated parameter change.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

FIG. 13B is a schematic of the visualization of anatomical structures via a spectral surgical visualization system, according to at least one aspect of the present disclosure.

FIGS. 13C-13E depict illustrative hyperspectral identifying signatures to differentiate anatomy from obscurants, wherein FIG. 13C is a graphical representation of a ureter signature versus obscurants, FIG. 13D is a graphical representation of an artery signature versus obscurants, and FIG. 13E is a graphical representation of a nerve signature versus obscurants, according to at least one aspect of the present disclosure.

Figure 14:
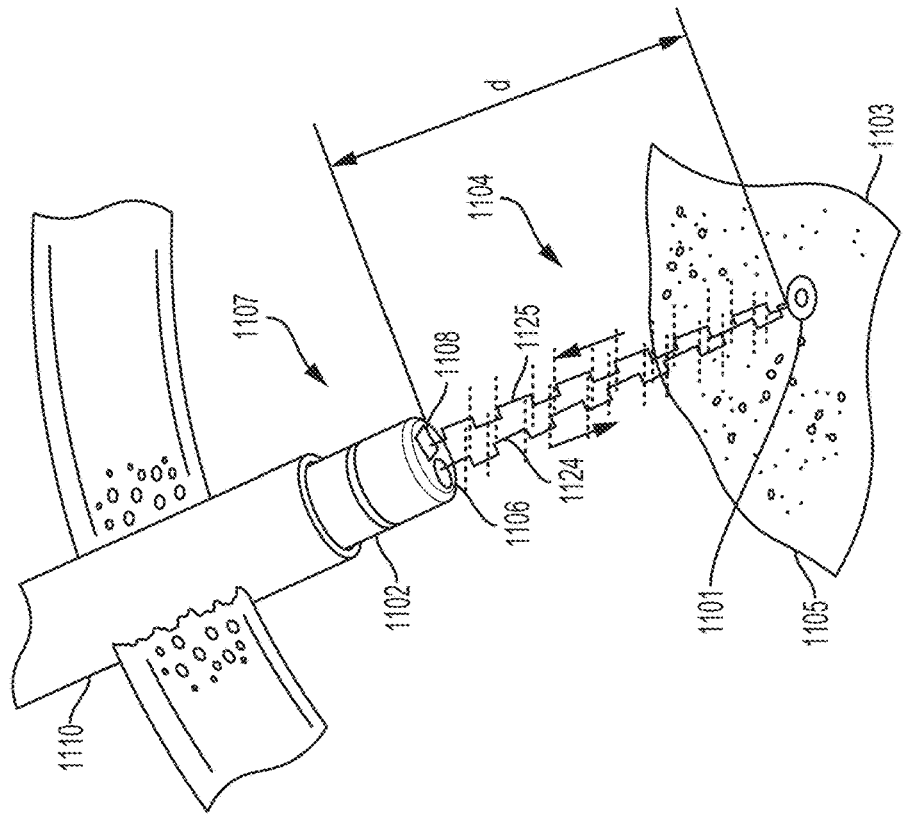

FIG. 14 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 15:
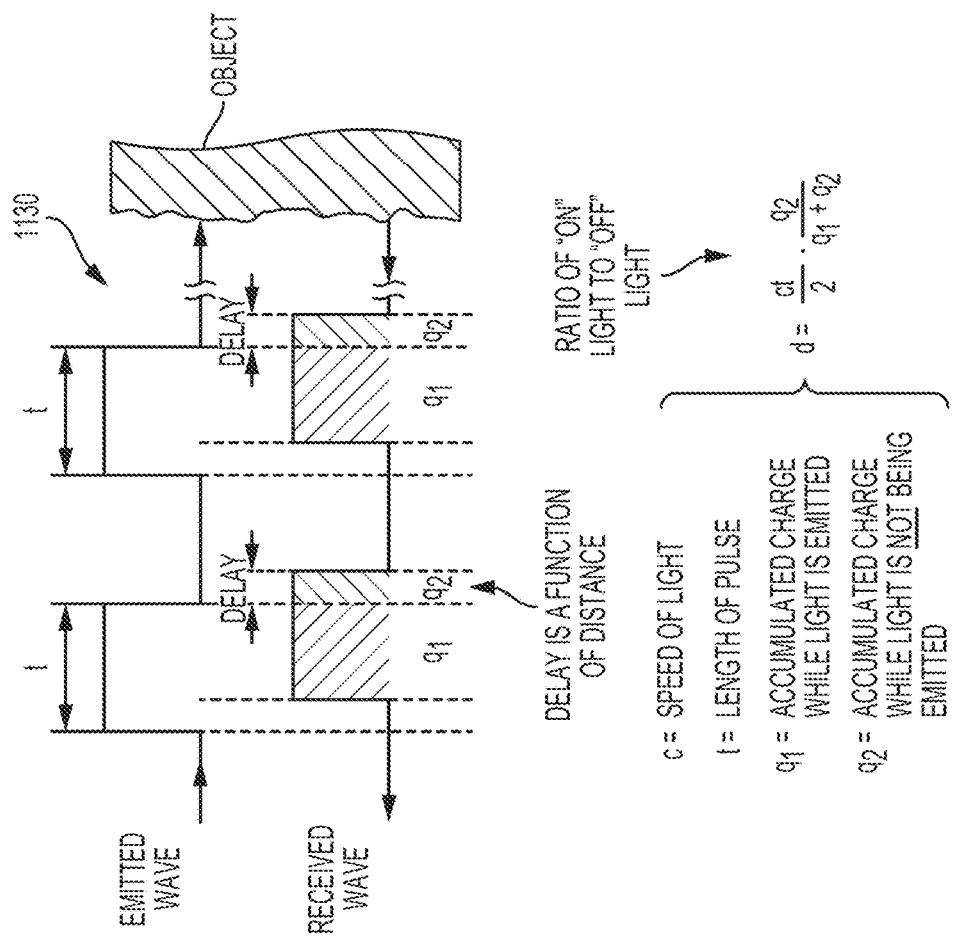

FIG. 15 is a schematic of an emitted wave, a received wave, and a delay between the emitted wave and the received wave of the NIR time-of-flight measurement system of FIG. 17A, according to at least one aspect of the present disclosure.

Figure 16:
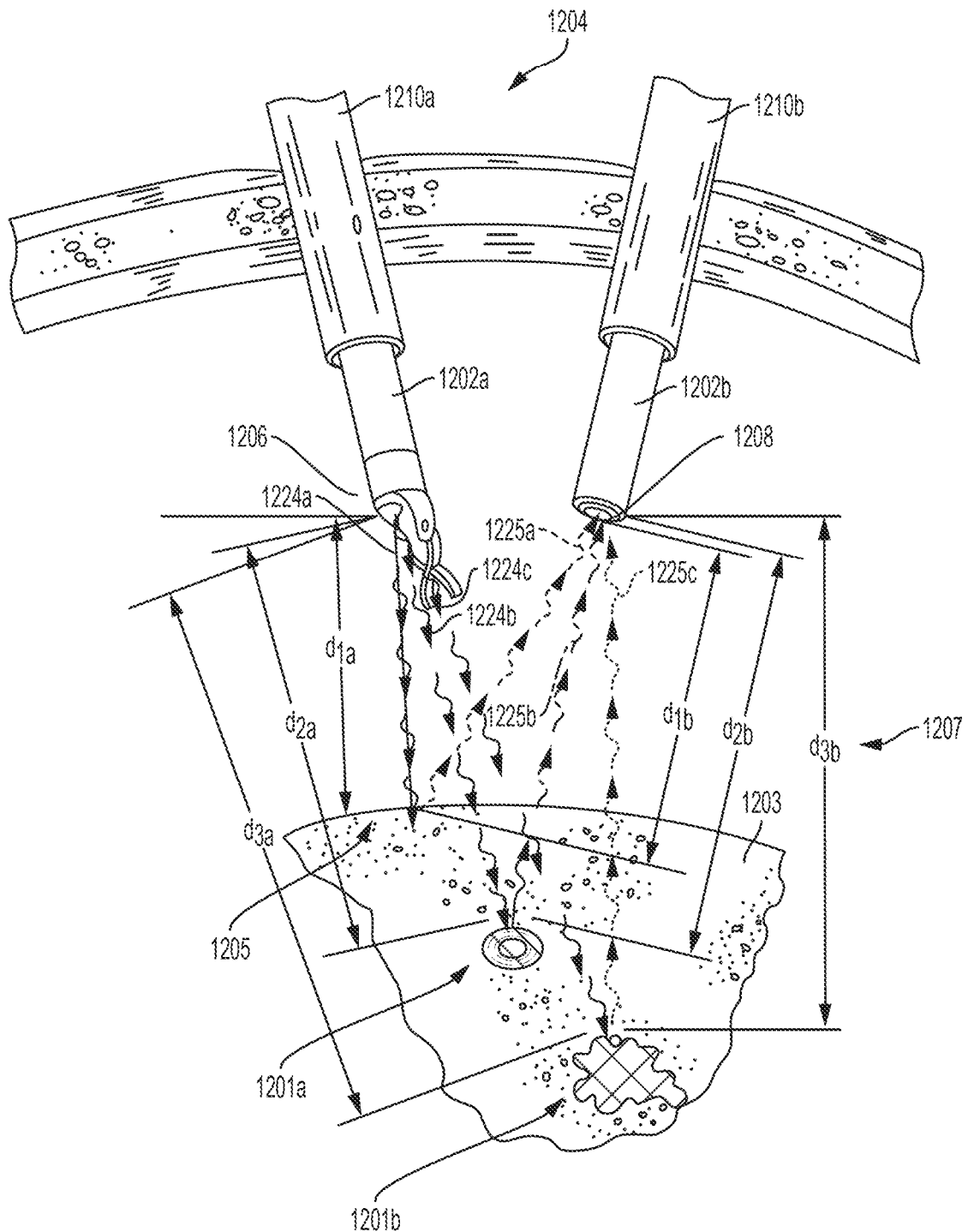

FIG. 16 illustrates a NIR time-of-flight measurement system configured to sense a distance to different structures, the time-of-flight measurement system including a transmitter (emitter) and a receiver (sensor) on separate devices, according to at least one aspect of the present disclosure.

Figure 17:
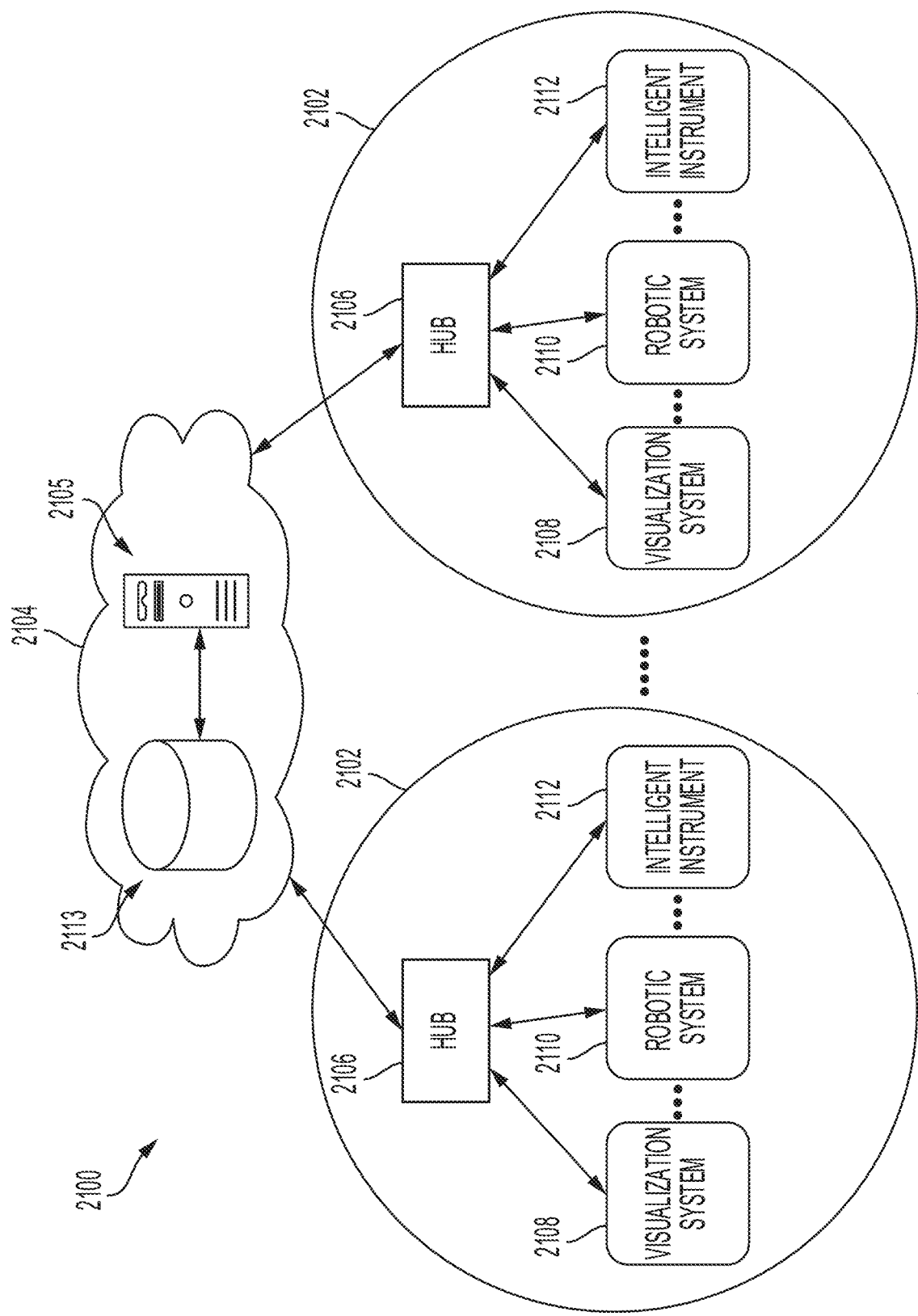

FIG. 17 is a block diagram of a computer-implemented interactive surgical system, according to at least one aspect of the present disclosure.

Figure 18:
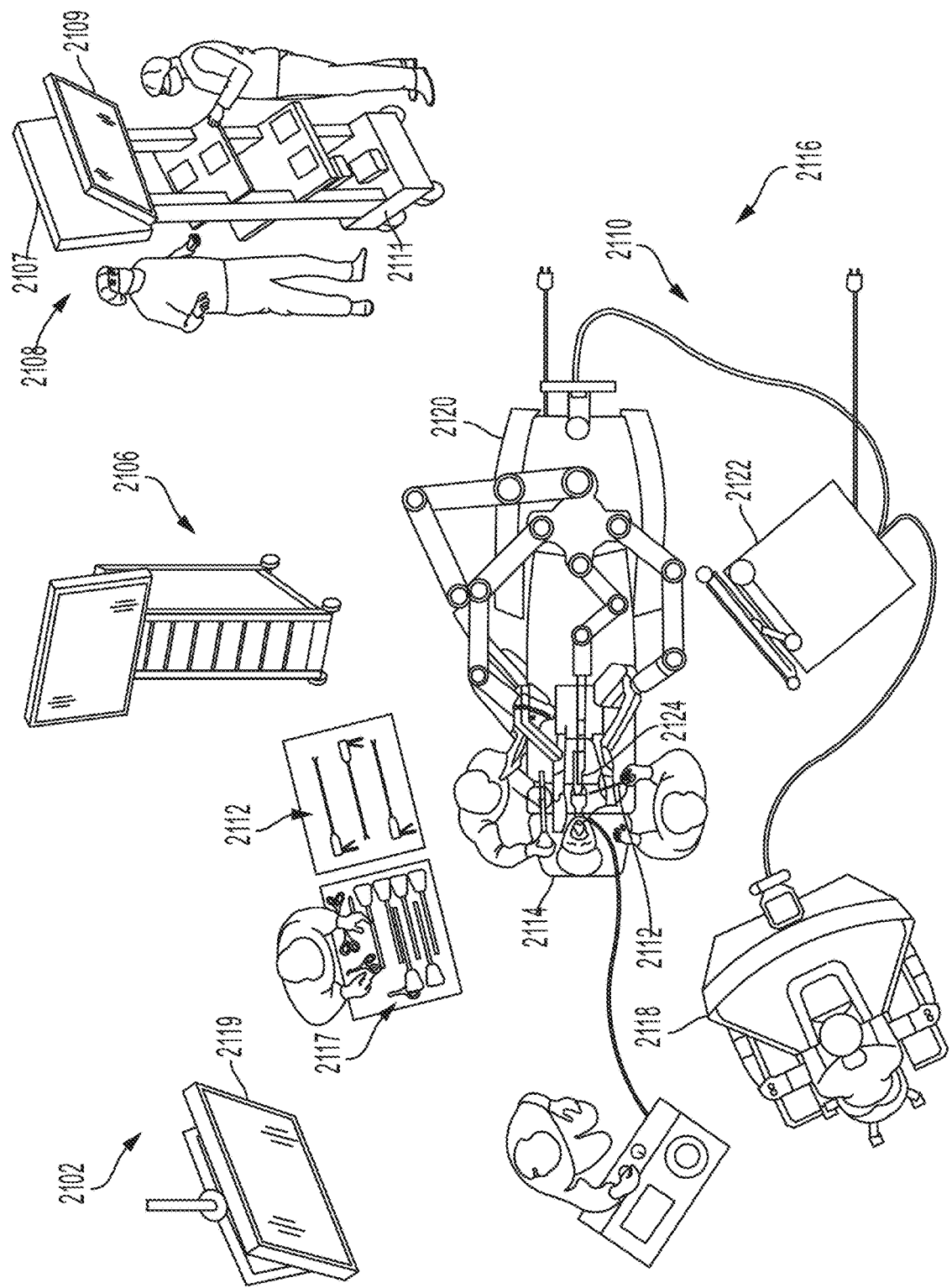

FIG. 18 is a surgical system being used to perform a surgical procedure in an operating room, according to at least one aspect of the present disclosure.

Figure 19:
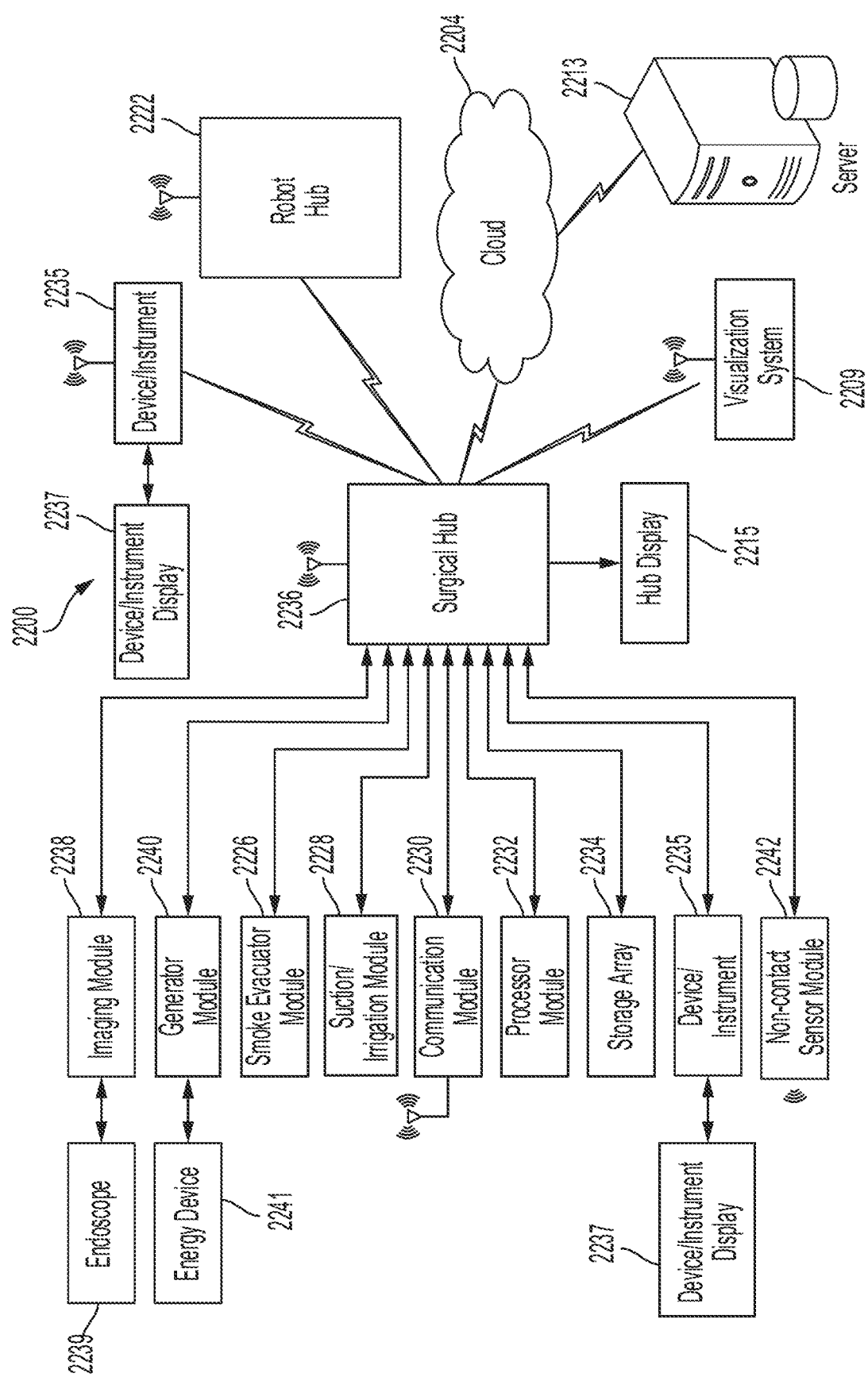

FIG. 19 illustrates a computer-implemented interactive surgical system, according to at least one aspect of the present disclosure.

Figure 20:
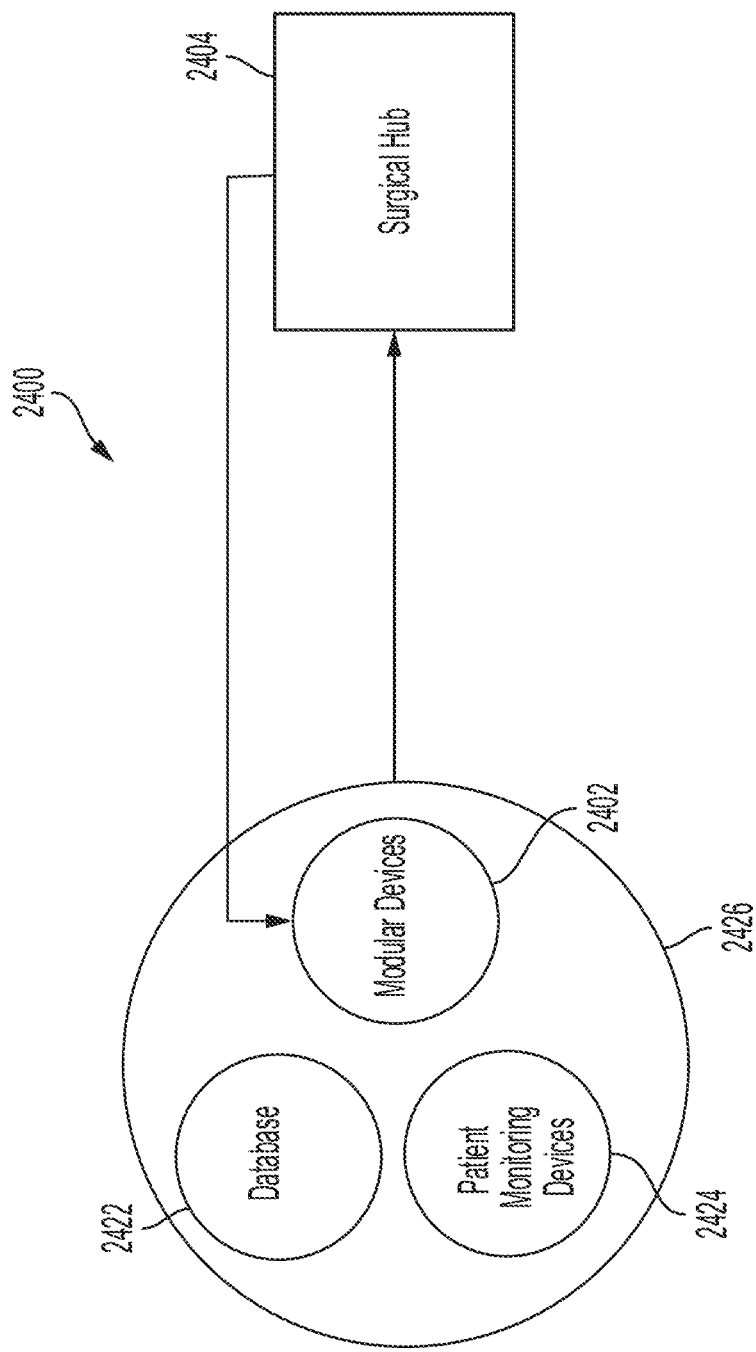

FIG. 20 illustrates a diagram of a situationally aware surgical system, according to at least one aspect of the present disclosure.

FIG. 21 illustrates a timeline depicting situational awareness of a hub, according to at least one aspect of the present disclosure.

Figure 22:

FIG. 22 is a logic flow diagram of a process depicting a control program or a logic configuration for correlating visualization data with instrument data, in accordance with at least one aspect of the present disclosure.

Figure 23:
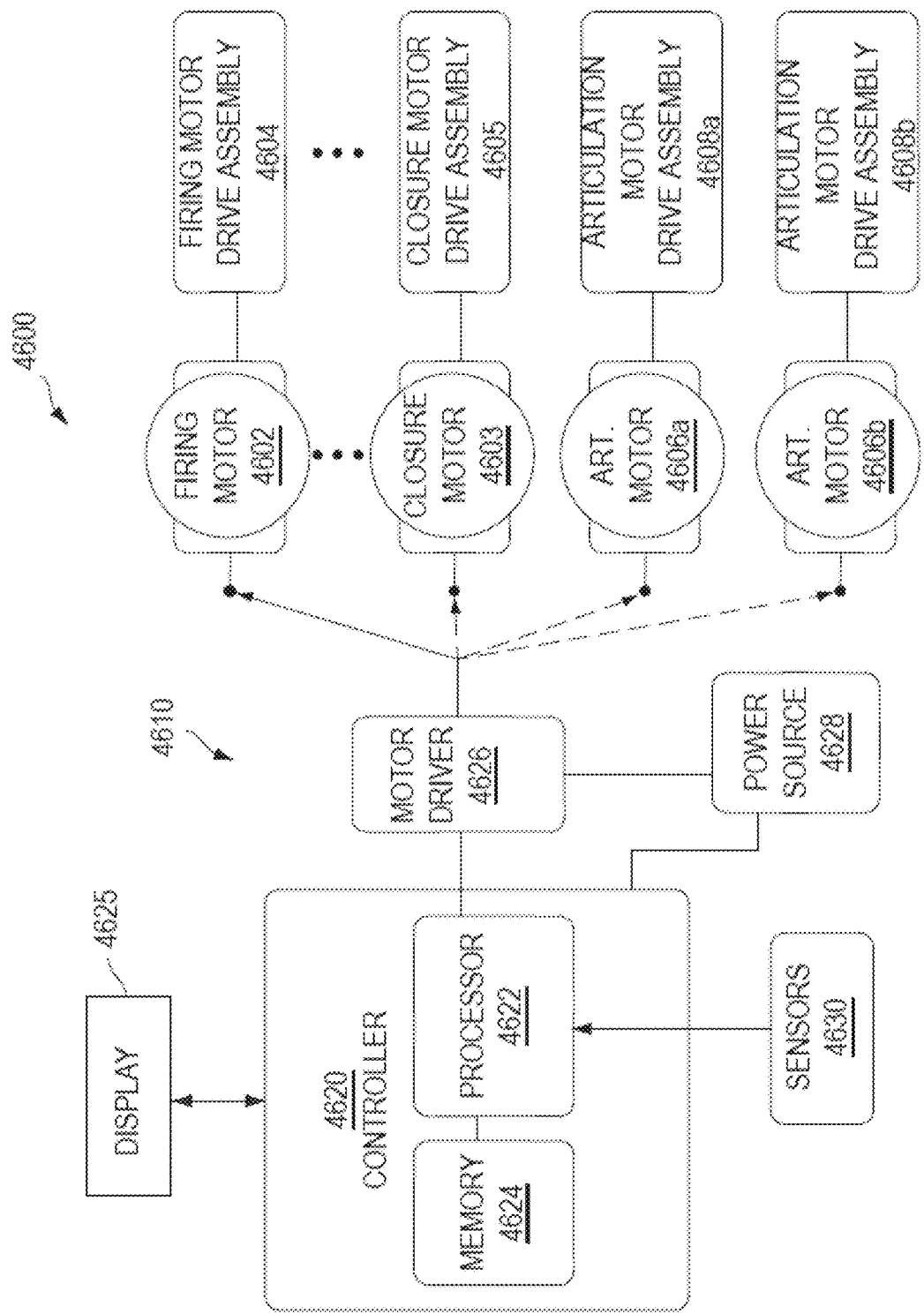

FIG. 23 is a schematic diagram of a surgical instrument, in accordance with at least one aspect of the present disclosure.

Figure 24:
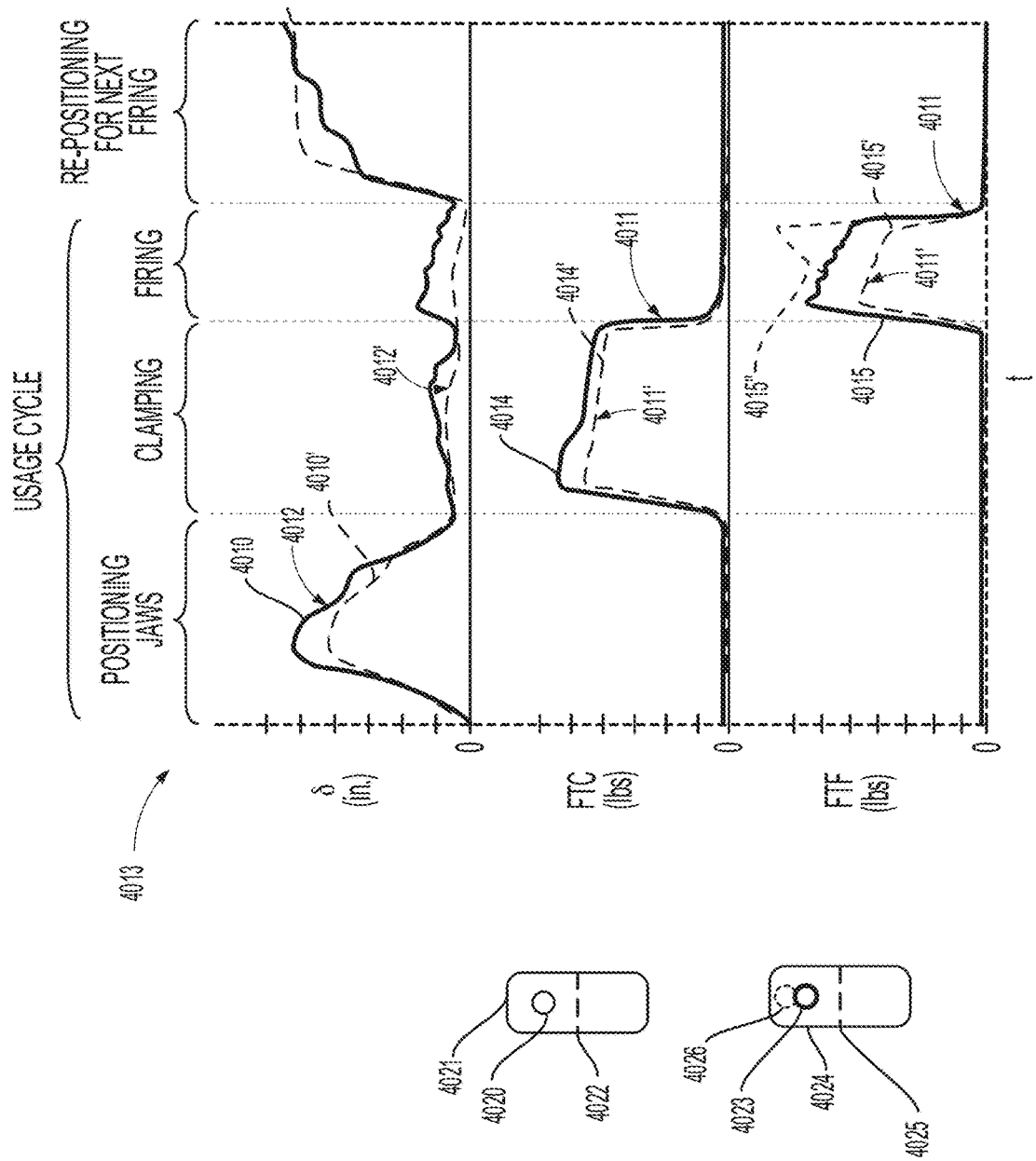

FIG. 24 is a graph depicting a composite data set and Force-to-Close ("FTC") and Force-to-Fire ("FTF") virtual gauges, in accordance with at least one aspect of the present disclosure.

Figure 25B:
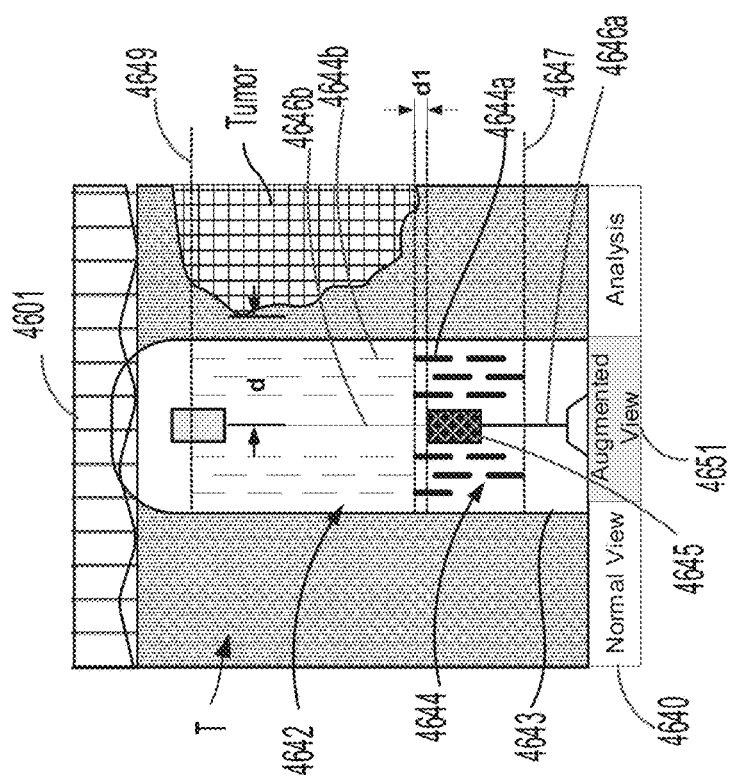
Figure 25A:
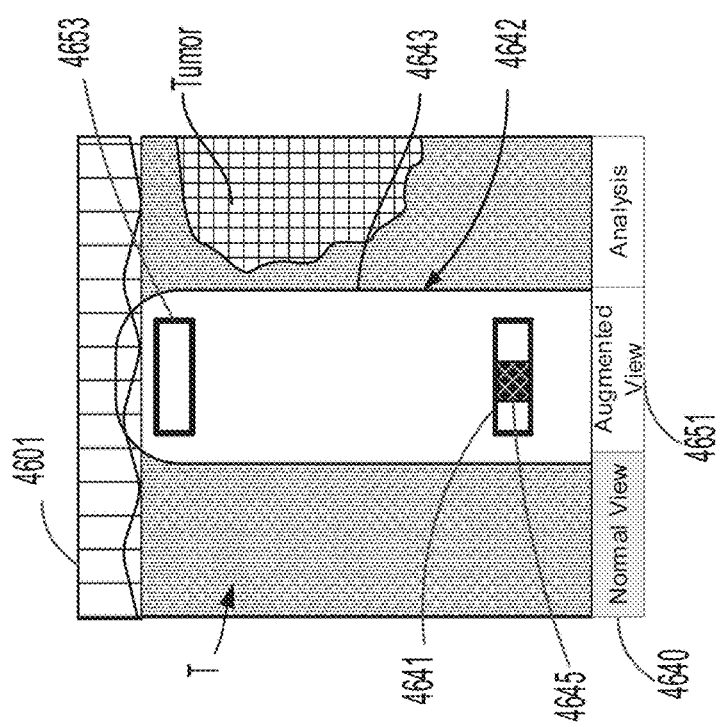

FIG. 25A illustrates a normal view of a screen of a visualization system displaying a live feed of an end effector in a surgical field of a surgical procedure, in accordance with at least one aspect of the present disclosure.

FIG. 25B illustrates an augmented view of a screen of a visualization system displaying a live feed of an end effector in a surgical field of a surgical procedure, in accordance with at least one aspect of the present disclosure.

Figure 26:
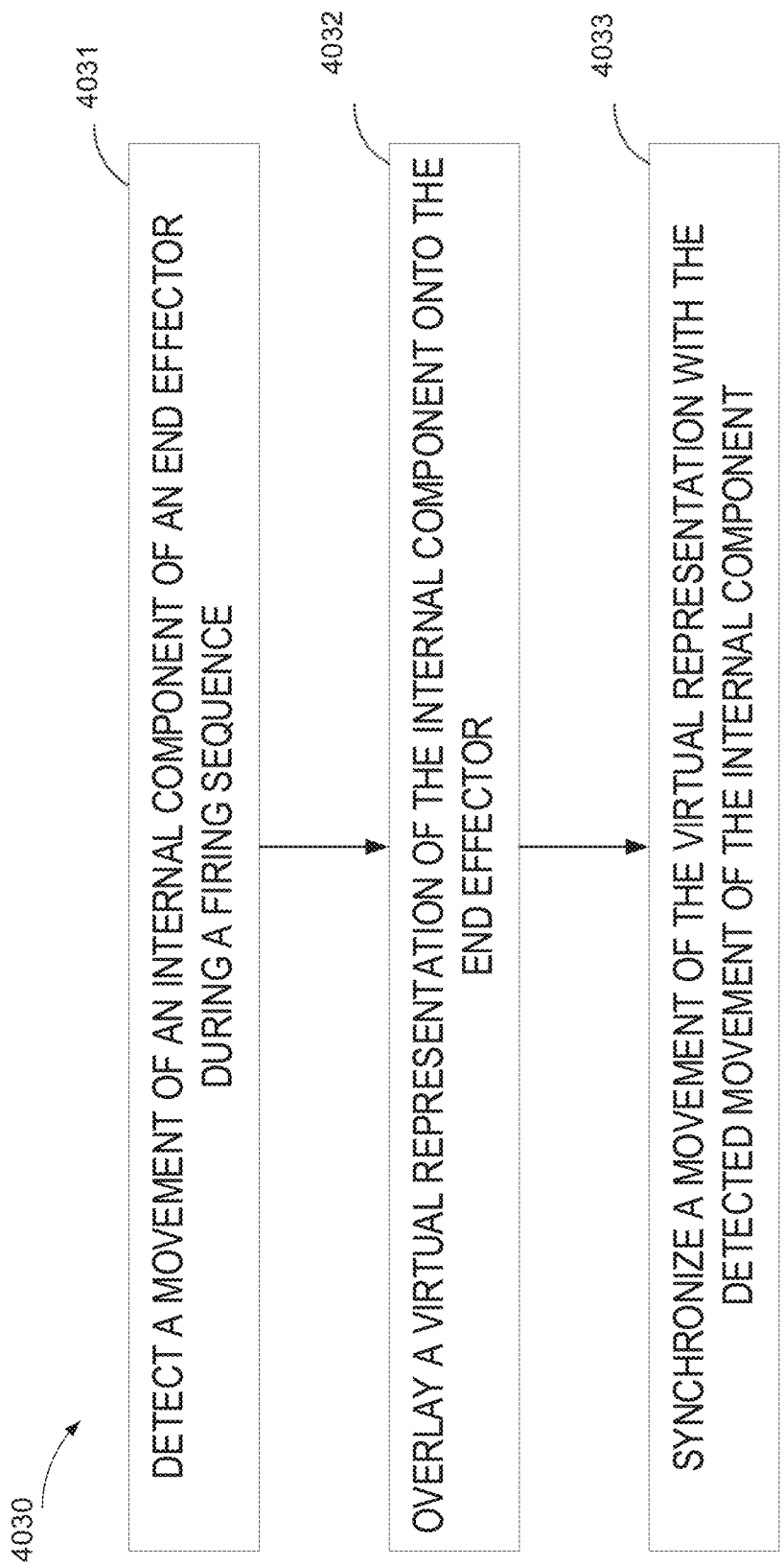

FIG. 26 is a logic flow diagram of a process depicting a control program or a logic configuration for synchronizing movement of a virtual representation of an end-effector component with actual movement of the end-effector component, in accordance with at least one aspect of the present disclosure.

Figure 27:
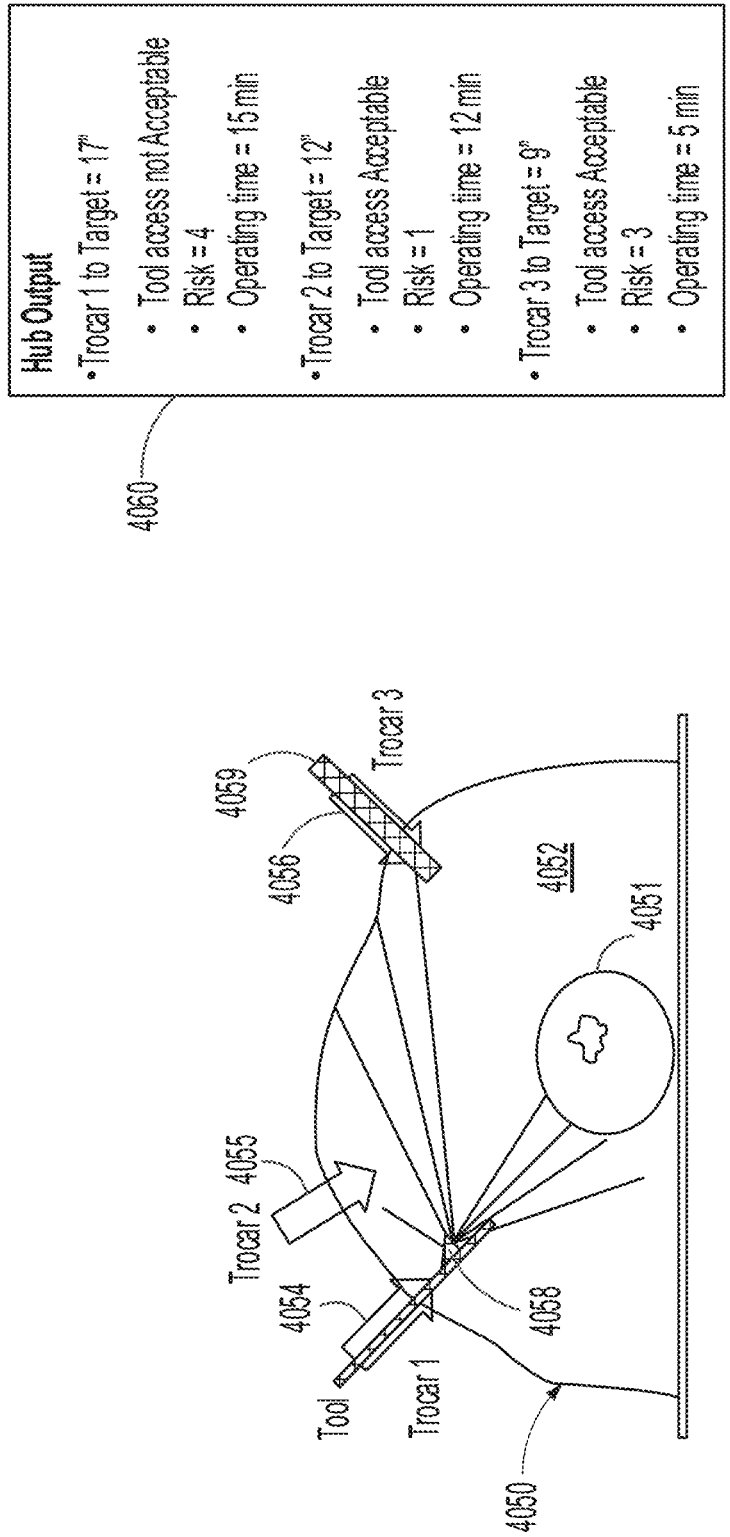

FIG. 27 illustrates a body wall and an anatomical structure in a cavity beneath the body wall, with trocars penetrating through the body wall into the cavity, and a screen displaying trocar distances from the anatomical structure, risks associated with presenting surgical instruments through the trocars, and the estimated operating times associated therewith, in accordance with at least one aspect of the present disclosure.

Figure 28:
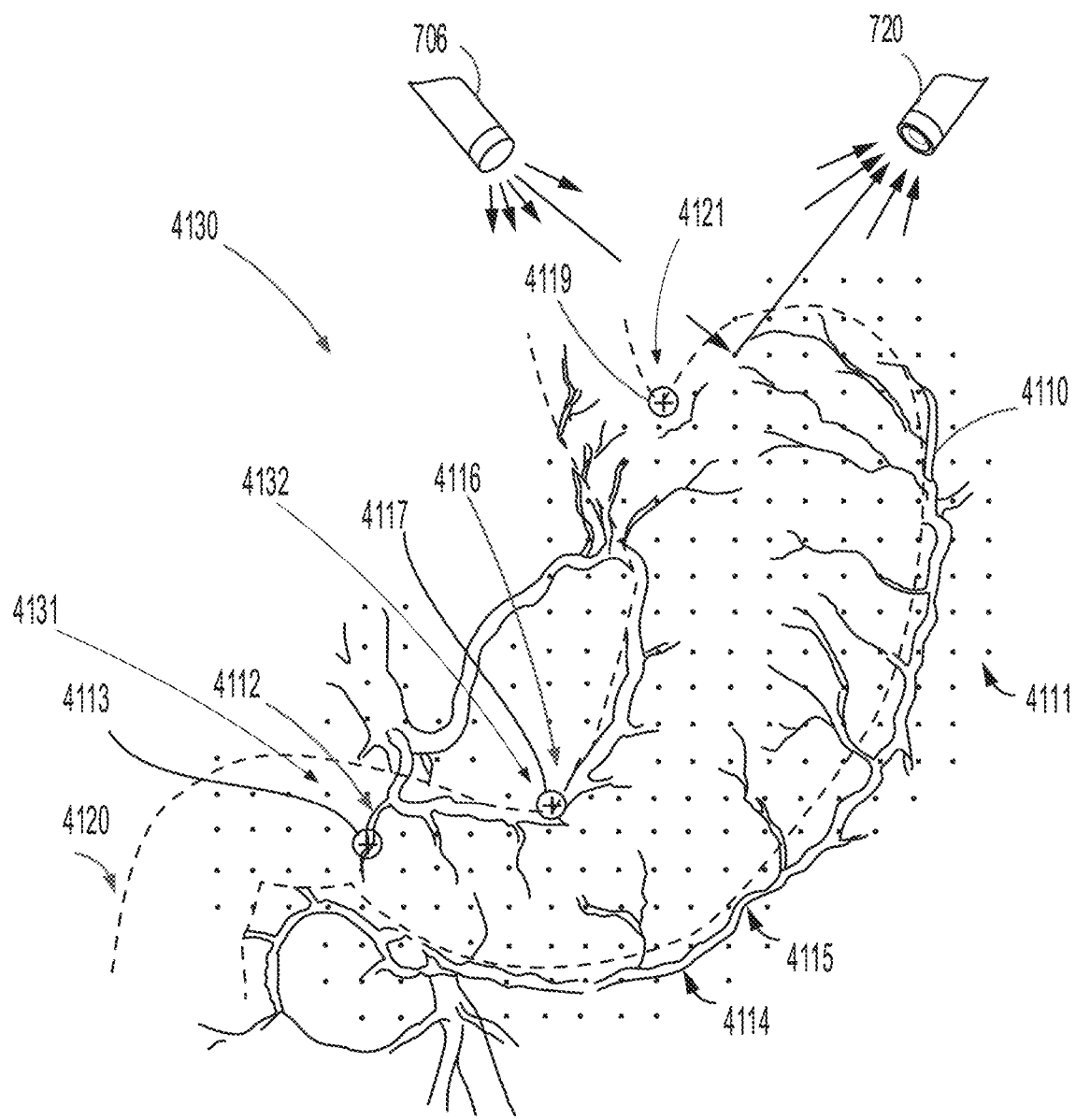

FIG. 28 illustrates a virtual three-dimensional ("3D") construct of a stomach exposed to structured light from a structured light projector, in accordance with at least aspect of the present disclosure.

Figure 29:
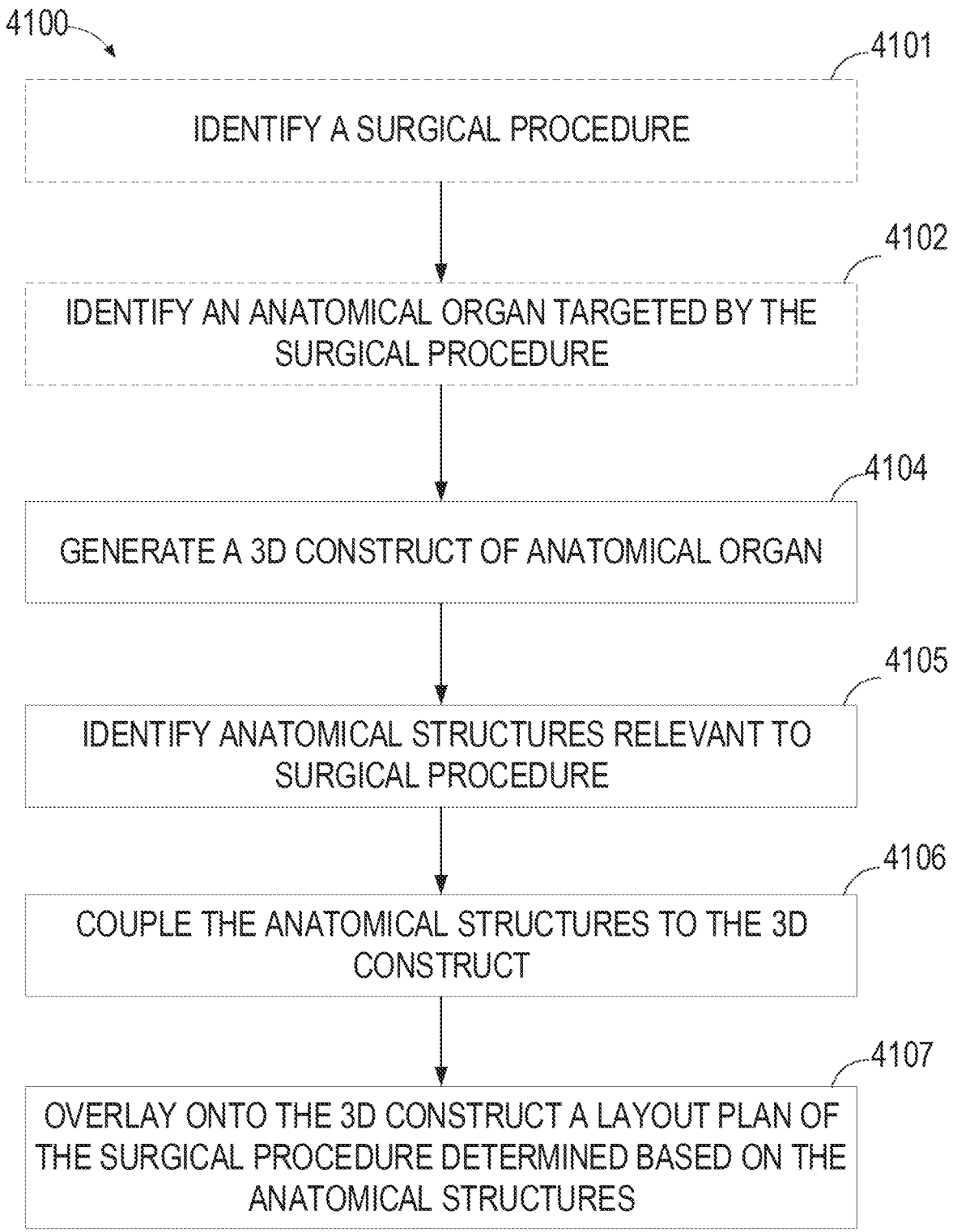

FIG. 29 is a logic flow diagram of a process depicting a control program or a logic configuration for correlating visualization data with instrument data, wherein boxes with broken lines denote alternative implementations of the process, in accordance with at least one aspect of the present disclosure.

Figure 30:
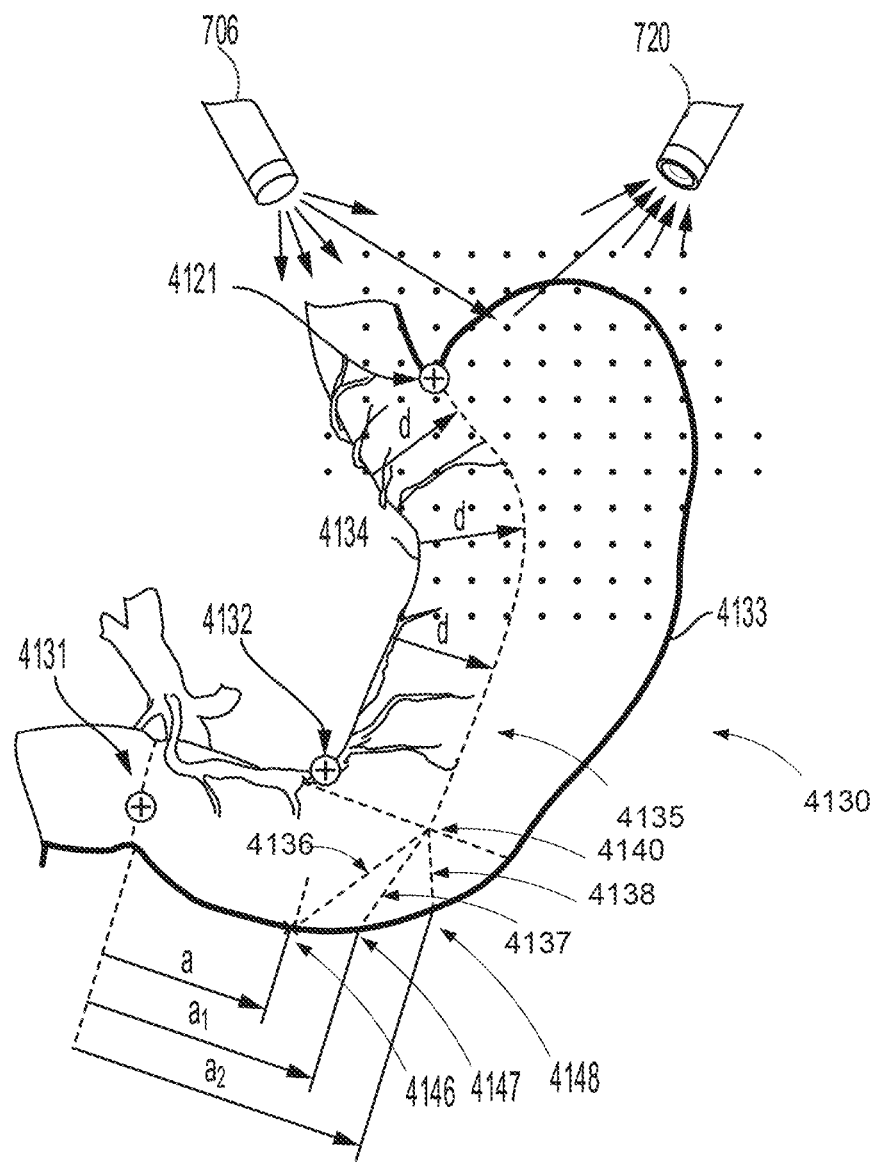

FIG. 30 illustrates a virtual 3D construct of a stomach exposed to structured light from a structured light projector, in accordance with at least aspect of the present disclosure.

Figure 31:
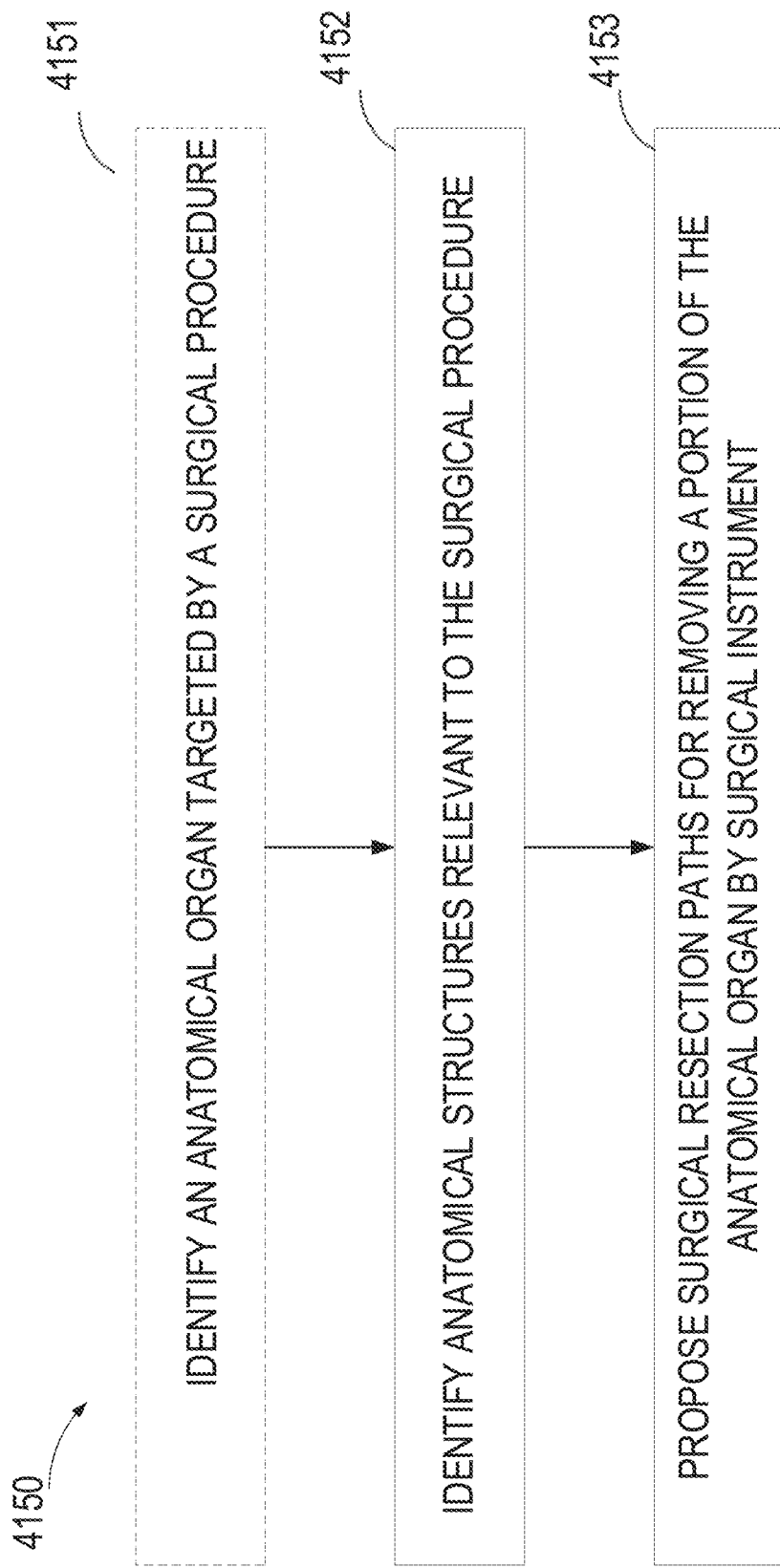

FIG. 31 is a logic flow diagram of a process depicting a control program or a logic configuration for proposing resection paths for removing a portion of an anatomical organ, wherein boxes with broken lines denote alternative implementations of the process, in accordance with at least one aspect of the present disclosure.

FIG. 32A illustrates a live view of a surgical field on a screen of a visualization system at the onset of a surgical procedure, in accordance with at least one aspect of the present disclosure.

FIG. 32B is an expanded view of a portion of the surgical field of FIG. 32A outlining a proposed surgical resection path overlaid onto the surgical field, in accordance with at least one aspect of the present disclosure.

FIG. 32C illustrates the live view of the surgical field of FIG. 32B at forty-three minutes beyond the onset of the surgical procedure, in accordance with at least one aspect of the present disclosure.

FIG. 32D illustrates an expanded view of the surgical field of FIG. 32C outlining a modification the proposed surgical resection path, in accordance with at least one aspect of the present disclosure.

Figure 33:
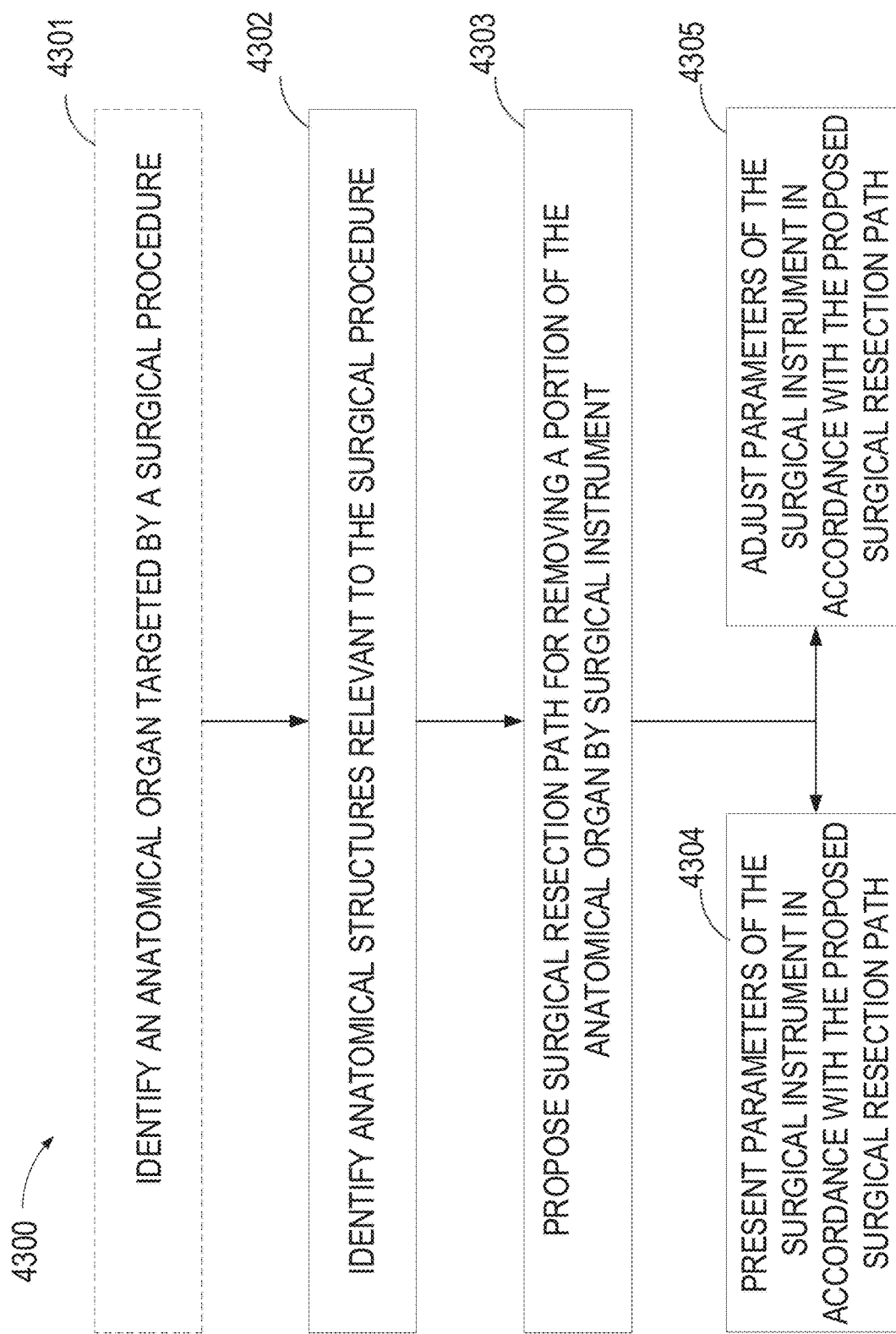

FIG. 33 is a logic flow diagram of a process depicting a control program or a logic configuration for presenting parameters of a surgical instrument onto, or near, a proposed surgical resection path, wherein boxes with broken lines denote alternative implementations of the process, in accordance with at least one aspect of the present disclosure.

Figure 34:
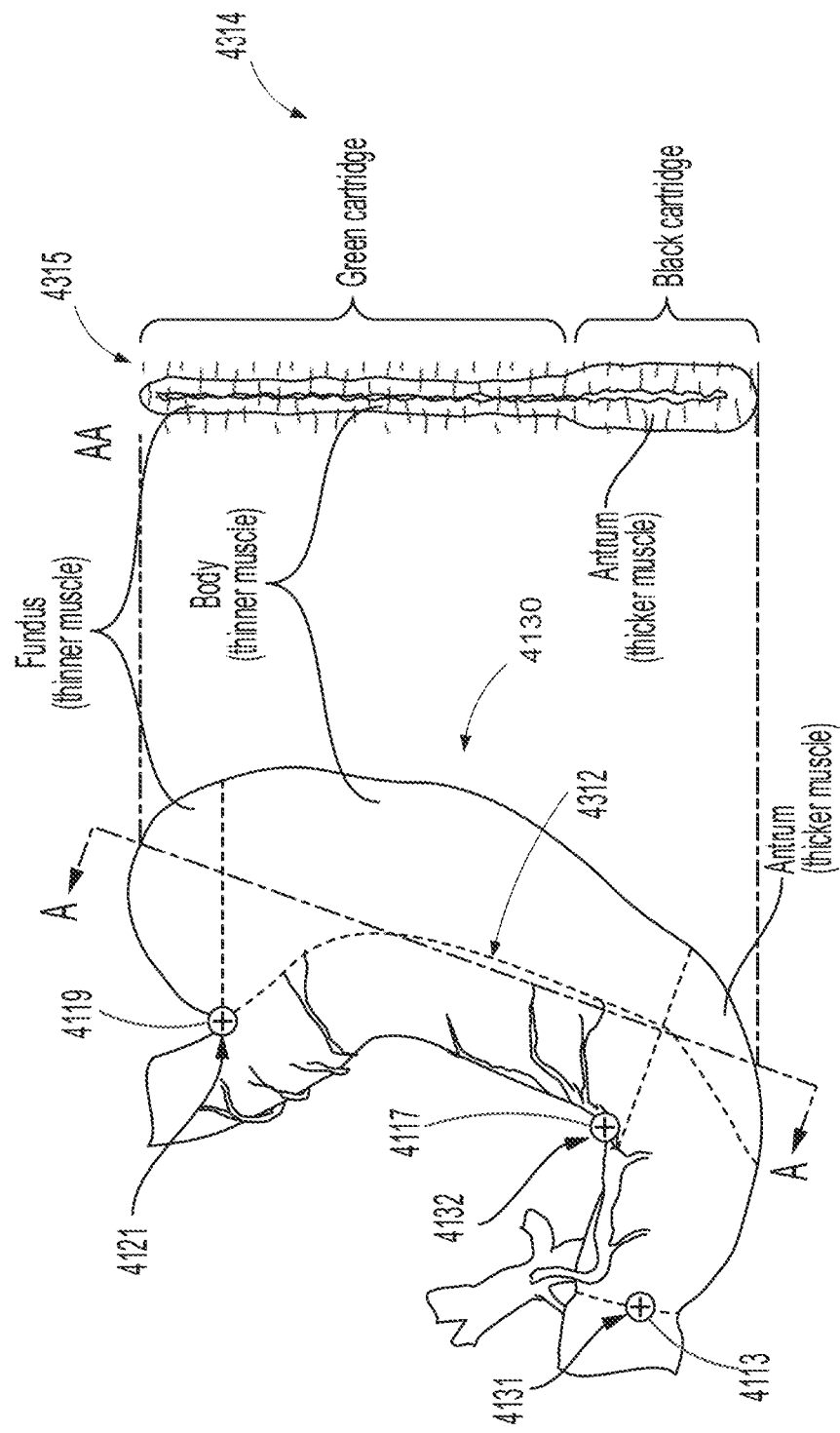

FIG. 34 illustrates a virtual 3D construct of a stomach of a patient undergoing a sleeve gastrectomy, in accordance with at least one aspect of the present disclosure.

Figure 35:
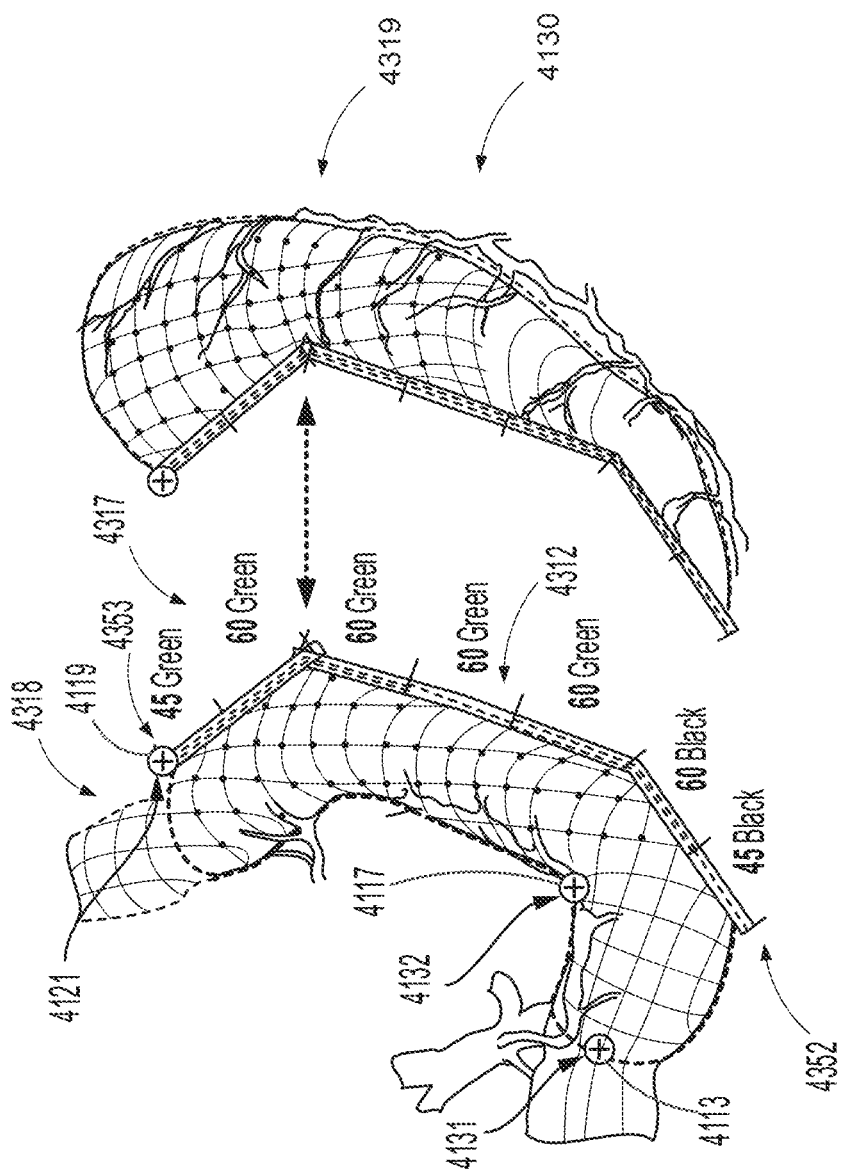

FIG. 35 illustrates a completed virtual resection of the stomach of FIG. 34.

Figures 36A, 36B, 36C:
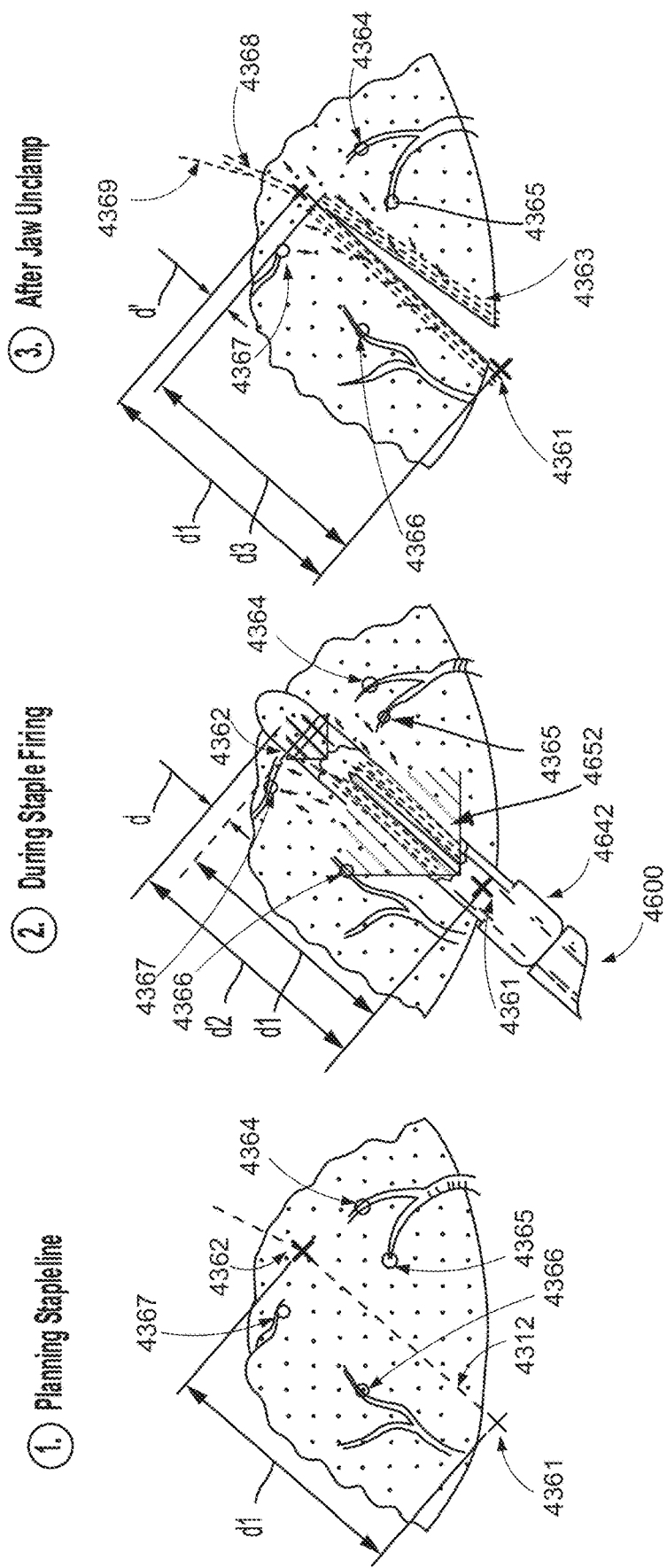

FIGS. 36A-36C illustrate firing of a surgical stapling instrument, in accordance with at least one aspect of the present disclosure.

Figure 37:
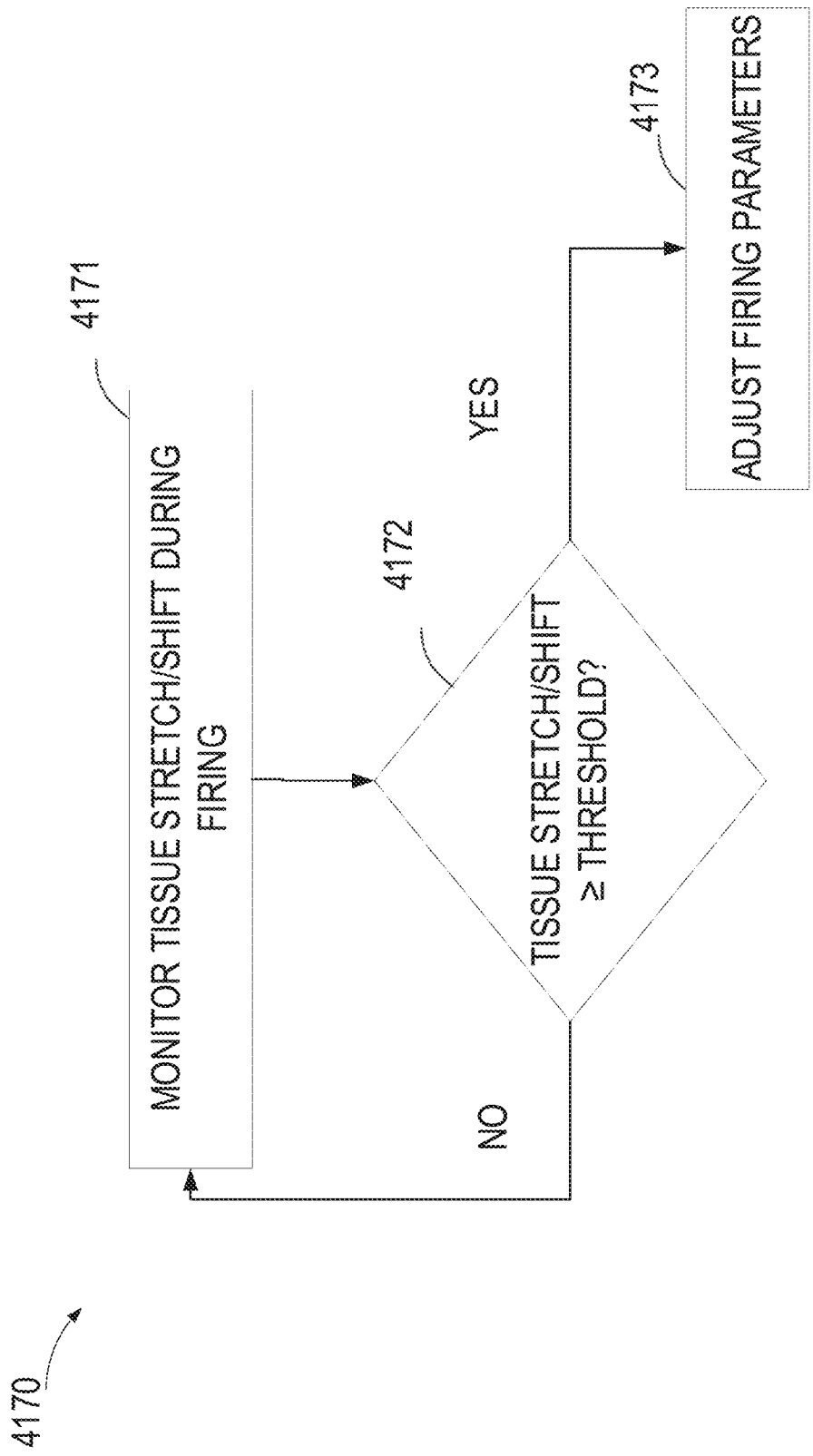

FIG. 37 is a logic flow diagram of a process depicting a control program or a logic configuration for adjusting firing speed of a surgical instrument, in accordance with at least one aspect of the present disclosure.

Figure 38:
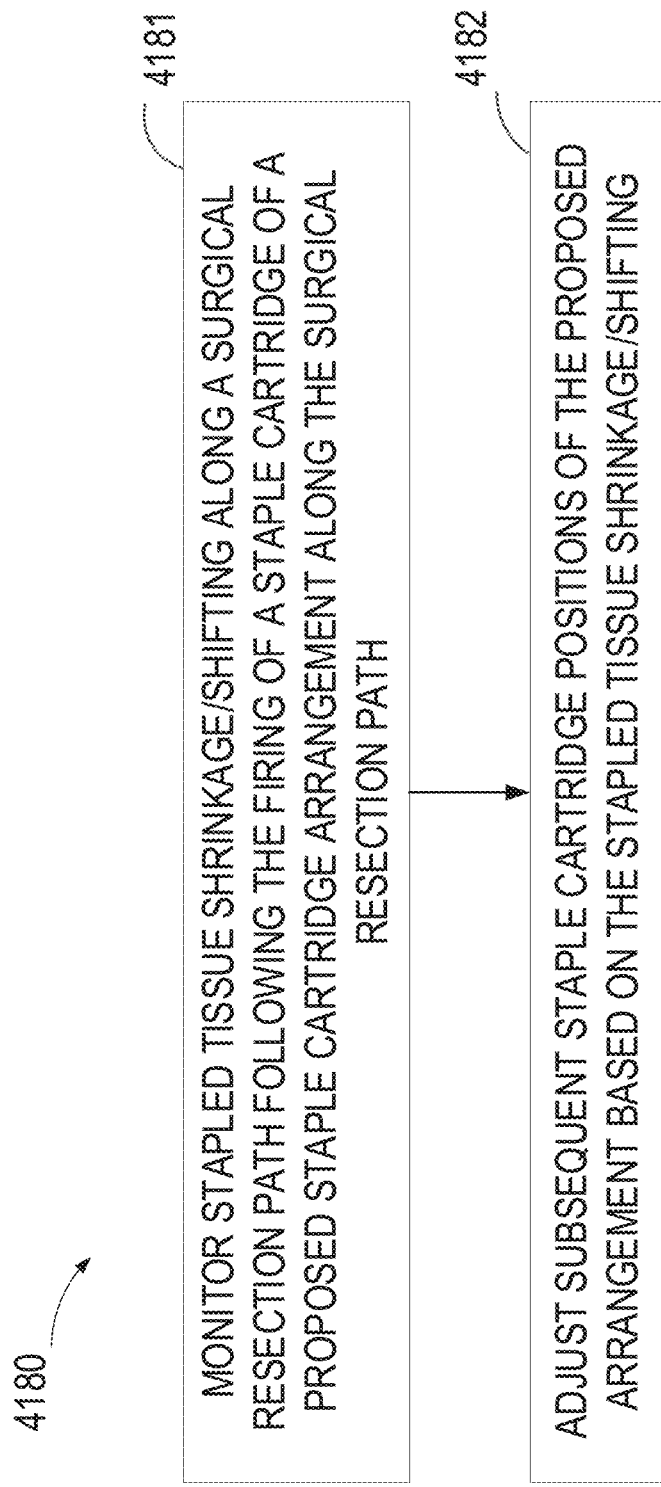

FIG. 38 is a logic flow diagram of a process depicting a control program or a logic configuration for a proposed staple cartridge arrangement along a proposed surgical resection path, in accordance with at least one aspect of the present disclosure.

Figure 39:
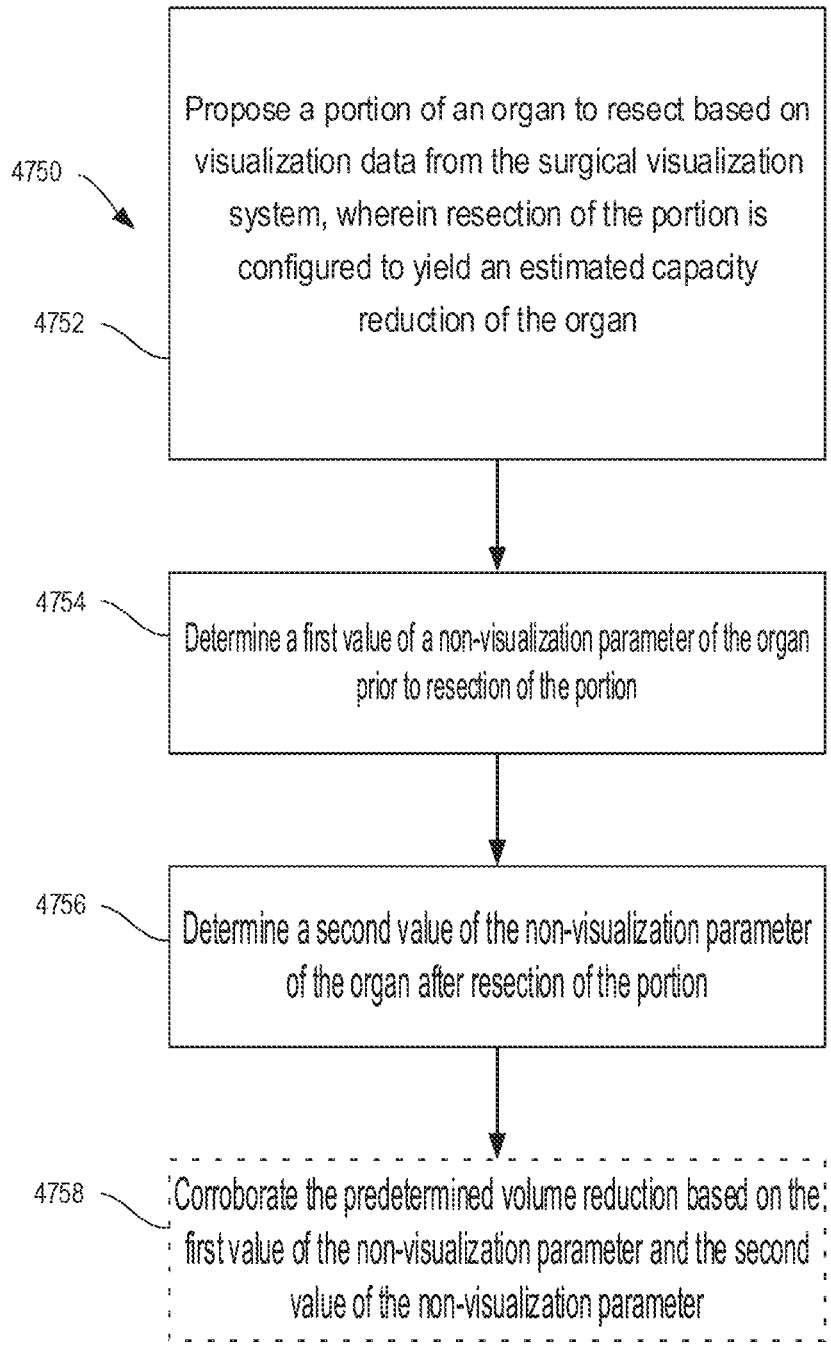

FIG. 39 is a logic flow diagram of a process depicting a control program or a logic configuration for proposing a surgical resection of an organ portion, in accordance with at least one aspect of the present disclosure.

Figure 40:
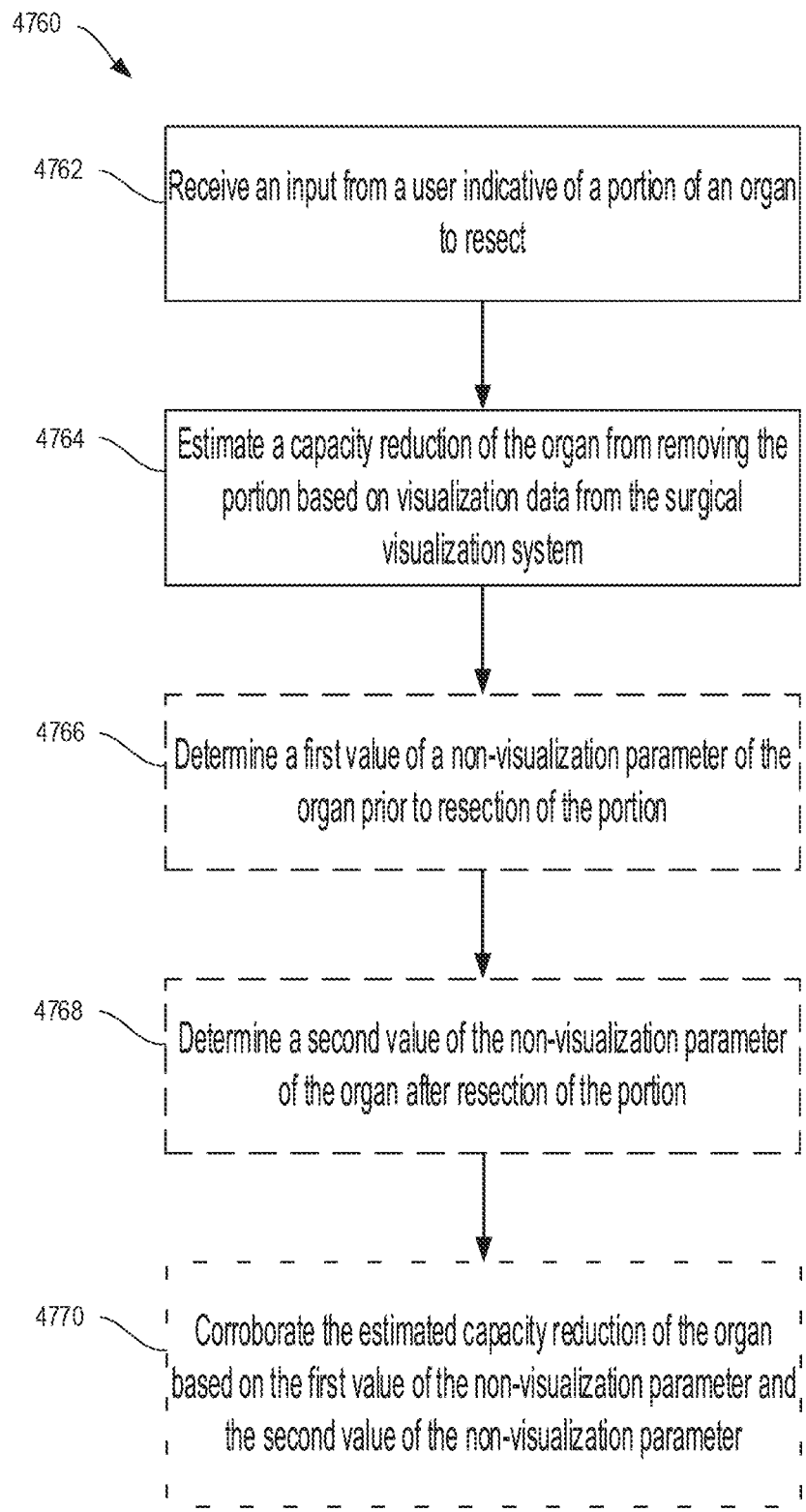

FIG. 40 is a logic flow diagram of a process depicting a control program or a logic configuration for estimating a capacity reduction of an organ resulting from the removal of a selected portion of the organ, in accordance with at least one aspect of the present disclosure.

Figure 41B:
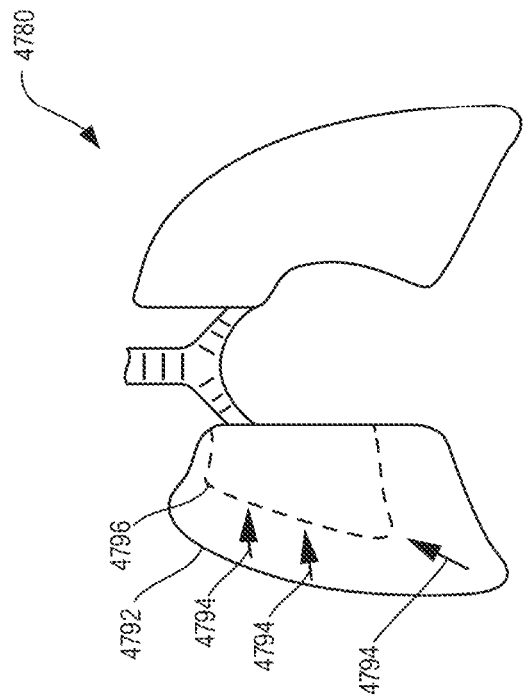
Figure 41A:
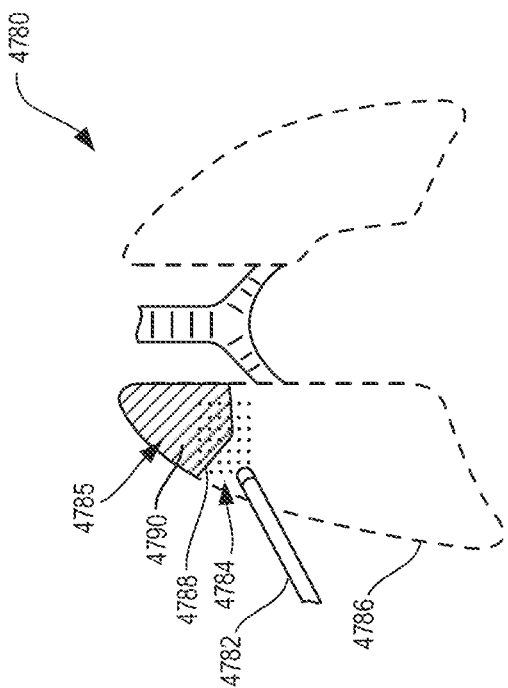

FIG. 41A illustrates a patient's lungs exposed to structured light, which includes a portion to be resected during a surgical procedure, in accordance with at least one aspect of the present disclosure.

FIG. 41B illustrates the patient's lungs of FIG. 41A after resection of the portion, in accordance with at least one aspect of the present disclosure.

Figure 41C:
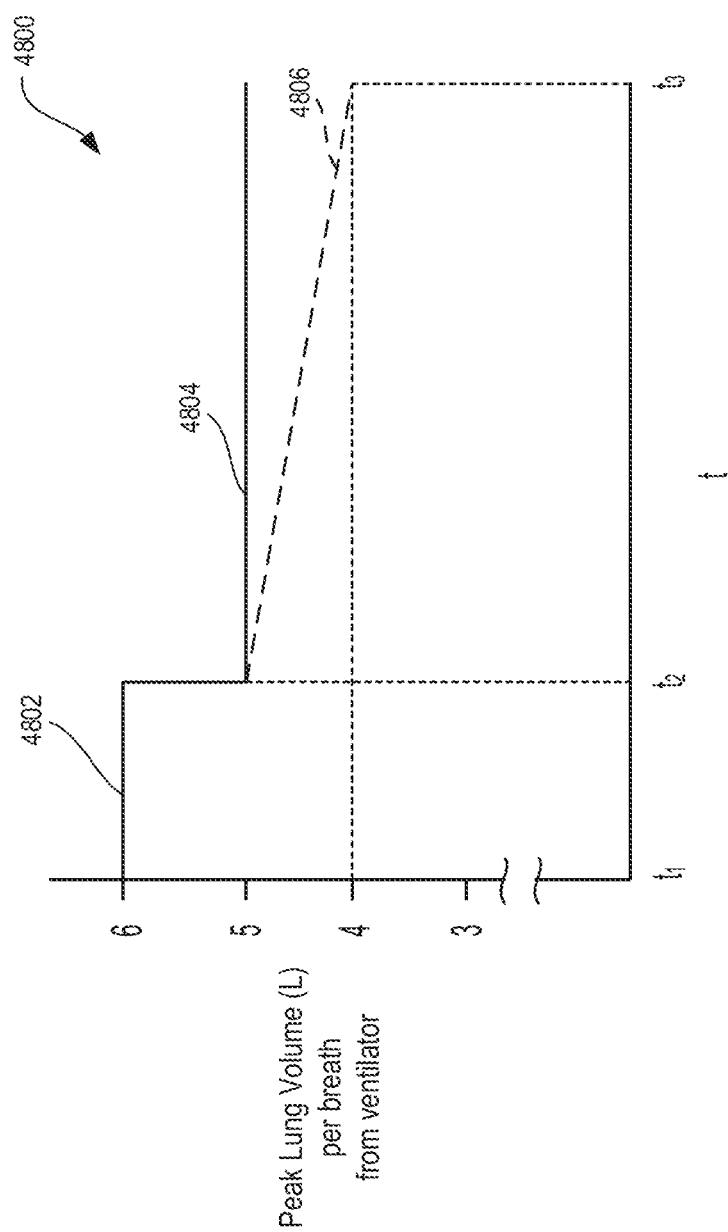

FIG. 41C illustrates a graph measuring peak lung volume of the patient's lungs from FIGS. 41A and 41B prior to and after the resection of the portion of the lung, in accordance with at least one aspect of the present disclosure.

Figure 42:
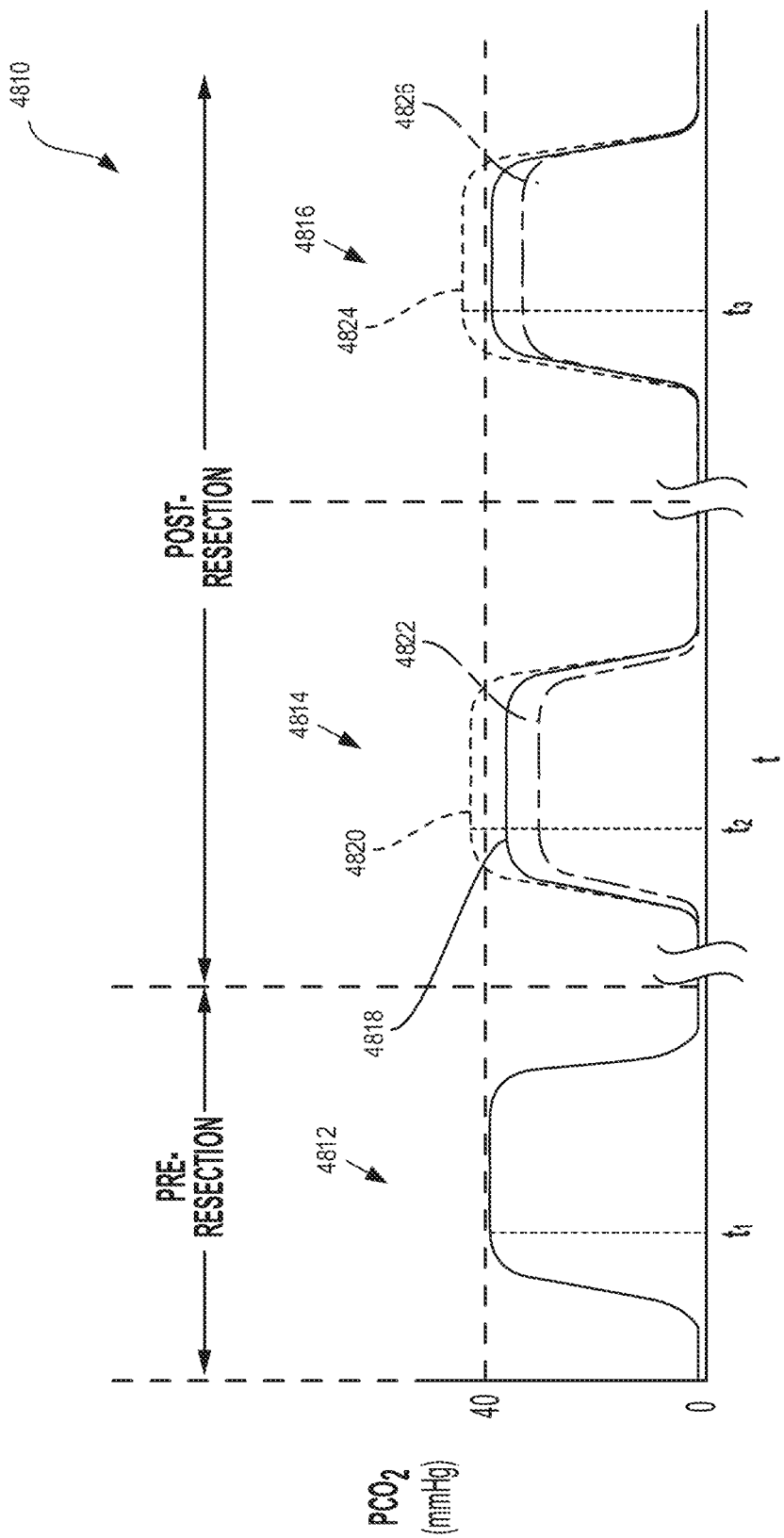

FIG. 42 illustrates a graph measuring partial pressure of carbon dioxide ("$PCO_2$") in a patient's lungs prior to, immediately after, and a minute after, resection of a portion of the lung, in accordance with at least one aspect of the present disclosure.

Figure 43:
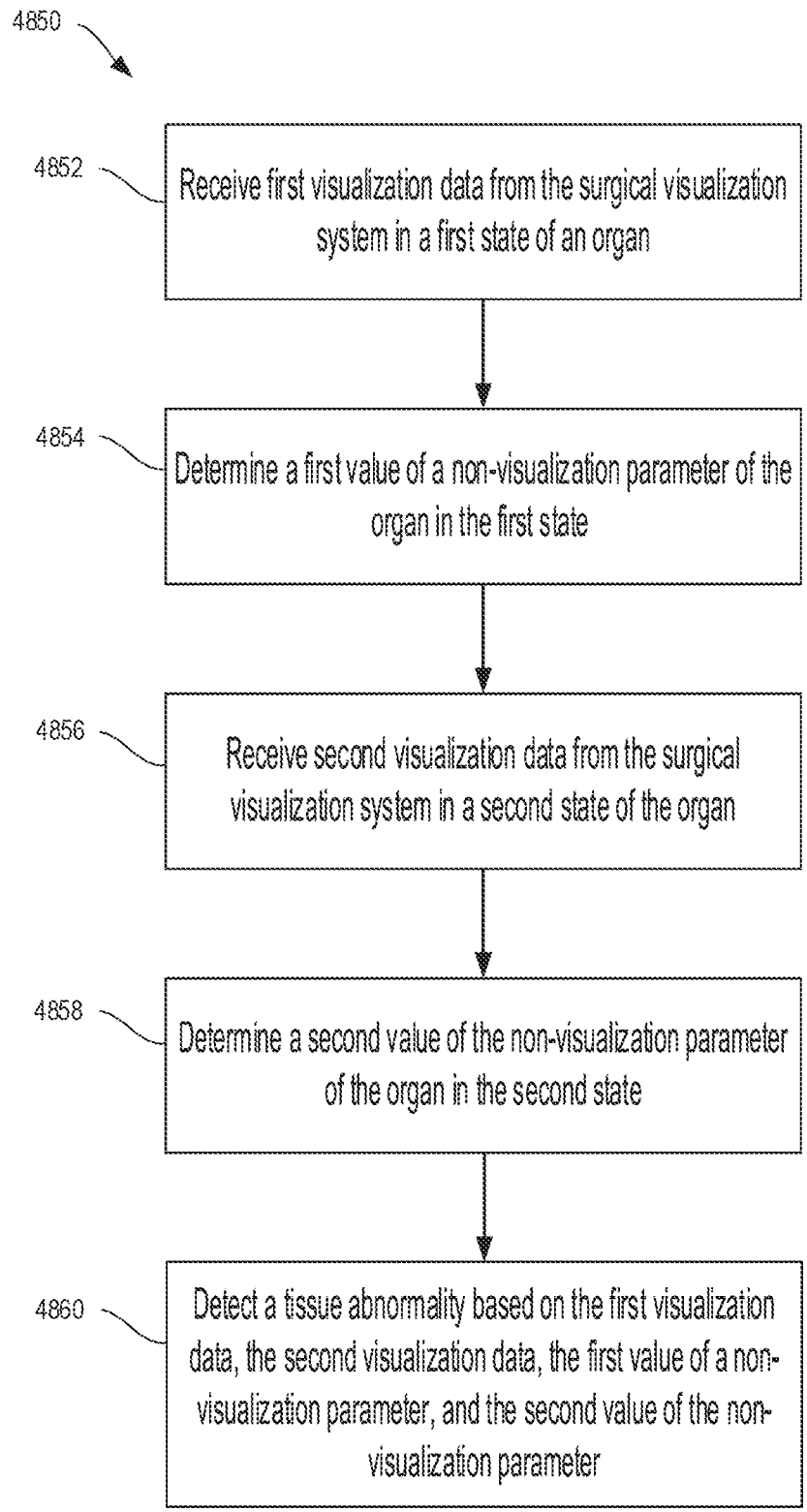

FIG. 43 is a logic flow diagram of a process depicting a control program or a logic configuration for detecting a tissue abnormality using visualization data and non-visualization data, in accordance with at least one aspect of the present disclosure.

Figure 44B:
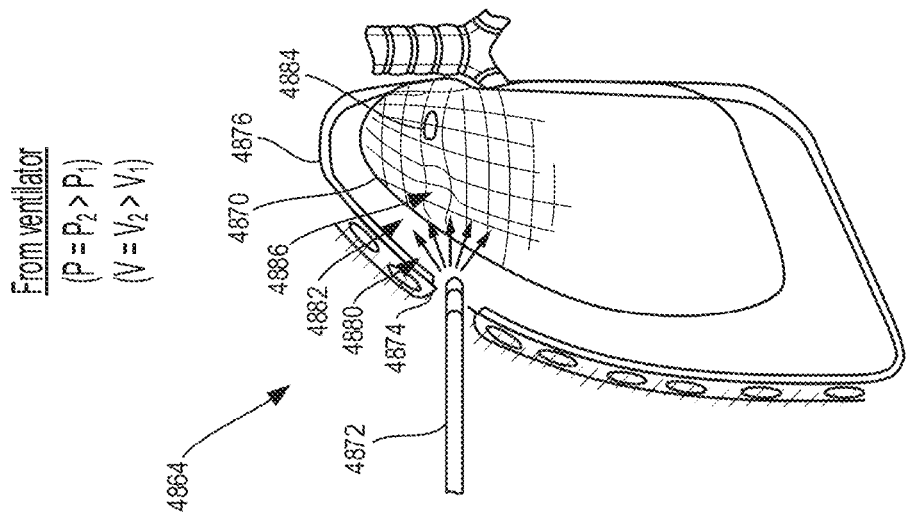
Figure 44A:
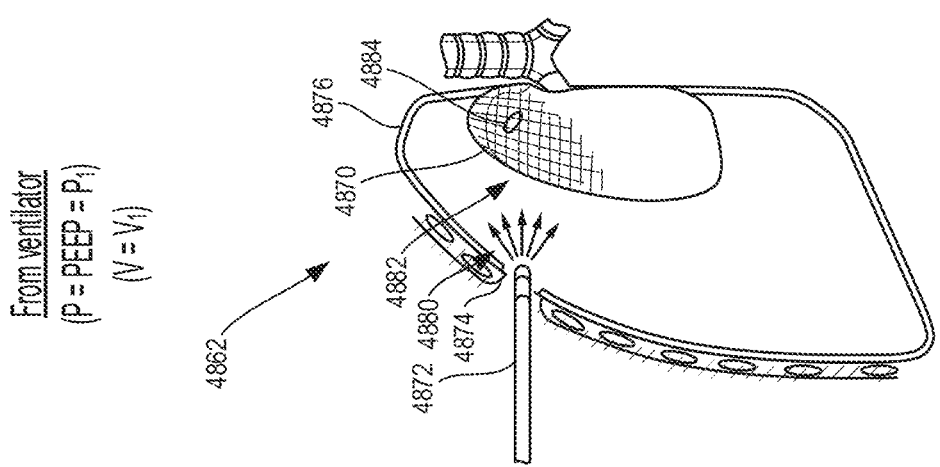

FIG. 44A illustrates a right lung in a first state with an imaging device emitting a pattern of light onto the surface thereof, in accordance with at least one aspect of the present disclosure.

FIG. 44B illustrates the right lung of FIG. 44A in a second state with the imaging device emitting a pattern of light onto the surface thereof, in accordance with at least one aspect of the present disclosure.

Figure 44D:
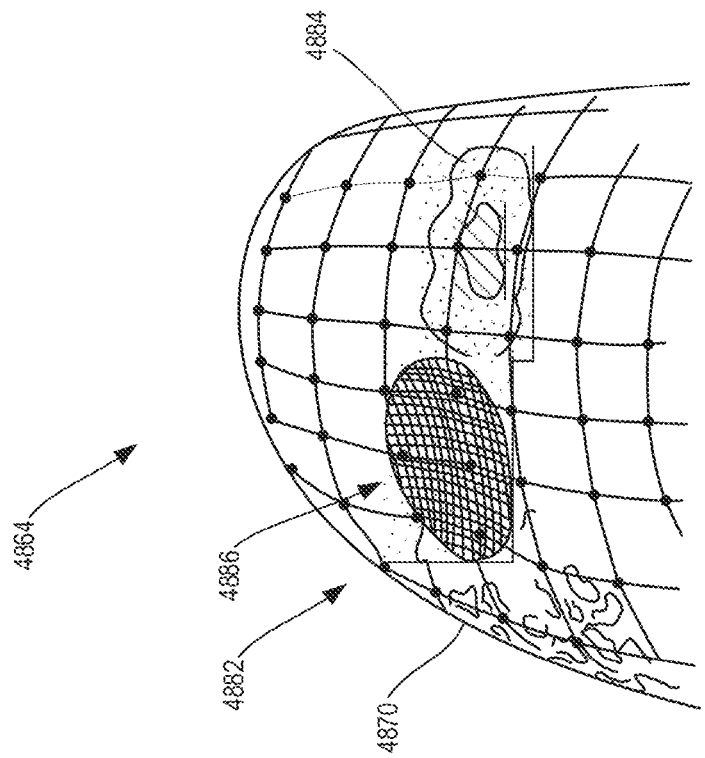
Figure 44C:
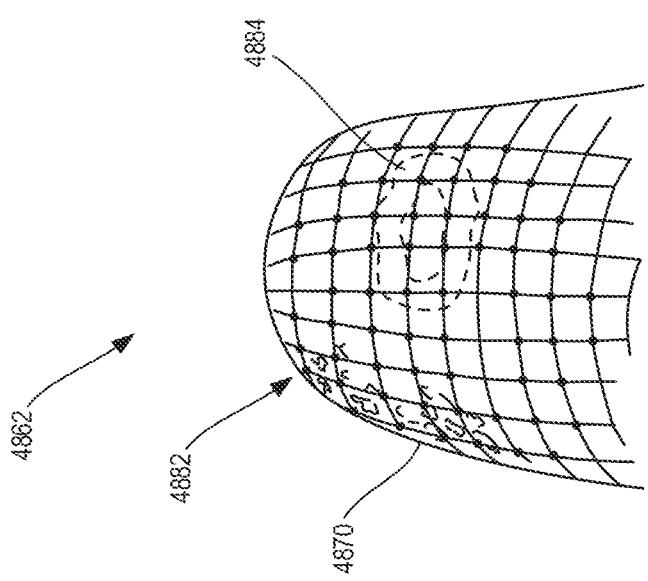

FIG. 44C illustrates a top portion of the right lung of FIG. 44A, in accordance with at least one aspect of the present disclosure.

FIG. 44D illustrates a top portion of the right lung of FIG. 44B, in accordance with at least one aspect of the present disclosure.

Figure 45:
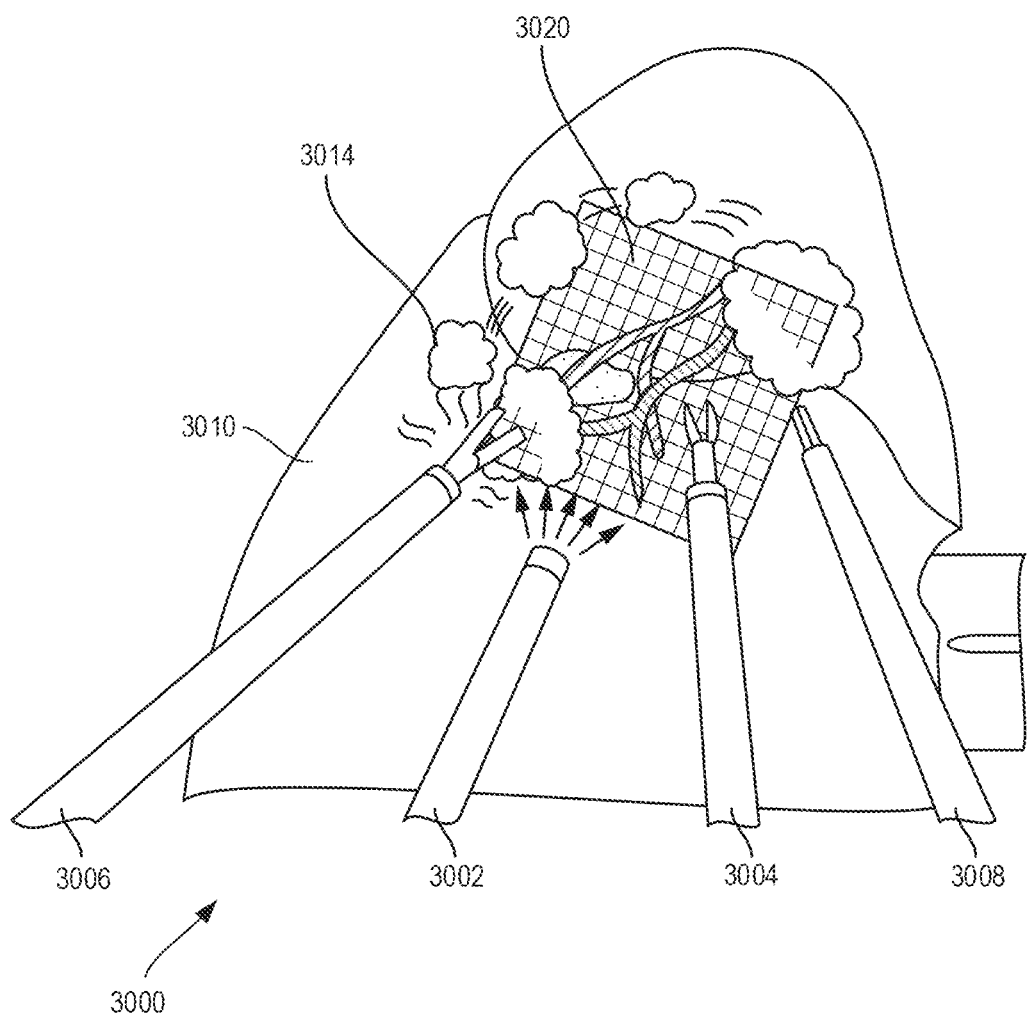

FIG. 45 is a diagram of a surgical system during the performance of a surgical procedure, in accordance with at least one aspect of the present disclosure.

Figure 46:
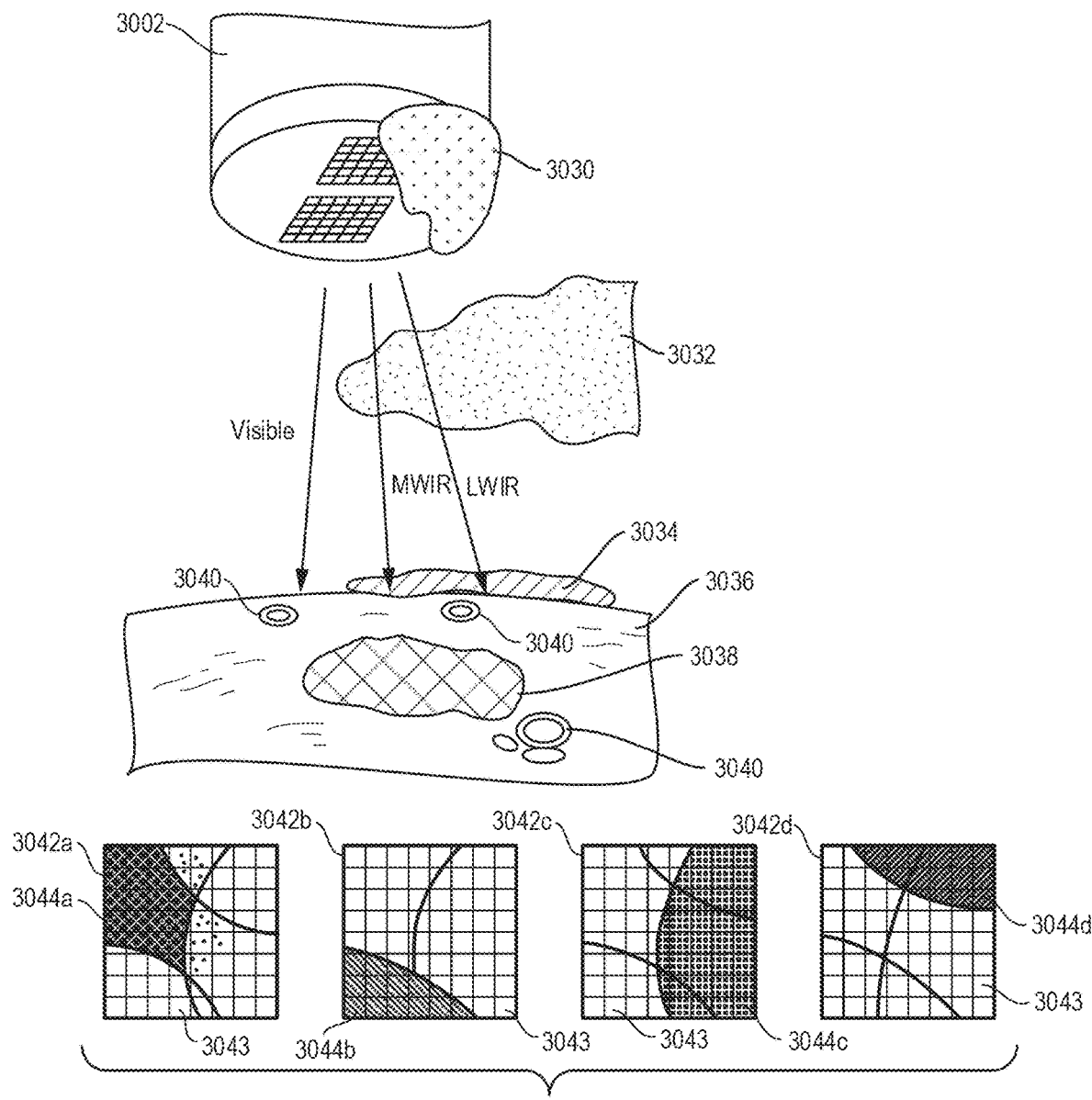

FIG. 46 is a diagram of an imaging device faced with multiple obscurants, in accordance with at least one aspect of the present disclosure.

Figure 47:
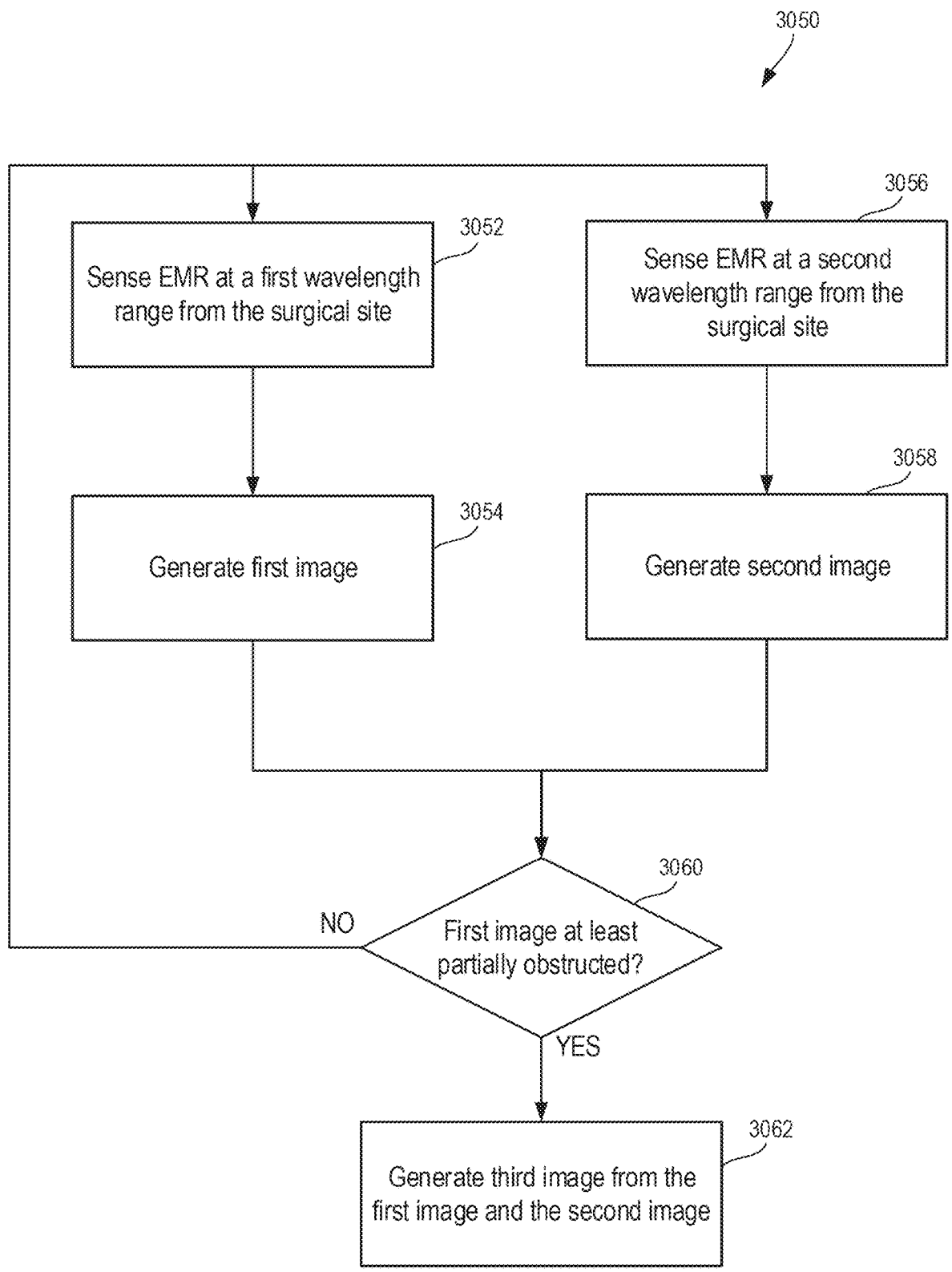

FIG. 47 is a logic flow diagram of a process for generating fused images utilizing a multispectral EMR source, in accordance with at least one aspect of the present disclosure.

Figure 48:
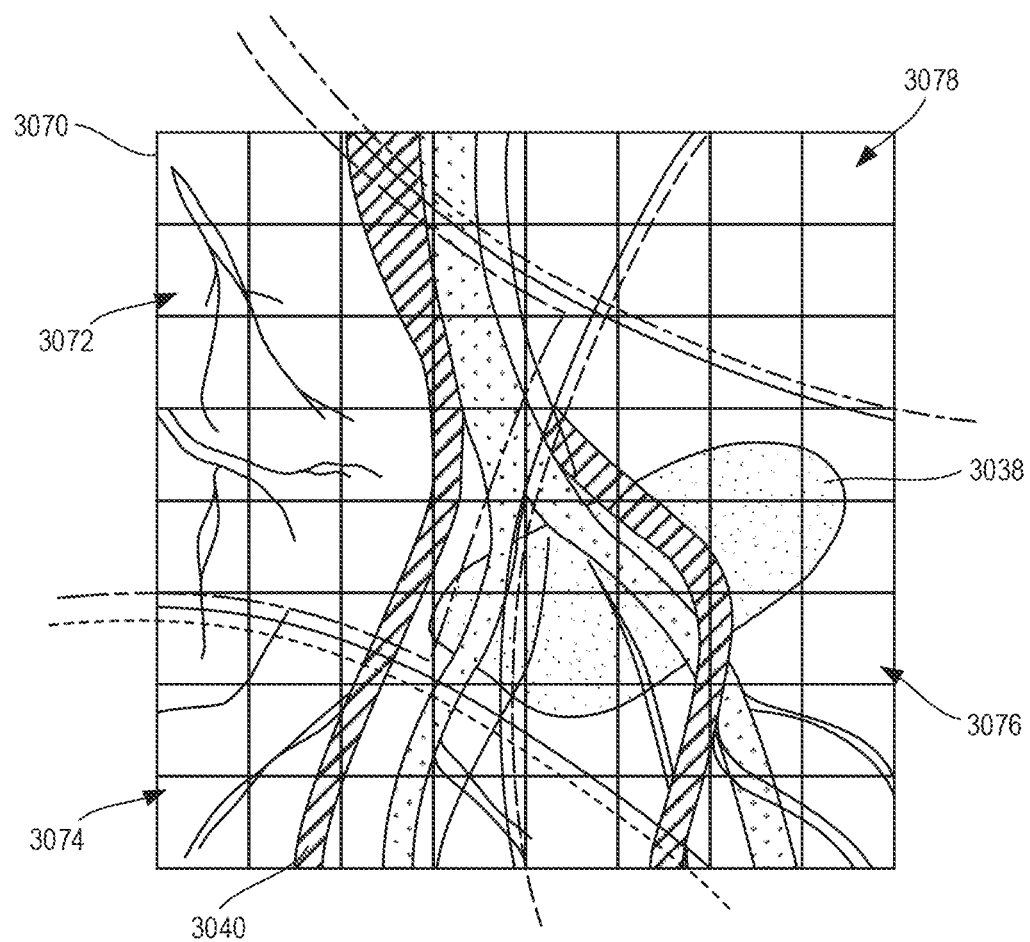

FIG. 48 is a diagram of a fused image generated from a multispectral EMR source, in accordance with at least one aspect of the present disclosure.

Figure 49:
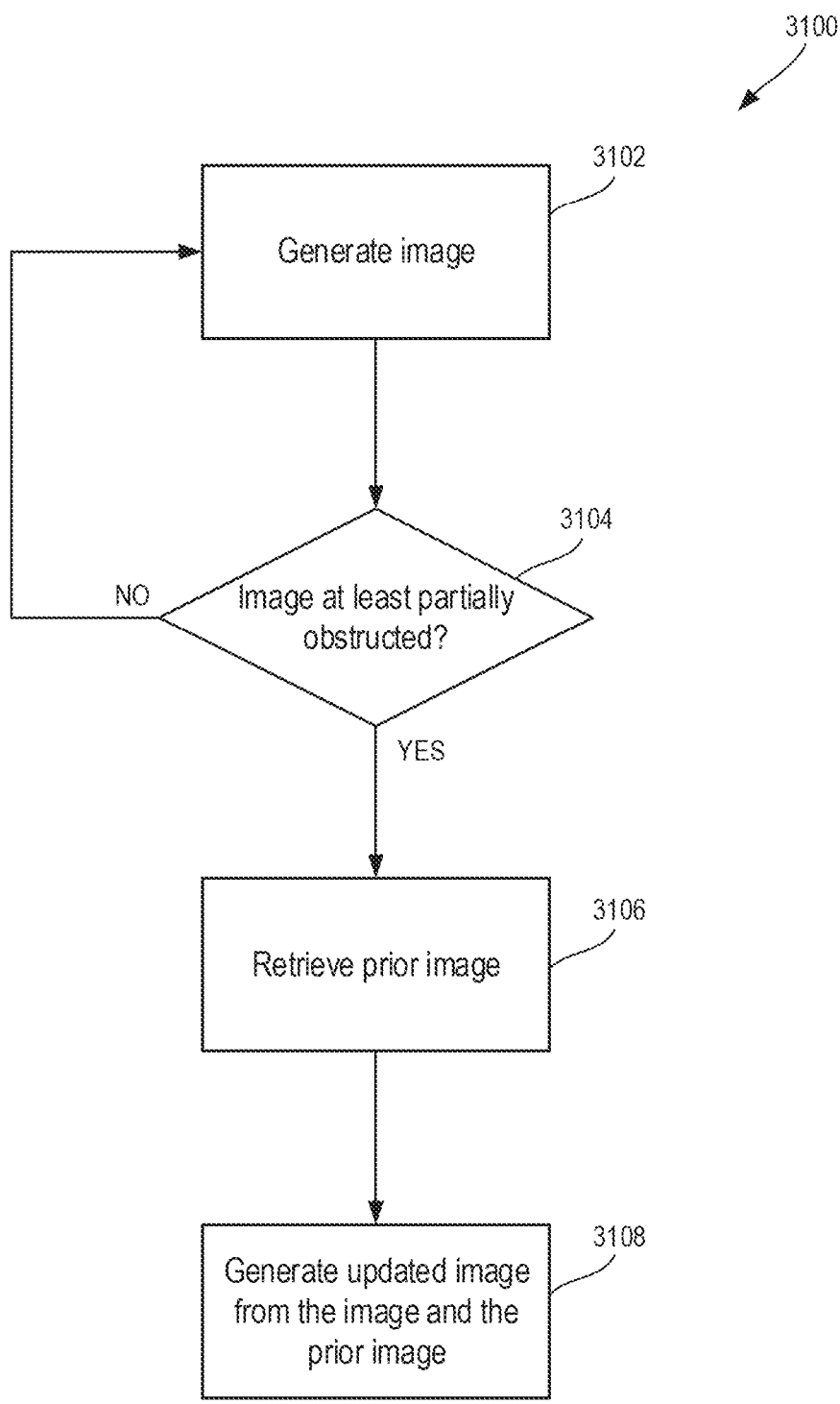

FIG. 49 is a logic flow diagram of a process for generating fused images utilizing multiple image frames, in accordance with at least one aspect of the present disclosure.

Figure 50:
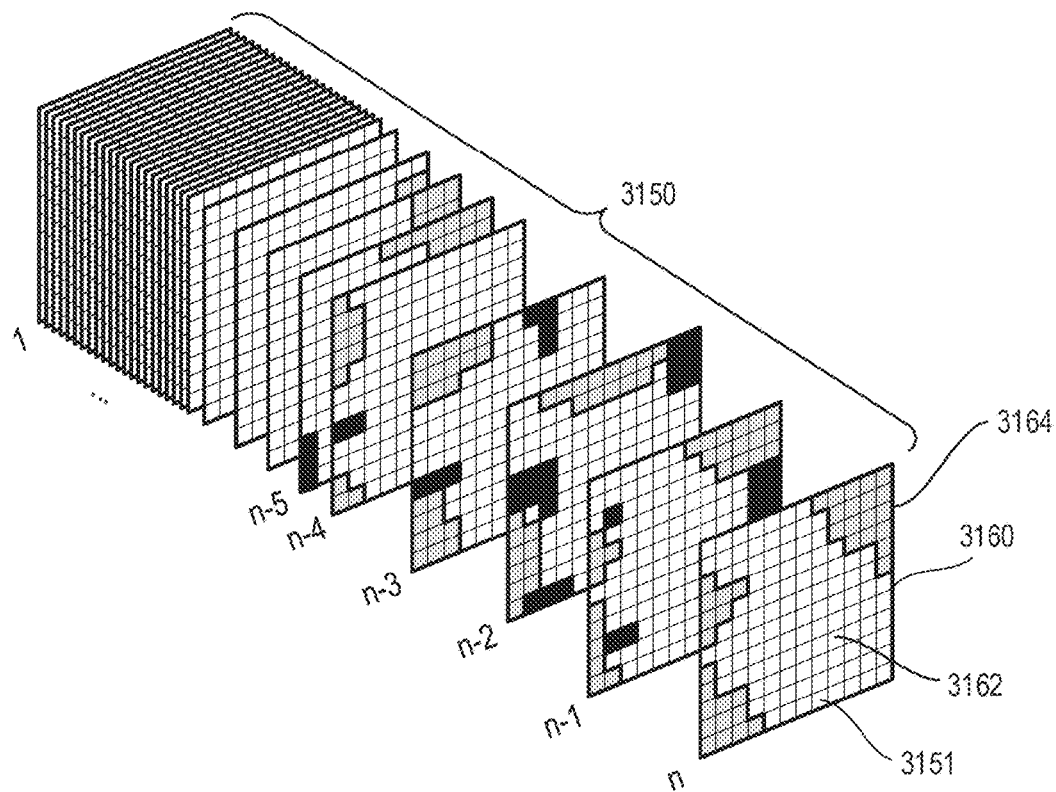

FIG. 50 is a diagram of a series of image frames, in accordance with at least one aspect of the present disclosure.

Figure 51:
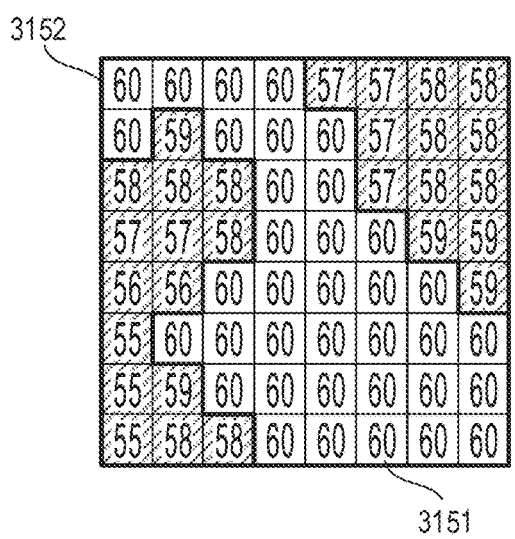

FIG. 51 is a diagram of a fused image, in accordance with at least one aspect of the present disclosure.

Figure 52:
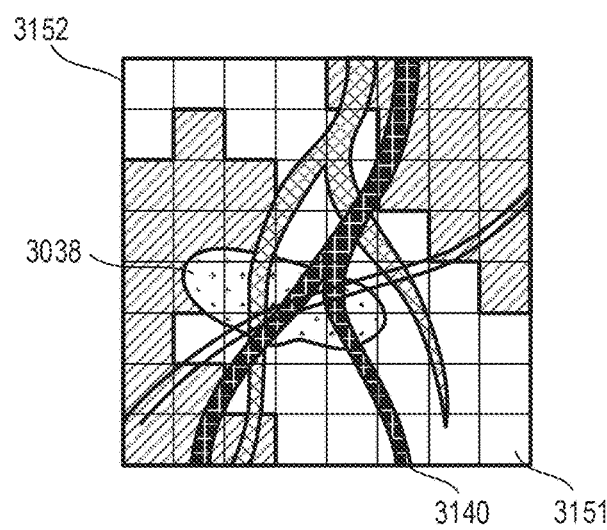

FIG. 52 is a diagram of a fused image as visualized to a user, in accordance with at least one aspect of the present disclosure.

Figure 53:
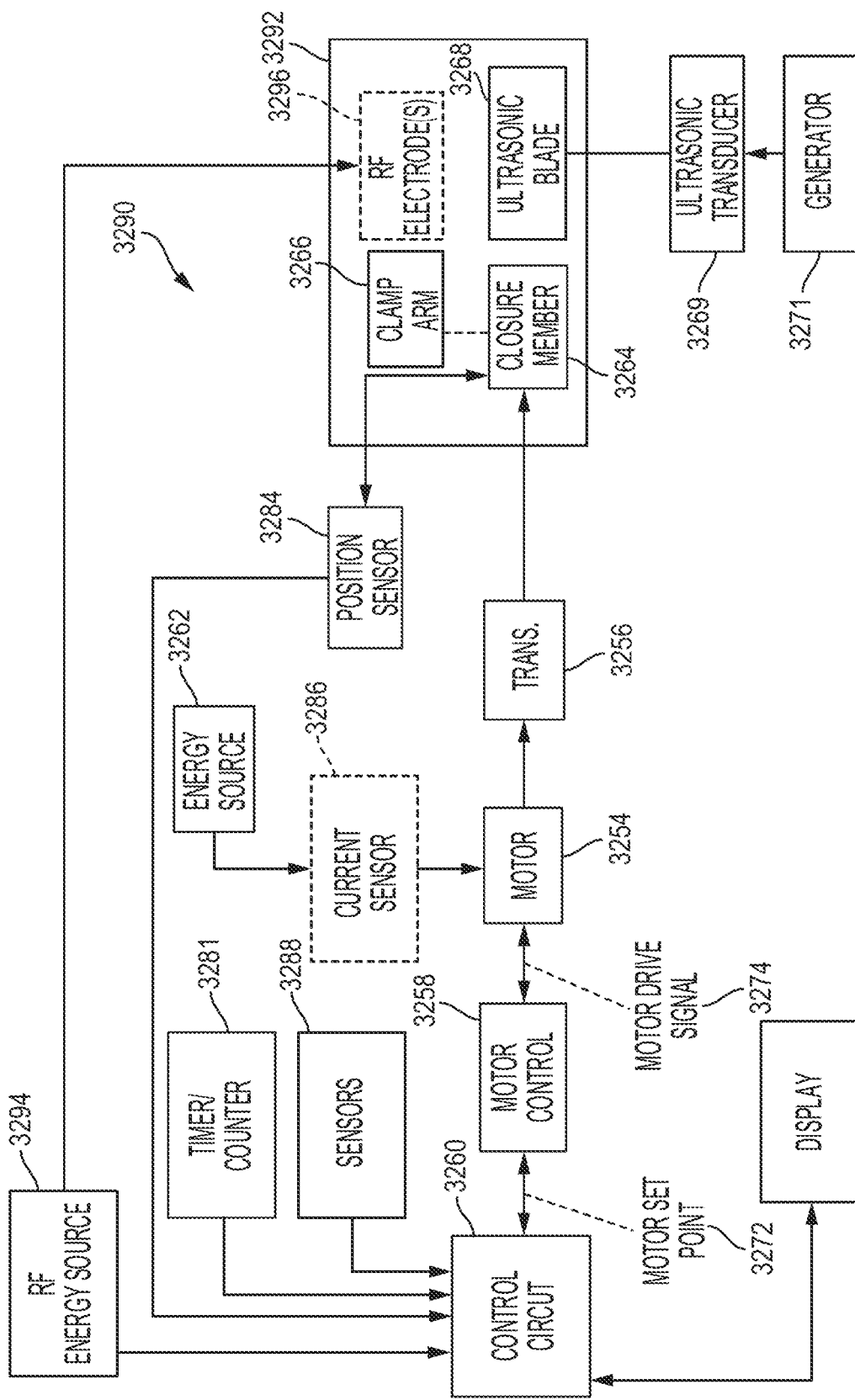

FIG. 53 is schematic diagram of a surgical instrument, in accordance with at least one aspect of the present disclosure.

Figure 54:
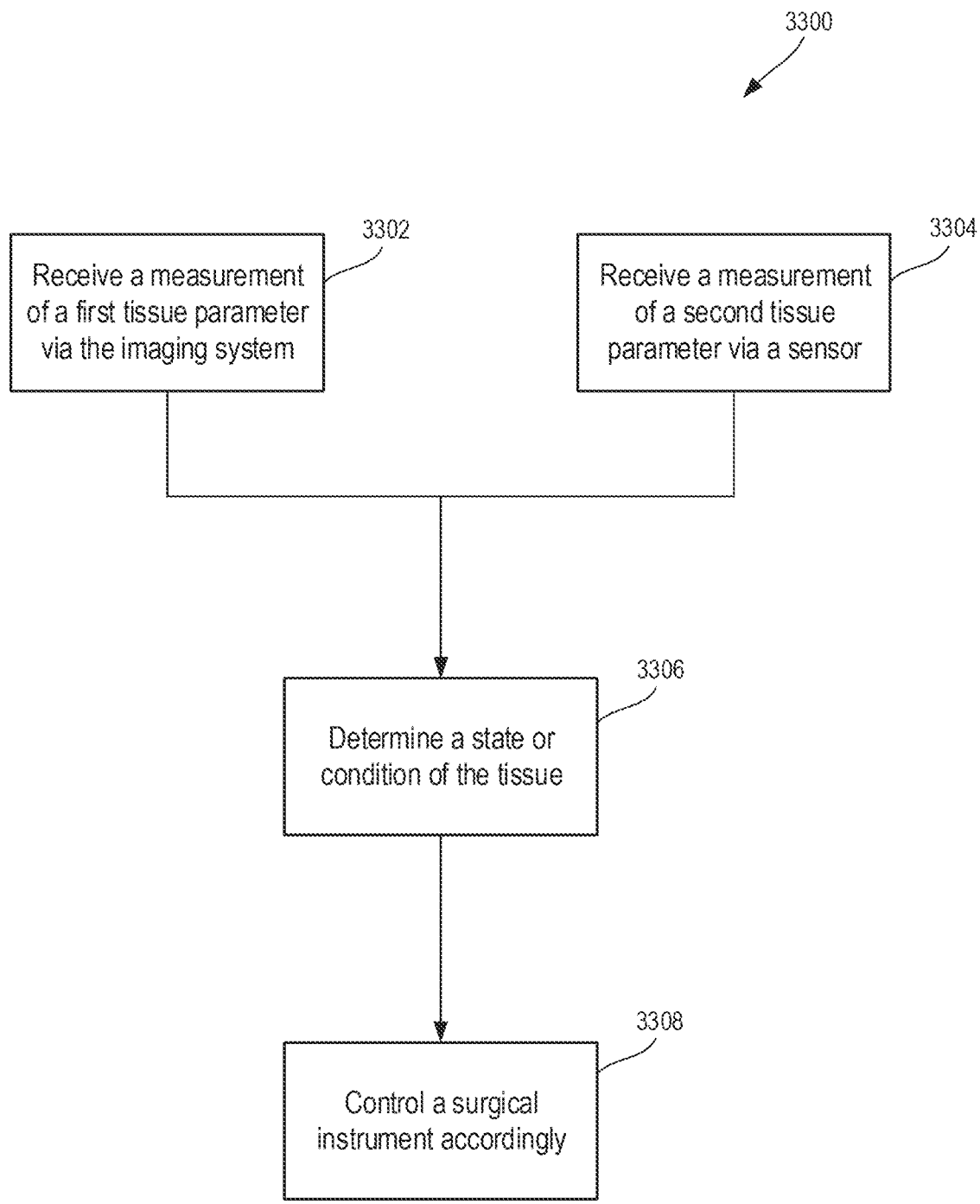

FIG. 54 is a logic flow diagram of a process for controlling a surgical system based on multiple sensed parameters, in accordance with at least one aspect of the present disclosure.

Figure 55:
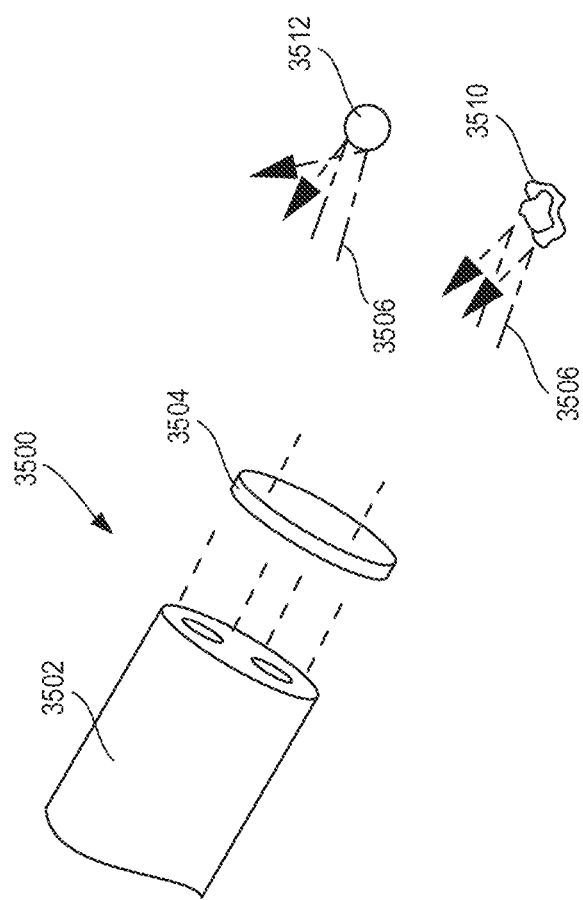

FIG. 55 is a diagram of a polarizing EMR source for detecting different particulate types, in accordance with at least one aspect of the present disclosure.

Figure 56A:
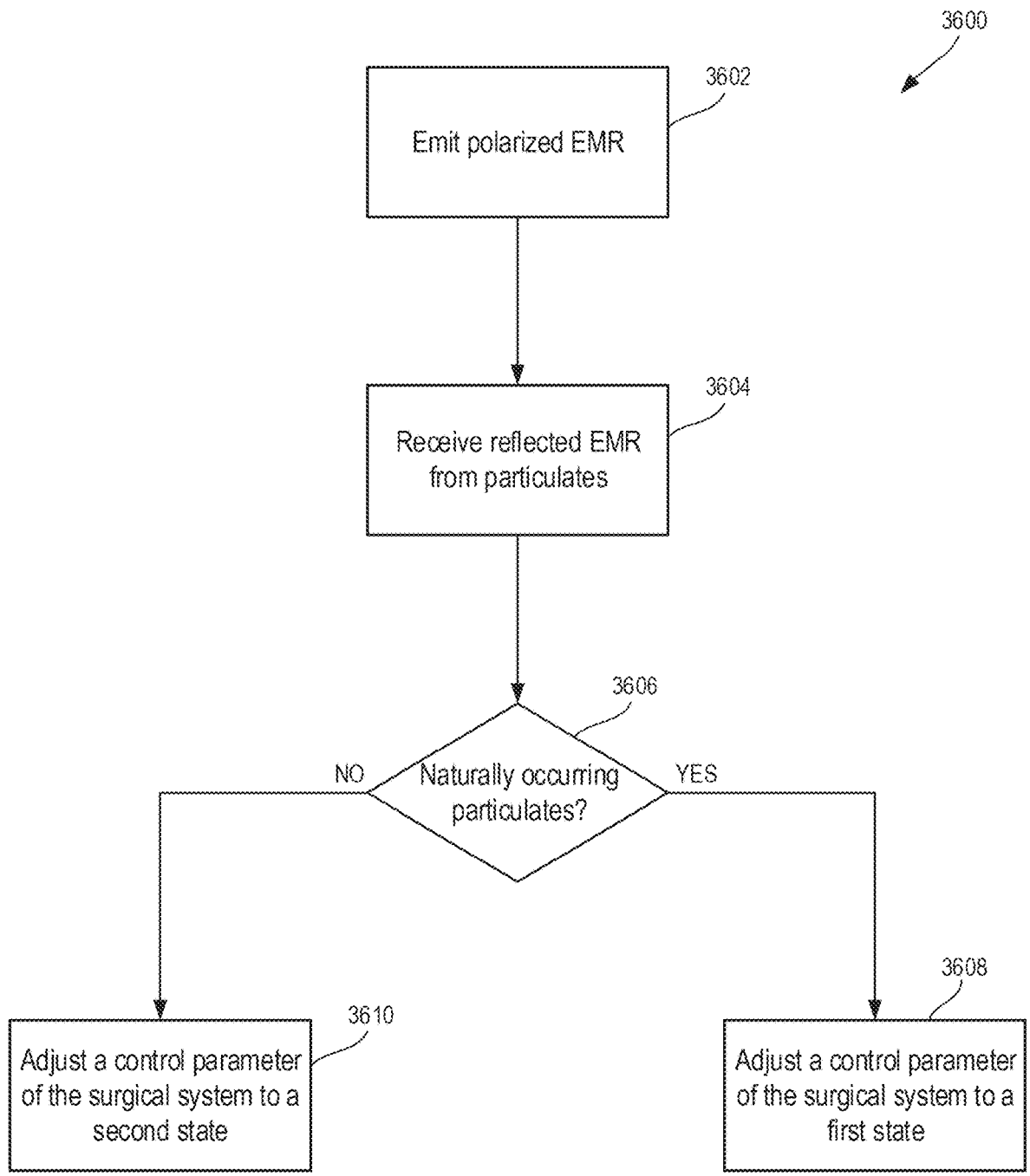

FIG. 56A is a logic flow diagram of a process for controlling a surgical system according to detected particulate types, in accordance with at least one aspect of the present disclosure.

Figure 56B:
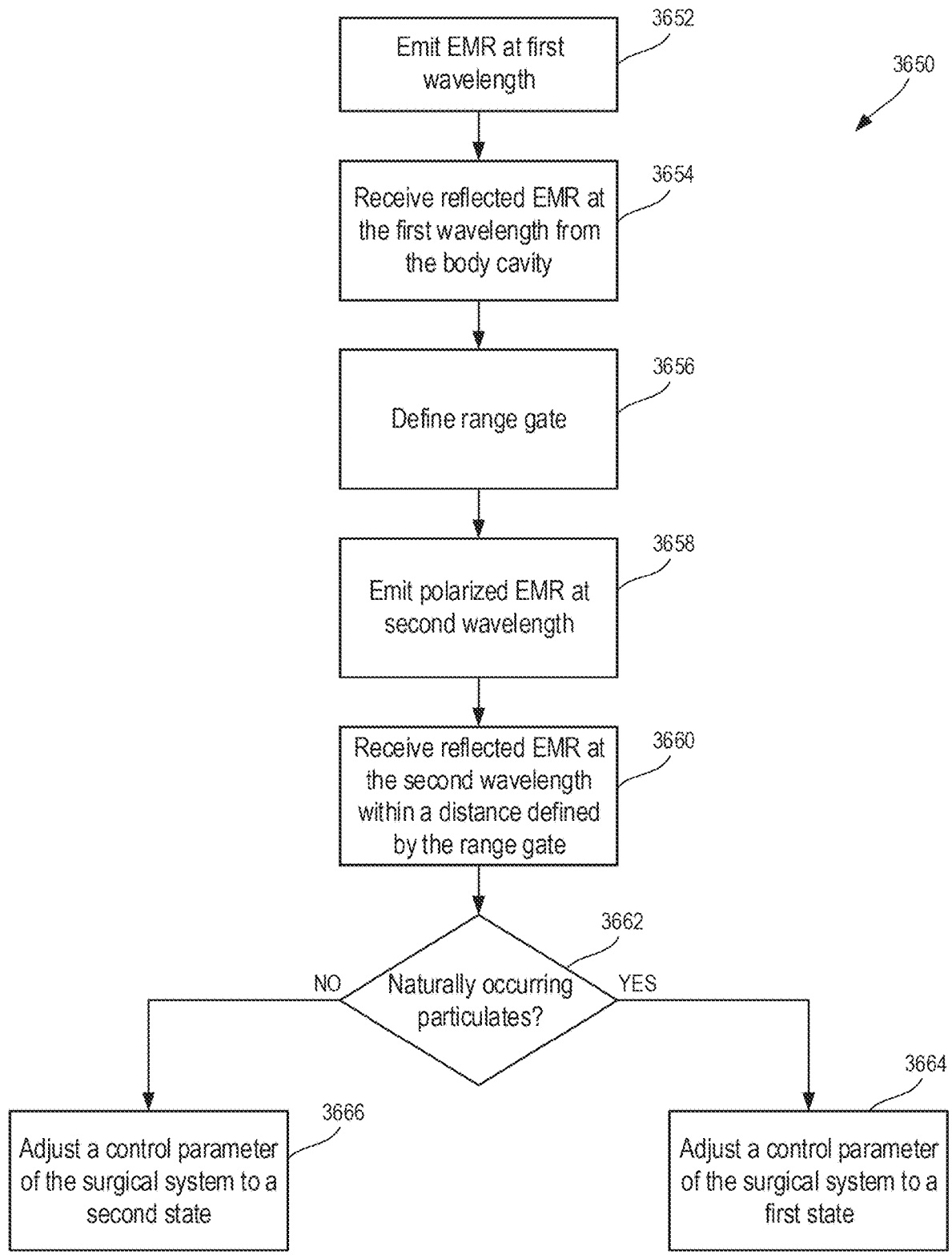

FIG. 56B is a logic flow diagram of a process for controlling a surgical system according to detected particulate types detected within a defined range gate, in accordance with at least one aspect of the present disclosure.

FIG. 57A is a pixel array of an image sensor detecting airborne particulates, in accordance with at least one aspect of the present disclosure.

FIG. 57B is a pixel array of an image sensor detecting airborne particulates that have moved from the positions shown in FIG. 57A, in accordance with at least one aspect of the present disclosure.

FIG. 57C is a pixel array of an image sensor indicating the generalized movement vector of the particulates shown in FIG. 57B, in accordance with at least one aspect of the present disclosure.

FIG. 58 illustrates a change in airborne particulate cloud state corresponding to FIGS. 57A-57C, in accordance with at least one aspect of the present disclosure.

Figure 59:
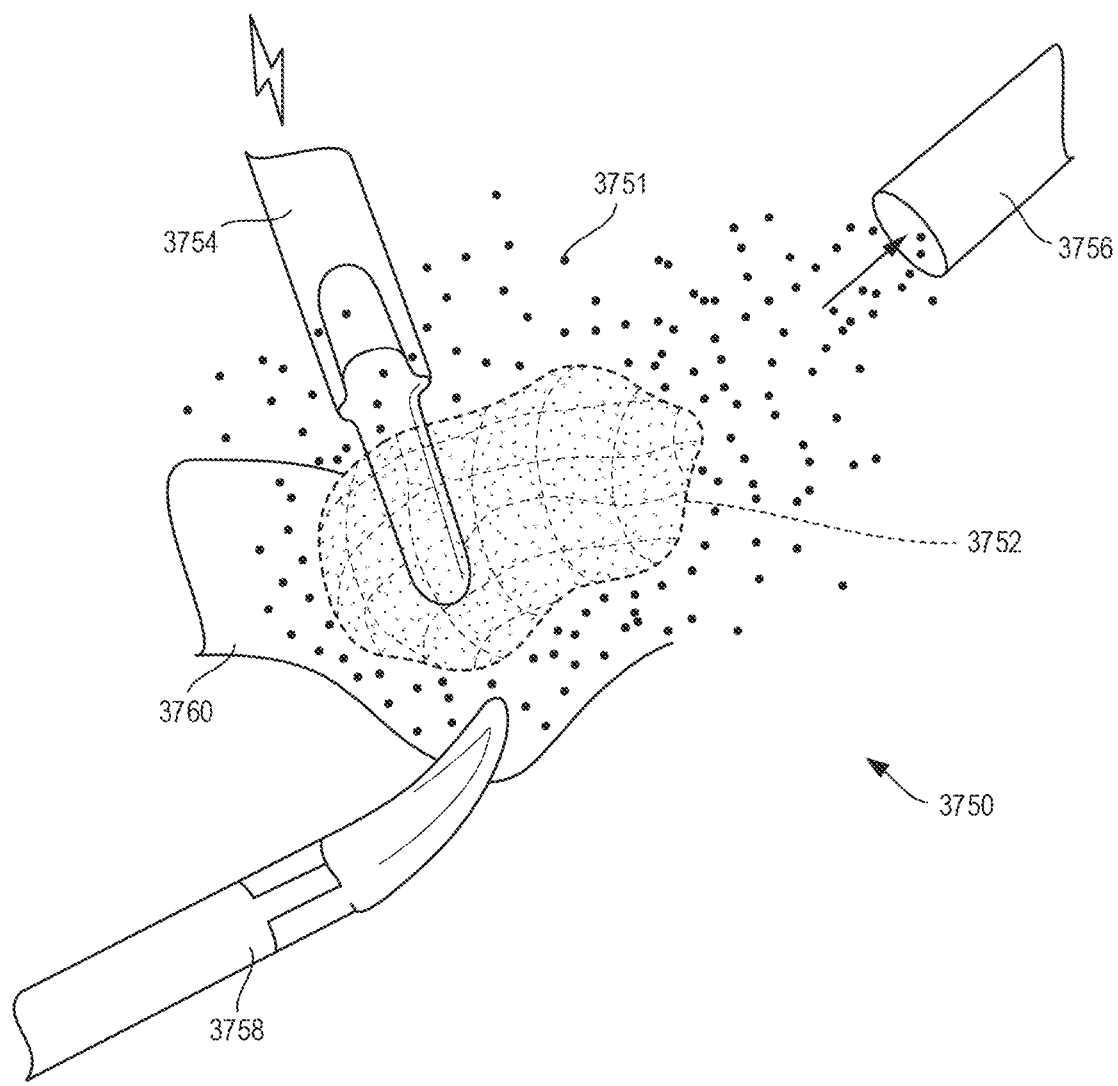

FIG. 59 is a diagram of a surgical system during the performance of a surgical procedure in which a particulate cloud is being generated, in accordance with at least one aspect of the present disclosure.

Figure 60:
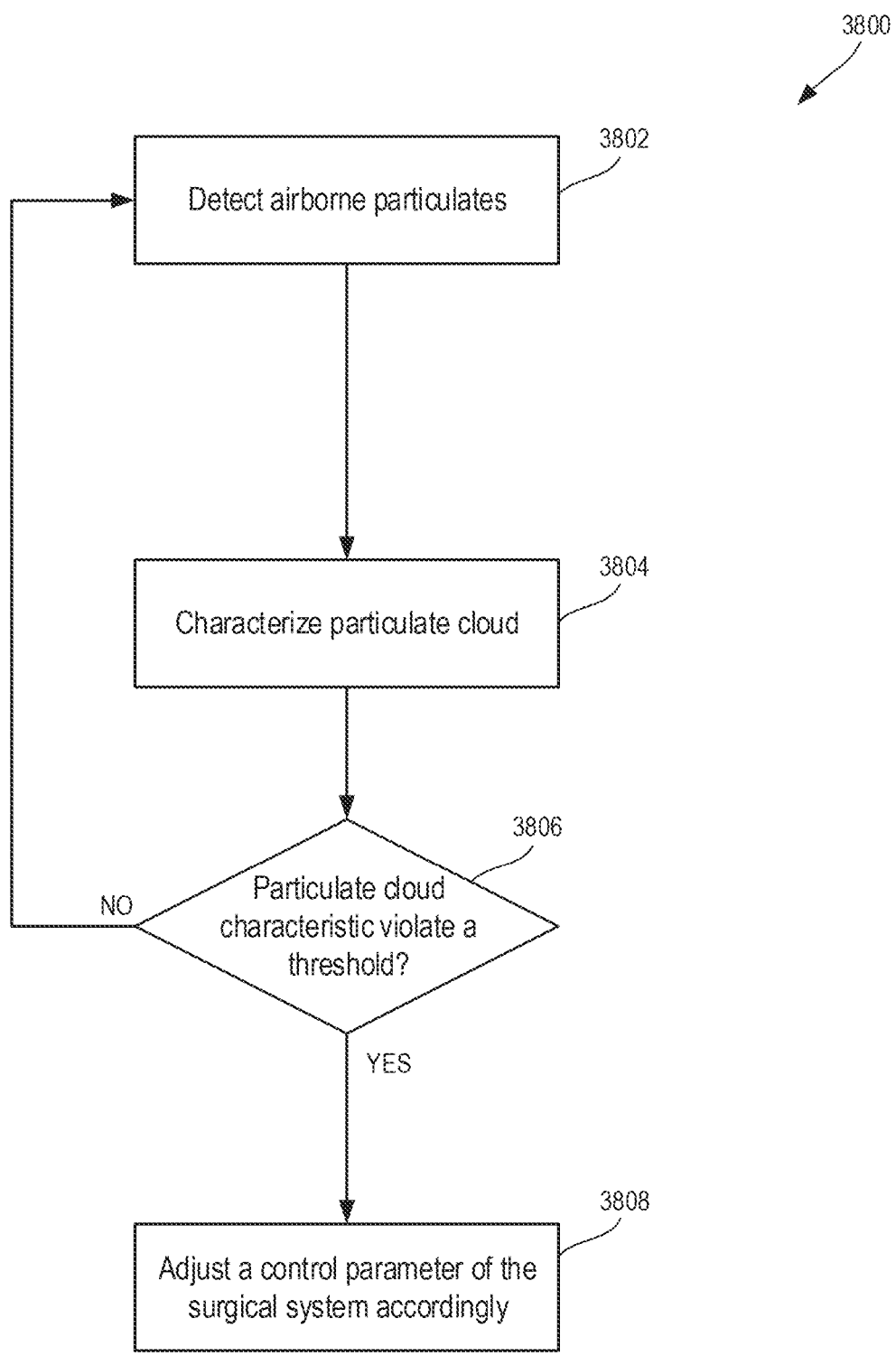

FIG. 60 is a logic flow diagram of a process for controlling a surgical system according to particulate cloud characteristics, in accordance with at least one aspect of the present disclosure.

Figure 61:
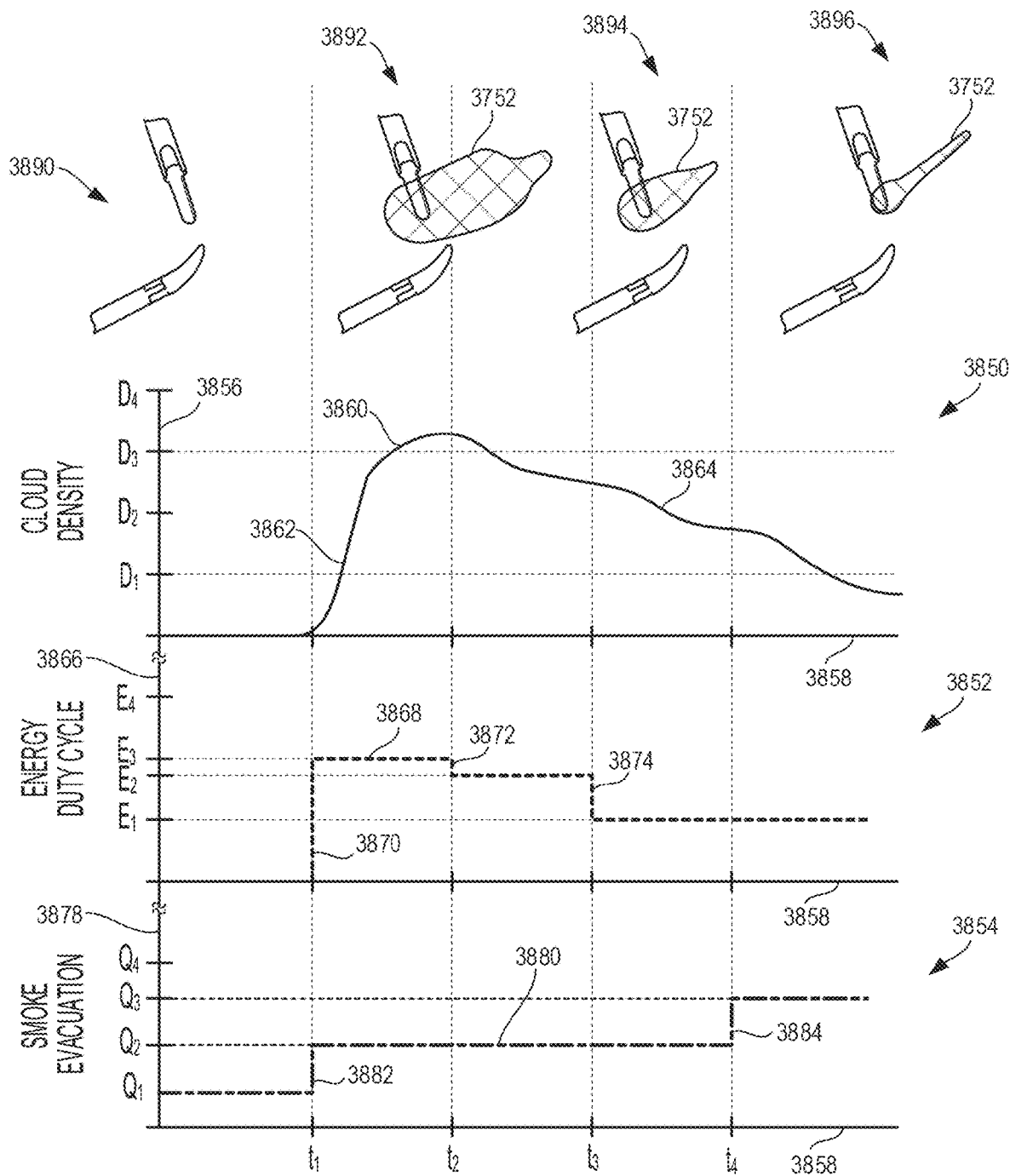

FIG. 61 is a series of graphs illustrating the adjustment of control parameters based on particulate cloud characteristics, in accordance with at least one aspect of the present disclosure.

Figure 62:
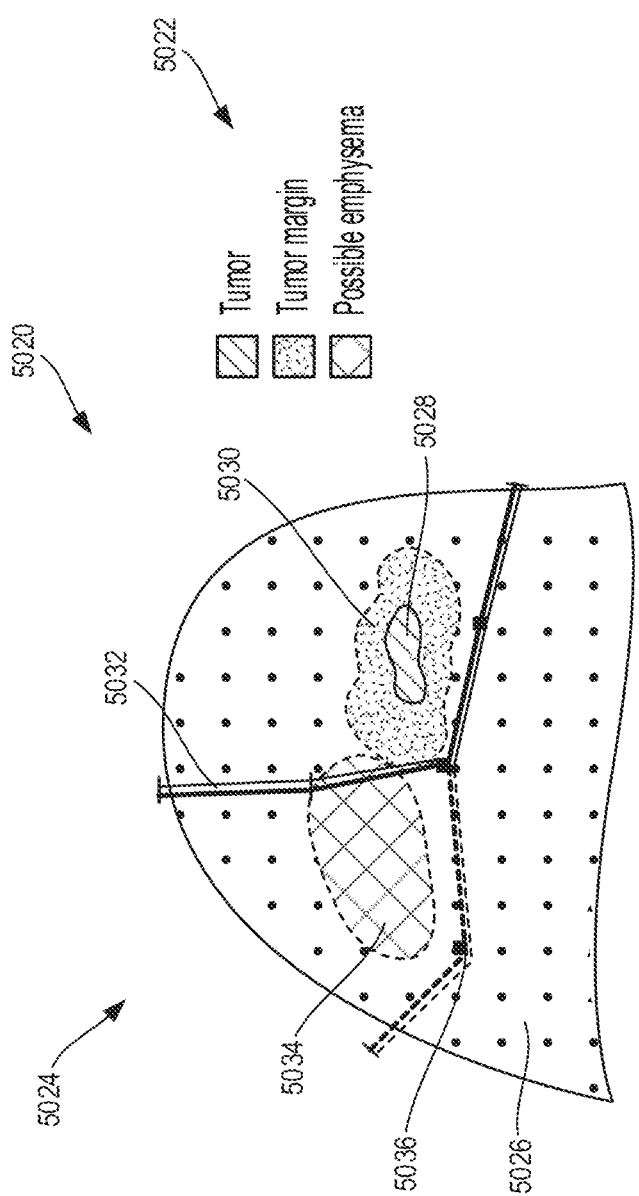

FIG. 62 is a display of a surgical visualization system shown in accordance with at least one aspect of the present disclosure.

Figure 63B:
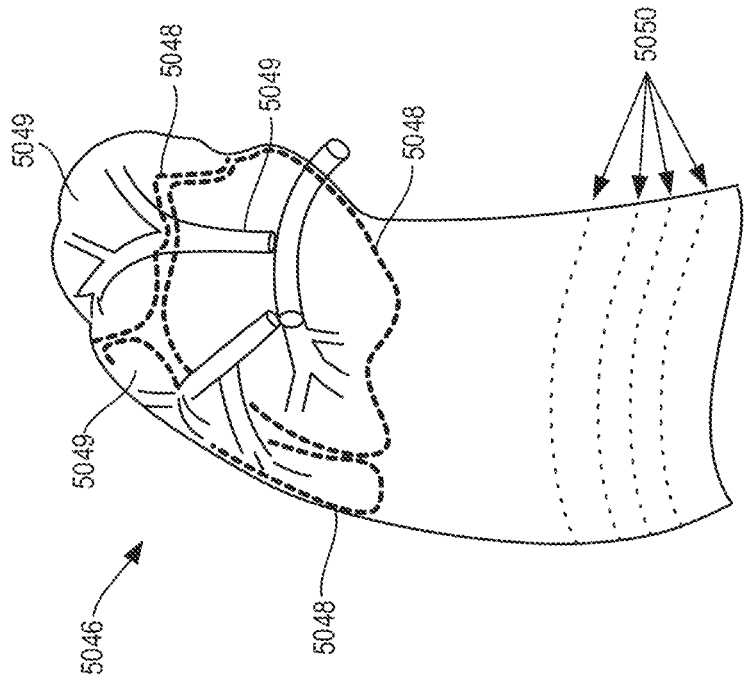
Figure 63A:
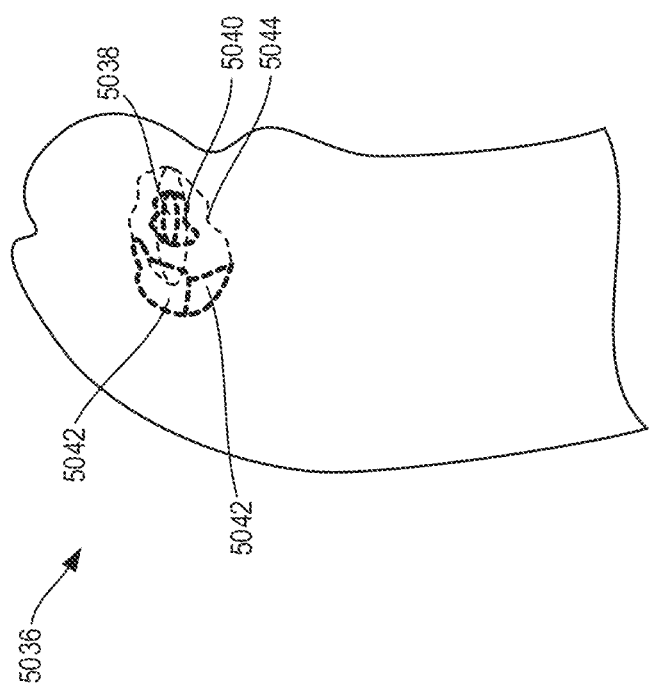

FIG. 63A is a model of an anatomical structure generated by a surgical visualization system shown in accordance with at least one aspect of the present disclosure.

FIG. 63B is a display of the model of FIG. 63A shown in accordance with at least one aspect of the present disclosure.

FIG. 64A is another model of an anatomical structure generated by a surgical visualization system shown in accordance with at least one aspect of the present disclosure.

FIG. 64B is a display of the model of FIG. 64A shown in accordance with at least one aspect of the present disclosure.

Figure 65:
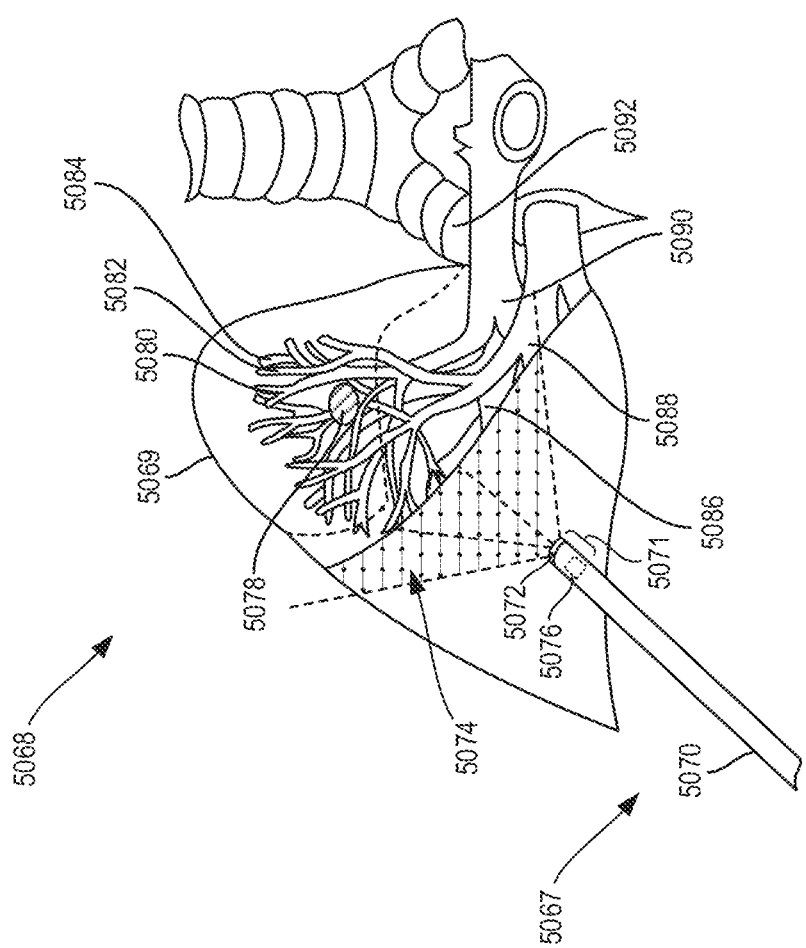

FIG. 65 is another model of an anatomical structure generated by a surgical visualization system shown in accordance with at least one aspect of the present disclosure.

Figure 66:
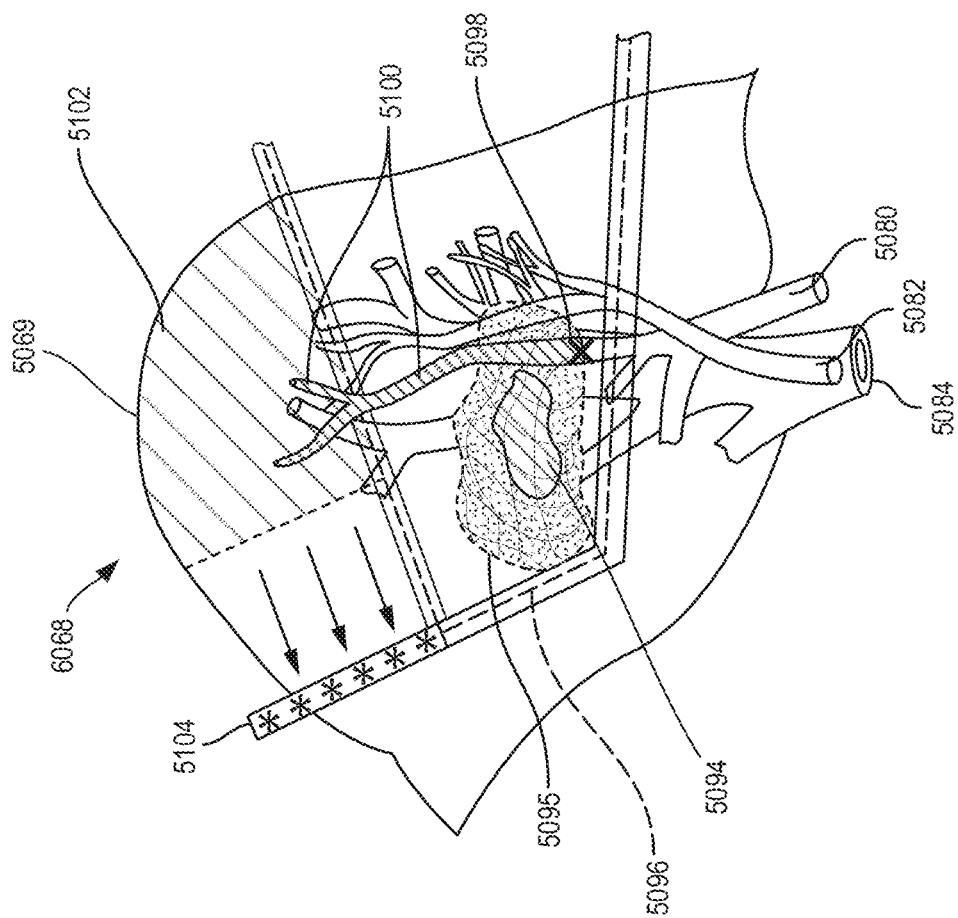

FIG. 66 is a display of the model of FIG. 65 shown in accordance with at least one aspect of the present disclosure.

Figure 67:
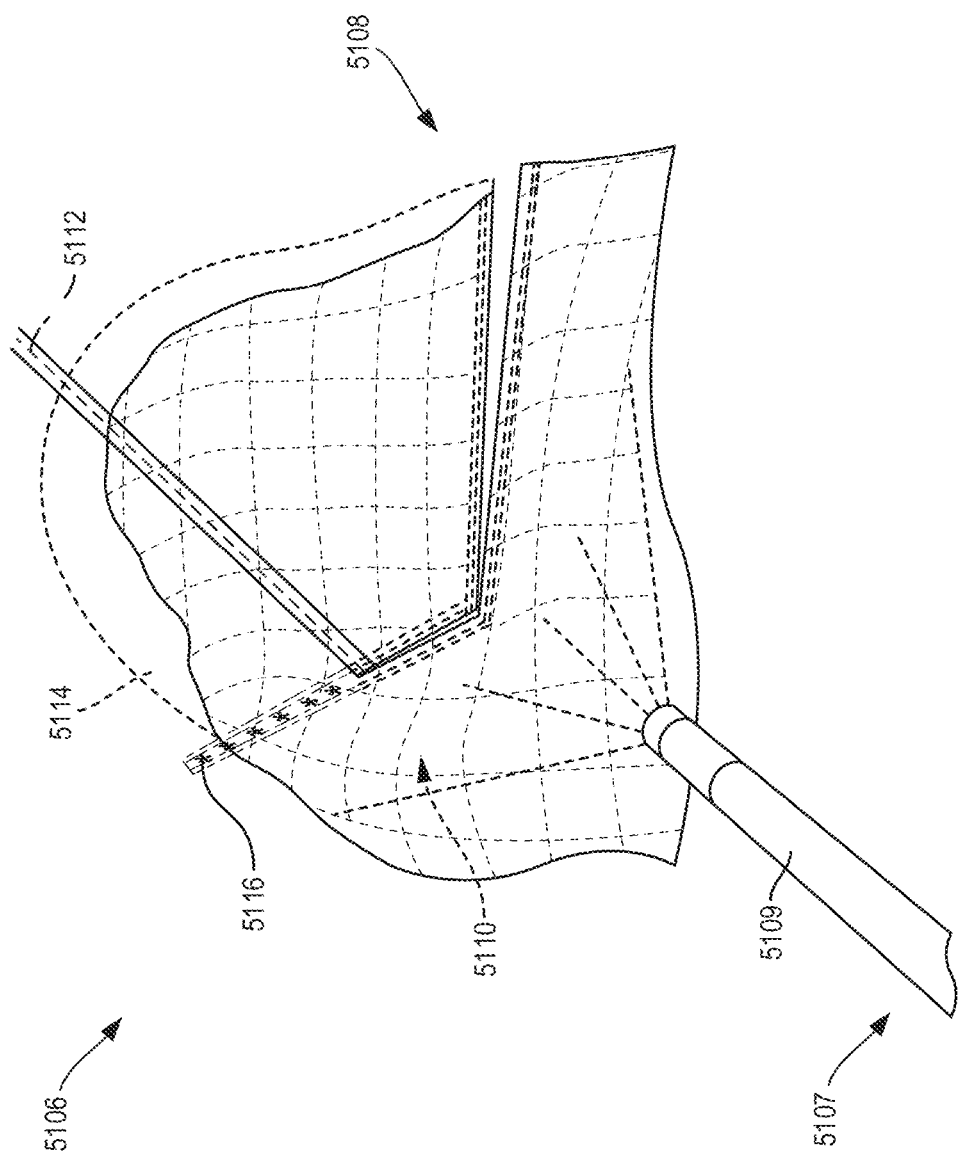

FIG. 67 is a display of another model of an anatomical structure generated by a surgical visualization system shown in accordance with at least one aspect of the present disclosure.

Figure 68:
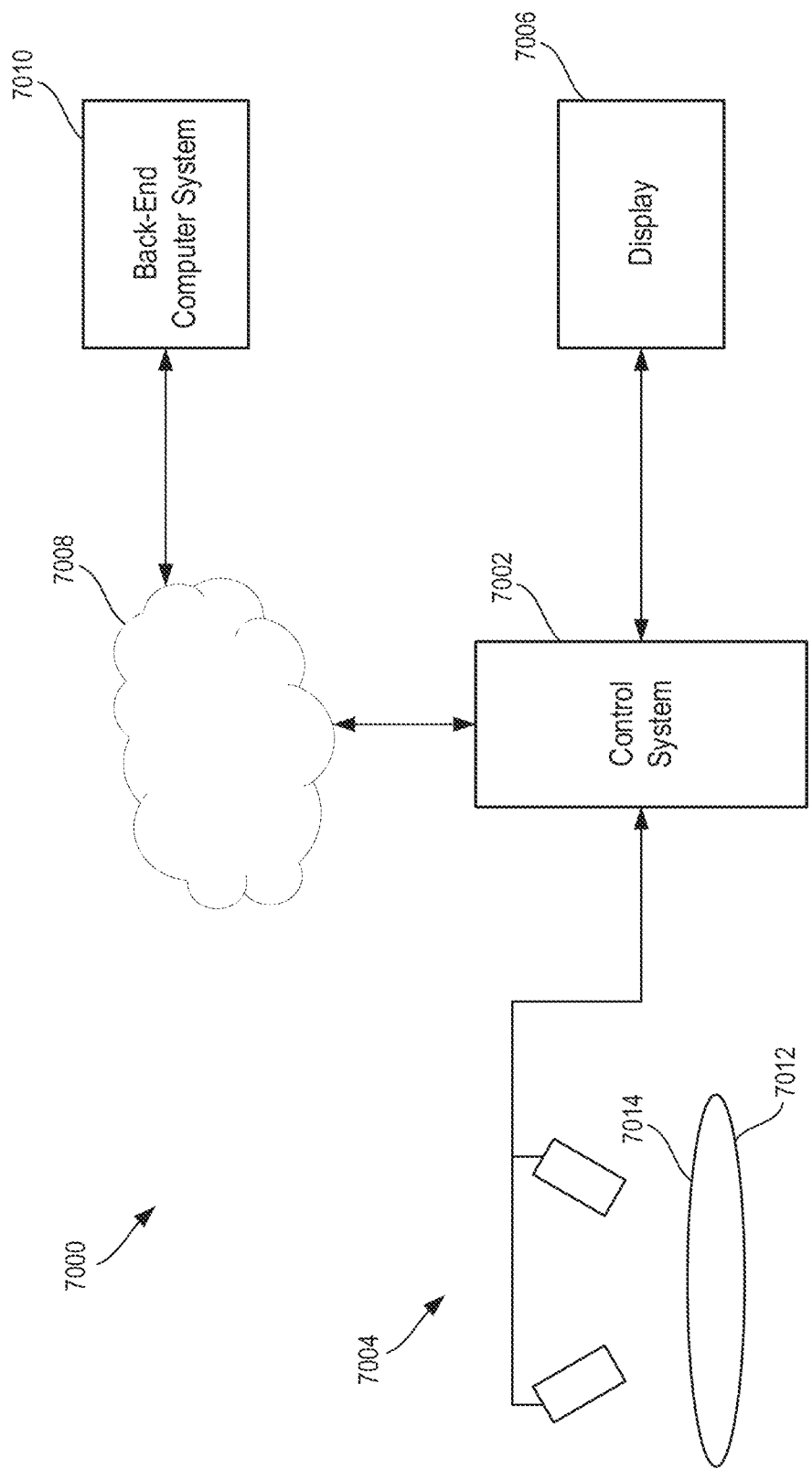

FIG. 68 is a diagram of a surgical system, in accordance with at least one aspect of the present disclosure.

Figure 69:
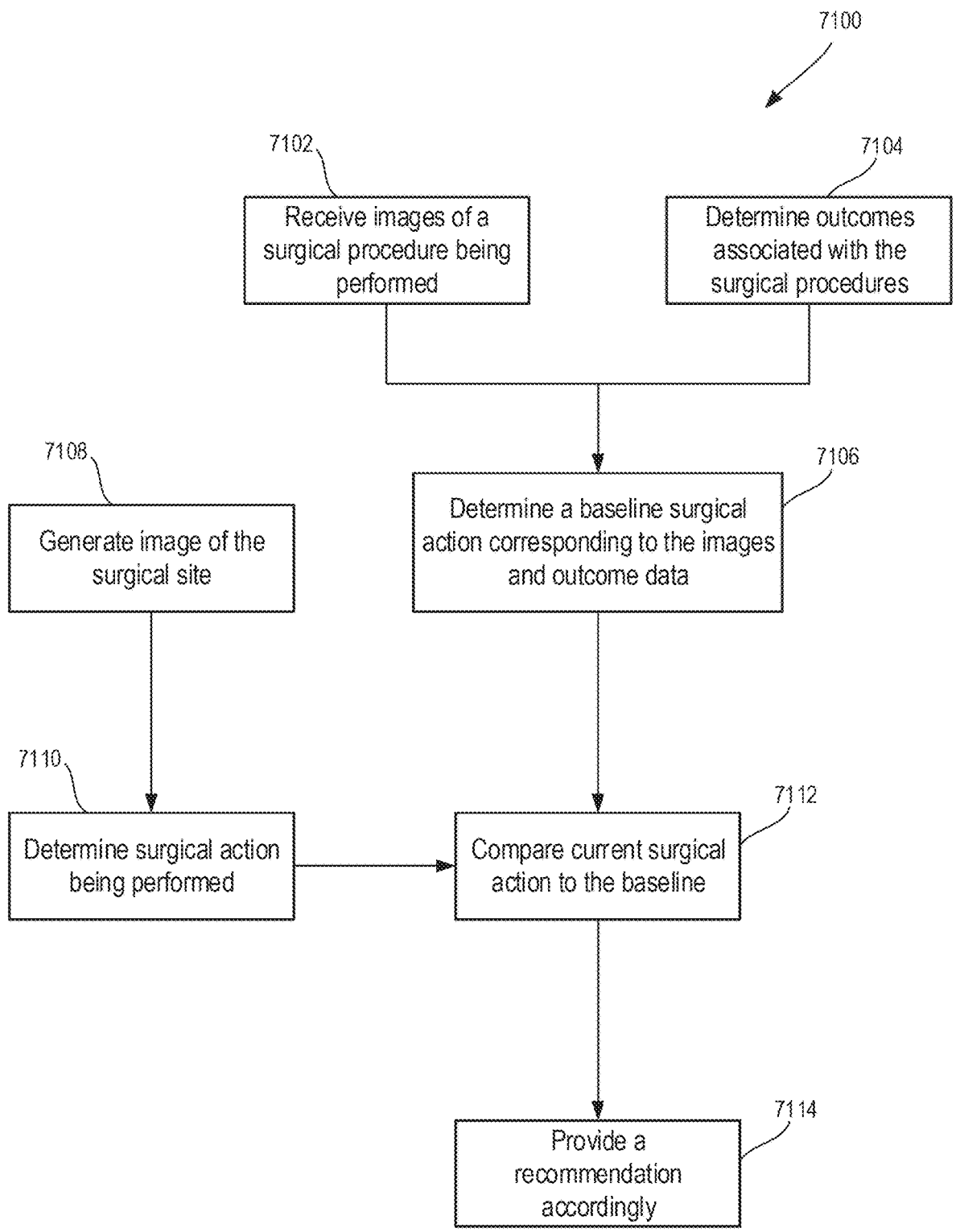

FIG. 69 is a logic flow diagram of a process for providing dynamic surgical recommendations to users, in accordance with at least one aspect of the present disclosure.

Figure 70:
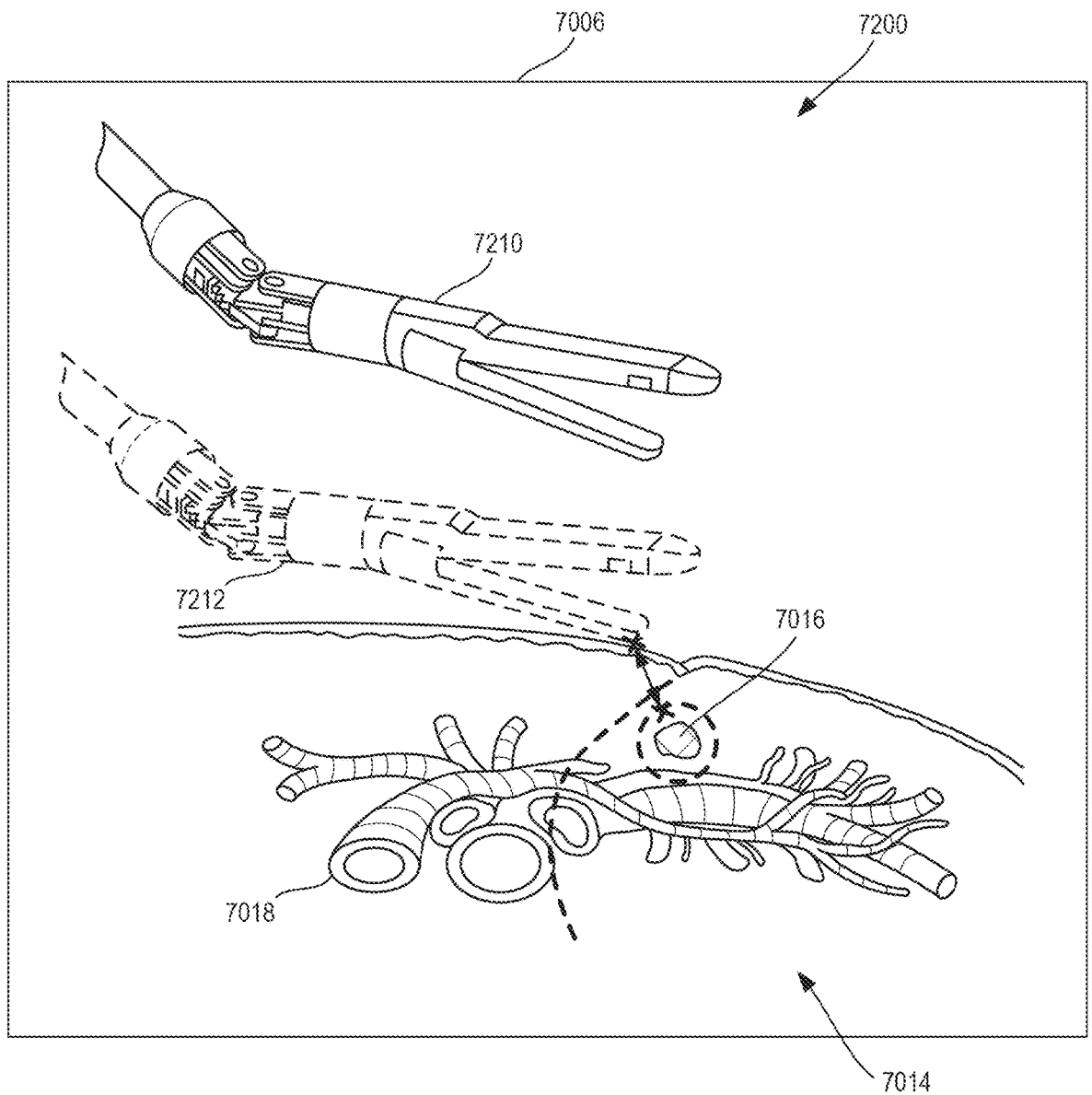

FIG. 70 is a surgical visualization displaying a recommended surgical instrument position, in accordance with at least one aspect of the present disclosure.

Figure 71:
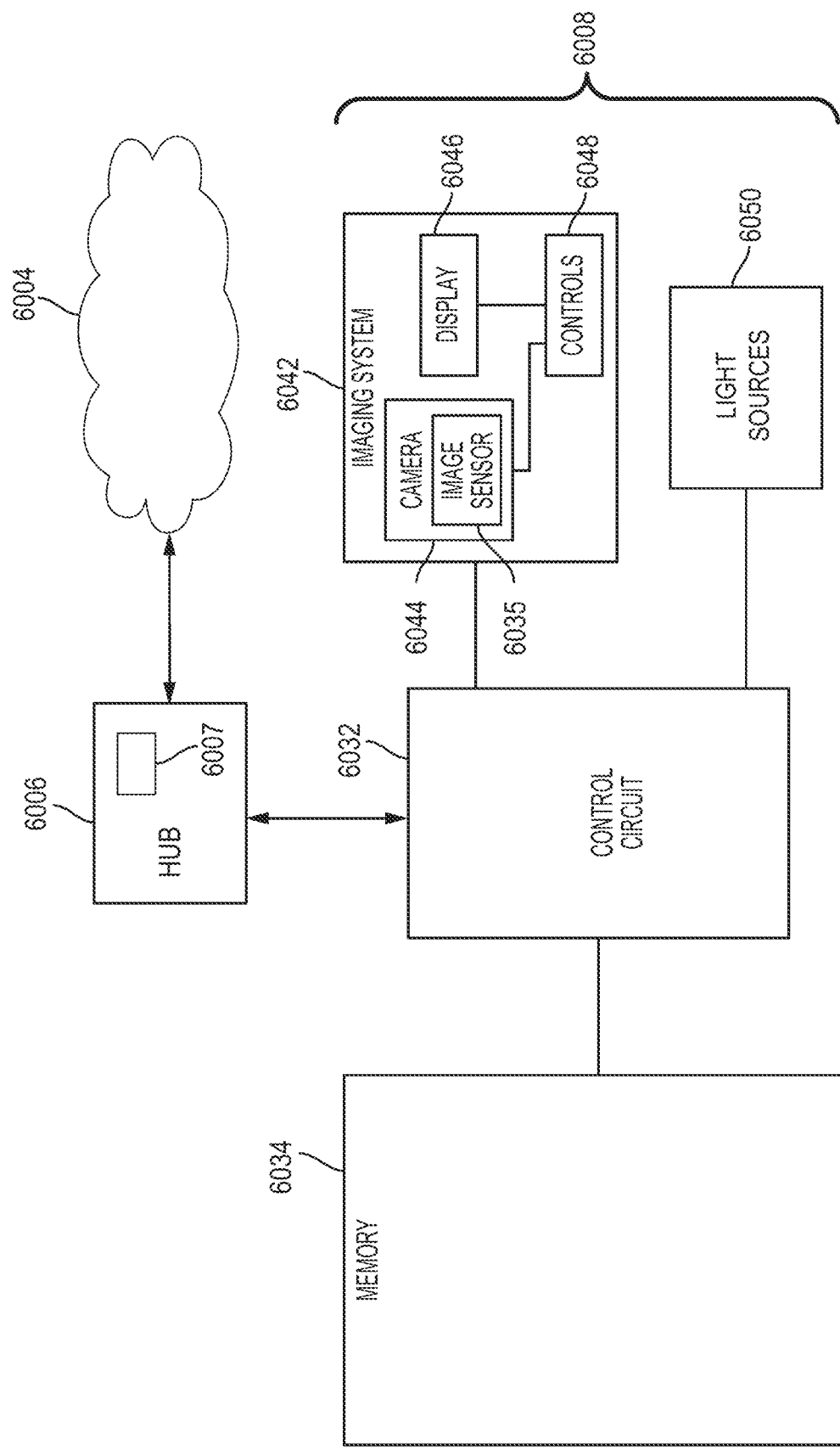

FIG. 71 is a schematic showing portions of a computer-implemented interactive surgical system including an adaptive surgical visualization system, according to at least one aspect of the present disclosure.

Figure 72:
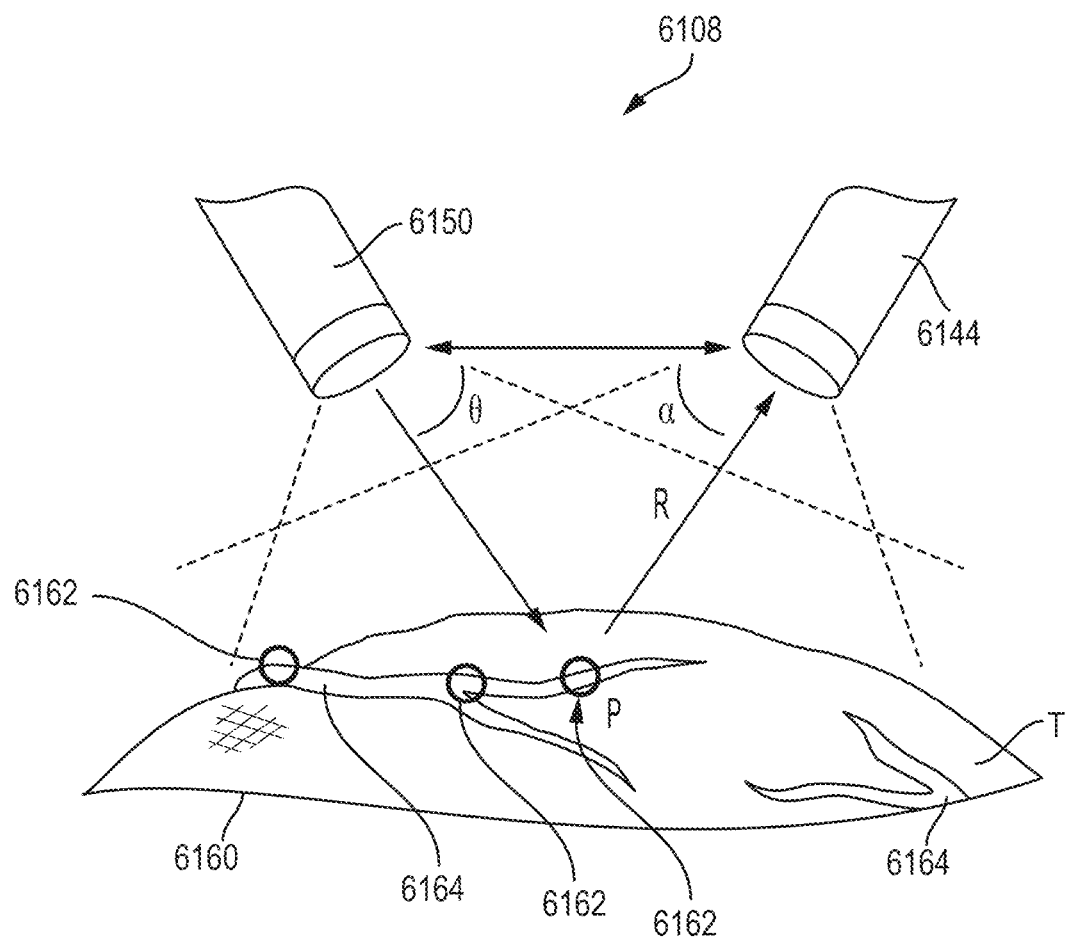

FIG. 72 is a schematic of a surgical visualization system including a structured light projector and a camera, according to at least one aspect of the present disclosure.

Figure 73:
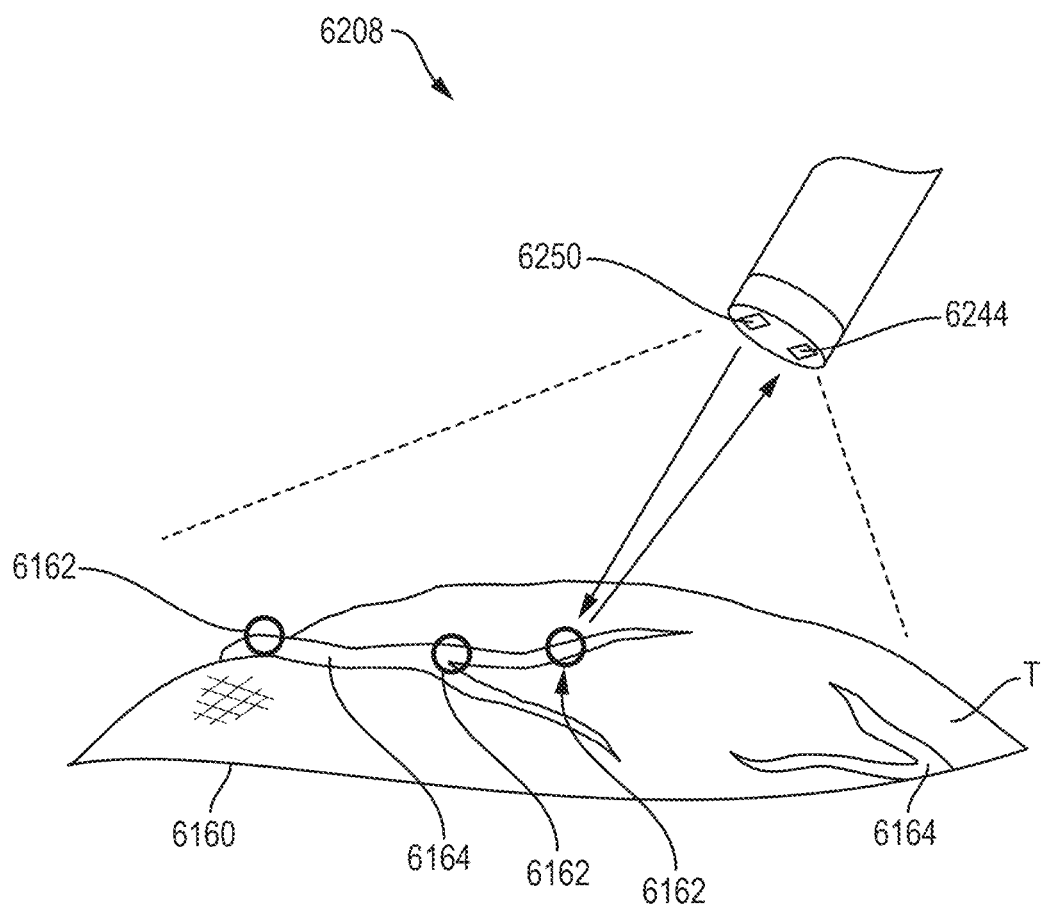

FIG. 73 is a schematic of a surgical visualization system including a surgical device including a structured light projector and a camera, according to at least one aspect of the present disclosure.

Figure 74A:
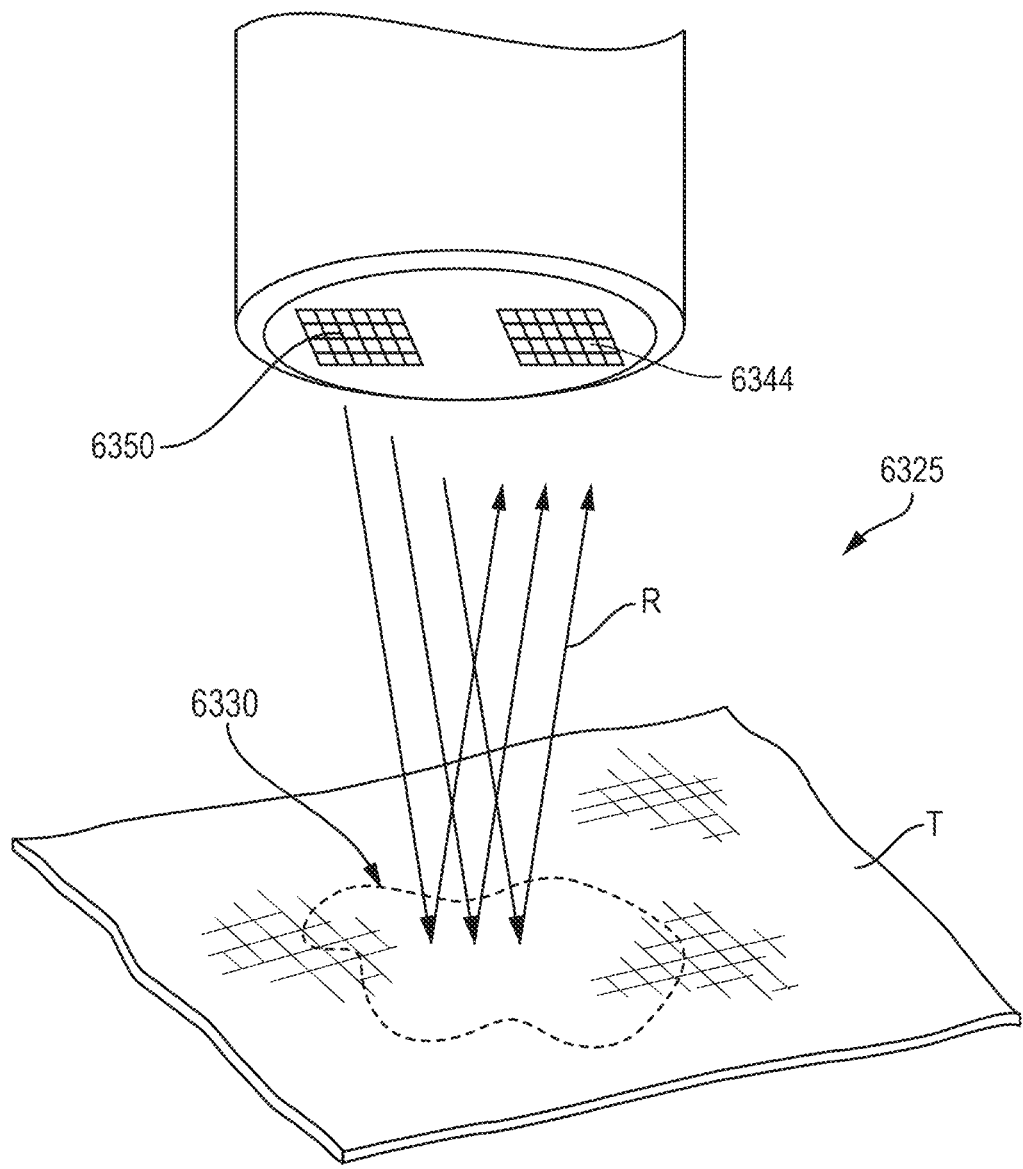

FIG. 74A is a schematic of a surgical device for visualizing tissue and depicting an expected refractivity, according to at least one aspect of the present disclosure.

Figure 74B:
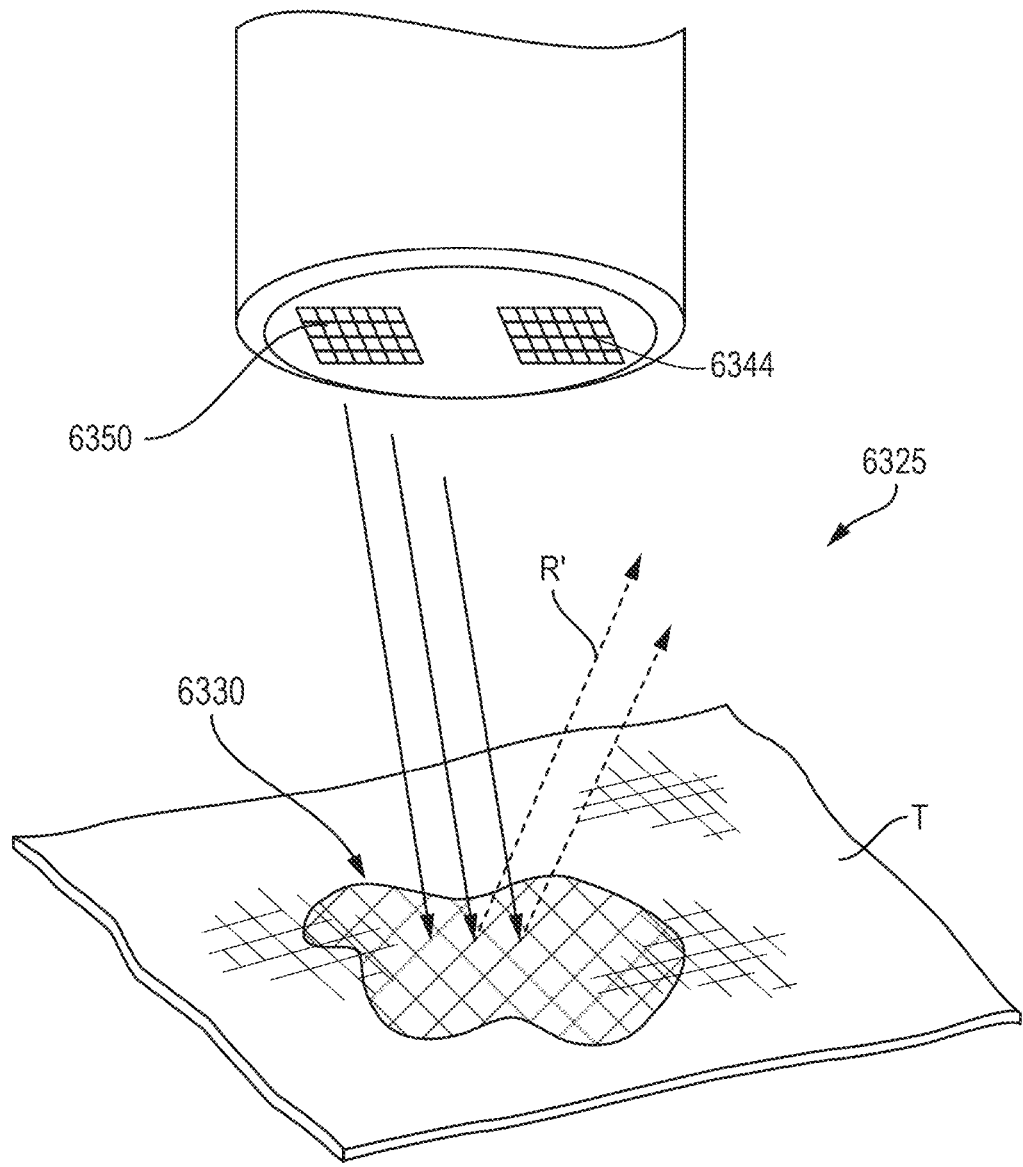

FIG. 74B is a schematic of the surgical device of FIG. 74B depicting the actual refractivity, according to at least one aspect of the present disclosure.

Figure 75:
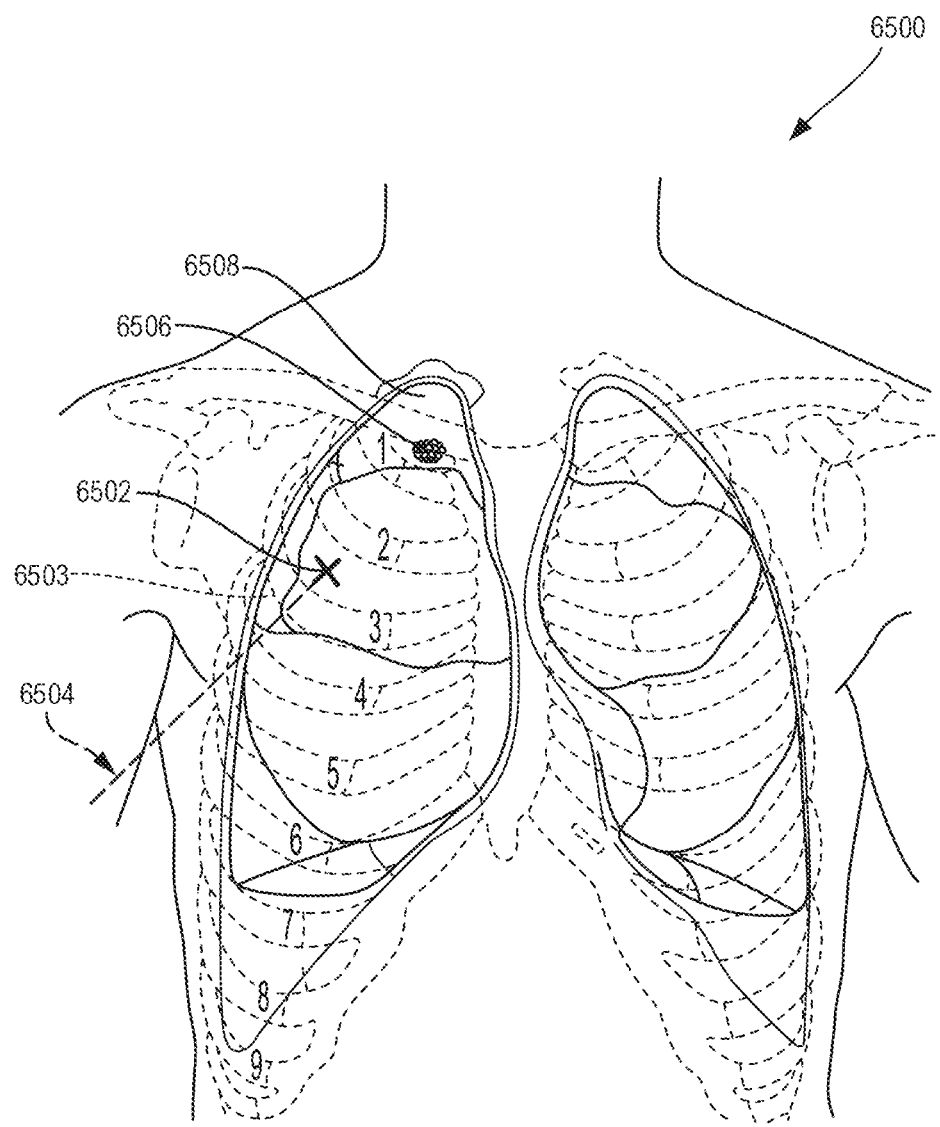

FIG. 75 is a diagram of a surgical instrument access path for a video-assisted thoracoscopic surgery (VATS) procedure, in accordance with at least one aspect of the present disclosure.

Figure 76:
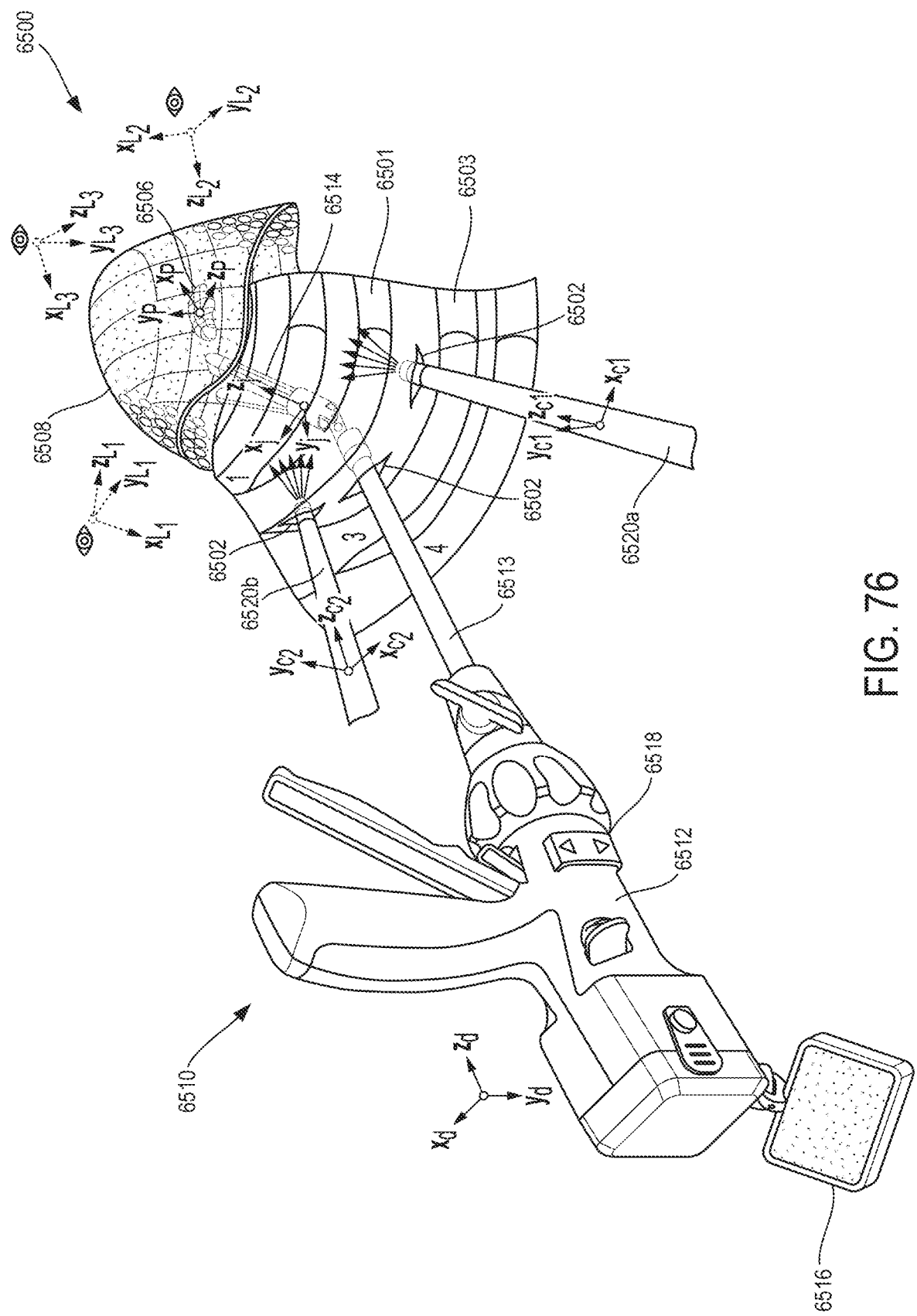

FIG. 76 is a diagram of various coordinate systems associated with a VATS procedure, in accordance with at least one aspect of the present disclosure.

Figure 77:
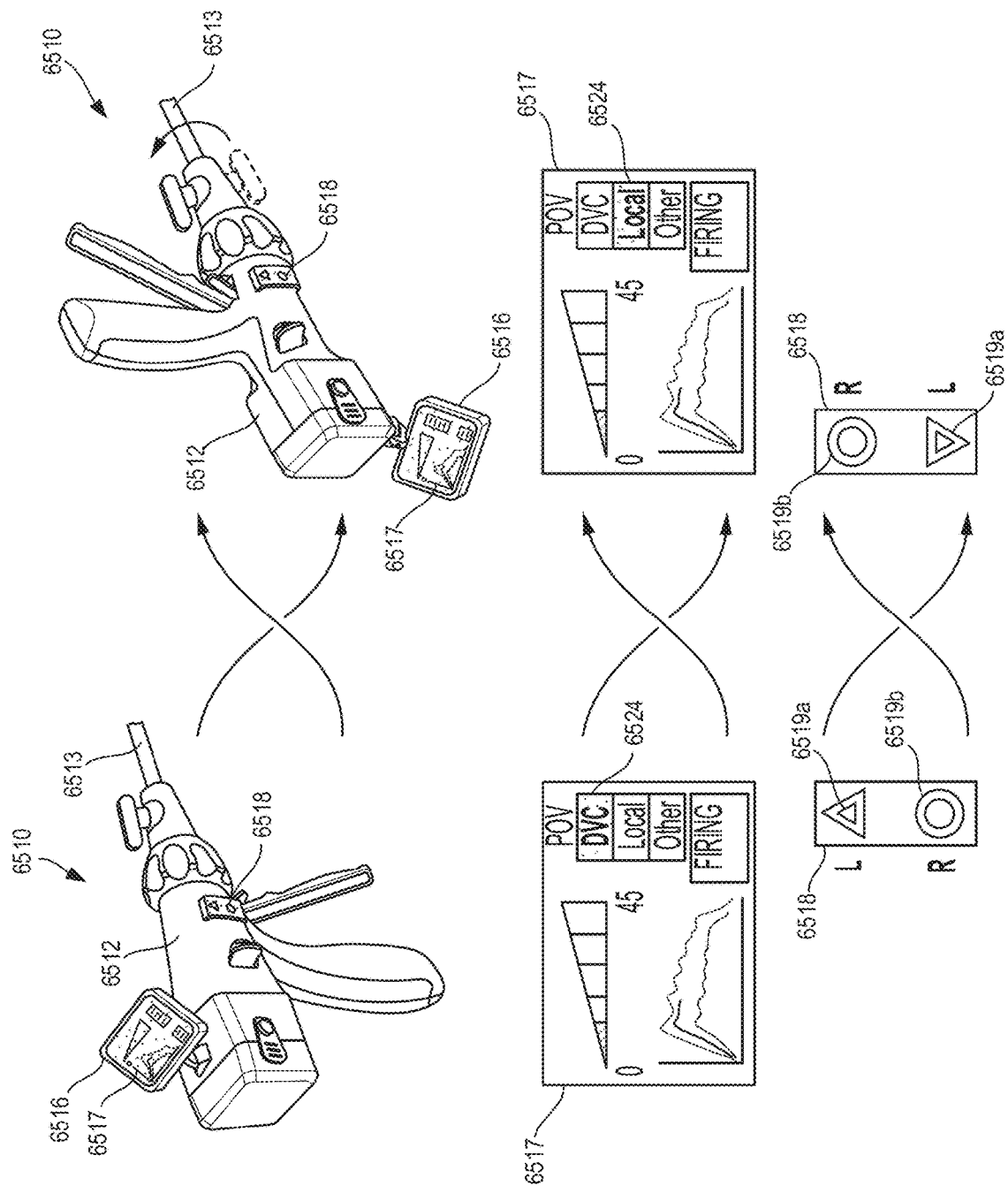

FIG. 77 is a diagram depicting the change in orientation of a display and user controls in response to a change in orientation of the surgical instrument, in accordance with at least one aspect of the present disclosure.

Figure 78:
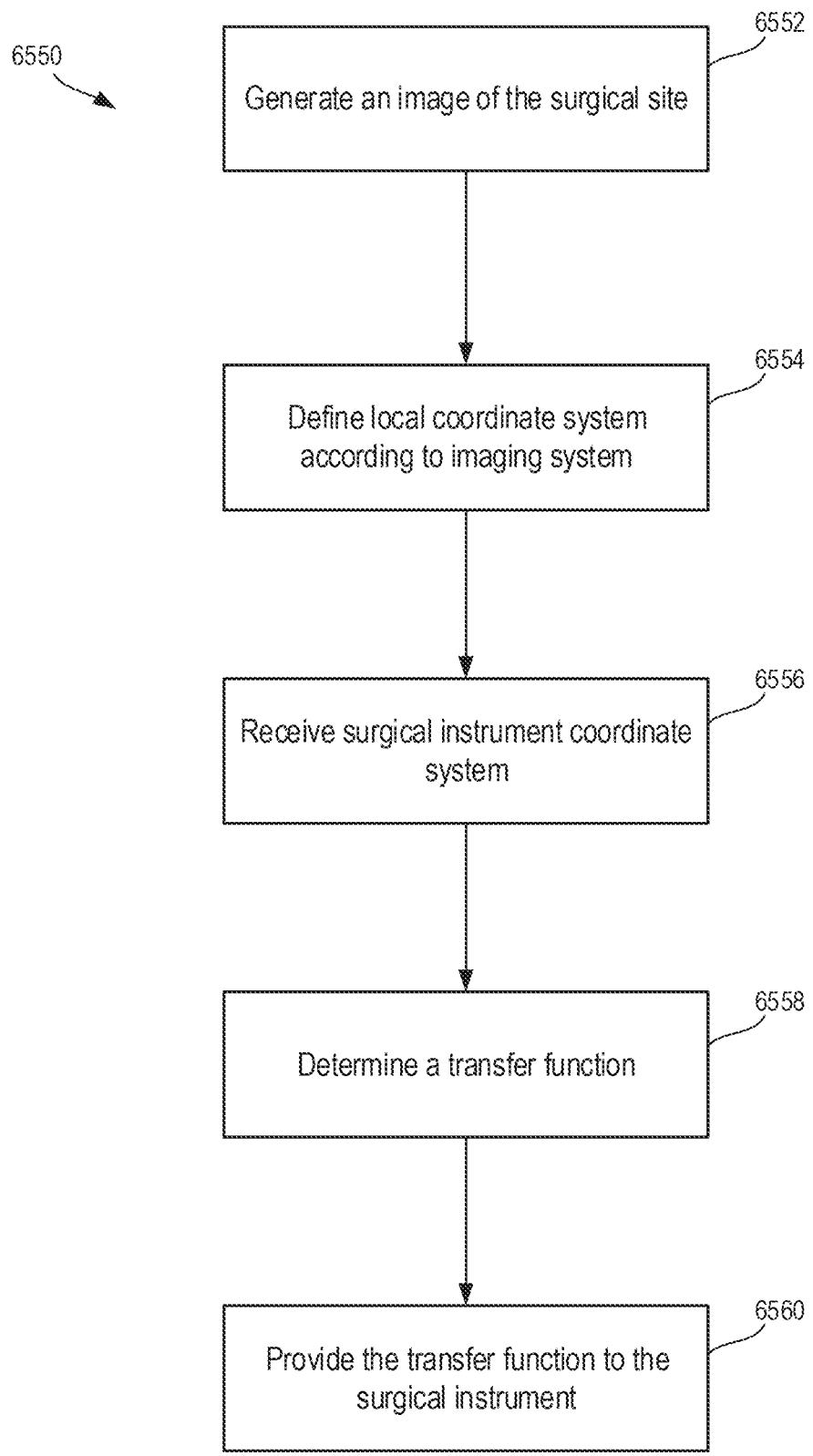

FIG. 78 is a logic flow diagram of a process of adjusting a display and/or user control according to a displayed coordinate system, in accordance with at least one aspect of the present disclosure.

Figure 79:
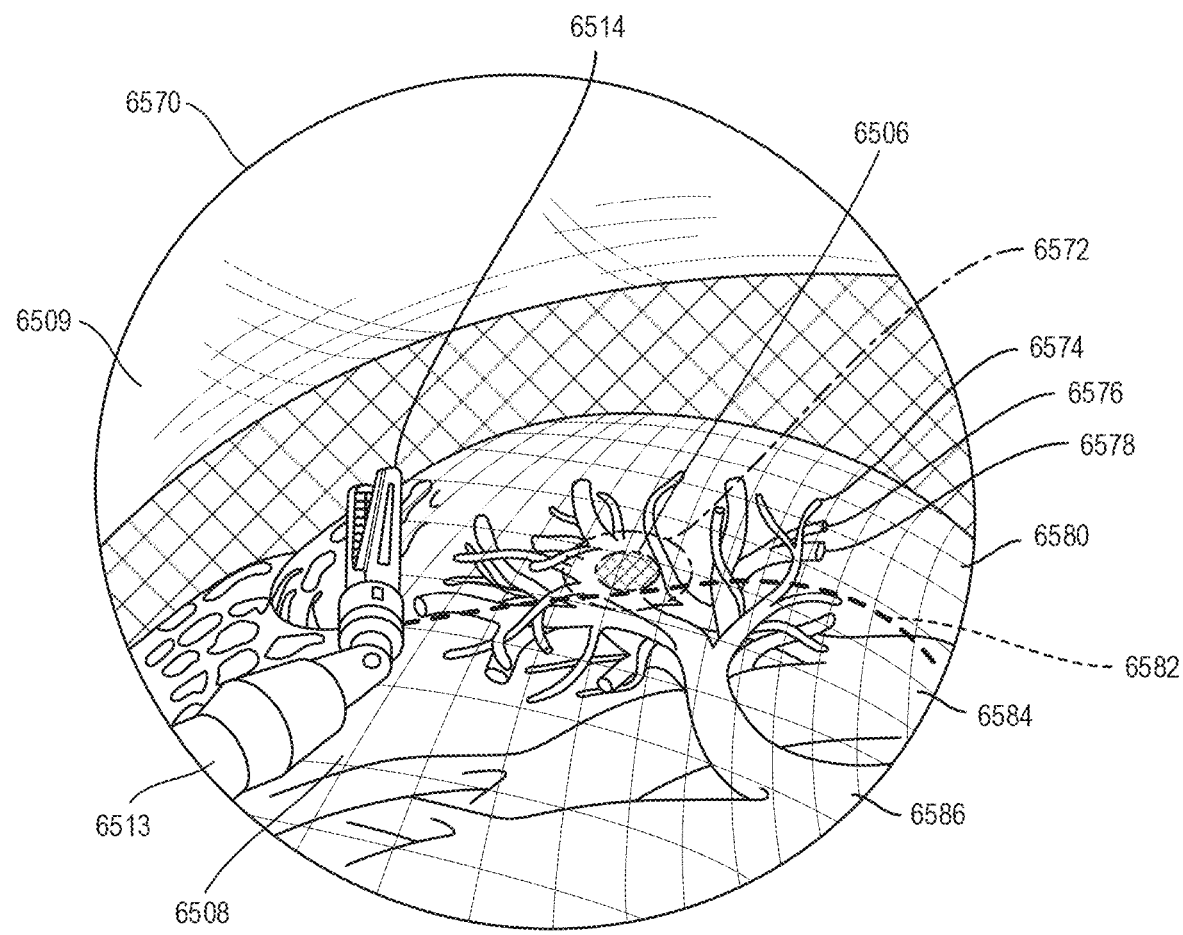

FIG. 79 depicts a camera view of the surgical procedure of FIG. 76, in accordance with at least one aspect of the present disclosure.

Figure 80:
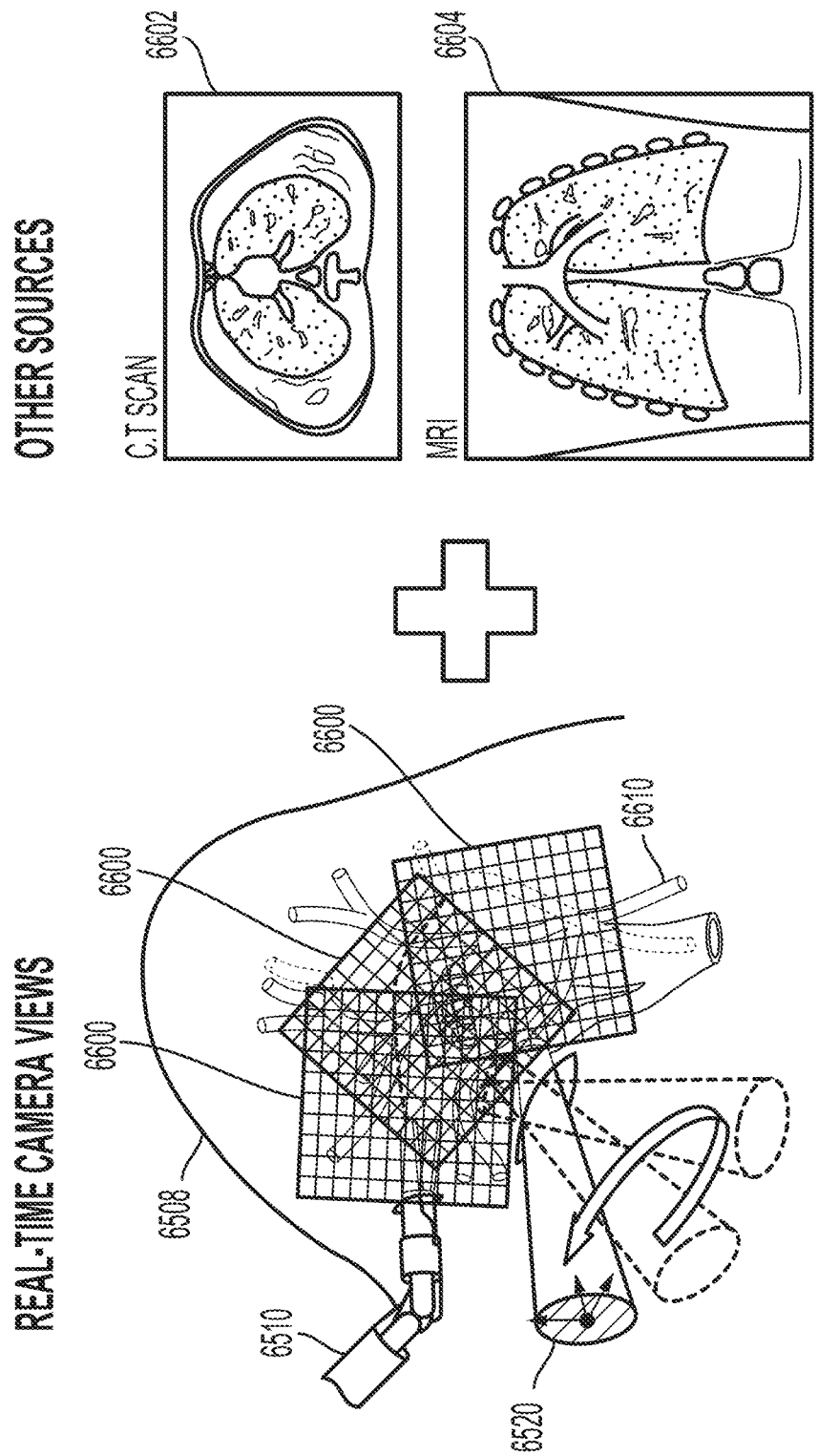

FIG. 80 is a diagram of image sources from which a three-dimensional (3D) representation of a surgical site can be generated, in accordance with at least one aspect of the present disclosure.

Figure 81:
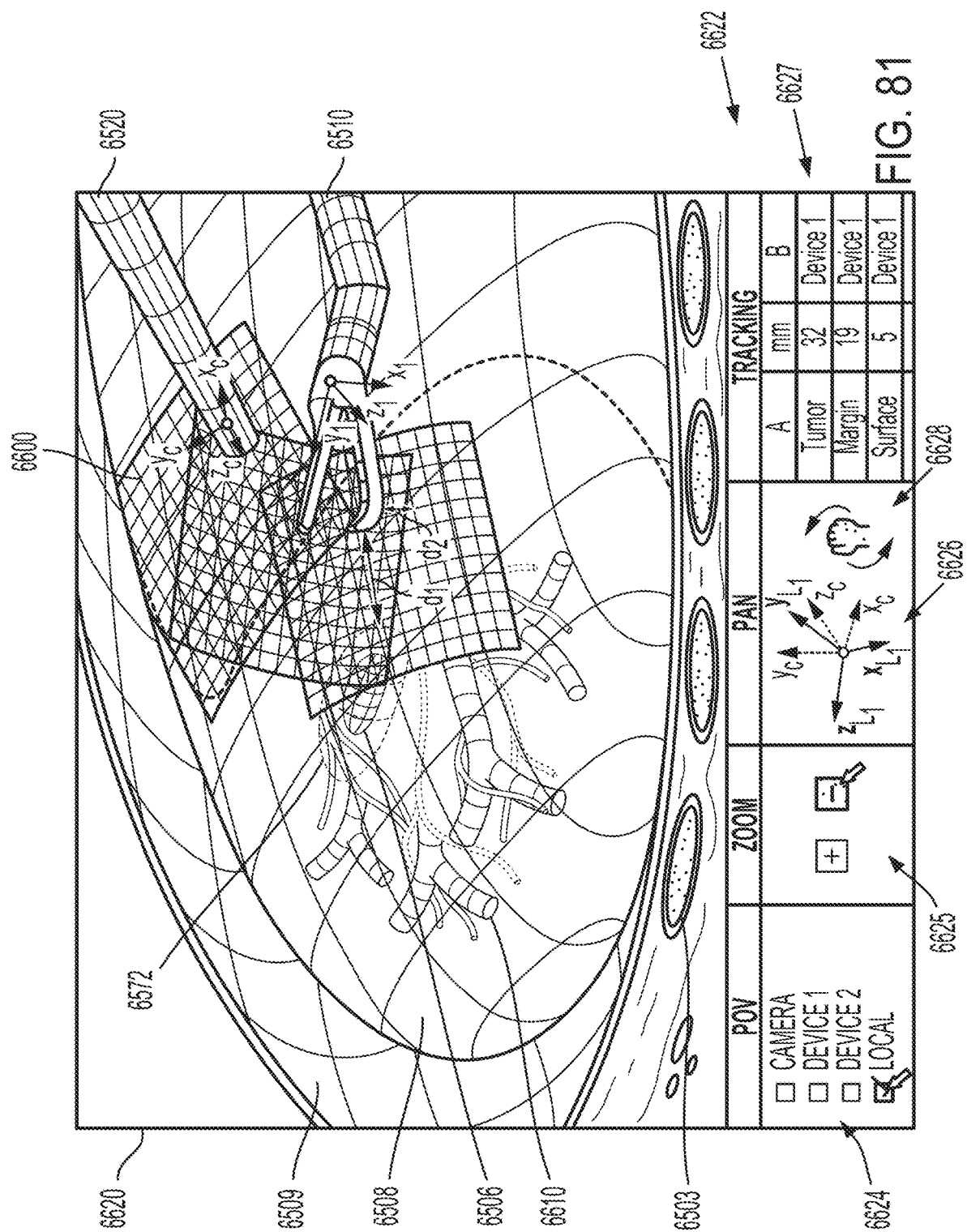

FIG. 81 is a visualization display and graphical user interface (GUI) of the surgical procedure of FIG. 76 provided by an imaging system, in accordance with at least one aspect of the present disclosure.

Figure 82:
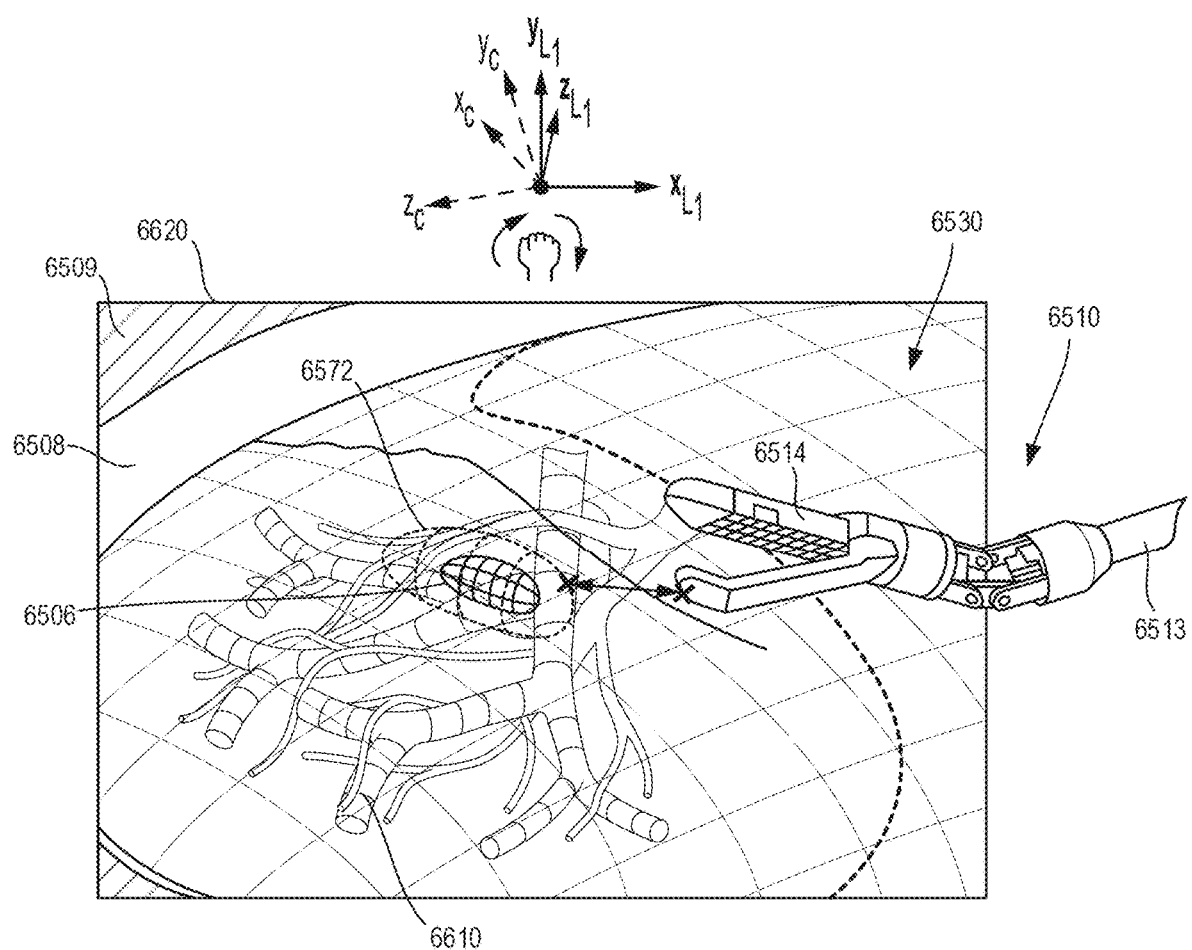

FIG. 82 is the visualization display of FIG. 81 adjusted to a first point of view (POV), in accordance with at least one aspect of the present disclosure.

Figure 83:
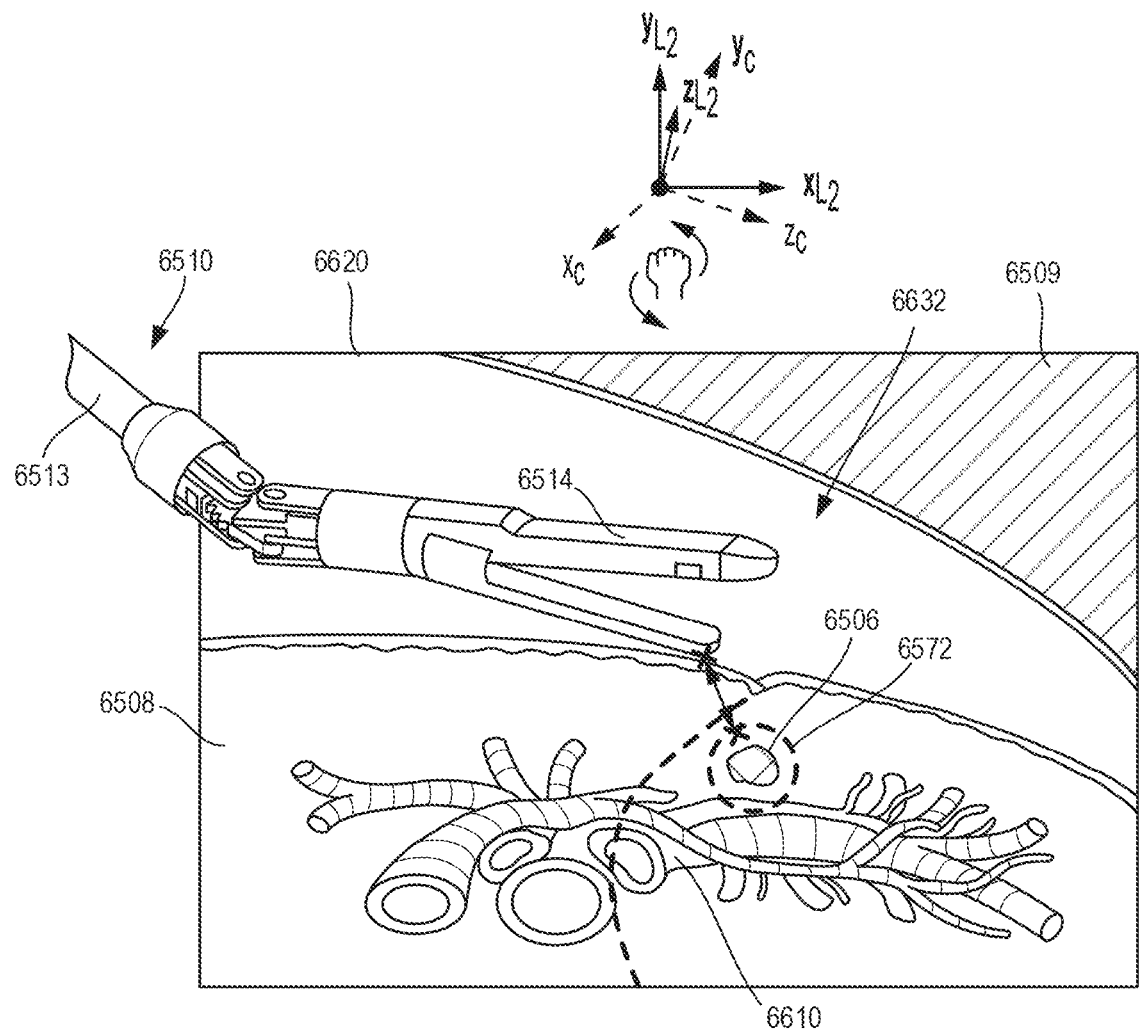

FIG. 83 is the visualization display of FIG. 81 adjusted to a second POV, in accordance with at least one aspect of the present disclosure.

Figure 84:
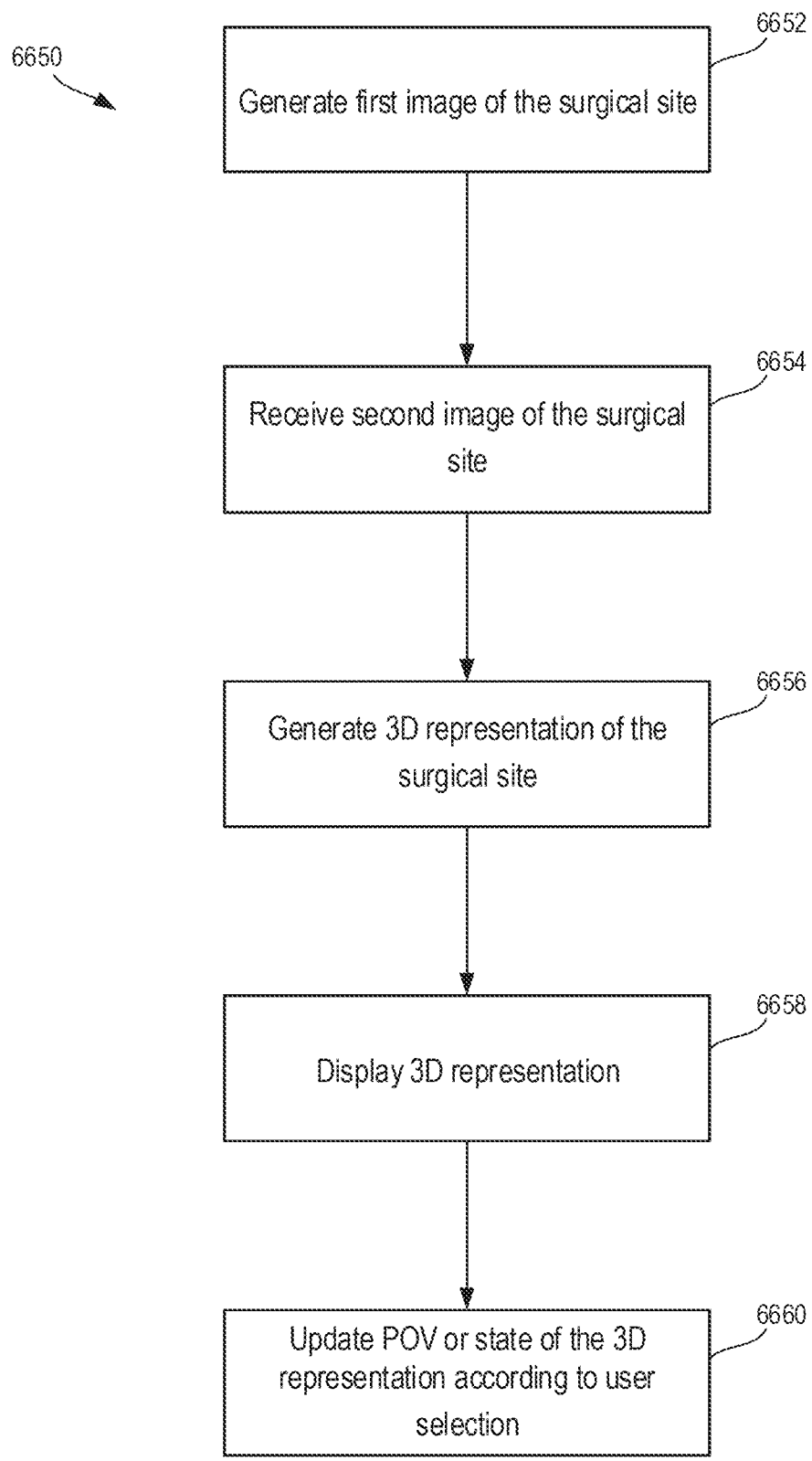

FIG. 84 is a logic flow diagram of a process of controlling a visualization display, in accordance with at least one aspect of the present disclosure.

Figure 85:
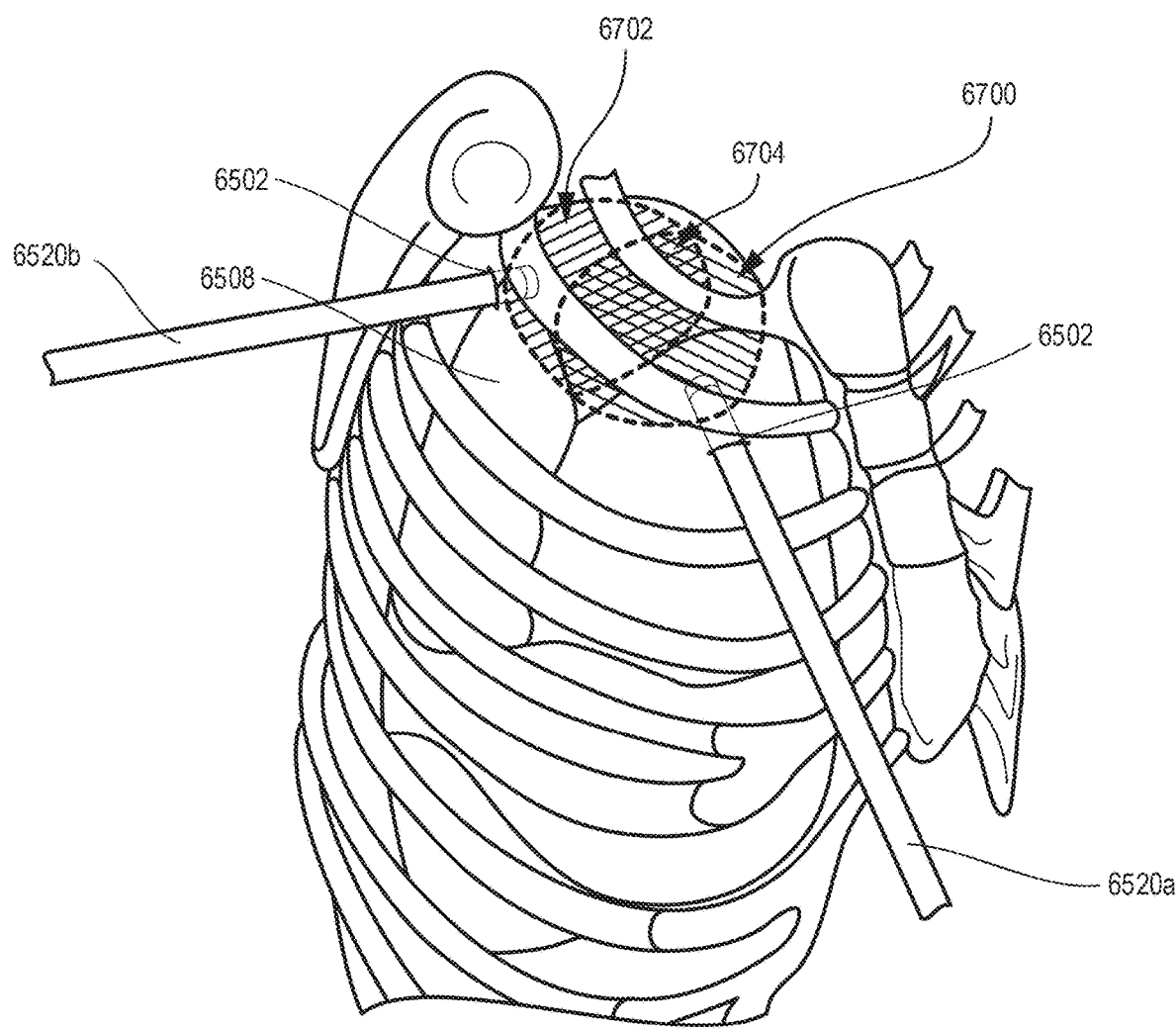

FIG. 85 is a diagram of a VATS procedure utilizing two cameras, in accordance with at least one aspect of the present disclosure.

Figure 86:
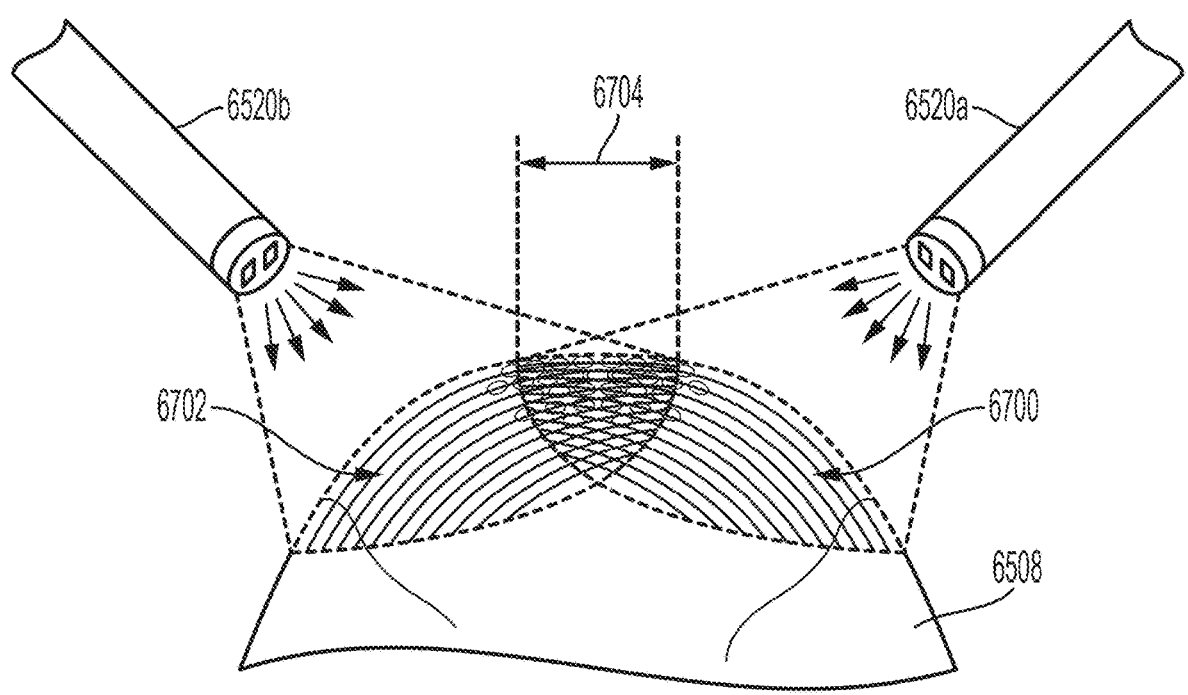

FIG. 86 is a diagram of a lung being imaged during the VATS procedure of FIG. 85, in accordance with at least one aspect of the present disclosure.

Figure 87:
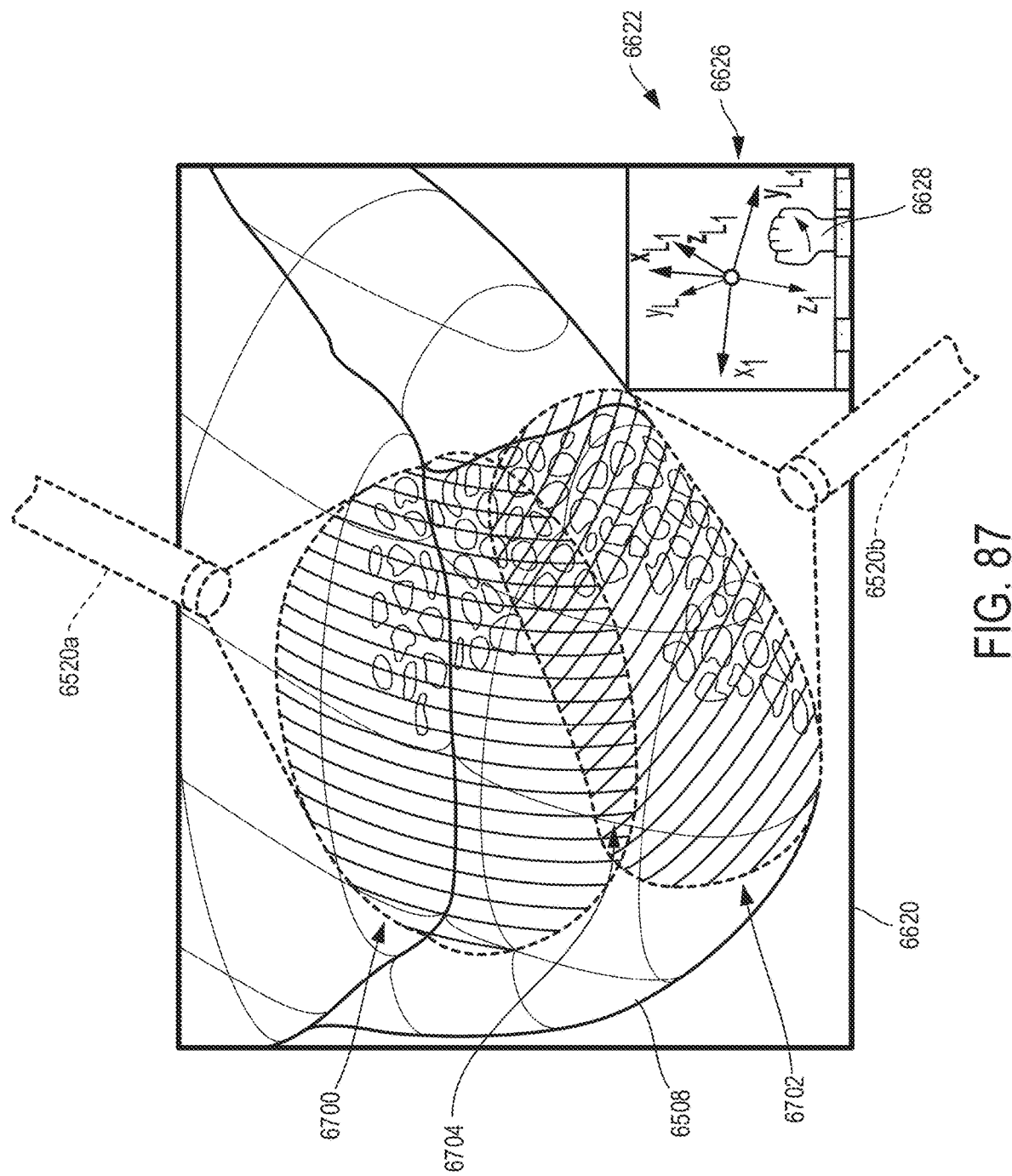

FIG. 87 is a visualization display and GUI of the VATS procedure of FIGS. 85 and 86, in accordance with at least one aspect of the present disclosure.

Figure 88:
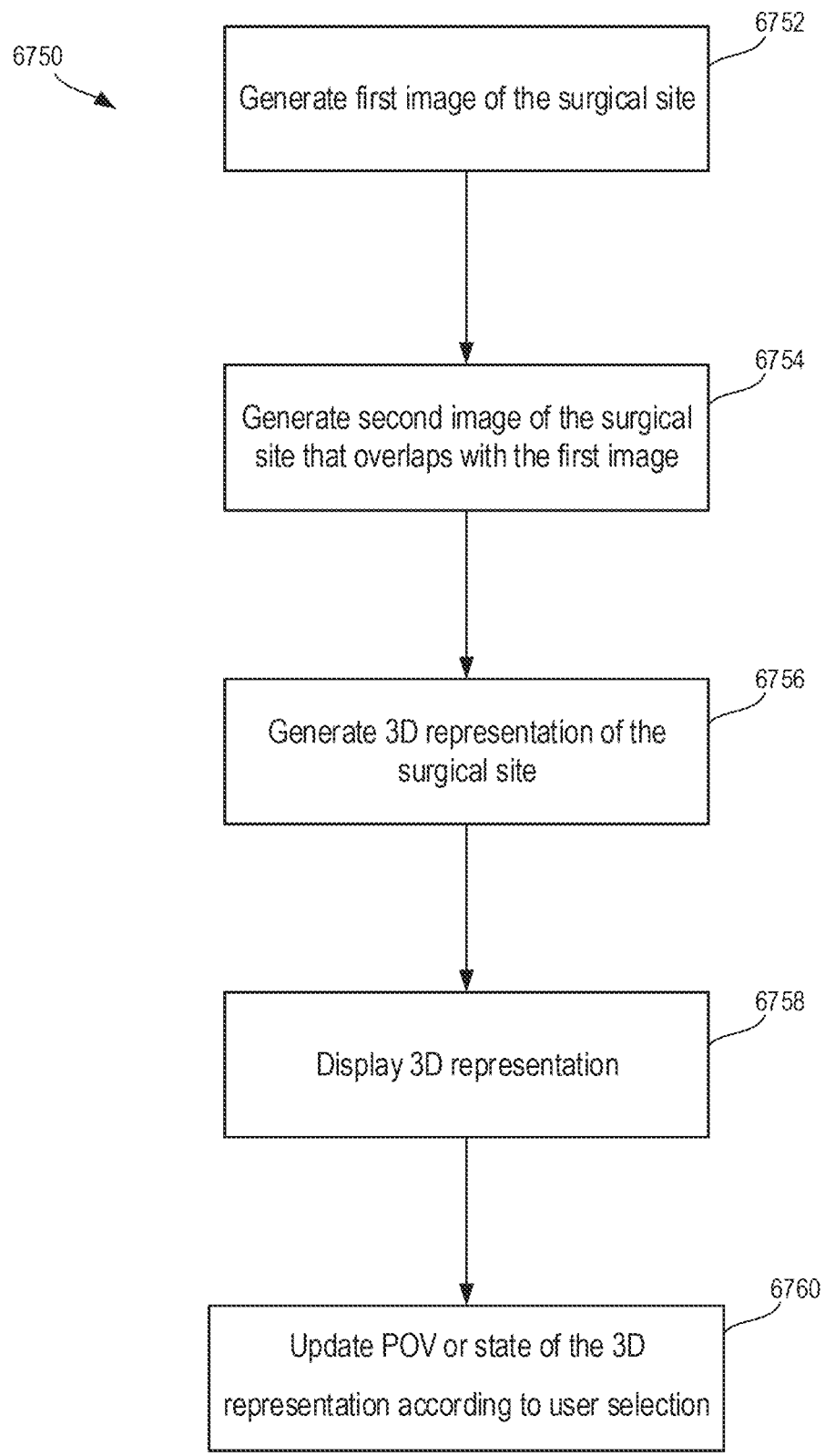

FIG. 88 is a logic flow diagram of a process of controlling a visualization display, in accordance with at least one aspect of the present disclosure.

Figure 89:
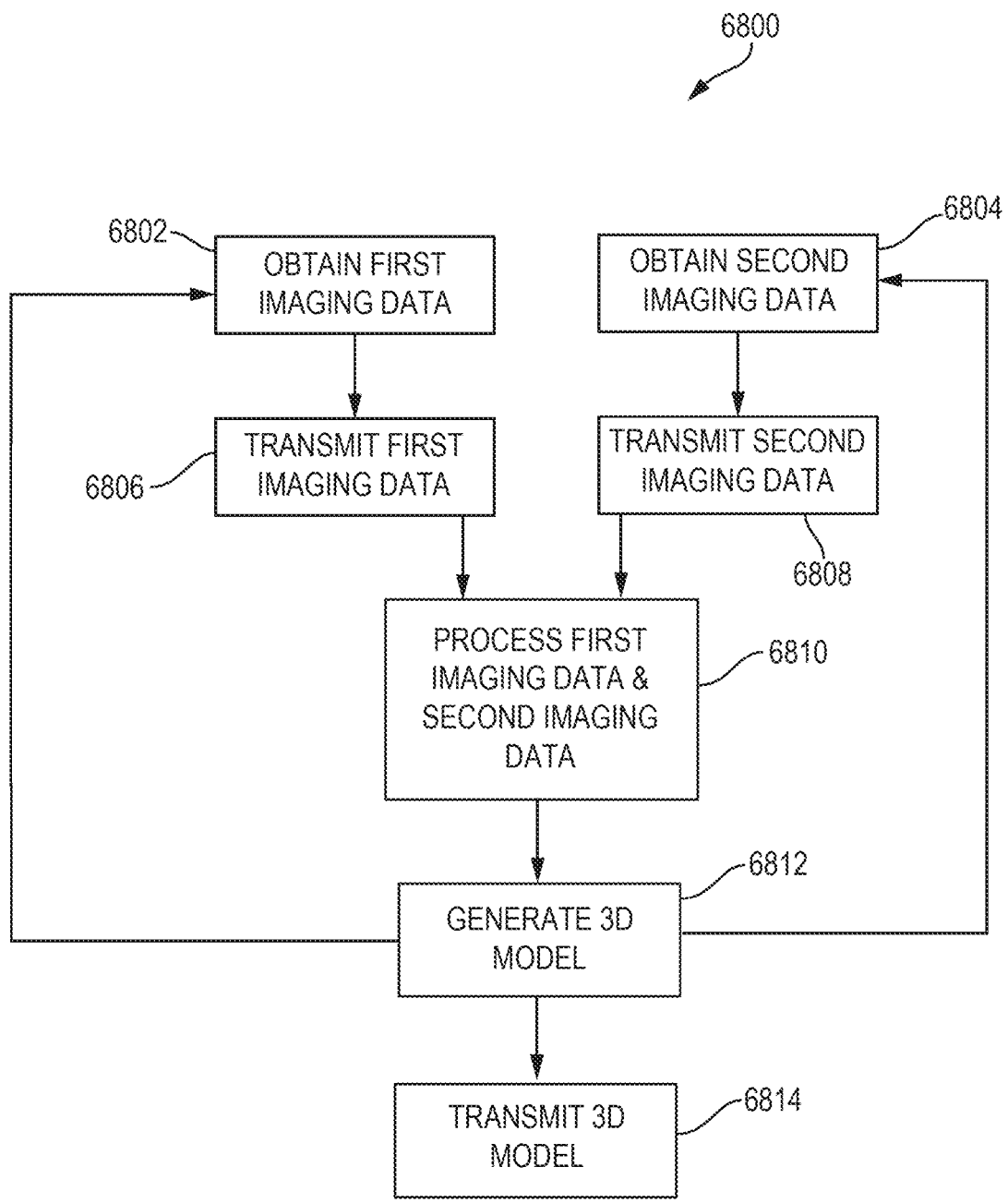

FIG. 89 is a logic flow diagram of a process of conveying three-dimensional models to a clinician, in accordance with at least one aspect of the present disclosure.

DESCRIPTION

Applicant of the present application owns the following U.S. Patent Applications, filed Dec. 30, 2019, each of which is herein incorporated by reference in its entirety:

U.S. patent application Ser. No. 16/729,803, titled ADAPTIVE VISUALIZATION BY A SURGICAL SYSTEM;

U.S. patent application Ser. No. 16/729,790, titled SURGICAL SYSTEM CONTROL BASED ON MULTIPLE SENSED PARAMETERS;

U.S. patent application Ser. No. 16/729,796, titled ADAPTIVE SURGICAL SYSTEM CONTROL ACCORDING TO SURGICAL SMOKE PARTICLE CHARACTERISTICS;

U.S. patent application Ser. No. 16/729,737, titled ADAPTIVE SURGICAL SYSTEM CONTROL ACCORDING TO SURGICAL SMOKE CLOUD CHARACTERISTICS;

U.S. patent application Ser. No. 16/729,740, titled SURGICAL SYSTEMS CORRELATING VISUALIZATION DATA AND POWERED SURGICAL INSTRUMENT DATA;

U.S. patent application Ser. No. 16/729,751, titled SURGICAL SYSTEMS FOR GENERATING THREE DIMENSIONAL CONSTRUCTS OF ANATOMICAL ORGANS AND COUPLING IDENTIFIED;

U.S. patent application Ser. No. 16/729,735, titled SURGICAL SYSTEM FOR OVERLAYING SURGICAL INSTRUMENT DATA ONTO A VIRTUAL THREE DIMENSIONAL CONSTRUCT OF AN ORGAN;

U.S. patent application Ser. No. 16/729,729, titled SURGICAL SYSTEMS FOR PROPOSING AND CORROBORATING ORGAN PORTION REMOVALS;

U.S. patent application Ser. No. 16/729,778, titled SYSTEM AND METHOD FOR DETERMINING, ADJUSTING, AND MANAGING RESECTION MARGIN ABOUT A SUBJECT TISSUE;

U.S. patent application Ser. No. 16/729,744, titled VISUALIZATION SYSTEMS USING STRUCTURED LIGHT;

U.S. patent application Ser. No. 16/729,747, titled DYNAMIC SURGICAL VISUALIZATION SYSTEMS; and U.S. patent application Ser. No. 16/729,772, titled ANALYZING SURGICAL TRENDS BY A SURGICAL SYSTEM.

Applicant of the present application owns the following U.S. Patent Applications, filed on Mar. 15, 2019, each of which is herein incorporated by reference in its entirety:

U.S. patent application Ser. No. 16/354,417, titled INPUT CONTROLS FOR ROBOTIC SURGERY, now U.S. Patent Application Publication No. 2020/0289219;

U.S. patent application Ser. No. 16/354,420, titled DUAL MODE CONTROLS FOR ROBOTIC SURGERY, now U.S. Patent Application Publication No. 2020/0289228;

U.S. patent application Ser. No. 16/354,422, titled MOTION CAPTURE CONTROLS FOR ROBOTIC SURGERY, now U.S. Patent Application Publication No. 2020/0289216;

U.S. patent application Ser. No. 16/354,440, titled ROBOTIC SURGICAL SYSTEMS WITH MECHANISMS FOR SCALING SURGICAL TOOL MOTION ACCORDING TO TISSUE PROXIMITY, now U.S. Patent Application Publication No. 2020/0289220;

U.S. patent application Ser. No. 16/354,444, titled ROBOTIC SURGICAL SYSTEMS WITH MECHANISMS FOR SCALING CAMERA MAGNIFICATION ACCORDING TO PROXIMITY OF SURGICAL TOOL TO TISSUE, now U.S. Patent Application Publication No. 2020/0289205;

U.S. patent application Ser. No. 16/354,454, titled ROBOTIC SURGICAL SYSTEMS WITH SELECTIVELY LOCKABLE END EFFECTORS, now U.S. Patent Application Publication No. 2020/0289221;

U.S. patent application Ser. No. 16/354,461, titled SELECTABLE VARIABLE RESPONSE OF SHAFT MOTION OF SURGICAL ROBOTIC SYSTEMS, now U.S. Patent Application Publication No. 2020/0289222;

U.S. patent application Ser. No. 16/354,470, titled SEGMENTED CONTROL INPUTS FOR SURGICAL ROBOTIC SYSTEMS, now U.S. Patent Application Publication No. 2020/0289223;

U.S. patent application Ser. No. 16/354,474, titled ROBOTIC SURGICAL CONTROLS HAVING FEEDBACK CAPABILITIES, now U.S. Patent Application Publication No. 2020/0289229;

U.S. patent application Ser. No. 16/354,478, titled ROBOTIC SURGICAL CONTROLS WITH FORCE FEEDBACK, now U.S. Patent Application Publication No. 2020/0289230; and U.S. patent application Ser. No. 16/354,481, titled JAW COORDINATION OF ROBOTIC SURGICAL CONTROLS, now U.S. Patent Application Publication No. 2020/0289217.

Applicant of the present application also owns the following U.S. Patent Applications, filed on Sep. 11, 2018, each of which is herein incorporated by reference in its entirety:

U.S. patent application Ser. No. 16/128,179, titled SURGICAL VISUALIZATION PLATFORM, now U.S. Pat. No. 11,000,270;

U.S. patent application Ser. No. 16/128,180, titled CONTROLLING AN EMITTER ASSEMBLY PULSE SEQUENCE, now U.S. Patent Application Publication No. 2020/0015900;

U.S. patent application Ser. No. 16/128,198, titled SINGULAR EMR SOURCE EMITTER ASSEMBLY, now U.S. Patent Application Publication No. 2020/0015668;

U.S. patent application Ser. No. 16/128,207, titled COMBINATION EMITTER AND CAMERA ASSEMBLY, now U.S. Patent Application Publication No. 2020/0015925;

U.S. patent application Ser. No. 16/128,176, titled SURGICAL VISUALIZATION WITH PROXIMITY TRACKING FEATURES, now U.S. Patent Application Publication No. 2020/0015899;

U.S. patent application Ser. No. 16/128,187, titled SURGICAL VISUALIZATION OF MULTIPLE TARGETS, now U.S. Patent Application Publication No. 2020/0015903;

U.S. patent application Ser. No. 16/128,192, titled VISUALIZATION OF SURGICAL DEVICES, now U.S. Pat. No. 10,792,034;

U.S. patent application Ser. No. 16/128,163, titled OPERATIVE COMMUNICATION OF LIGHT, now U.S. Patent Application Publication No. 2020/0015897;

U.S. patent application Ser. No. 16/128,197, titled ROBOTIC LIGHT PROJECTION TOOLS, now U.S. Patent Application Publication No. 2020/0015924;

U.S. patent application Ser. No. 16/128,164, titled SURGICAL VISUALIZATION FEEDBACK SYSTEM, now U.S. Patent Application Publication No. 2020/0015898;

U.S. patent application Ser. No. 16/128,193, titled SURGICAL VISUALIZATION AND MONITORING, now U.S. Patent Application Publication No. 2020/0015906;

U.S. patent application Ser. No. 16/128,195, titled INTEGRATION OF IMAGING DATA, now U.S. Patent Application Publication No. 2020/0015907;

U.S. patent application Ser. No. 16/128,170, titled ROBOTICALLY-ASSISTED SURGICAL SUTURING SYSTEMS, now U.S. Pat. No. 10,925,598;

U.S. patent application Ser. No. 16/128,183, titled SAFETY LOGIC FOR SURGICAL SUTURING SYSTEMS, now U.S. Patent Application Publication No. 2020/0015901;

U.S. patent application Ser. No. 16/128,172, titled ROBOTIC SYSTEM WITH SEPARATE PHOTOACOUSTIC RECEIVER, now U.S. Patent Application Publication No. 2020/0015914; and U.S. patent application Ser. No. 16/128,185, titled FORCE SENSOR THROUGH STRUCTURED LIGHT DEFLECTION, now U.S. Patent Application Publication No. 2020/0015902.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, now U.S. Patent Application Publication No. 2019/0201111;

U.S. patent application Ser. No. 15/940,676, titled AUTOMATIC TOOL ADJUSTMENTS FOR ROBOT-ASSISTED SURGICAL PLATFORMS, now U.S. Pat. No. 11,013,563;

U.S. patent application Ser. No. 15/940,711, titled SENSING ARRANGEMENTS FOR ROBOT-ASSISTED SURGICAL PLATFORMS, now U.S. Patent Application Publication No. 2019/0201120; and U.S. patent application Ser. No. 15/940,722, titled CHARACTERIZATION OF TISSUE IRREGULARITIES THROUGH THE USE OF MONO-CHRO- MATIC LIGHT REFRACTIVITY, now U.S. Patent Application Publication No. 2019/0200905.

Applicant of the present application owns the following U.S. Patent Applications, filed on Dec. 4, 2018, the disclosure of each of which is herein incorporated by reference in its entirety:

- U.S. patent application Ser. No. 16/209,395, titled METHOD OF HUB COMMUNICATION, now U.S. Patent Application Publication No. 2019/0201136;
- U.S. patent application Ser. No. 16/209,403, titled METHOD OF CLOUD BASED DATA ANALYTICS FOR USE WITH THE HUB, now U.S. Patent Application Publication No. 2019/0206569;
- U.S. patent application Ser. No. 16/209,407, titled METHOD OF ROBOTIC HUB COMMUNICATION, DETECTION, AND CONTROL, now U.S. Patent Application Publication No. 2019/0201137;
- U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;
- U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;
- U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;
- U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;
- U.S. patent application Ser. No. 16/209,447, titled METHOD FOR SMOKE EVACUATION FOR SURGICAL HUB, now U.S. Patent Application Publication No. 2019/0201045;
- U.S. patent application Ser. No. 16/209,453, titled METHOD FOR CONTROLLING SMART ENERGY DEVICES, now U.S. Patent Application Publication No. 2019/0201046;
- U.S. patent application Ser. No. 16/209,458, titled METHOD FOR SMART ENERGY DEVICE INFRASTRUCTURE, now U.S. Patent Application Publication No. 2019/0201047;
- U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;
- U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;
- U.S. patent application Ser. No. 16/209,490, titled METHOD FOR FACILITY DATA COLLECTION AND INTERPRETATION, now U.S. Patent Application Publication No. 2019/0206564; and
- U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Surgical Visualization System

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. It should be noted that throughout the following disclosure, any reference to "light," unless specifically in reference to visible light, can include electromagnetic radiation (EMR) or photons in the visible and/or non-visible portions of the EMR wavelength spectrum. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
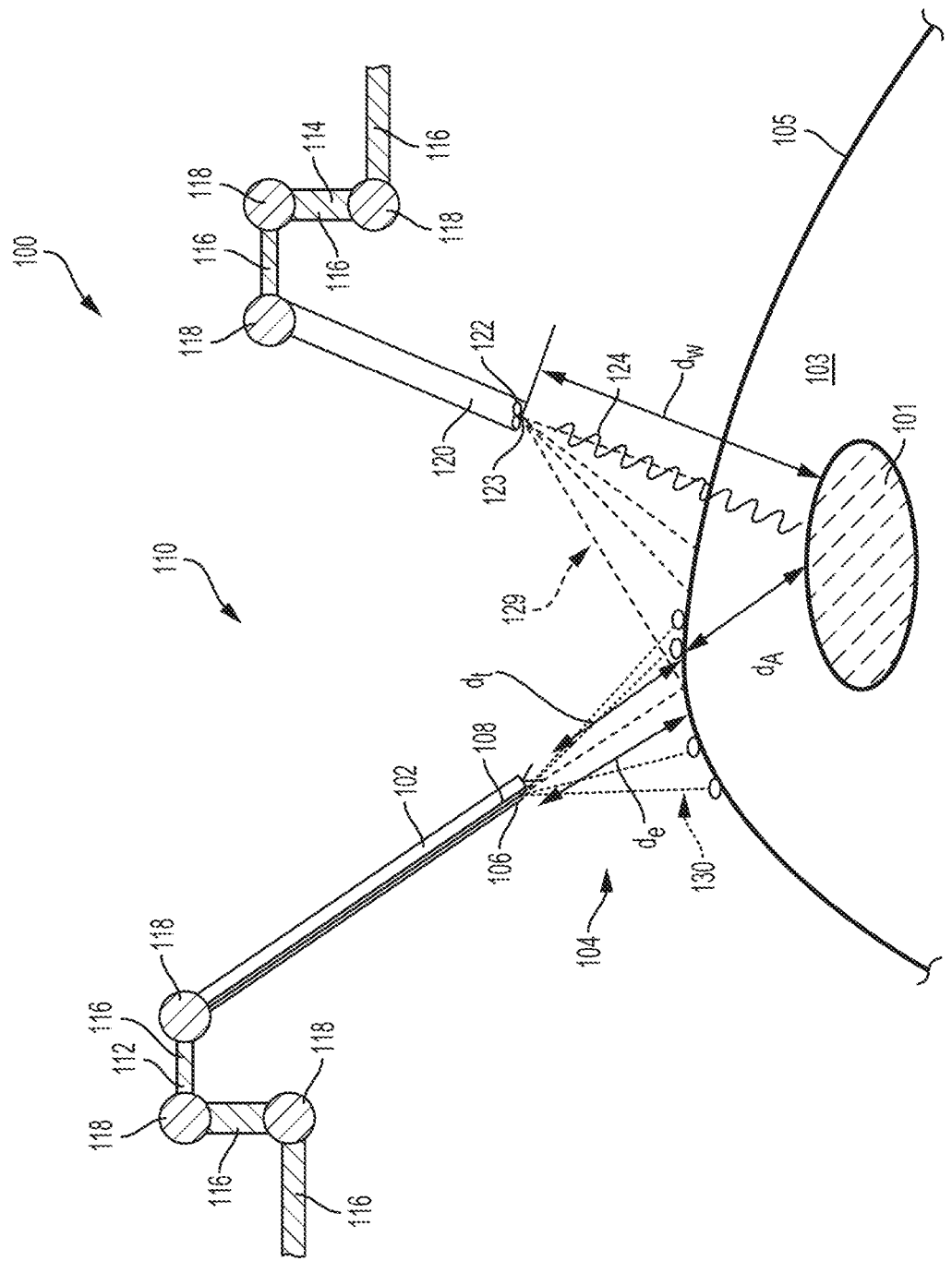
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
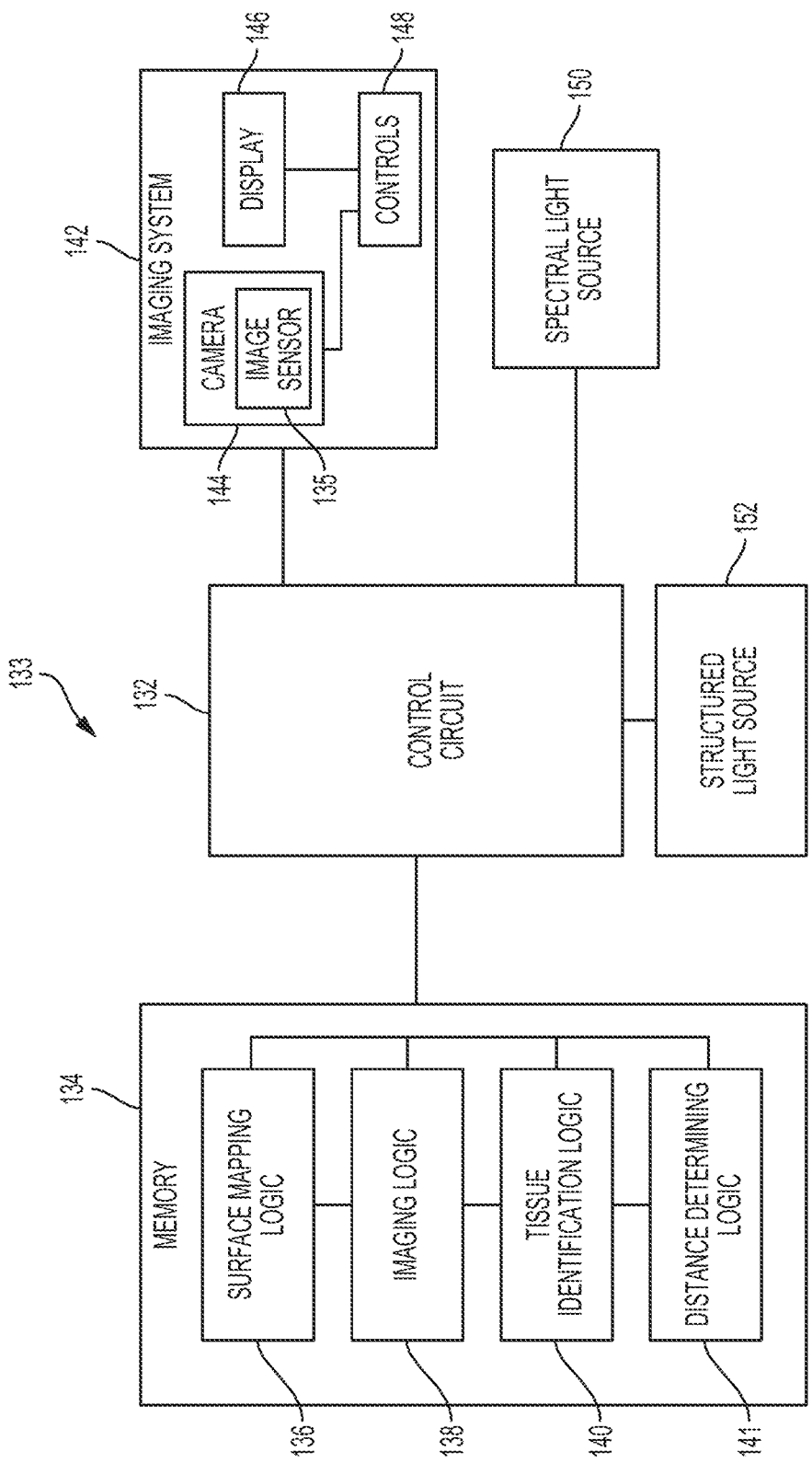
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
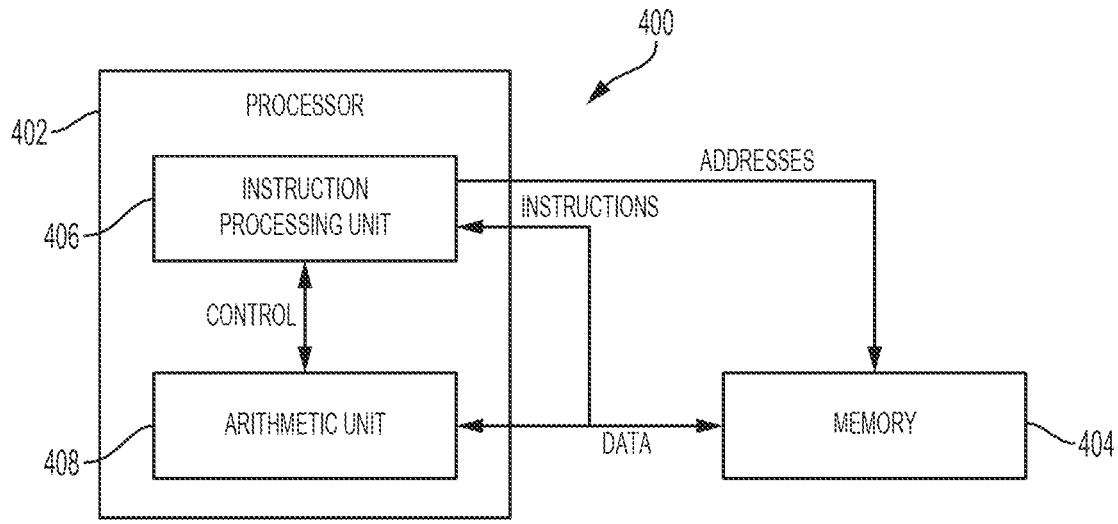
FIG. 2A illustrates a control circuit configured to control aspects of a surgical visualization system, according to at least one aspect of the present disclosure.
Figure 2B:
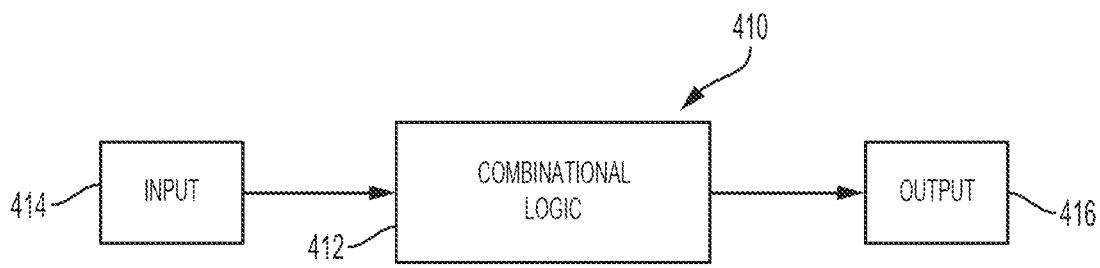
FIG. 2B illustrates a combinational logic circuit configured to control aspects of a surgical visualization system, according to at least one aspect of the present disclosure.
Figure 2C:
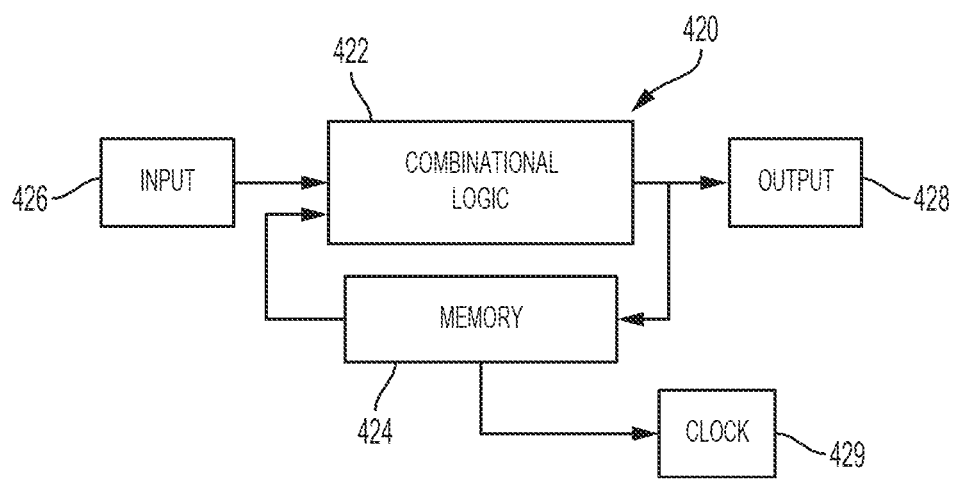
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned U.S. Patent Applications, including U.S. patent application Ser. No. 16/128,192, titled VISUALIZATION OF SURGICAL DEVICES, filed Sep. 11, 2018, for example, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
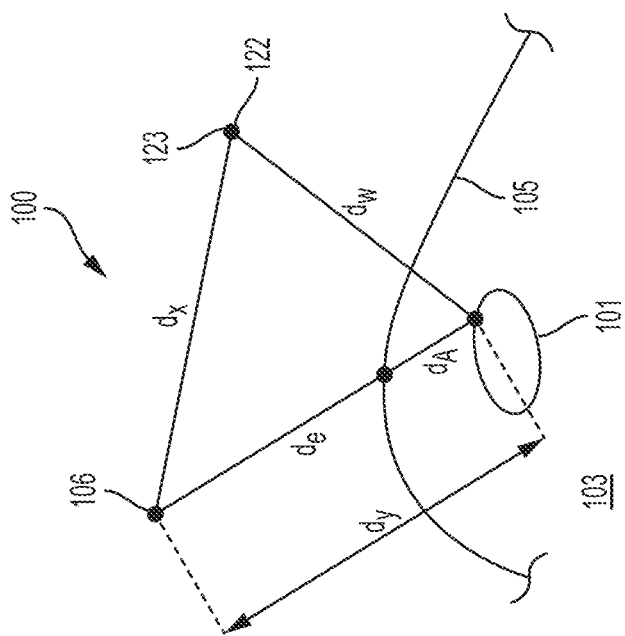
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
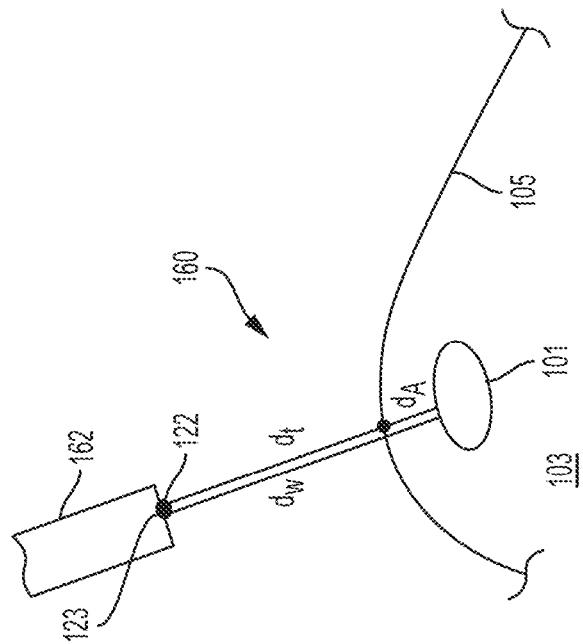
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figure 6:
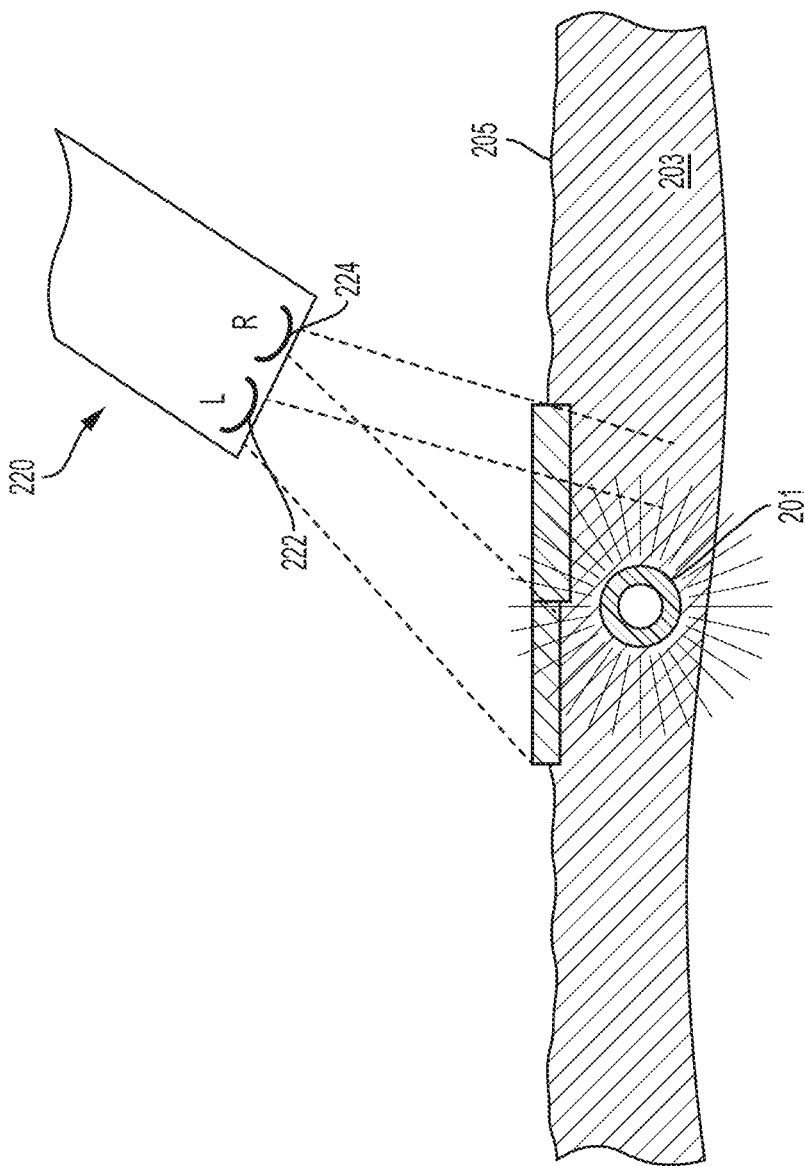
FIG. 6 is a schematic of a surgical visualization system including a three-dimensional camera, wherein the surgical visualization system is configured to identify a critical structure that is embedded within tissue, according to at least one aspect of the present disclosure.
Figures 7A, 7B:
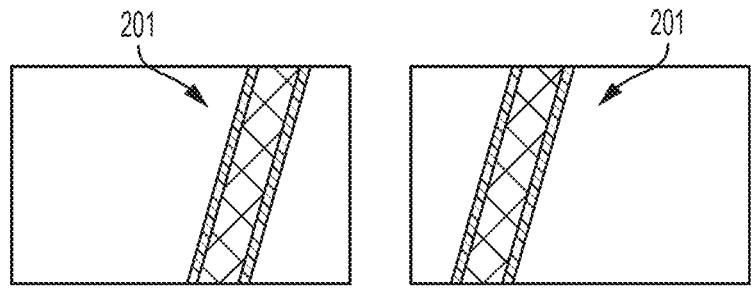
Figure 8:
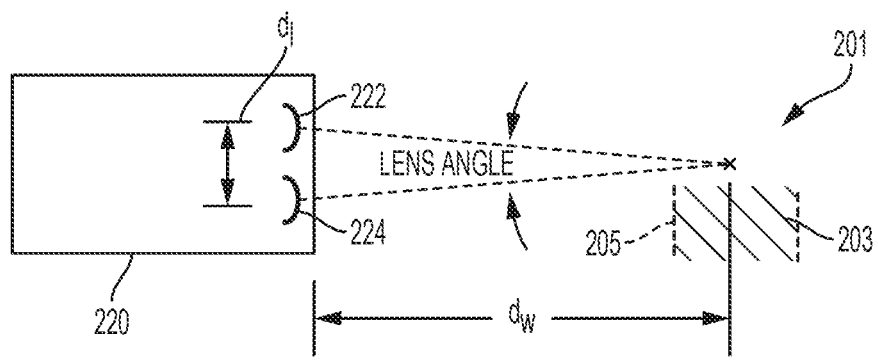
FIG. 8 is a schematic of the surgical visualization system of FIG. 6, in which a camera-to-critical structure distance $d_w$ from the three-dimensional camera to the critical structure can be determined, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
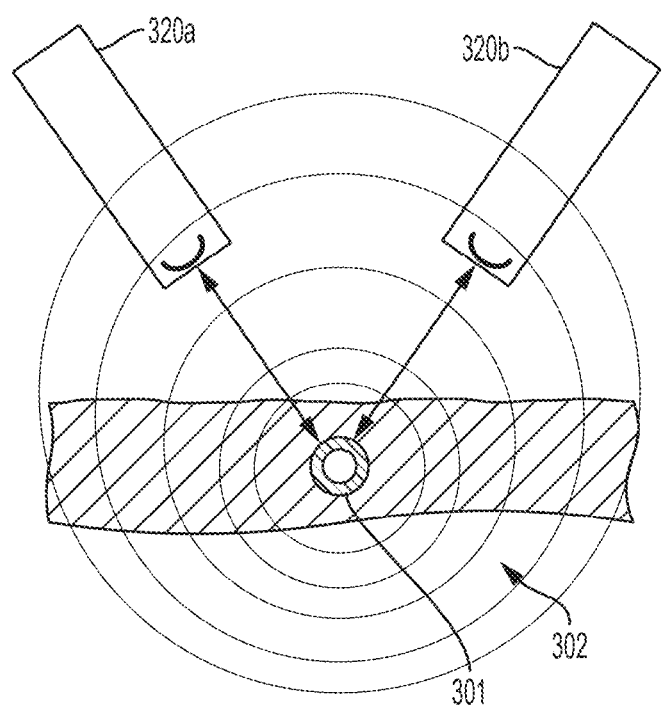
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
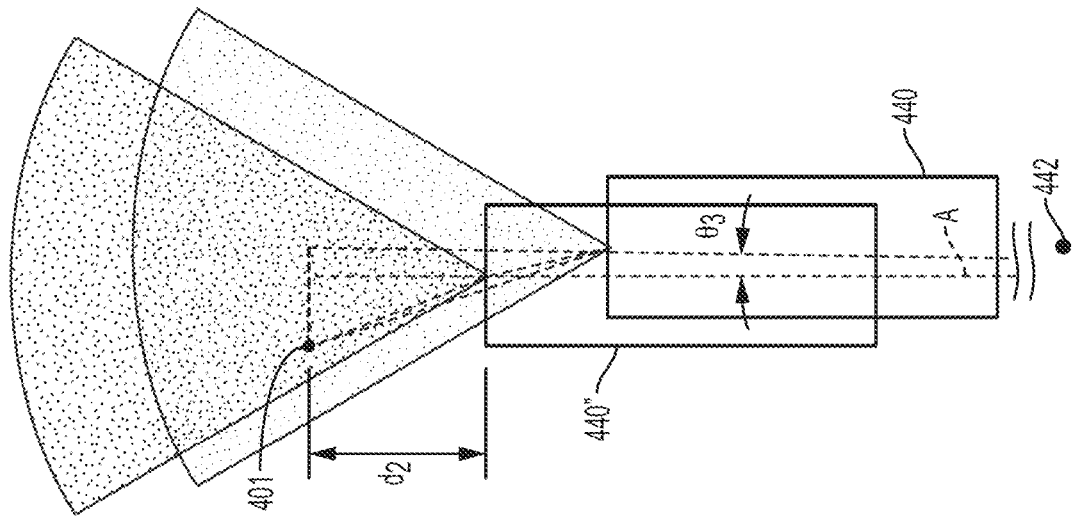
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
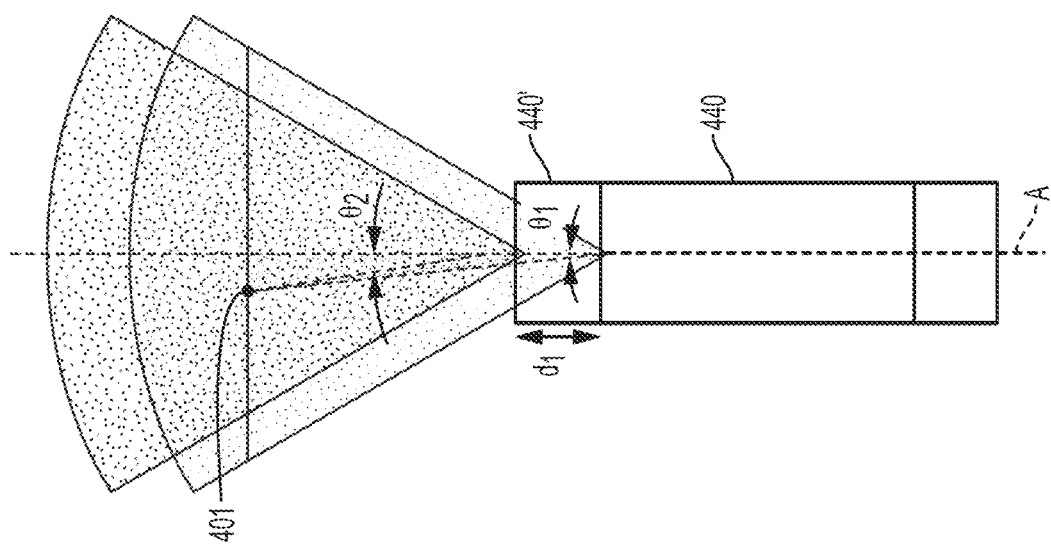
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
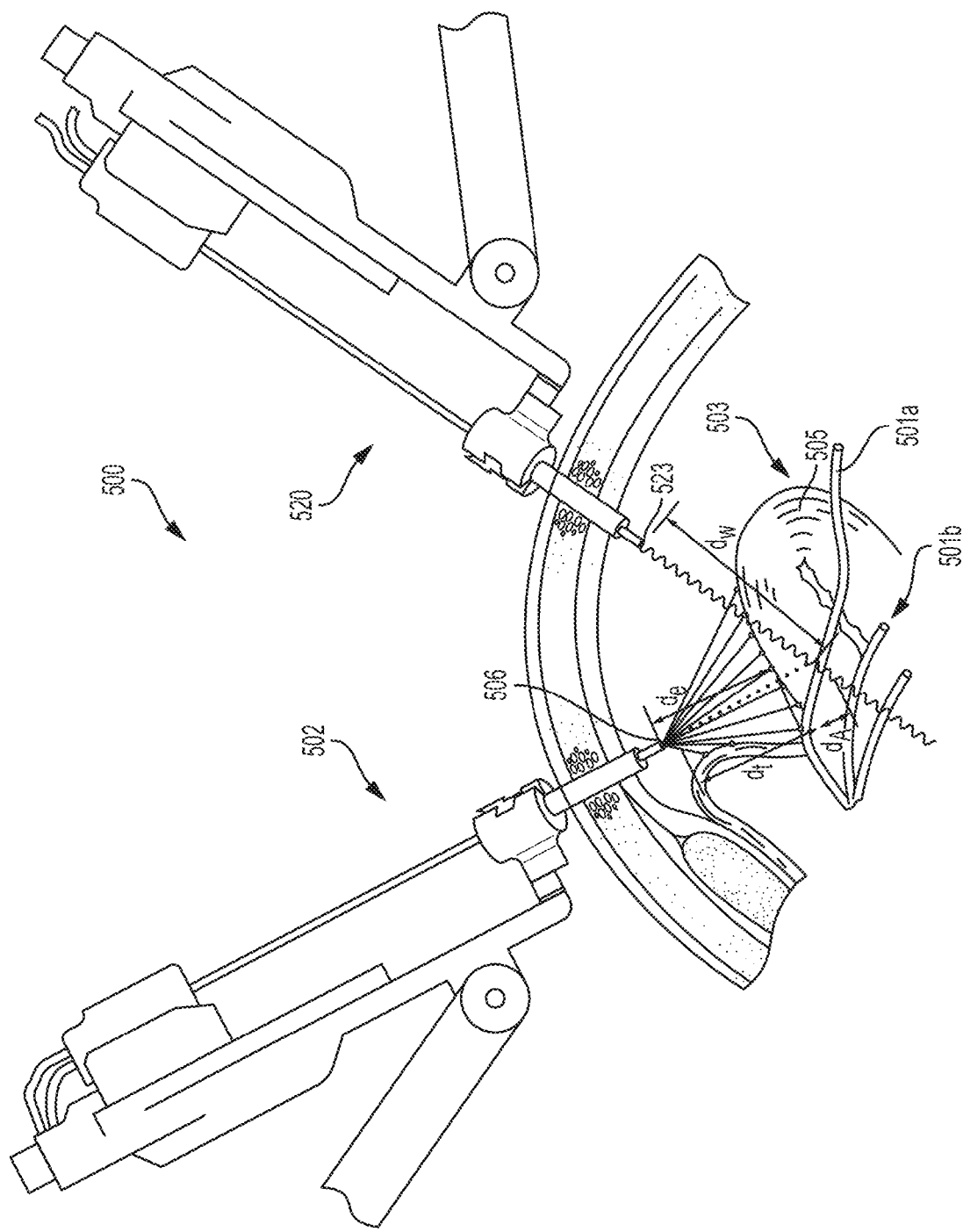
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera-to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
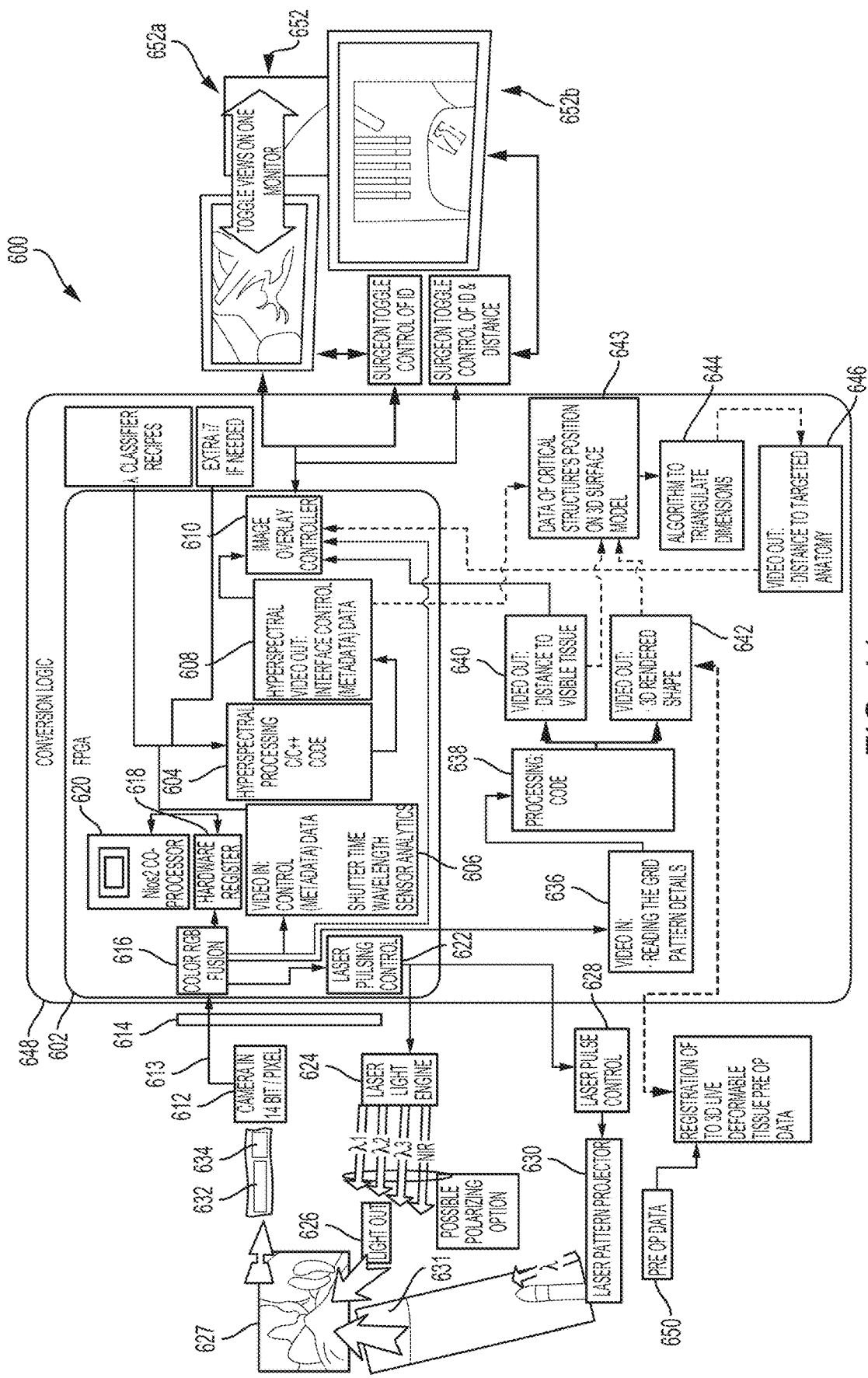
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned U.S. Patent Applications, including U.S. patent application Ser. No. 16/128,195, titled INTEGRATION OF IMAGING DATA, filed Sep. 11, 2018, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
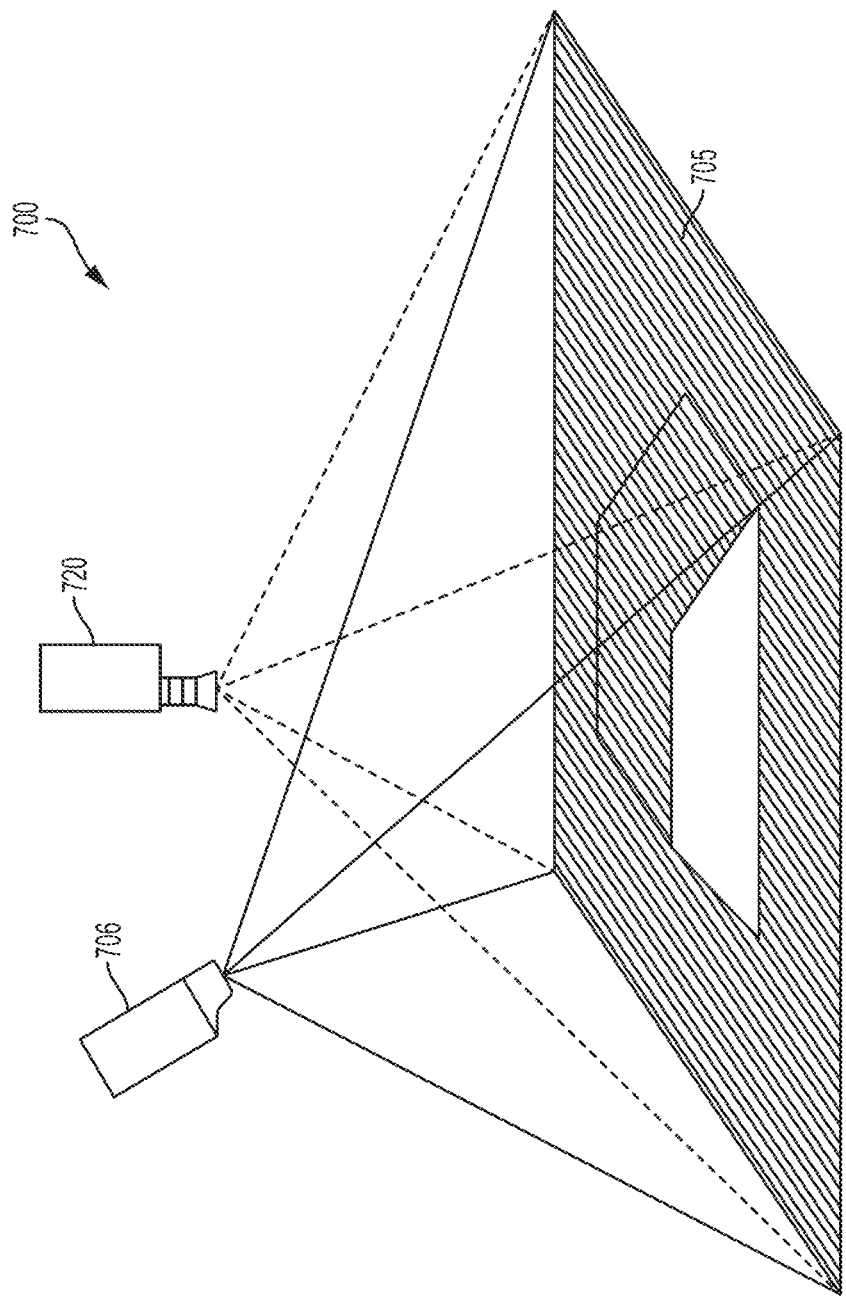
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13A:
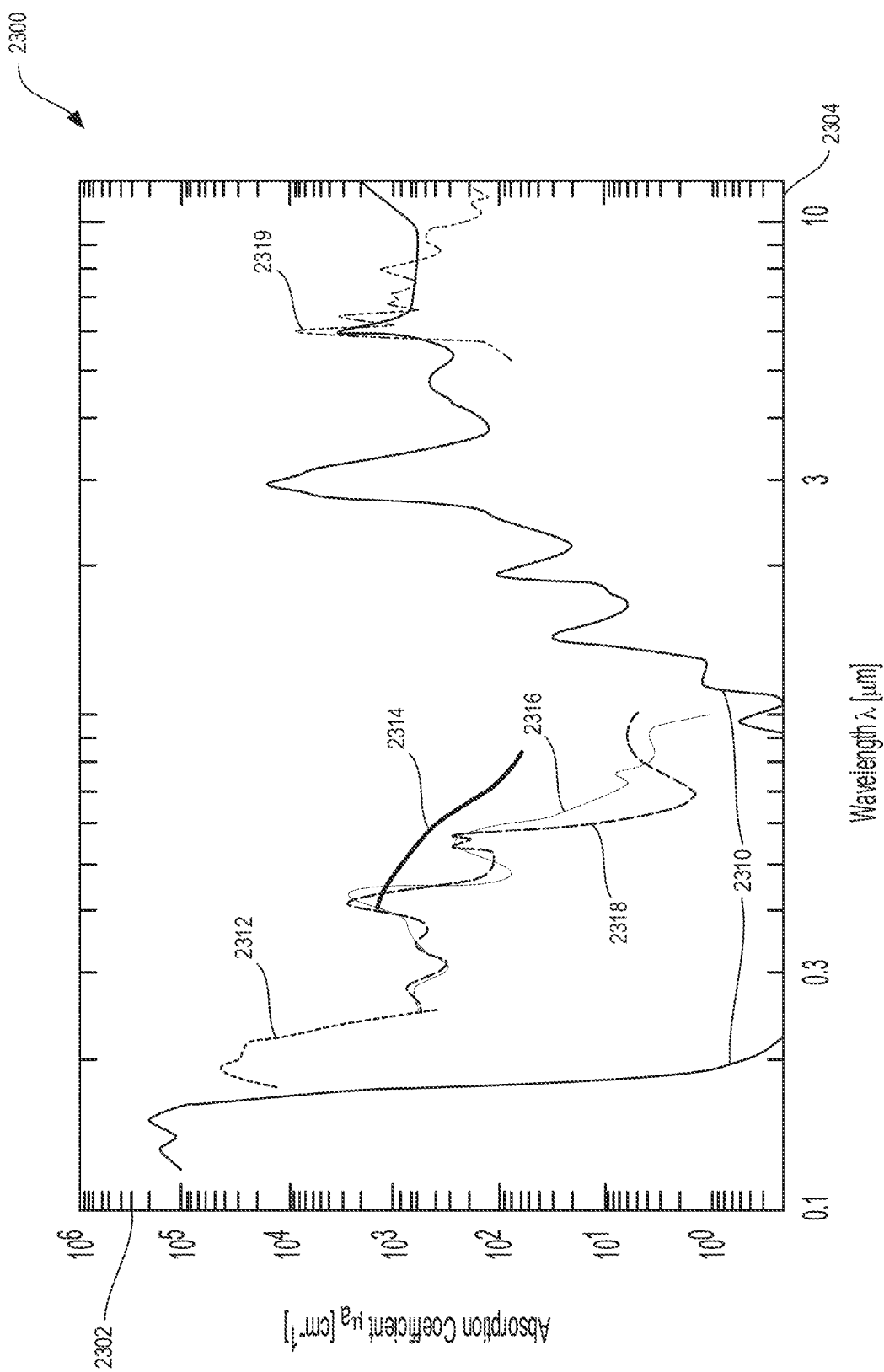
FIG. 13A is a graph of absorption coefficient verse wavelength for various biological materials, according to at least one aspect of the present disclosure.

As noted above, the various surgical visualization systems described herein can be utilized to visualize various different types of tissues and/or anatomical structures, including tissues and/or anatomical structures that may be obscured from being visualized by EMR in the visible portion of the spectrum. In one aspect, the surgical visualization systems can utilize a spectral imaging system to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be further configured to characterize the tissue type of the tissue being visualized based upon the particular combination of constituent materials. To illustrate, FIG. 13A is a graph 2300 depicting how the absorption coefficient of various biological materials varies across the EMR wavelength spectrum. In the graph 2300, the vertical axis 2303 represents absorption coefficient of the biological material (e.g., in $cm^{-1}$) and the horizontal axis 2304 represents EMR wavelength (e.g., in μm). The graph 2300 further illustrates a first line 2310 representing the absorption coefficient of water at various EMR wavelengths, a second line 2312 representing the absorption coefficient of protein at various EMR wavelengths, a third line 2314 representing the absorption coefficient of melanin at various EMR wavelengths, a fourth line 2316 representing the absorption coefficient of deoxygenated hemoglobin at various EMR wavelengths, a fifth line 2318 representing the absorption coefficient of oxygenated hemoglobin at various EMR wavelengths, and a sixth line 2319 representing the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system can be configured to emit EMR at a number of different wavelengths, determine the constituent materials of the tissue based on the detected absorption EMR absorption response at the different wavelengths, and then characterize the tissue type based on the particular detected combination of constituent materials.

An illustration of the utilization of spectral imaging techniques to visualize different tissue types and/or anatomical structures is shown in FIG. 13B. In FIG. 13B, a spectral emitter 2320 (e.g., spectral light source 150) is being utilized by an imaging system to visualize a surgical site 2325. The EMR emitted by the spectral emitter 2320 and reflected from the tissues and/or structures at the surgical site 2325 can be received by an image sensor 135 (FIG. 2) to visualize the tissues and/or structures, which can be either visible (e.g., be located at the surface of the surgical site 2325) or obscured (e.g., underlay other tissue and/or structures at the surgical site 2325). In this example, an imaging system 142 (FIG. 2) can visualize a tumor 2332, an artery 2334, and various abnormalities 2338 (i.e., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system 142, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Further, the imaging system 142 can be configured to tailor or update the displayed surgical site visualization according to the identified tissue and/or structure types. For example, the imaging system 142 can display a margin 2330a associated with the tumor 2332 being visualized on a display screen (e.g., display 146). The margin 2330a can indicate the area or amount of tissue that should be excised to ensure complete removal of the tumor 2332. The control system 133 (FIG. 2) can be configured to control or update the dimensions of the margin 2330a based on the tissues and/or structures identified by the imaging system 142. In the illustrated example, the imaging system 142 has identified multiple abnormalities 2338 within the FOV. Accordingly, the control system 133 can adjust the displayed margin 2330a to a first updated margin 2330b having sufficient dimensions to encompass the abnormalities 2338. Further, the imaging system 142 has also identified an artery 2334 partially overlapping with the initially displayed margin 2330a (as indicated by the highlighted region 2336 of the artery 2334). Accordingly, the control system 133 can adjust the displayed margin 2330a to a second updated margin 2330c having sufficient dimensions to encompass the relevant portion of the artery 2334.

Tissues and/or structures can also be imaged or characterized according to their reflective characteristics, in addition to or in lieu of their absorptive characteristics described above with respect to FIGS. 13A and 13B, across the EMR wavelength spectrum. For example, FIGS. 13C-13E illustrate various graphs of reflectance of different types of tissues or structures across different EMR wavelengths. FIG. 13C is a graphical representation 1050 of an illustrative ureter signature versus obscurants. FIG. 13D is a graphical representation 1052 of an illustrative artery signature versus obscurants. FIG. 13E is a graphical representation 1054 of an illustrative nerve signature versus obscurants. The plots in FIGS. 13C-13E represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

In various instances, select wavelengths for spectral imaging can be identified and utilized based on the anticipated critical structures and/or obscurants at a surgical site (i.e., "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 14 and 15, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 15, for example, which can be measured by the receiver 1108.

Based on the delay between the emitted wave 1124 and the received wave 1125, the time-of-flight sensor system 1104 is configured to determine the distance d (FIG. 14). A time-of-flight timing diagram 1130 for the emitter 1106 and the receiver 1108 of FIG. 14 is shown in FIG. 15. The delay is a function of the distance d and the distance d is given by:

$$d = \frac{ct}{2} \cdot \frac{q_2}{q_1 + q_2}$$

where:
- c=the speed of light;
- t=length of pulse;
- $q_1$=accumulated charge while light is emitted; and
- $q_2$=accumulated charge while light is not being emitted.

As provided herein, the time-of-flight of the waveforms 1124, 1125 corresponds to the distance d in FIG. 14. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
- $d_A$=the depth of the critical structure 1101;
- $d_w$=the distance from the emitter 1106 to the critical structure 1101 (d in FIG. 14); and
- $d_t$=the distance from the emitter 1106 (on the distal end of the surgical device 1102) to the surface 1105 of the obscuring tissue 1103.

In one aspect of the present disclosure, referring now to FIG. 16, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the -receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described in various U.S. Patent Applications, which are incorporated by reference herein in the present disclosure.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}, d_{2a}, d_{3a}, d_{1b}, d_{2b}, d_{2c}$ indicated in FIG. 16.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}, d_{2a}, d_{3a}, d_{1b}, d_{2b}, d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}, d_{2a}, d_{3a}, d_{1b}, d_{2b}, d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 16, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 16, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization systems disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure(s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

In various instances, clinicians may not know the location of a critical structure with respect to a surgical tool. For example, when a critical structure is embedded in tissue, the clinician may be unable to ascertain the location of the critical structure. In certain instances, a clinician may want to keep a surgical device outside a range of positions surrounding the critical structure and/or away from the visible tissue covering the hidden critical structure. When the location of a concealed critical structure is unknown, the clinician may risk moving too close to the critical structure, which can result in inadvertent trauma and/or dissection of the critical structure and/or too much energy, heat, and/or tension in proximity of the critical structure. Alternatively, the clinician may stay too far away from a suspected location of the critical structure and risk affecting tissue at a less desirable location in an effort to avoid the critical structure.

A surgical visualization system is provided that presents surgical device tracking with respect to one or more critical structures. For example, the surgical visualization system can track the proximity of a surgical device with respect to a critical structure. Such tracking can occur intraoperatively, in real-time, and/or in near real-time. In various instances, the tracking data can be provided to the clinicians via a display screen (e.g. a monitor) of an imaging system.

In one aspect of the present disclosure, a surgical visualization system includes a surgical device comprising an emitter configured to emit a structured light pattern onto a visible surface, an imaging system comprising a camera configured to detect an embedded structure and the structured light pattern on the visible surface, and a control circuit in signal communication with the camera and the imaging system, wherein the control circuit is configured to determine a distance from the surgical device to the embedded structure and provide a signal to the imaging system indicative of the distance. For example, the distance can be determined by computing a distance from the camera to the critical structure that is illuminated with fluoroscopy technology and based on a three-dimensional view of the illuminated structure provided by images from multiple lenses (e.g. a left-side lens and a right-side lens) of the camera. The distance from the surgical device to the critical structure can be triangulated based on the known positions of the surgical device and the camera, for example. Alternative means for determining the distance to an embedded critical structure are further described herein. For example, NIR time-of-flight distance sensors can be employed. Additionally or alternatively, the surgical visualization system can determine a distance to visible tissue overlying/covering an embedded critical structure. For example, the surgical visualization system can identify a hidden critical structure and augment a view of the hidden critical structure by depicting a schematic of the hidden critical structure on the visible structure, such as a line on the surface of the visible tissue. The surgical visualization system can further determine the distance to the augmented line on the visible tissue.

By providing the clinician with up-to-date information regarding the proximity of the surgical device to the concealed critical structure and/or visible structure, as provided by the various surgical visualization systems disclosed herein, the clinician can make more informed decisions regarding the placement of the surgical device relative to the concealed critical structure. For example, the clinician can view the distance between the surgical device and the critical structure in real-time/intraoperatively and, in certain instances, an alert and/or warning can be provided by the imaging system when the surgical device is moved within a predefined proximity and/or zone of the critical structure. In certain instances, the alert and/or warning can be provided when the trajectory of the surgical device indicates a likely collision with a "no-fly" zone in the proximity of the critical structure (e.g. within 1 mm, 2 mm, 5 mm, 10 mm, 20 mm or more of the critical structure). In such instances, the clinician can maintain momentum throughout the surgical procedure without requiring the clinician to monitor a suspected location of the critical structure and the surgical device's proximity thereto. As a result, certain surgical procedures can be performed more quickly, with fewer pauses/interruptions, and/or with improved accuracy and/or certainty, for example. In one aspect, the surgical visualization system can be utilized to detect tissue variability, such as the variability of tissue within an organ to differentiate tumors/cancerous tissue/unhealthy tissue from healthy tissue. Such a surgical visualization system can maximize the removal of the unhealthy tissue while minimizing the removal of the healthy tissue.

Surgical Hub System

The various visualization or imaging systems described herein can be incorporated into a surgical hub system, such as is illustrated in connection with FIGS. 17-19 and described in further detail below.

Referring to FIG. 17, a computer-implemented interactive surgical system 2100 includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. In one example, as illustrated in FIG. 17, the surgical system 2102 includes a visualization system 2108, a robotic system 2110, and a handheld intelligent surgical instrument 2112, which are configured to communicate with one another and/or the hub 2106. In some aspects, a surgical system 2102 may include an M number of hubs 2106, an N number of visualization systems 2108, an O number of robotic systems 2110, and a P number of handheld intelligent surgical instruments 2112, where M, N, O, and P are integers greater than or equal to one.

FIG. 18 depicts an example of a surgical system 2102 being used to perform a surgical procedure on a patient who is lying down on an operating table 2114 in a surgical operating room 2116. A robotic system 2110 is used in the surgical procedure as a part of the surgical system 2102. The robotic system 2110 includes a surgeon's console 2118, a patient side cart 2120 (surgical robot), and a surgical robotic hub 2122. The patient side cart 2120 can manipulate at least one removably coupled surgical tool 2117 through a minimally invasive incision in the body of the patient while the surgeon views the surgical site through the surgeon's console 2118. An image of the surgical site can be obtained by a medical imaging device 2124, which can be manipulated by the patient side cart 2120 to orient the imaging device 2124. The robotic hub 2122 can be used to process the images of the surgical site for subsequent display to the surgeon through the surgeon's console 2118.

Other types of robotic systems can be readily adapted for use with the surgical system 2102. Various examples of robotic systems and surgical tools that are suitable for use with the present disclosure are described in various U.S. Patent Applications, which are incorporated by reference herein in the present disclosure.

Various examples of cloud-based analytics that are performed by the cloud 2104, and are suitable for use with the present disclosure, are described in various U.S. Patent Applications, which are incorporated by reference herein in the present disclosure.

In various aspects, the imaging device 2124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 2124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 2124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in various U.S. Patent Applications that are incorporated by reference herein in the present disclosure. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 2124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 2108 includes one or more imaging sensors, one or more image-processing units, one or more storage arrays, and one or more displays that are strategically arranged with respect to the sterile field, as illustrated in FIG. 18. In one aspect, the visualization system 2108 includes an interface for HL7, PACS, and EMR. Various components of the visualization system 2108 are described in various U.S. Patent Applications that are incorporated by reference herein in the present disclosure.

As illustrated in FIG. 18, a primary display 2119 is positioned in the sterile field to be visible to an operator at the operating table 2114. In addition, a visualization tower 21121 is positioned outside the sterile field. The visualization tower 21121 includes a first non-sterile display 2107 and a second non-sterile display 2109, which face away from each other. The visualization system 2108, guided by the hub 2106, is configured to utilize the displays 2107, 2109, and 2119 to coordinate information flow to operators inside and outside the sterile field. For example, the hub 2106 may cause the visualization system 2108 to display a snapshot of a surgical site, as recorded by an imaging device 2124, on a non-sterile display 2107 or 2109, while maintaining a live feed of the surgical site on the primary display 2119. The snapshot on the non-sterile display 2107 or 2109 can permit a non-sterile operator to perform a diagnostic step relevant to the surgical procedure, for example.

In one aspect, the hub 2106 is also configured to route a diagnostic input or feedback entered by a non-sterile operator at the visualization tower 21121 to the primary display 2119 within the sterile field, where it can be viewed by a sterile operator at the operating table. In one example, the input can be in the form of a modification to the snapshot displayed on the non-sterile display 2107 or 2109, which can be routed to the primary display 2119 by the hub 2106.

Referring to FIG. 18, a surgical instrument 2112 is being used in the surgical procedure as part of the surgical system 2102. The hub 2106 is also configured to coordinate information flow to a display of the surgical instrument 2112, as is described in various U.S. Patent Applications that are incorporated by reference herein in the present disclosure. A diagnostic input or feedback entered by a non-sterile operator at the visualization tower 21121 can be routed by the hub 2106 to the surgical instrument display 2115 within the sterile field, where it can be viewed by the operator of the surgical instrument 2112. Example surgical instruments that are suitable for use with the surgical system 2102 are described in various U.S. Patent Applications that are incorporated by reference herein in the present disclosure.

FIG. 19 illustrates a computer-implemented interactive surgical system 2200. The computer-implemented interactive surgical system 2200 is similar in many respects to the computer-implemented interactive surgical system 2100. The surgical system 2200 includes at least one surgical hub 2236 in communication with a cloud 2204 that may include a remote server 2213. In one aspect, the computer-implemented interactive surgical system 2200 comprises a surgical hub 2236 connected to multiple operating theater devices such as, for example, intelligent surgical instruments, robots, and other computerized devices located in the operating theater. The surgical hub 2236 comprises a communications interface for communicably coupling the surgical hub 2236 to the cloud 2204 and/or remote server 2213. As illustrated in the example of FIG. 19, the surgical hub 2236 is coupled to an imaging module 2238 that is coupled to an endoscope 2239, a generator module 2240 that is coupled to an energy device 2421, a smoke evacuator module 2226, a suction/irrigation module 2228, a communication module 2230, a processor module 2232, a storage array 2234, a smart device/instrument 2235 optionally coupled to a display 2237, and a non-contact sensor module 2242. The operating theater devices are coupled to cloud computing resources and data storage via the surgical hub 2236. A robot hub 2222 also may be connected to the surgical hub 2236 and to the cloud computing resources. The devices/instruments 2235, visualization systems 2209, among others, may be coupled to the surgical hub 2236 via wired or wireless communication standards or protocols, as described herein. The surgical hub 2236 may be coupled to a hub display 2215 (e.g., monitor, screen) to display and overlay images received from the imaging module, device/instrument display, and/or other visualization systems 208. The hub display also may display data received from devices connected to the modular control tower in conjunction with images and overlaid images.

Situational Awareness

The various visualization systems or aspects of visualization systems described herein can be utilized as part of a situational awareness system that can be embodied or executed by a surgical hub 2106, 2236 (FIGS. 17-19). In particular, characterizing, identifying, and/or visualizing surgical instruments or other surgical devices (including their positions, orientations, and actions), tissues, structures, users, and other things located within the surgical field or the operating theater can provide contextual data that can be utilized by a situational awareness system to infer the type of surgical procedure or a step thereof being performed, the type of tissue(s) and/or structure(s) being manipulated by the surgeon, and so on. This contextual data can then be utilized by the situational awareness system to provide alerts to users, suggest subsequent steps or actions for the users to undertake, prepare surgical devices in anticipation for their use (e.g., activate an electrosurgical generator in anticipation of an electrosurgical instrument being utilized in a subsequent step of the surgical procedure), control surgical instruments intelligently (e.g., customize surgical instrument operational parameters based on each patient's particular health profile), and so on.

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control modular device incorrectly or suboptimally given the particular context-free sensed data. Modular devices can include any surgical devices that is controllable by a situational awareness system, such as visualization system devices (e.g., a camera or display screen), surgical instruments (e.g., an ultrasonic surgical instrument, an electrosurgical instrument, or a surgical stapler), and other surgical devices (e.g., a smoke evacuator). For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 20 illustrates a diagram of a situationally aware surgical system 2400, in accordance with at least one aspect of the present disclosure. In some exemplifications, the data sources 2426 include, for example, the modular devices 2402 (which can include sensors configured to detect parameters associated with the patient and/or the modular device itself), databases 2422 (e.g., an EMR database containing patient records), and patient monitoring devices 2424 (e.g., a blood pressure (BP) monitor and an electrocardiography (EKG) monitor).

A surgical hub 2404, which may be similar to the hub 106 in many respects, can be configured to derive the contextual information pertaining to the surgical procedure from the data based upon, for example, the particular combination(s) of received data or the particular order in which the data is received from the data sources 2426. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2404 to derive or infer information related to the surgical procedure from received data can be referred to as "situational awareness." In one exemplification, the surgical hub 2404 can incorporate a situational awareness system, which is the hardware and/or programming associated with the surgical hub 2404 that derives contextual information pertaining to the surgical procedure from the received data.

The situational awareness system of the surgical hub 2404 can be configured to derive the contextual information from the data received from the data sources 2426 in a variety of different ways. In one exemplification, the situational awareness system includes a pattern recognition system, or machine learning system (e.g., an artificial neural network), that has been trained on training data to correlate various inputs (e.g., data from databases 2422, patient monitoring devices 2424, and/or modular devices 2402) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2402. In one exemplification, the contextual information received by the situational awareness system of the surgical hub 2404 is associated with a particular control adjustment or set of control adjustments for one or more modular devices 2402. In another exemplification, the situational awareness system includes a further machine learning system, lookup table, or other such system, which generates or retrieves one or more control adjustments for one or more modular devices 2402 when provided the contextual information as input.

A surgical hub 2404 incorporating a situational awareness system provides a number of benefits for the surgical system 2400. One benefit includes improving the interpretation of sensed and collected data, which would in turn improve the processing accuracy and/or the usage of the data during the course of a surgical procedure. To return to a previous example, a situationally aware surgical hub 2404 could determine what type of tissue was being operated on; therefore, when an unexpectedly high force to close the surgical instrument's end effector is detected, the situationally aware surgical hub 2404 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2404 could infer whether a surgical procedure being performed is a thoracic or an abdominal procedure, allowing the surgical hub 2404 to determine whether the tissue clamped by an end effector of the surgical stapling and cutting instrument is lung (for a thoracic procedure) or stomach (for an abdominal procedure) tissue. The surgical hub 2404 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2404 could determine whether the surgical site is under pressure (by determining that the surgical procedure is utilizing insufflation) and determine the procedure type. As a procedure type is generally performed in a specific body cavity, the surgical hub 2404 could then control the motor rate of the smoke evacuator appropriately for the body cavity being operated in. Thus, a situationally aware surgical hub 2404 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 2404 could determine whether the surgical procedure is an arthroscopic procedure. The surgical hub 2404 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2404 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2404 can be configured to adjust the energy level for the ultrasonic surgical instrument or RF electrosurgical instrument throughout the course of a surgical procedure, rather than just on a procedure-by-procedure basis. A situationally aware surgical hub 2404 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2426 to improve the conclusions that the surgical hub 2404 draws from one data source 2426. A situationally aware surgical hub 2404 could augment data that it receives from the modular devices 2402 with contextual information that it has built up regarding the surgical procedure from other data sources 2426. For example, a situationally aware surgical hub 2404 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2404 can be further configured to compare a physiologic measurement (e.g., blood pressure sensed by a BP monitor communicably connected to the surgical hub 2404) with the visual or image data of hemostasis (e.g., from a medical imaging device 124 (FIG. 2) communicably coupled to the surgical hub 2404) to make a determination on the integrity of the staple line or tissue weld. In other words, the situational awareness system of the surgical hub 2404 can consider the physiological measurement data to provide additional context in analyzing the visualization data. The additional context can be useful when the visualization data may be inconclusive or incomplete on its own.

Another benefit includes proactively and automatically controlling the paired modular devices 2402 according to the particular step of the surgical procedure that is being performed to reduce the number of times that medical personnel are required to interact with or control the surgical system 2400 during the course of a surgical procedure. For example, a situationally aware surgical hub 2404 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2404 could determine whether the current or subsequent step of the surgical procedure requires a different view or degree of magnification on the display according to the feature(s) at the surgical site that the surgeon is expected to need to view. The surgical hub 2404 could then proactively change the displayed view (supplied by, e.g., a medical imaging device for the visualization system 108) accordingly so that the display automatically adjusts throughout the surgical procedure.

As yet another example, a situationally aware surgical hub 2404 could determine which step of the surgical procedure is being performed or will subsequently be performed and whether particular data or comparisons between data will be required for that step of the surgical procedure. The surgical hub 2404 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2404 could determine whether the operating theater is setup properly or optimally for the surgical procedure to be performed. The surgical hub 2404 can be configured to determine the type of surgical procedure being performed, retrieve the corresponding checklists, product location, or setup needs (e.g., from a memory), and then compare the current operating theater layout to the standard layout for the type of surgical procedure that the surgical hub 2404 determines is being performed. In one exemplification, the surgical hub 2404 can be configured to compare the list of items for the procedure scanned by a suitable scanner for example and/or a list of devices paired with the surgical hub 2404 to a recommended or anticipated manifest of items and/or devices for the given surgical procedure. If there are any discontinuities between the lists, the surgical hub 2404 can be configured to provide an alert indicating that a particular modular device 2402, patient monitoring device 2424, and/or other surgical item is missing. In one exemplification, the surgical hub 2404 can be configured to determine the relative distance or position of the modular devices 2402 and patient monitoring devices 2424 via proximity sensors, for example. The surgical hub 2404 can compare the relative positions of the devices to a recommended or anticipated layout for the particular surgical procedure. If there are any discontinuities between the layouts, the surgical hub 2404 can be configured to provide an alert indicating that the current layout for the surgical procedure deviates from the recommended layout.

As another example, a situationally aware surgical hub 2404 could determine whether the surgeon (or other medical personnel) was making an error or otherwise deviating from the expected course of action during the course of a surgical procedure. For example, the surgical hub 2404 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2404 determined is being performed. In one exemplification, the surgical hub 2404 can be configured to provide an alert indicating that an unexpected action is being performed or an unexpected device is being utilized at the particular step in the surgical procedure.

Overall, the situational awareness system for the surgical hub 2404 improves surgical procedure outcomes by adjusting the surgical instruments (and other modular devices 2402) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2402 in the surgical theater according to the specific context of the procedure.

Referring now to FIG. 21, a timeline 2500 depicting situational awareness of a hub, such as the surgical hub 106 or 206 (FIGS. 1-11), for example, is depicted. The timeline 2500 is an illustrative surgical procedure and the contextual information that the surgical hub 106, 206 can derive from the data received from the data sources at each step in the surgical procedure. The timeline 2500 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 2502 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 2504, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 2506, the medical personnel scan the patient band via a scanner that is communicably connected to the surgical hub 106, 206. The surgical hub 106, 206 can then confirm the patient's identity based on the scanned data.

Fourth step 2508, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 2510, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 2512, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 2512, the pre-operative portion of the lung segmentectomy procedure is completed and the operative portion begins.

Seventh step 2514, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 2516, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 2504 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 2518, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 2520, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 2522, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 2524, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 2524, the incisions are closed up and the post-operative portion of the procedure begins.

Thirteenth step 2526, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 2528 is that the medical personnel remove the various patient monitoring devices from the patient. The surgical hub 2106, 2236 can thus infer that the patient is being transferred to a recovery room when the hub loses EKG, BP, and other data from the patient monitoring devices. As can be seen from the description of this illustrative procedure, the surgical hub 2106, 2236 can determine or infer when each step of a given surgical procedure is taking place according to data received from the various data sources that are communicably coupled to the surgical hub 2106, 2236.

Situational awareness is further described in various U.S. Patent Applications that are incorporated by reference herein in the present disclosure, which is herein incorporated by reference in its entirety. In certain instances, operation of a robotic surgical system, including the various robotic surgical systems disclosed herein, for example, can be controlled by the hub 2106, 2236 based on its situational awareness and/or feedback from the components thereof and/or based on information from the cloud 2104 (FIG. 17).

FIG. 22 is a logic flow diagram of a process 4000 depicting a control program or a logic configuration for correlating visualization data with instrument data, in accordance with at least one aspect of the present disclosure. The process 4000 is generally executed during a surgical procedure and includes: receiving or deriving 4001 a first data set, visualization data, from a surgical visualization system indicative of a visual aspect of the surgical instrument relative to a surgical field, receiving or deriving 4002 a second data set, instrument data, from the surgical instrument indicative of a functional aspect of the surgical instrument, and correlating 4003 the first data set with the second data set.

In at least one example, correlating the visualization data with the instrument data is implemented by developing a composite data set from the visualization data and the instrument data. The process 4000 may further include comparing the composite data set to another composite data set, which can be received from an external source and/or can be derived from previously collected composite data sets. In at least one example, the process 4000 includes displaying a comparison of the two composite data sets, as described in greater detail below.

The visualization data of the process 4000 can be indicative of a visual aspect of the end effector of the surgical instrument relative to tissue in the surgical field. Additionally, or alternatively, the visualization data can be indicative of a visual aspect of the tissue being treated by the end effector of the surgical instrument. In at least one example, the visualization data represents one or more positions of the end effector, or a component thereof, relative to the tissue in the surgical field. Additionally, or alternatively, the visualization data may represent one or more movements of the end effector, or a component thereof, relative to the tissue in the surgical field. In at least one example, the visualization data represents one or more changes in shape, dimensions, and/or color of the tissue being treated by the end effector of the surgical instrument.

In various aspects, the visualization data is derived from a surgical visualization system (e.g. visualization system 100, 160, 500, 2108). The visualization data can be derived from various measurements, readings, and/or any other suitable parameters monitored and/or captured by a surgical visualization system, as described in greater detail in connection with FIGS. 1-18. In various examples, the visualization data is indicative of one or more visual aspects of tissue in a surgical field and/or one more visual aspects of a surgical instrument relative to the tissue in the surgical field. In certain examples, the visualization data represents or identifies position and/or movement of an end effector of the surgical instrument relative to a critical structure (e.g. the critical structure 101 in FIG. 1) in the surgical field. In certain examples, the visualization data is derived from surface mapping data, imaging data, tissue identification data, and/or distance data computed by surface mapping logic 136, imaging logic 138, tissue identification logic 140, or distance determining logic 141 or any combinations of the logic 136, 138, 140, and 141.

In at least one example, the visualization data is derived from tissue identification and geometric surface mapping performed by the visualization system 100 in combination with a distance sensor system 104, as described in greater detail in connection with FIG. 1. In at least one example, the visualization data is derived from measurements, readings, or any other sensor data captured by the imaging device 120. As described in connection with FIG. 1, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths.

Additionally, or alternatively, the visualization data can be derived from measurements, readings, or any suitable sensor data captured by any suitable imaging device that includes a camera or imaging sensor that is configured to detect visible light, spectral light waves (visible or invisible), and a structured light pattern (visible or invisible), for example. In at least one example, the visualization data is derived from a visualization system 160 that includes an optical waveform emitter 123 and an waveform sensor 122 that is configured to detect the reflected waveforms, as described in greater detail in connection with FIGS. 3-4 and 13-16. In yet another example, the visualization data is derived from a visualization system that includes a three-dimensional (3D) camera and associated electronic processing circuits such as, for example, the visualization system 500. In yet another example, the visualization data is derived from a structured (or patterned) light system 700, which is described in greater detail in connection with FIG. 12. The foregoing examples can be used alone or in combination to derive the visualization data of the process 4000.

The instrument data of the process 4000 can be indicative of one or more operations of one or more internal components of the surgical instrument. In at least one example, the instrument data represents one or more operational parameters of an internal component of the surgical instrument. The instrument data may represent one or more positions and/or one or more movements of one or more internal components of the surgical instrument. In at least one example, the internal component is a cutting member configured to cut the tissue during a firing sequence of the surgical instrument. Additionally, or alternatively, the internal component can include one or more staples configured to be fired into the tissue during the firing sequence of the surgical instrument.

In at least one example, the instrument data represents one or more operations of one or more components of one or more drive assemblies of the surgical instrument such as, for example, an articulation drive assembly, a closure drive assembly, a rotation drive assembly, and/or a firing drive assembly. In at least one example, the instrument data set represents one or more operations of one or more drive members of the surgical instrument such as, for example, an articulation drive member, a closure drive member, a rotation drive member, and/or a firing drive member.

FIG. 23 is a schematic diagram of an example surgical instrument 4600 for use with the process 4000 that is similar in many respects to other surgical instruments or tools described by the present disclosure such as, for example, the surgical instrument 2112. For brevity, various aspects of the process 4000 are only described by the present disclosure using a handheld surgical instrument. However, this is not limiting. Such aspects of the process 4000 can be equally implemented using a robotic surgical tool such as, for example, the surgical tool 2117.

The surgical instrument 4600 includes a plurality of motors, which can be activated to perform various functions. The plurality of motors of surgical instrument 4600 can be activated to cause firing, closure, and/or articulation motions in the end effector. The firing, closure, and/or articulation motions can be transmitted to an end effector of the surgical instrument 4600 through a shaft assembly, for example. In other examples, however, a surgical instrument for use with the process 4000 can be configured to perform one or more of the firing, closure, and articulation motions manually. In at least one example, the surgical instrument 4600 includes an end effector that treats tissue by deploying staples into the tissue. In another example, the surgical instrument 4600 includes an end effector that treats tissue by applying therapeutic energy to the tissue.

In certain instances, the surgical instrument 4600 includes a firing motor 4602. The firing motor 4602 may be operably coupled to a firing motor drive assembly 4604, which can be configured to transmit firing motions, generated by the firing motor 4602 to the end effector, in particular to move a firing member in the form of an I-beam, for example, which may include a cutting member. In certain instances, the firing motions generated by the firing motor 4602 may cause the staples to be deployed from a staple cartridge into tissue captured by the end effector and, optionally, cause the cutting member of the I-beam to be advanced to cut the captured tissue, for example.

In certain instances, the surgical instrument or tool may include a closure motor 4603. The closure motor 4603 may be operably coupled to a closure motor drive assembly 4605 which can be configured to transmit closure motions, generated by the closure motor 4603 to the end effector, in particular to displace a closure tube to close the anvil and compress tissue between the anvil and the staple cartridge. The closure motions may cause the end effector to transition from an open configuration to an approximated configuration to capture tissue, for example.

In certain instances, the surgical instrument or tool may include one or more articulation motors 4606a, 4606b, for example. The articulation motors 4606a, 4606b may be operably coupled to respective articulation motor drive assemblies 4608a, 4608b, which can be configured to transmit articulation motions generated by the articulation motors 4606a, 4606b to the end effector. In certain instances, the articulation motions may cause the end effector to articulate relative to the shaft, for example.

In certain instances, the surgical instrument or tool may include a control module 4610 which can be employed with a plurality of motors of the surgical instrument 4600. Each of the motors 4602, 4603, 4606a, 4606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 23, the control module 4610 may comprise a motor driver 4626 which may comprise one or more H-Bridge FETs. The motor driver 4626 may modulate the power transmitted from a power source 4628 to a motor coupled to the control module 4610 based on input from a microcontroller 4620 (the "controller"), for example. In certain instances, the controller 4620 can be employed to determine the current drawn by the motor, for example, while the motor is coupled to the control module 4610, as described above.

In certain instances, the controller 4620 may include a microprocessor 4622 (the "processor") and one or more non-transitory computer-readable mediums or memory units 4624 (the "memory"). In certain instances, the memory 4624 may store various program instructions, which when executed may cause the processor 4622 to perform a plurality of functions and/or calculations described herein. In certain instances, one or more of the memory units 4624 may be coupled to the processor 4622, for example. In various instances, the processor 4622 may control the motor driver 4626 to control the position, direction of rotation, and/or velocity of a motor that is coupled to the control module 4610.

In certain instances, one or more mechanisms and/or sensors such as, for example, sensors 4630 can be configured to detect forces (Force-to-Close "FTC") applied by the jaws of an end effector of the surgical instrument 4600 to tissue captured between the jaws. FTC can be transmitted to the jaws of the end effector through the closure motor drive assembly 4605. Additionally, or alternatively, the sensors 4630 can be configured to detect forces (Force-to-Fire "FTF") applied to the end effector through the firing motor drive assembly 4604. In various examples, the sensors 4630 can be configured to sense closure actuation (e.g., motor current and FTC), firing actuation (e.g., motor current and FTF), articulation (e.g., the angular position of the end effector), and rotation of the shaft or the end effector.

One or more aspects of the process 4000 can be executed by one or more of the control circuits (e.g. control circuit 132, 400, 410, 420, 602, 622, 2108, 4620) described by the present disclosure. In at least one example, one or more aspects of the process 4000 are executed by a control circuit (e.g. control circuit 400 of FIG. 2A) that includes a processor and a memory storing a set of computer-executable instructions that, when executed by the processor, cause the processor to perform the one or more aspects of the process 4000. Additionally, or alternatively, one or more aspects of the process 4000 can be executed by a combinational logic circuit (e.g. control circuit 410 of FIG. 2B) and/or a sequential logic circuit (e.g. control circuit 420 of FIG. 2C). Furthermore, the process 4000 can be executed by any suitable circuitry with any suitable hardware and/or software components that may be located in or associated with various suitable systems described by the present disclosure.

In various aspects, the process 4000 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4000 can be a component of a visualization system (e.g. visualization system 100, 160, 500, 2108), and can be in communication with a surgical instrument (e.g. surgical instrument 2112, 4600) to receive the instrument data therefrom. The communication between the surgical instrument and the control circuit of the visualization system can be a direct communication, or the instrument data can be routed to the visualization system through a surgical hub 2106, for example. In at least one example, the control circuit executing one or more aspects of the process 4000 can be a component of a surgical hub 2106.

Referring to FIG. 24, in various examples, visualization data 4010 is correlated with instrument data 4011 by developing a composite data set 4012 from the visualization data 4010 and the instrument data 4011. FIG. 24 displays a current user's composite data set 4012 in a Graph 4013, which is developed from the current user's visualization data 4010 and the current user's instrument data 4011. Graph 4013 illustrates visualization data 4010 that represents a first usage cycle of a surgical instrument 4600, which involves jaw positioning, clamping, and firing of the surgical instrument 4600. Graph 4013 also depicts visualization data 4010 that represents the beginning of a second usage cycle of the surgical instrument 4600 where the jaws are repositioned for a second clamping and firing of the surgical instrument 4600. Graph 4013 further depicts the current user's instrument data 4011 in the form of FTC data 4014, correlated to clamping visualization data, and FTF data 4015, correlated to firing visualization data.

As described above, the visualization data 4010 is derived from a visualization system (e.g. visualization system 100, 160, 500, 2108), and can represent, for example, the distance between the end effector of the surgical instrument 4600 and a critical structure in a surgical field during positioning, clamping, and/or firing of the end effector of the surgical instrument 4600. In at least one example, the visualization system identifies the end effector, or components thereof, in the surgical field, identifies a critical structure in the surgical field, and tracks the position of the end effector, or components thereof, with respect to the critical structure or with respect to tissue around the critical structure. In at least one example, the visualization system identifies jaws of the end effector in a surgical field, identifies a critical structure in the surgical field, and tracks the position of the jaws with respect to the critical structure or with respect to tissue around the critical structure within the surgical.

In at least one example, the critical structure is a tumor. To remove the tumor, surgeons generally prefer to cut tissue along a safety margin around the tumor to ensure that the entire tumor is removed. In such example, the visualization data 4010 can represent the distance between the jaws of the end effector and the safety margin of the tumor during positioning, clamping, and/or firing of the surgical instrument 4600.

The process 4000 may further include comparing a current user's composite data set 4012 to another composite data set 4012', which can be received from an external source and/or can be derived from previously collected composite data sets. Graph 4013 illustrates a comparison between the current user's composite data set 4012 and another composite data set 4012' that includes visualization data 4010' and instrument data 4011' including FTC data 4014' and FTF data 4015'. The comparison can be presented to a user of the surgical instrument 4600 in real time in the form of the graph 4013, or any other suitable format. The control circuit executing one or more aspects of the process 4000 may cause the comparison of two composite data sets to be displayed on any suitable screen within the operating room such as a screen of the visualization system, for example. In at least one example, the comparison can be displayed alongside the real-time video of the surgical field captured on any suitable screen within the operating room. In at least one example, the control circuit is configured to adjust an instrument parameter to address a detected deviation between the first composite data set and the second composite data set.

Furthermore, a control circuit (e.g. control circuit 132, 400, 410, 420, 602, 622, 2108, 4620) executing one or more aspects of the process 4000 may further cause current statuses of instrument data such as, for example, FTF data and/or FTC data to be displayed against best practice equivalents. In the example illustrated in FIG. 24, a current value of FTC—represented by a circle 4020—is depicted in real time against a gauge 4021 with an indicator 4022 representing a best practice FTC. Likewise, a current value of FTF—represented by a circle 4023—is depicted against a gauge 4024 with an indicator 4025 representing a best practice FTF. Such information can be overlaid onto the video feed of the surgical field in real time.

The example illustrated in FIG. 24 alerts the user that the current FTC is higher than the best practice FTC and that the current FTF is also higher than the best practice FTF. The control circuit executing one or more aspects of the process 4000 may further alert the current user of the surgical instrument 4600—using an audible, visual, and/or haptic alerting mechanism—if the current value of the FTF and/or FTC reaches and/or moves beyond a predetermined threshold.

In certain instances, a control circuit (e.g. control circuit 132, 400, 410, 420, 602, 622, 2108, 4620) executing one or more aspects of the process 4000 may further provide a current user of the surgical instrument 4600 with a projected instrument data based on current investment data. For example, as illustrated in FIG. 24, a projected FTF 4015" is determined based on a current value of the FTF, and is further displayed on the graph 4013 against current FTF 4015 and previously collected FTF'. Additionally, or alternatively, a projected FTF circle 4026 can be displayed against the gauge 4024, as illustrated in FIG. 24.

In various aspects, previously collected composite data sets and/or best practice FTF and/or FTC are determined from previous uses of the surgical instrument 4600 in the same surgical procedure and/or other surgical procedures performed by the user, other users within the hospitals, and/or users in other hospitals. Such data can be made available to a control circuit (e.g. control circuit 132, 400, 410, 420, 602, 622, 2108, 4620) executing one or more aspects of the process 4000 by importation from a cloud 104, for example.

In various aspects, a control circuit (e.g. control circuit 132, 400, 410, 420, 602, 622, 2108, 4620) executing one or more aspects of the process 4000 can cause feedback measurements of tissue thickness, compression, and stiffness to be visually overlaid onto a screen that displays a live feed of the surgical instrument 4600 in the surgical field as the jaws of the end effector begin to deform the tissue captured therebetween during the clamping phase. The visual overlay correlates the visualization data representing tissue deformation to changes in clamping force over time. The correlation helps a user confirm proper cartridge selection, determine the time to start firing, as well as determine a suitable firing speed. The correlation can further inform an adaptive clamping algorithm. Adaptive firing speed changes can be informed by measured forces as well as changes in tissue motions immediately adjacent the jaws of the surgical instrument 4600 (e.g. principal strains, tissue slippage, etc.) while a gauge or meter that communicates the results is overlaid on the screen that displays a live feed of the end effector in the surgical field.

Further to the above, the kinematics of the surgical instrument 4600 can also instruct instrument operation relative to another use or user. The kinematics can be ascertained via accelerometers, torque sensors, force sensors, motor encoders, or any other suitable sensors, and can yield various force, velocity, and/or acceleration data of the surgical instrument, or components thereof, for correlation with corresponding visualization data.

In various aspects, a control circuit (e.g. control circuit 132, 400, 410, 420, 602, 622, 2108, 4620) executing one or more aspects of the process 4000 may cause an alternate surgical technique to be presented, if a deviation from the best-practice surgical technique is detected from the visualization data and/or the instrument data. In at least one example, an adaptive display of instrument movement, force, tissue impendence, and results from proposed alternative techniques are presented. Where the visualization data indicates detection of a blood vessel and a clip applier in the surgical field, a control circuit (e.g. control circuit 132, 400, 410, 420, 602, 622, 2108, 4620) executing one or more aspects of the process 4000 may further ensure perpendicularity of the blood vessel with respect to the clip applier. The control circuit may suggest changing position, orientation, and/or roll angle to achieve the desired perpendicularity.

In various aspects, a control circuit (e.g. control circuit 132, 400, 410, 420, 602, 622, 2108, 4620) may execute the process 4000 by comparing real-time visualization data to pre-surgical planning simulations. The user can utilize pre-operative patient scans to simulate a surgical approach. The pre-surgical planning simulations can allow a user to follow a particular pre-surgical plan based on training runs. The control circuit can be configured to correlate fiducial landmarks of the pre-operative scans/simulations with current visualization data. In at least one example, the control circuit may employ boundary tracking of an object to establish the correlation.

As a surgical instrument interacts with tissue and deforms surface geometry, the change in surface geometry as a function of the surgical instrument's position can be computed. For a given change in the surgical instrument's position upon contact with the tissue, the corresponding change in tissue geometry can depend on the sub-surface structures in the tissue region contacted by the surgical instrument. For example, in thoracic procedures, the change in tissue geometry in regions with airway substructures is different than regions with parenchyma substructures. Generally, stiffer substructures yield a smaller change in surface tissue geometry in response to a given change in the surgical instrument's position. In various aspects, a control circuit (e.g. control circuit 132, 400, 410, 420, 602, 622, 2108, 4620) can be configured to compute a running average of the change in the surgical instrument position versus change in surface geometry for the given patient to give patient-specific differences. Additionally, or alternatively, the computed running average can be compared to a second set of previously collected data. In certain instances, a surface reference can be selected when no change in surface geometry is measured per change in tool position. In at least one example, a control circuit can be configured to determine the location of a substructure based on detected surface geometry changes in response to a given contact between a tissue region and a surgical instrument.

Furthermore, a control circuit (e.g. control circuit 132, 400, 410, 420, 602, 622, 2108, 4620) can be configured to maintain a set instrument-tissue contact throughout a tissue treatment based on the correlation between the set instrument-tissue contact and one or more tissue-surface geometry changes associated with the set instrument-tissue contact. For example, the end effector of a surgical instrument 4600 may clamp tissue between its jaws at a desired compression setting the instrument-tissue contact. A corresponding change in tissue-surface geometry can be detected by the visualization system. Furthermore, a control circuit (e.g.

control circuit 132, 400, 410, 420, 602, 622, 2108, 4620) can derive visualization data indicative of the change in tissue-surface geometry associated with the desired compression. The control circuit can further cause a motor setting of the closure motor 4603 (FIG. 22) to be automatically adjusted to maintain the change in tissue-surface geometry associated with the desired compression. This arrangement requires a continuous interaction between the surgical instrument 4600 and visualization system to maintain the change in tissue-surface geometry associated with the desired compression by continuously adjusting the jaw compression against the tissue based on the visualization data.

In yet another example, where the surgical instrument 4600 is a robotic tool attached to a robotic arm of a robotic surgical system (e.g. robotic system 110), the robotic surgical system can be configured to automatically adjust one or more components of the robotic surgical system to maintain a set surface contact with tissue based on visualization data derived from a detected change in surface geometry of the tissue in response to the set surface contact with the tissue.

In various examples, the visualization data can be used in combination with measured instrument data to maintain contact between the tissue either in position or load control allowing the user to manipulate the tissue to apply a predefined load to the tissue while moving the instrument relative to the tissue. The user could specify that they wish to maintain contact or maintain a pressure and the visual tracking of the instrument along with the internal loading of the instrument could be used to enable repositioning without changing the fixed parameters.

Referring to FIGS. 25A and 25B, a screen 4601 of the visualization system (e.g. visualization system 100, 160, 500, 2108) displays a real-time video feed of a surgical field during a surgical procedure. An end effector 4642 of the surgical instrument 4600 includes jaws clamping tissue near a tumor identified in the surgical field via an overlaid MRI image, for example. The jaws of the end effector 4642 comprise an anvil 4643 and a channel housing a staple cartridge. At least one of the anvil 4643 and the channel is movable relative to the other to capture tissue between the anvil 4643 and the staple cartridge. The captured tissue is then stapled via staples 4644 deployable from the staple cartridge during a firing sequence of the surgical instrument 4600. In addition, the captured tissue is cut via a cutting member 4645 advanced distally during the firing sequence but slightly behind the staple deployment.

As apparent in FIG. 25A, during the firing sequence, the captured tissue, and positions and/or movements of certain internal components of the end effector 4642 such as staples 4644 and cutting member 4645, may not visible in a normal view 4640 of the live feed on the screen 4601. Certain end effectors include windows 4641, 4653 that permit a partial view of the cutting member 4645 in the beginning and the end of the firing sequence but not during the firing sequence. Accordingly, a user of the surgical instrument 4600 is unable to track the firing sequence progress on the screen 4601.

FIG. 26 is a logic flow diagram of a process 4030 depicting a control program or a logic configuration for synchronizing movement of a virtual representation of an end-effector component with actual movement of the end-effector component, in accordance with at least one aspect of the present disclosure. The process 4030 is generally executed during a surgical procedure and includes detecting 4031 a movement of an internal component of an end effector during the firing sequence, presenting, for example by overlaying 4032, a virtual representation of the internal component onto the end effector, and synchronizing 4033 a movement of the virtual representation on the screen 4601 with the detected movement of the internal component.

One or more aspects of the process 4030 can be executed by one or more of the control circuits (e.g. control circuit 132, 400, 410, 420, 602, 622, 2108, 4620) described by the present disclosure. In at least one example, one or more aspects of the process 4030 are executed by a control circuit (e.g. control circuit 400 of FIG. 2A) that includes a processor and a memory storing a set of computer-executable instructions that, when executed by the processor, cause the processor to perform the one or more aspects of the process 4030. Additionally, or alternatively, one or more aspects of the process 4030 can be executed by a combinational logic circuit (e.g. control circuit 410 of FIG. 2B) and/or a sequential logic circuit (e.g. control circuit 420 of FIG. 2C). Furthermore, the process 4030 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4030 may receive instrument data indicative of the movement of an internal component of an end effector 4642 during a firing sequence thereof. The movement of the internal component can be tracked using conventional rotary encoders of the firing motor 4602, for example. In other examples, the movement of the internal component can be tracked by a tracking system that employs an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety. In certain examples, the movement of the internal component can be tracked using one or more position sensors that may comprise any number of magnetic sensing elements, such as, for example, magnetic sensors classified according to whether they measure the total magnetic field or the vector components of the magnetic field.

In various aspects, the process 4030 includes an overlay trigger. In at least one example, the overlay trigger can be detecting that a tissue is captured by the end effector 4642. If tissue captured by the end effector 4642 is detected, the process 4030 overlays, onto the end effector 4642, a virtual representation of the cutting member 4645 at a starting position. The process 4030 further includes projecting staple lines, outlining where staples will be deployed into the captured tissue. Furthermore, in response to an activation of the firing sequence by the user, the process 4030 causes the virtual representation of the cutting member 4645 to move distally mimicking actual movement of the cutting member 4645 within the end effector 4642. As the staples are deployed, the process 4030 converts unfired staples to fired staples, thereby allowing the user to visually track staple deployment and cutting member 4645 advancement in real-time.

In various examples, a control circuit (e.g. control circuit 132, 400, 410, 420, 602, 622, 2108, 4620) executing one or more aspects of the process 4030 may detect that a tissue is captured by the end effector 4642 from instrument data indicative of the force applied by the closure motor 4603 (FIG. 22) to the jaws of the end effector 4642 through the closure motor drive assembly 4605, for example. The control circuit may further determine the position of the end effector within the surgical field from visualization data derived from a visualization system (e.g. visualization system 100, 160, 500, 2108). In at least one example, the end effector position can be determined with respect to a reference point in the tissue such as, for example, a critical structure.

In any event, the control circuit causes a virtual representation of the internal component to be overlaid onto the end effector 4642 on the screen 4601 at a position commensurate with the position of the internal component within the end effector. The control circuit further causes the projected virtual representation of the internal component to move synchronously with the internal component during the firing sequence. In at least one example, the synchronization is improved by the integration of markings on the end effector 4642 that the control circuit can use as reference points for determining where to overlay the virtual representation.

FIG. 25B illustrates an augmented view 4651 of the live feed of the surgical field on the screen 4601. In the augmented view 4651 of the example of FIG. 25B, virtual representations of the staples 4644 and cutting member 4645 are overlaid onto the end effector 4642 during the firing sequence. The overlay distinguishes fired staples 4644a from unfired staples 4644b, and distinguishes a completed cutline 4646a from a projected cutline 4646b, which tracks the firing sequence progress. The overlay further shows the beginning of the staple lines 4647, and a projected end 4649 of the staple lines in the cutline that will not reach the end of the tissue. Furthermore, based on the overlay of the tumor MRI image, a safe margin distance "d" between the tumor and the projected cutline 4646b is measured and presented with the overlay. The overlaid safe margin distance "d" assures the user that all of the tumor will be removed.

As illustrated in FIG. 25B, the control circuit is configured to cause the visualization system to continuously reposition the virtual representation of the internal component to correlate with the actual movement of the internal component. In the example of FIG. 25B, the overlay shows the completed cutline 4646a slightly lagging behind the fired staple lines 4644a by a distance "d1", which assures the user that the firing sequence is progressing properly.

Referring now to FIG. 27, a visualization system (e.g. visualization system 100, 160, 500, 2108) can employ tool lighting 4058 and cameras 4059 to detect and/or define trocar locations. Based on determined trocar locations, a user can be directed to the most suitable trocar port for completing an intended function based on time efficiency, location of a critical structure, and/or avoidance or risk.

FIG. 27 illustrates three trocar positions (Trocar 1, Trocar 2, Trocar 3) extending through a body wall 4050 at different positions and orientations with respect to the body wall and with respect to a critical structure 4051 in a cavity 4052 inside the body wall 4050. The trocars are represented by arrows 4054, 4055, 4056. The lighting tool 4058 could be used to detect trocar locations by using cascading light or image on surrounding environment. Additionally, a light source of a lighting tool 4058 could be a rotatable light source. In at least one example, the light source of the lighting tool 4058 and the camera 4059 are utilized to detect distance of trocars relative to target location such as, for example, the critical structure 4051. In various examples, the visualization system could suggest a location change of an instrument if a more preferred instrument location is determined based on the visualization data derived from the camera 4059 recording of the light projected by the light source of the lighting tool 4058. A screen 4060 can display the distance between a trocar and a target tissue, whether a tool access through the trocar is acceptable, risk associated with utilizing the trocar, and/or expected operating time using the trocar, which can aid a user in selecting an optimal trocar for introducing a surgical tool into the cavity 4052.

In various aspects, a surgical hub (e.g. surgical hub 2106, 2122) may recommend an optimal trocar for insertion of a surgical tool into the cavity 4052 based on user characteristics, which can be received from a user database, for example. The user characteristics include user hand dominance, patient-side user preference, and/or user physical characteristics (e.g. height, arm length, range of motion). The surgical hub may utilize these characteristics, position and orientation data of the available trocars, and/or position data of a critical structure to select an optimal trocar for insertion of a surgical tool in an effort to reduce user fatigue and increase efficiency. In various aspects, the surgical hub may further cause a surgical instrument to invert its controls if the user inverts the end-effector orientation.

The surgical hub can reconfigure outputs of the surgical instrument based on visualization data. For example, the surgical hub may prohibit an activation of a therapeutic energy output of a surgical instrument if the visualization data indicates that the surgical instrument is being retracted, or is being utilized to perform a different task.

In various aspects, the visualization system can be configured to track blood surface or estimation of blood volume based reflective IR or red wavelength to delineate blood from non-blood surfaces and surface geometry measurements. This could be reported as an absolute static measure or as a rate of change to provide quantitative data on amount and degree of change of bleeding.

Referring to FIG. 28, various elements of a visualization system (e.g. visualization system 100, 160, 500, 2108) such as, for example, a structured light projector 706 and a camera 720 can be used to generate visualization data of an anatomical organ to generate a virtual 3D construct 4130 of the anatomical organ.

As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

FIG. 29 is a logic flow diagram of a process 4100 depicting a control program or a logic configuration, in accordance with at least one aspect of the present disclosure. In various instances, the process 4100 identifies 4101 a surgical procedure and identifies 4102 an anatomical organ targeted by the surgical procedure. The process 4100 further generates 4104 a virtual 3D construct 4130 of at least a portion of the anatomical organ, identifies 4105 anatomical structures of at least a portion of the anatomical organ which are relevant to the surgical procedure, couples 4106 the anatomical structures to the virtual 3D construct 4130, and overlays 4107 onto the virtual 3D construct 4130 a layout plan of the surgical procedure that is determined based on the anatomical structures.

One or more aspects of the process 4100 can be executed by one or more of the control circuits (e.g. control circuit 132, 400, 410, 420, 602, 622, 2108, 4620) described by the present disclosure. In at least one example, one or more aspects of the process 4100 are executed by a control circuit (e.g. control circuit 400 of FIG. 2A) that includes a processor and a memory storing a set of computer-executable instructions that, when executed by the processor, cause the processor to perform the one or more aspects of the process 4100. Additionally, or alternatively, one or more aspects of the process 4100 can be executed by a combinational logic circuit (e.g. control circuit 410 of FIG. 2B) and/or a sequential logic circuit (e.g. control circuit 420 of FIG. 2C). Furthermore, one or more aspects of the process 4100 can be executed by any suitable circuitry with any suitable hardware and/or software components that may be located in or associated with various suitable systems described by the present disclosure.

In various aspects, the process 4100 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4100 can be a component of a visualization system (e.g. visualization system 100, 160, 500, 2108).

A control circuit (e.g. control circuit 132, 400, 410, 420, 602, 622, 2108, 4620) executing one or more aspects of the process 4100 may identify 4101 a surgical procedure and/or identify 4102 an anatomical organ targeted by the surgical procedure by retrieving such information from a database storing the information, or obtaining the information directly from user input. In at least one example, the database is stored in a cloud-based system (e.g., the cloud 2104 that may include a remote server 2113 coupled to a storage device 2105). In at least one example, the database comprises hospital EMRs.

In one aspect, the surgical system 2200 comprises a surgical hub 2236 connected to multiple operating theater devices such as, for example, a visualization system (e.g. visualization system 100, 160, 500, 2108) located in the operating theater. In at least one example, the surgical hub 2236 comprises a communications interface for communicably coupling the surgical hub 2236 to the visualization system, the cloud 2204, and/or the remote server 2213. A control circuit of the surgical hub 2236 executing one or more aspects of the process 4100 may identify 4101 a surgical procedure and/or identify 4102 an anatomical organ targeted by the surgical procedure by retrieving such information from a database stored in the cloud 2204, and/or the remote server 2213.

The control circuit executing one or more aspects of the process 4100 may cause a visualization system (e.g. visualization system 100, 160, 500, 2108) to perform an initial scan of at least a portion of the anatomical organ to generate 4104 a three-dimensional ("3D") construct 4130 of at least a portion of the anatomical organ targeted by the surgical procedure. In the example illustrated in FIG. 28, the anatomical organ is a stomach 4110. The control circuit may cause one or more elements of the visualization system such as, for example, a structured light projector 706 and a camera 720 utilize structured light 4111 to generate visualization data by performing a scan of at least a portion of the anatomical organ when the camera(s) are introduced into the body. The current visualization data, pre-operative data (e.g. patient scans and other relevant clinical data), visualization data from previous similar surgical procedures performed on the same or other patients, and/or user input can be leveraged to generate a 3D construct of at least a portion of the anatomical organ.

Furthermore, a control circuit executing one or more aspects of the process 4100 identifies 4105 anatomical structures of at least a portion of the anatomical organ, which are relevant to the surgical procedure. In at least one example, a user may select the anatomical structures using any suitable input device. Additionally, or alternatively, the visualization system may include one or more imaging devices 120 with spectral cameras (e.g. a hyperspectral camera, multispectral camera, or selective spectral camera), which are configured to detect reflected spectral waveforms and generate images based on the molecular response to the different wavelengths. Optical absorption or refractive properties of the tissue can be utilized by the control circuit to distinguish different tissue types of the anatomical organ and, thereby, identify the relevant anatomical structures. In addition, current visualization data, pre-operative data (e.g. patient scans and other relevant clinical data), stored visualization data from previous similar surgical procedures performed on the same or other patients, and/or user input can be leveraged by the control circuit to identify the relevant anatomical structures.

The identified anatomical structures can be anatomical structures in a surgical field and/or anatomical structures are selected by a user. In various examples, position tracking of the relevant anatomical structures can be expanded beyond a current visibility view of a camera directed at the surgical field. In one example, this is achieved by using common visible coupled landmarks or through the use of secondary coupled movement tracking. The secondary tracking could be accomplished through a secondary imaging source, calculation of scope movement, and/or through pre-established beacons that are measures by a second visualization system, for example.

As described above in greater detail in connection with FIG. 14, a visualization system can utilize a structured light projector 706 to cast an array of patterns or lines in which the camera 720 could determine a distance to a target location. The visualization system can then emit a known size pattern or line at a set distance equal to the determined distance. In addition, a spectral camera can determine a size of the pattern, which can vary depending on the optical absorption or refractive properties of the tissue at the target location. The difference between the known size and the determined size is indicative of tissue density at the target location, which is indicative of tissue type at the target location. A control circuit executing one or more aspects of the process 4100 may identify the relevant anatomical structures based, at least in part, on determined tissue densities at target locations.

In at least one example, a detected abnormality in the tissue density can be associated with a disease state. Furthermore, the control circuit select, update, or modify one or more settings of a surgical instrument treating the tissue based on the tissue density detected via visualization data. For example, the control circuit may change various clamping and/or firing parameters of a surgical stapler utilized to staple and cut the tissue. In at least one example, the control circuit may slow down the firing sequence and/or allow more clamping time based on the tissue density detected by the visualization data. In various examples, the control circuit may alert a user of the surgical instrument to the abnormal tissue density by, for example, displaying over a screen, instructions to reduce bite size, increase or decrease the energy delivery output for an electrosurgical instrument, and adjust the amount the jaw closure. In another example, if the visualization data indicate that the tissue is a fatty tissue, the instructions could be to increase power to reduce energy application time.

Furthermore, identification of the surgical procedure type can facilitate target organ identification by the control circuit. For example, if the procedure is a left upper lobectomy, it is highly likely that the lung is the target organ. Accordingly, the control circuit will only consider visualization data and non-visualization data relevant to the lung and/or tools that are generally used in such procedure. In addition, knowledge of the procedure type better enables other image fusion algorithms that inform tumor location and staple line placement, for example.

In various aspects, knowledge of surgical table position and/or insufflation pressure can be used by a control circuit executing one or more aspects of the process 4100 to establish a baseline position of a target anatomical organ and/or relevant anatomical structures identified from visualization data. Motion of the surgical table (e.g., moving the patient from a flat position to a reverse Trendelenburg position) can cause deformation of anatomical structures, which can be tracked, and compared to a baseline, to continuously inform target organ and/or relevant anatomical structures locations and states. Likewise, changes in insufflation pressure within a body cavity can interfere with baseline visualization data of a target organ and/or relevant anatomical structures within the body cavity.

A control circuit (e.g. control circuit 132, 400, 410, 420, 602, 622, 2108, 4620) may execute one or more aspects of a process that derives baseline visualization data of a target organ and/or relevant anatomical structures of a patient on a surgical table during a surgical procedure, determines a change in the surgical table position, and re-derives the baseline visualization data of the target organ and/or the relevant anatomical structures of the patient in the new position.

Likewise, a control circuit (e.g. control circuit 132, 400, 410, 420, 602, 622, 2108, 4620) may execute one or more aspects of a process that derives baseline visualization data of a target organ and/or relevant anatomical structures of a patient on a surgical table during a surgical procedure, determines a change in insufflation pressure in the patient's body cavity, and re-derives the baseline visualization data of the target organ and/or the relevant anatomical structures of the patient under the new insufflation pressure.

In various instances, the control circuit executing one or more aspects of the process 4100 may couple identified anatomical structures to the virtual 3D construct by overlaying landmarks or signs onto the virtual 3D construct of the organ to indicate positions of the anatomical structures, as illustrated in FIG. 28. The control circuit may also cause user defined structures and tissue planes to be overlaid onto the virtual 3D construct. In various aspects, a hierarchy of tissue types can be established to organize the anatomical structures identified on the virtual 3D construct. Table 1, which is provided below, sets forth example hierarchies for the lung and the stomach.

| ORGAN | TIER 1 | TIER 2 | TIER 3 |
|---|---|---|---|
| Lung | Left Lung | Left upper lobe | Segments in the left upper lobe, major vessels/airways |

-continued

| ORGAN | TIER 1 | TIER 2 | TIER 3 |
|---|---|---|---|
| Stomach | Stomach | Fundus, antrum, pylorus | Angle of His, Angularis Incisura, Greater/Lesser Curvature |

In various aspects, relevant anatomical structures that are identified on a virtual 3D construct can be renamed and/or repositioned by a user to correct errors or for preference. In at least one example, corrections can be voice activated. In at least one example, corrections are recorded for future machine learning.

Further to the above, a control circuit (e.g. control circuit 132, 400, 410, 420, 602, 622, 2108, 4620) executing one or more aspects of the process 4100 may overlay 4107 a surgical procedure layout plan (e.g. layout plan 4120) onto the virtual 3D construct of the target organ (e.g. stomach 4110). In at least one example, the virtual 3D construct is displayed on a separate screen of the visualization system from the screen displaying the live feed/view of the surgical field. In another example, one screen may alternate displaying the live feed of the surgical field and the 3D construct. In such example, a user can use any suitable input device to alternate between the two views.

In the example illustrated in FIG. 28, the control circuit has determined that the surgical procedure is a sleeve gastrectomy procedure, and that the target organ is the stomach. In an initial scan of the abdominal cavity, the control circuit identifies the stomach, liver, spleen, greater curvature of the stomach, and pylorus using visualization data such as, for example, structured light data and/or spectral data. This is informed by knowledge of the procedure and the structures of interest.

Visualization data such as, for example, structured light data and/or spectral data can be utilized by the control circuit to identify the stomach 4110, liver, and/or the spleen by comparing current structured light data with stored structured light data previously associated with such organs. In at least one example, a control circuit (e.g. control circuit 132, 400, 410, 420, 602, 622, 2108, 4620) can utilize structured light data that represent signature anatomical contours of an organ and/or spectral data that represent signature subsurface tissue characteristics to identify anatomical structures relevant to a surgical procedure layout plan (e.g. layout plan 4120).

In at least one example, visualization data could be utilized to identify the pyloric vein 4112, which indicates the position 4113 of the pylorus 4131, identify the gastric-omental vessel 4114, which indicates the position 4115 of the greater curvature of the stomach 4110, identify the bend 4116 in the right gastric vein, which indicates the position 4117 of the angle of incisura 4132, and/or identify a position 4119 of the Angle of His 4121. The control circuit may assign landmarks to one or more of the identified position. In at least one example, as illustrated in FIG. 28 the control circuit causes the visualization system to overlay landmarks onto the positions 4113, 4117, 4119 on a virtual 3D construct of stomach 4110 generated using visualization data, as described above. In various aspects, the landmarks can be synchronously overlaid onto the virtual 3D construct and the surgical field views to allow the user to switch between the views without losing sight of the landmarks. The user may zoom out in the view of the screen displaying the virtual 3D construct to show the overall layout plan or may zoom in to show a portion analogous to the surgical field view. The control circuit may continuously track and update the landmarks.

In a sleeve gastrectomy, the surgeon typically staples stomach tissue at, or about, 4 cm from the pylorus. Prior to stapling, an energy device is introduced into the abdominal cavity of the patient in the beginning of the sleeve gastrectomy procedure to dissect the gastroepiploic artery and omentum away from the greater curvature at, or about, 4 cm from the pylorus. A control circuit that has identified the position 4113, as described above, may automatically cause an overlay of an end effector of the energy device at, or about, 4 cm from the position 4113. The overlay of the end effector of the energy device, or any suitable landmark, at, or about, 4 cm from the pylorus identifies a starting position of the sleeve gastrectomy.

As the surgeon dissects along the greater curvature of the stomach, the control circuit causes the landmark at position 4113 and/or the overlaid end effector of the energy device to be removed. As the surgeon approaches the spleen, a distance indicator is automatically overlaid onto the virtual 3D construct view and/or the surgical field view. The control circuit may cause the distance indicator to identify a 2 cm distance from the spleen. The control circuit may cause the distance indicator to flash and/or change colors when the dissection path reaches, or is about to reach, 2 cm from the spleen, for example. The distance indicator overlay remains until the user reaches to the position 4119 at the Angle of His 4121.

Referring to FIG. 30, once a surgical stapler is introduced into the abdominal cavity, the control circuit may utilize visualization data to identify the pylorus 4131, Angular Incisura 4132, greater curvature 4133 of the stomach 4110, lesser curvature 4134 of the stomach 4110, and/or other anatomical structure relevant to the sleeve gastrectomy procedure. An overlay of a bougie can be shown as well. Introduction of a surgical instrument into a body cavity (e.g. introduction of the surgical stapler into the abdominal cavity), can be detected by a control circuit from visualization data indicative of visual cues on the end effector, such as distinctive colors, signs, and/or shapes. The control circuit can identify the surgical instrument in a database storing such visual cues and corresponding visual cues. Alternatively, the control circuit may prompt a user to identify the surgical instrument inserted into the body cavity. Alternatively, a surgical trocar facilitating access to the body cavity may include one or more sensors for detecting a surgical instrument inserted therethrough. In at least one example, the sensors comprise an RFID reader configured to identify the surgical instrument from an RFID chip on the surgical instrument.

In addition to the landmarks identifying relevant anatomical structures, the visualization system may also overlay a procedure layout plan 4135, which can be in the form a recommended treatment path, onto the 3D critical structure and/or onto the surgical field view. In the example of FIG. 30, the surgical procedure is a sleeve gastrectomy, and the procedure layout plan 4135 is in the form of three resection paths 4136, 4137, 4138 and corresponding outcome volumes of the resulting sleeves.

As illustrated in FIG. 30, distances (a, $a_1$, $a_2$) from the pylorus 4131 to starting points for making the sleeves. Each starting point yields a different sleeve size (e.g. 400cc, 425cc, 450cc for the starting points 4146, 4147, 4148, at distances a, $a_1$, $a_2$ from pylorus 4131, respectively). In one example, the control circuit prompts the user to enter a size selection and, in response, present a procedure layout plan, which can be in the form of a resection path, which yields the selected sleeve size. In another example, as illustrated in FIG. 30, the control circuit presents a plurality of resection paths 4136, 4137, 4138 and corresponding sleeve sizes. The user may then select one of the proposed resection paths 4136, 4137, 4138 and, in response, the control circuit removes the unselected resection paths.

In yet another example, the control circuit allows the user to make adjustments to a proposed resection path on a screen showing the resection path overlaid onto the virtual 3D construct and/or the surgical field. The control circuit may calculate a sleeve size based on the adjustments. Alternatively, in another example, the user is permitted to select a starting point, for forming the sleeve, at a desired distance from the pylorus 4131. In response, the control circuit calculates a sleeve size based on the selected starting point.

Presenting resection paths can be achieved by causing the visualization system to overlay the resection paths onto the virtual 3D construct view and/or the surgical field view, for example. Conversely, removing proposed resection paths can be achieved by causing the visualization system to remove the overlay of such resection paths from the virtual 3D construct view and/or the surgical field view.

Referring still to FIG. 30, in certain examples, once an end effector of a surgical stapler clamps the stomach tissue between a starting point, selected from proposed starting points 4146, 4147, 4147, and an end position 4140, at a predefined distance from the Angle of incisura 4132, the control circuit presents information about the clamping and/or firing the surgical stapler. In at least one example, as illustrated in FIG. 24, a composite data set 4012 from the visualization data 4010 and the instrument data 4011 can be displayed. Additionally, or alternatively, FTC and/or FTF values can be displayed. For example, a current value of FTC—represented by a circle 4020—can be depicted in real time against a gauge 4021 with an indicator 4022 representing a best practice FTC. Likewise, a current value of FTF—represented by a circle 4023—can be depicted against a gauge 4024 with an indicator 4025 representing a best practice FTF.

After the surgical stapler is fired, recommendations for new cartridge selections can be presented onto the screen of the surgical stapler or any of the screens of the visualization system, as described below in greater detail. When the surgical stapler is removed from the abdominal cavity, reloaded with a selected staple cartridge, and reintroduced into the abdominal cavity, distance indicators—identifying a constant distance (d) from a plurality of points along the lesser curvature 4134 of the stomach 4110 to the selected resection path—are overlaid onto the virtual 3D construct view and/or the surgical field view. To ensure a proper orientation of the end effector of the surgical stapler, the distance from the target of the distal end of the end effector of the surgical stapler, as well as the distance from the proximal end to the previously fired staple lines are overlaid onto the virtual 3D construct view and/or the surgical field view. This process is repeated until the resection is complete.

One or more of the distances proposed and/or calculated by the control circuit can be determined based on stored data. In at least one example, the stored data includes preoperative data, user preference data, and/or data from previously performed surgical procedures by the user or other users.

Referring to FIG. 31, a process 4150 depicting a control program or a logic configuration for proposing resection paths for removing a portion of an anatomical organ, in accordance with at least one aspect of the present disclosure. The process 4150 identifies 4151 an anatomical organ targeted by the surgical procedure, identifies 4152 anatomical structures of the anatomical organ which are relevant to the surgical procedure, and proposes 4153 surgical resection paths for removing a portion of the anatomical organ by the surgical instrument, as described in greater detail elsewhere herein in connection with the process 4100. The surgical resection paths are determined based on the anatomical structures. In at least one example, the surgical resection path comprise different starting points.

One or more aspects of the process 4150 can be executed by one or more of the control circuits (e.g. control circuit 132, 400, 410, 420, 602, 622, 2108, 4620) described by the present disclosure. In at least one example, one or more aspects of the process 4150 are executed by a control circuit (e.g. control circuit 400 of FIG. 2A) that includes a processor and a memory storing a set of computer-executable instructions that, when executed by the processor, cause the processor to perform the one or more aspects of the process 4150. Additionally, or alternatively, one or more aspects of the process 4150 can be executed by a combinational logic circuit (e.g. control circuit 410 of FIG. 2B) and/or a sequential logic circuit (e.g. control circuit 420 of FIG. 2C). Furthermore, the process 4150 can be executed by any suitable circuitry with any suitable hardware and/or software components that may be located in or associated with various suitable systems described by the present disclosure.

Referring to FIGS. 32A-32D, a control circuit (e.g. control circuit 132, 400, 410, 420, 602, 622, 2108, 4620) executing on or more aspects of the process 4100 or the process 4150 may utilize dynamic visualization data to update or modify a surgical procedure layout plan in real time during implementation. In at least one example, the control circuit modifies a set resection path (FIG. 32B) for removing a portion of an organ or an abnormality (e.g. a tumor or region) by a surgical instrument to an alternative resection path (FIG. 32D) based on the dynamic visualization data from one or more imaging devices of a visualization system (e.g. visualization system 100, 160, 500, 2108) tracking progress of the tissue being resected and surrounding tissue. The resection path modification can be triggered by a shift in the position of a critical structure (e.g. a blood vessel) into the resection path. For instance, the tissue resection process can sometimes lead to tissue inflammation that changes the tissue shape and/or volume, which can cause a critical structure (e.g. a blood vessel) to shift position. Dynamic visualization data enable the control circuit to detect position and/or volume changes of critical structures and/or relevant anatomical structure near a set resection path. If the changes in position and/or volume cause the critical structures to shift into, or within a safe margin from, the resection path, the control circuit modifies the set resection path by selecting, or at least recommending, an alternative resection path of the surgical instrument.

FIG. 32A illustrates a live view 4201 of a surgical field on a screen 4230 of the visualization system. A surgical instrument 4200 is introduced into the surgical field to remove a target region 4203. An initial plan layout 4209 for removing the region is overlaid onto the live view 4201, as illustrated in the expanded view of the region 4203 in FIG. 32B. The region 4203 is surrounded by critical structures 4205, 4206, 4207, 4208. The initial plan layout 4209, as illustrated in FIG. 32B, extends a resection path around the region 4203 at a predefined safe margin from the region 4203. The resection path avoids crossing over or passing through a critical structure by extending either on the outside (e.g critical structure 4208) or on the inside (e.g. critical structure 4206) of the critical structure. As described above, the initial plan layout 4209 is determined by the control circuit based on visualization data from visualization system.

FIG. 32C illustrates a live view 4201' of the surgical field on the screen 4230 of the visualization system at a later time (00:43). An end effector 4202 of the surgical instrument 4200 resects tissue along the predefined resection path defined by the layout plan 4209. A volume change of tissue including the region 4203 due tissue inflammation, for example, causes critical structures 4206 and 4208 to be shifted into the predefined resection path. In response, the control circuit proposes an alternative resection path 4210 that navigates around the critical structures 4206, 4208, which protects the critical structures 4206, 4208 from being damaged, as illustrated in FIG. 32D. In various examples, alternative resection paths can be proposed to optimize the amount of healthy tissue that would remain and provide user with guidance to ensure they did not hit critical structures which would minimize bleeding and, therefore, reducing surgery time and pressure of dealing with unintended situations, while balancing that against the impacts on remaining organ volume.

In various aspects, a control circuit executing one or more aspects of one or more of the processes described by the present disclosure may receive and/or derive visualization data from multiple imaging devices of a visualization system. The visualization data facilitates tracking of critical structures that are outside the live view of the surgical field. Common landmarks can allow the control circuit to consolidate the visualization data from multiple imaging devices of the visualization system. In at least one example, secondary tracking of critical structures outside a live view of the surgical filed, for example, could be achieved through a secondary imaging source, calculation of scope movement, or through pre-established beacons/landmarks that are measure by a second system.

Referring generally to FIGS. 33-35, a logic flow diagram of a process 4300 depicts a control program or a logic configuration for presenting, or overlaying, parameters of a surgical instrument onto, or near, a proposed surgical resection path, in accordance with at least one aspect of the present disclosure. The process 4300 is generally executed during a surgical procedure and includes identifying 4301 an anatomical organ targeted by the surgical procedure, identifying 4302 anatomical structures relevant to the surgical procedure from visualization data from at least one imaging device, and proposing 4303 a surgical resection path for removing a portion of the anatomical organ by a surgical instrument. In at least one example, the surgical resection path is determined based on the anatomical structures. The process 4300 further includes presenting 4304 parameters of the surgical instrument in accordance with the surgical resection path. Additionally, or alternatively, the process 4300 further includes adjusting 4305 parameters of the surgical instrument in accordance with the surgical resection path.

One or more aspects of the process 4300 can be executed by one or more of the control circuits (e.g. control circuit 132, 400, 410, 420, 602, 622, 2108, 4620) described by the present disclosure. In at least one example, one or more aspects of the process 4300 are executed by a control circuit (e.g. control circuit 400 of FIG. 2A) that includes a processor and a memory storing a set of computer-executable instructions that, when executed by the processor, cause the processor to perform the one or more aspects of the process 4030. Additionally, or alternatively, one or more aspects of the process 4300 can be executed by a combinational logic circuit (e.g. control circuit 410 of FIG. 2B) and/or a sequential logic circuit (e.g. control circuit 420 of FIG. 2C). Furthermore, the process 4300 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4300 may identify 4301 an anatomical organ targeted by the surgical procedure, identify 4302 anatomical structures relevant to the surgical procedure from visualization data from at least one imaging device of a visualization system (e.g. visualization system 100, 160, 500, 2108), and/or propose 4303 a surgical resection path for removing a portion of the anatomical organ by a surgical instrument (e.g. surgical instrument 4600), as described elsewhere herein in connection with the processes 4150 (FIG. 31), 4100 (FIG. 29). Furthermore, the control circuit executing one or more aspects of the process 4300 may propose or recommend one or more parameters of the surgical instrument in accordance with the proposed 4303 surgical resection path. In at least one example, the control circuit presents 4304 the recommended parameters of the surgical instrument by overlaying such parameters onto, or near, the proposed surgical path, as illustrated in FIGS. 34 and 35.

FIG. 34 illustrates a virtual 3D construct 4130 of a stomach of a patient undergoing a sleeve gastrectomy performed using a surgical instrument 4600, in accordance with at least one aspect of the present disclosure. As described in greater detail in connection with FIG. 28, for example, various elements of a visualization system (e.g. visualization system 100, 160, 500, 2108) such as, for example, a structured light projector 706 and a camera 720 can be used to generate visualization data to create the virtual 3D construct 4130. Relevant anatomical structures (e.g. pylorus 4131, Angular Incisura 4132, Angle of His 4121) are identified from visualization data from one or more imaging devices of the visualization system. In at least one example, landmarks are assigned to positions 4113, 4117, 4119 of such anatomical structures by overlaying the landmarks onto the virtual 3D construct 4130.

In addition, a surgical resection path 4312 is proposed 4303 based on the identified anatomical structures. In at least one example, the control circuit overlays the surgical resection path 4312 onto the virtual 3D construct 4130, as illustrated in FIG. 34. As described in greater detail elsewhere herein, adjustments can be automatically made to proposed surgical paths based on desired volume outputs. In addition, adjustments can be automatically made to projected margins based on critical structures and/or tissue abnormalities automatically identified by the control circuit from the visualization data.

In various aspects, the control circuit executing at least one aspect of the process 4300 presents parameters 4314 of the surgical instrument that are selected in accordance with the proposed 4303 surgical resection path 4312. In the example illustrated in FIG. 34, the parameters 4314 are indicative of staple cartridges automatically selected for use with the surgical instrument 4600 in performing the sleeve gastrectomy based on the proposed 4303 surgical resection path. In at least one example, the parameters 4314 comprise at least one of a staple cartridge size, a staple cartridge color, a staple cartridge type, and a staple cartridge length. In at least one example, the control circuit presents 4304 the parameters 4314 of the surgical instrument 4600 by overlaying such parameters onto, or near, the proposed 4303 surgical resection path 4312, as illustrated in FIGS. 34 and 35.

In various aspects, the control circuit executing at least one aspect of the process 4300 presents tissue parameters 4315 along one or more portions of the surgical resection path 4312. In the example illustrated in FIG. 34, the tissue parameters 4315 are tissue thicknesses presented by displaying a cross-section taken along the line A-A, which represents tissue thicknesses along at least a portion of the surgical resection path 4312. In various aspects, the staple cartridges utilized by the surgical instrument 4600 can be selected in accordance with the tissue parameters 4315. For example, as illustrated in FIG. 34, a black cartridge, which comprises a larger staple size, is selected for use with the thicker muscle tissue of the Antrum, and a green cartridge, which comprises a smaller staple size, is selected for use with the heart muscle tissue of the body and fundus portions of the stomach.

The tissue parameters 4315 include at least one of a tissue thickness, a tissue type, and a volume outcome of the sleeve resulting from the proposed surgical resection path 4312. Tissue parameters 4315 can be derived from previously captured CT, ultrasound, and/or MRI images of the organ of the patient and/or from previously known average tissue thicknesses. In at least one example, the surgical instrument 4600 is an intelligent instrument (similar to the intelligent instrument 2112), and the tissue thicknesses and/or the selected staple cartridge information are transmitted to the surgical instrument 4600 for optimization of closure setting, firing settings, and/or any other suitable surgical instrument settings. In one example, the tissue thickness and/or the selected staple cartridge information can be transmitted to the surgical instrument 4600 from a surgical hub (e.g. surgical hub 2106, 2122) in communication with a visualization system (e.g. visualization system 100, 160, 500, 2108) and the surgical instrument 4600, as described in connection with FIGS. 17-19.

In various examples, the control circuit executing at least one aspect of the process 4300 proposes an arrangement 4317 of two or more staple cartridge sizes (e.g. 45 mm and 60 mm) in accordance with determined tissue thicknesses along at least a portion of the surgical resection path 4312. Furthermore, as illustrated in FIG. 35, the control circuit may further present the arrangement 4317 along the proposed 4303 surgical resection path 4312. Alternatively, the control circuit can present a suitable arrangement 4317 along a user-selected surgical resection path. The control circuit can determine tissue thicknesses along the user-selected resection path, as described above, and propose a staple cartridge arrangement in accordance with the tissue thicknesses.

In various aspects, the control circuit executing one or more aspects of the process 4300 may propose a surgical resection path, or optimize a selected surgical resection path, to minimize the number of staple cartridges in the staple cartridge arrangement 4317 without compromising the size of the resulting sleeve beyond a predetermined threshold. Reducing the number of spent cartridges reduces procedure time and cost, and reduces patient trauma.

Still referring to FIG. 35, the arrangement 4317 comprises a first staple cartridge 4352 and a last staple cartridge 4353 defining the beginning and end of the surgical resection path 4312. Where only a small portion of a last staple cartridge 4353 of a proposed staple cartridge arrangement 4317 is needed, the control circuit may adjust the surgical resection path 4312 to eliminate the need for the last staple cartridge 4353 without compromising the size of the resulting sleeve beyond a predetermined threshold.

In various examples, the control circuit executing at least one aspect of the process 4300 presents a virtual firing of the proposed staple cartridge arrangement 4317, which virtually separates the virtual 3D construct 4130 into a retained portion 4318 and a removed portion 4319, as illustrated in FIG. 35. The retained portion 4318 is a virtual representation of a sleeve that would result from implementation of the proposed surgical resection path 4312 by firing the staple cartridge arrangement 4317. The control circuit may further determine an estimate volume of the retained portion 4318 and/or the removed portion 4319. The volume of the retained portion 4318 represents the volume of the resulting sleeve. In at least one example, the volume of the retained portion 4318 and/or the removed portion 4319 is derived from the visualization data. In another example, the volume of the retained portion 4318 and/or the removed portion 4319 is determined from a database storing retained volumes, removed portion volumes, and corresponding surgical resection paths. The database can be constructed from surgical procedures previously performed on organs with the same, or at least similar, dimensions, which have been resected using the same, or at least similar, resection paths.

In various examples, a combination of predetermined average tissue thickness data based on the situational awareness of the organ, as described above in greater detail, in combination with volumetric analysis from the visualization source and CT, MRI, and/or ultrasound secondary imaging, if available for the patient, can be utilized to select a first staple cartridge for the arrangement 4317. Firings of subsequent staple cartridges in the arrangement 4317 can use instrument data from pervious firings, in addition to the visualization data, to optimize the firing parameters. The instrument data that could be used to supplement volume measurements include FTF, FTC, current draw by motors driving the firing and/or closure, end-effector closure gap, rate of firing, tissue impendence measurements across the jaws, and/or wait or pause time during use of the surgical instrument, for example.

In various examples, visualization data such as, for example, structured light data can be used to track surface geometry changes in tissue being treated by a surgical instrument (e.g. surgical instrument 4600). Additionally, visualization data such as, for example, spectral data can be used to track critical structures below the tissue surface. The structured data and/or the spectral data can be used to maintain a set instrument-tissue contact throughout the tissue treatment.

In at least one example, the end effector 4642 of the surgical instrument 4600 can be used to grasp tissue between its jaws. Once a desired tissue-instrument contact is confirmed by a user input, for example, the visualization data for the end effector and surrounding tissue, which are associated with the desired tissue-instrument contact, can be used to automatically maintain the desired tissue-surface contact throughout at least a portion of the tissue treatment. The desired tissue-surface contact can be automatically maintained by, for example, slight manipulations to position, orientation, and/or FTC parameters of the end effector 4642.

In the event the surgical instrument 4600 is a hand-held surgical instrument, position and/or orientation manipulations could be provided to a user in the form of instructions that could be presented on a display 4625 (FIG. 22) of the surgical instrument 4600, for example. An alert could also be issued by the surgical instrument 4600 when user manipulations are needed to reestablish the desired tissue-surface contact. Meanwhile, non-user manipulations such as, for example, manipulations to the FTC parameters and/or articulation angle can be communicated to the controller 4620 of the surgical instrument 4600 from the surgical hub 2106 or the visualization system 2108, for example. The controller 4620 could then cause the motor driver 4626 to implement the desired manipulations. In the event the surgical instrument 4600 is a surgical tool coupled to a robotic arm of a robotic system 2110, position and/or orientation manipulations could be communicated to the robotic system 2110 from the surgical hub 2106 or the visualization system 2108, for example.

Referring primarily to FIGS. 36A-36C, a firing of a surgical instrument 4600 loaded with a first staple cartridge 4652 in the staple cartridge arrangement 4317 is illustrated. In a first stage, as illustrated in FIG. 36A, a first landmark 4361 and a second landmark 4362 are overlaid onto the surgical resection path 4312. The landmarks 4361, 4362 are spaced apart a distance (d1) defined by the size (e.g. 45) of the staple cartridge 4652 which represents the length of a staple line 4363 to be deployed by the staple cartridge 4652 onto the surgical resection path 4312. The control circuit executing one or more aspects of the process 4300 can employ visualization data, as described in greater detail elsewhere herein, to overlay the landmarks 4361, 4362 onto the surgical resection path 4312, and continuously track and update their positions with respect to predetermined critical structures such as, for example, anatomical structures 4364, 4365, 4366, 4367.

During firing, as illustrated in FIG. 36B, staples of the staple line 4363 are deployed into tissue and the cutting member 4645 is advanced to cut the tissue along the surgical resection path 4312 between the landmarks 4361, 4362. In various instances, the advancement of the cutting member 4645 causes the tissue being treated to stretch and/or shift. Tissue stretching and/or shifting beyond a predetermined threshold indicates that the cutting member 4645 is moving too fast through the tissue being treated.

FIG. 37 is a logic flow diagram of a process 4170 depicting a control program or a logic configuration for adjusting a firing speed of a surgical instrument to address tissue stretching/shifting during firing. The process 4170 includes monitoring 4171 a tissue stretch/shift during firing of the surgical instrument and adjusting 4173 firing parameters if 4172 the tissue stretch/shift is greater than or equal to a predetermined threshold.

One or more aspects of the process 4170 can be executed by one or more of the control circuits (e.g. control circuit 132, 400, 410, 420, 602, 622, 2108, 4620) described by the present disclosure. In at least one example, one or more aspects of the process 4170 are executed by a control circuit (e.g. control circuit 400 of FIG. 2A) that includes a processor and a memory storing a set of computer-executable instructions that, when executed by the processor, cause the processor to perform the one or more aspects of the process 4170. Additionally, or alternatively, one or more aspects of the process 4170 can be executed by a combinational logic circuit (e.g. control circuit 410 of FIG. 2B) and/or a sequential logic circuit (e.g. control circuit 420 of FIG. 2C). Furthermore, the process 4170 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4170 monitors 4171 tissue stretch/shift during firing of the surgical instrument 4600 using visualization data from a visualization system (e.g. visualization system 100, 160, 500, 2108). In the example illustrated in FIG. 36B, a tissue stretch/shift (d) is monitored 4171 by tracking distortions in a structured light grid projected onto the tissue during firing and/or tracking the landmarks 4364, 4365, 4366, 4367, which represent positions of adjacent anatomical structure, using visualization data. Additionally, or alternatively, the tissue stretch (d) can be monitored 4171 by tracking the position of the landmark 4362 during firing. In the example of FIG. 36B, tissue stretch/shift (d) is the difference between the distance (d1) between the landmarks 4361, 4362 during firing and a distance (d2) between the landmarks 4361, 4362 during the firing. In any event, if 4172 the tissue stretch/shift (d) is greater than or equal to a predetermined threshold, the control circuit adjusts 4173 the firing parameters of the surgical instrument 4600 to reduce the tissue stretch/shift (d). For example, the control circuit may cause the controller 4620 to reduce the speed of the firing motor drive assembly 4604 by reducing current draw of the firing motor 4602, for example, which reduces the speed of advancement of the cutting member 4645. Additionally, or alternatively, the control circuit may cause the controller 4620 to pause the firing motor 4602 for a predetermined period of time to reduce the tissue stretch/shift (d).

Post firing, as illustrated in FIG. 36C, the jaws of the end effector 4642 are unclamped, and the stapled tissue shrinks due to the fired staples of the staple line 4363. FIG. 36C illustrates the projected staple line length defined by the distance (d1) and an actual staple line defined by a distance (d3) less than the distance (d1). The difference between the distances d1, d2 represents the shrinkage/shifting distance (d').

FIG. 38 is a logic flow diagram of a process 4180 depicting a control program or a logic configuration for adjusting a proposed staple cartridge arrangement along a proposed surgical resection path. The process 4180 includes monitoring 4081 stapled tissue shrinkage/shifting along a proposed surgical resection path following the firing of a staple cartridge of the proposed arrangement, and adjusting subsequent staple cartridge positions of the proposed arrangement along the proposed surgical resection path.

One or more aspects of the process 4180 can be executed by one or more of the control circuits (e.g. control circuit 132, 400, 410, 420, 602, 622, 2108, 4620) described by the present disclosure. In at least one example, one or more aspects of the process 4180 are executed by a control circuit (e.g. control circuit 400 of FIG. 2A) that includes a processor and a memory storing a set of computer-executable instructions that, when executed by the processor, cause the processor to perform the one or more aspects of the process 4180. Additionally, or alternatively, one or more aspects of the process 4180 can be executed by a combinational logic circuit (e.g. control circuit 410 of FIG. 2B) and/or a sequential logic circuit (e.g. control circuit 420 of FIG. 2C). Furthermore, the process 4180 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4180 monitors 4181 shrinkage/shifting of a stapled tissue along a proposed resection path 4312. In the example illustrated in FIG. 36C, a staple line 4363 is deployed into the tissue between the landmarks 4361, 4362 from a staple cartridge of the staple cartridge arrangement 4317. When the jaws of the end effector 4642 are unclamped, the stapled tissue shrinks/shifts a distance (d'). The distance (d') is the difference between the distance (d1) between the landmarks 4361, 4362 pre-firing, which represents a length of the staple line 4361 proposed by the arrangement 4317, and a distance (d3) representing the actual length of the staple line 4363.

To avoid gaps between consecutive staple lines, the control circuit adjusts subsequent staple cartridge positions of the proposed arrangement 4317 along the proposed surgical resection path 4312. For example, as illustrated in FIG. 36C an originally proposed staple line 4368 is removed and replaced with an updated staple line 4369 that extends through, or covers, the gap defined by the distance (d'). In various aspects, a tissue shrinkage/shift (d') is monitored 4181 by tracking distortions in a structured light grid projected onto the tissue after the jaws of the end effector 4642 are unclamped and/or tracking the landmarks 4364, 4365, 4366, 4367, which represent positions of adjacent anatomical structure, using visualization data. Additionally, or alternatively, the tissue shrinkage distance (d') can be monitored 4181 by tracking the position of the landmark 4362.

In various aspects, it may be desirable to corroborate visualization data derived from a surgical visualization system (e.g. visualization system 100, 160, 500, 2108) using non-visualization data from non-visualization systems and vice versa. In one example, a non-visualization system can include a ventilator, which can be configured to measure non-visualization data, such as volume, pressure, partial pressure of carbon dioxide ($PCO_2$), partial pressure of oxygen ($PO_2$), etc., of a patient's lungs. Corroborating visualization data with non-visualization data provides a clinician with greater confidence that the visualization data derived from the visualization system is accurate. In addition, corroborating the visualization data with the non-visualization data allows a clinician to better identify post-operative complications, as well as determine the overall efficiency of the organ, as will described in greater detail below. The corroboration may also be helpful in segmentectomy or complicated lobectomies without fissures.

In various aspects, a clinician may need to resect a portion of a patient's organ to remove a critical structure, such as a tumor, and/or other tissue. In one example, the patient's organ can be the right lung. A clinician may need to resect a portion of the patient's right lung in order to remove unhealthy tissue. However, the clinician may not want to remove too much of the patient's lung during the surgical procedure in order to ensure the lung's functionality is not too compromised. The lung's functionality can be assessed based on peak lung volume per breath, which represents peak lung capacity. In determining how much of the lung can be safely removed, the clinician is limited by a predetermined peak lung-capacity reduction beyond which the lung loses its viability, necessitating a full organ resection.

In at least one example, the surface area and/or volume of the lung is estimated from visualization data from surgical visualization system (e.g. visualization system 100, 160, 500, 2108). The lung surface area and/or volume can be estimated at peak lung capacity, or peak lung volume per breath. In at least one example, the lung surface area and/or volume can be estimated at multiple points throughout the inhalation/exhalation cycle. In at least one aspect, prior to resection of a portion of the lung, visualization data and non-visualization data can be utilized to correlate the surface area and/or volume of the lung determined by the visualization system with lung capacity as determined by a ventilator. Correlation data can be employed in developing a mathematical relation between the surface area and/or volume of the lung, as derived from visualization data, and the lung capacity, as determined by a ventilator, for example.

The relation can be employed in estimating the size of a lung portion that could be removed while maintaining the peak lung-capacity reduction at a value less than or equal to a predetermined threshold that sustains the viability of the lung.

FIG. 39 illustrates a logic flow diagram of a process 4750 for proposing a surgical resection of an organ portion, in accordance with at least one aspect of the present disclosure. The process 4750 is generally executed during a surgical procedure. The process 4750 may include proposing 4752 a portion of an organ to resect based on visualization data from the surgical visualization system, wherein resection of the portion is configured to yield an estimated capacity reduction of the organ. The process 4750 may further include determining 4754 a first value of a non-visualization parameter of the organ prior to resection of the portion and determining 4756 a second value of the non-visualization parameter of the organ after resection of the portion. Additionally, in certain examples, the process 4750 may further include corroborating 4758 the predetermined capacity reduction based on the first value of the non-visualization parameter and the second value of the non-visualization parameter.

One or more aspects of the process 4750 can be executed by one or more of the control circuits (e.g. control circuit 132, 400, 410, 420, 602, 622, 2108, 4620) described by the present disclosure. In at least one example, one or more aspects of the process 4750 are executed by a control circuit (e.g. control circuit 400 of FIG. 2A) that includes a processor and a memory storing a set of computer-executable instructions that, when executed by the processor, cause the processor to perform the one or more aspects of the process 4750. Additionally, or alternatively, one or more aspects of the process 4750 can be executed by a combinational logic circuit (e.g. control circuit 410 of FIG. 2B) and/or a sequential logic circuit (e.g. control circuit 420 of FIG. 2C). Furthermore, one or more aspects of the process 4750 can be executed by any suitable circuitry with any suitable hardware and/or software components that may be located in or associated with various suitable systems described by the present disclosure.

In various aspects, the process 4750 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4750 can be a component of a visualization system (e.g. visualization system 100, 160, 500, 2108).

FIG. 41A illustrates a set of patient's lungs 4780. In one embodiment, a clinician can utilize an imaging device 4782 to emit 4784 a pattern 4785 of light onto the surface of the patient's right lung 4786, such as stripes, grid lines, and/or dots, to enable the determination of the topography or landscape of the surface of the patient's right lung 4786. The imaging device can be similar in various respects to imaging device 120 (FIG. 1). As described elsewhere herein, projected light arrays can be employed to determine the shape defined by the surface of the patient's right lung 4786, and/or motion of the patient's right lung 4786 intraoperatively. In one embodiment, the imaging device 4782 can be coupled to the structured light source 152 of control system 133. In one embodiment, a surgical visualization system, such as surgical visualization system 100, could utilize the surface mapping logic 136 of control circuit 133, described elsewhere herein, to determine the topography or landscape of the surface of the patient's right lung 4786.

A clinician may provide a type of procedure that is to be performed, such as an upper right lobectomy, to a surgical system, such as surgical system 2100. In addition to providing the surgical procedure to be performed, the clinician may provide the surgical system with a maximum desired capacity of the organ to be removed during the surgical procedure. Based on the visualization data obtained from the imaging device 4782, the type of surgical procedure to be performed, and the maximum desired capacity to be removed, the surgical system can propose a resection path 4788 to remove a portion of the right lung 4790 that satisfies all of the clinician's inputs. Other methods of proposing surgical resection paths are described elsewhere herein. Any number of additional parameters can be considered by the surgical system in order to propose the resection path 4788.

In various instances, it may be desirable to ensure that the volume of the organ resected yields the desired capacity reduction from the patient's organ. In order to corroborate that the volume resected yields the desired capacity reduction, non-visualization data from non-visualization systems can be utilized. In one embodiment, a ventilator can be utilized to measure peak lung capacity in a patient over time.

In at least one example, a clinician may utilize the surgical system 2100 in a surgical procedure to remove a lung tumor. The control circuit may identify the tumor from visualization data, as described above in connection with FIGS. 13A-13E and may propose a surgical resection path that provides a safe margin around the tumor, as described above in connection with FIGS. 29-38. The control circuit may further estimate a volume of the lung at peak lung capacity. A ventilator can be utilized to measure the peak lung capacity prior to the surgical procedure. Using a predetermined mathematical correlation between visually estimated lung volume and lung capacity as detected by the ventilator, the control circuit is able to estimate a peak lung-capacity reduction associated with removing a portion of the lung, which includes the tumor and a safe margin of tissue around it. If the estimated lung capacity reduction is beyond a predetermined safety threshold, the control circuit can alert the clinician and/or propose a different surgical resection path that yields a lesser reduction in the lung capacity.

FIG. 41C illustrates a graph 4800 measuring a patient's peak lung capacity over time. Prior to resection of the portion of organ ($t_1$), a ventilator can measure peak lung capacity. In FIG. 41C, at time $t_1$ prior to resection of the portion 4790, the peak lung capacity is measured as being 6 L. In the example described above where the surgical procedure to be performed is an upper right lobectomy, a clinician may desire to only remove a volume of the patient's lung that yields a predetermined capacity reduction such that the patient's ability to breath is not compromised. In one embodiment, a clinician may desire to remove a portion yielding up to about 17% reduction of the patient's peak lung capacity, for example. Based on the surgical procedure and the desired capacity reduction, the surgical system can propose a surgical resection path 4788 that achieves removal of the lung portion while maintain peak lung capacity at a value greater than or equal to 83% of the un-resected peak lung capacity.

Utilizing ventilator data, as shown in FIG. 41C, the clinician can monitor the patient's peak lung capacity over time, such as prior to section 4802 and after resection 4804 of the portion of the lung 4790. At time $t_2$, the portion of the lung 4790 is resected along the proposed resection path 4788. As a result, the peak lung capacity measured by the ventilator drops. A clinician can corroborate with the ventilator data (pre-resection peak lung volume 4802 and post resection peak lung volume 4804) to ensure that the volume of the lung resected yields the desired capacity reduction from the lungs. As shown in FIG. 41C, after resection, the peak lung capacity has dropped to 5 L, which is approximately a 17% drop in peak lung capacity, which is approximately the same as the desired reduction in capacity. Using the ventilator data, the clinician has greater confidence that the actual reduction in capacity is aligned with the desired reduction in capacity achieved by the proposed surgical resection path 4788. In other embodiments, where there is a discrepancy between the non-visualization data and the visualization data, such as a larger drop in peak lung capacity than expected (too much lung resected) or a smaller drop in peak lung capacity than expected (not enough lung resected), the clinician can determine if appropriate action should be taken.

Referring now to FIG. 41B, the patient's right lung 4792 is shown after resection of the portion 4790. After resection of the portion 4790, the clinician may have inadvertently caused an air leak 4794, which results in air leaking into the space between the lung 4794 and chest wall, resulting in a pneumothorax 4796. As a result of the air leak 4794, the patient's peak lung volume per breath will steadily diminish over time as the right lung 4792 collapses. Dynamic surface area/volumetric analysis of the lung can be performed using the visualization data derived from a visualization system (e.g. visualization system 100, 160, 500, 2108) to detect an air leak by visually tracking a change in the volume of the lung. The volume and/or surface area of the lung can be tracked visually at one or more points during the inhalation/exhalation cycle to detect a volume change indicative of the air leak 4794. In one embodiment, as discussed above, projected light arrays from the imaging device 4782 can be employed to monitor motion of the patient's right lung 4786 over time, such as monitoring a decrease in size. In another embodiment, the surgical visualization system could utilize surface mapping logic, such as surface mapping logic 136, to determine the topography or landscape of the surface of the patient's right lung 4786 and monitor changes in the topography or landscape over time.

In one aspect, the clinician can utilize the non-visualization system, such as the ventilator, to corroborate the reduction in volume detected by the visualization system. Referring again to FIG. 41C, as described above, a patient's peak lung capacity can be measured prior to resection of the portion of the lung 4802 and after resection of the portion to corroborate the desired reduction in capacity aligns with the actual reduction in capacity of the lung. In the example described above where an air leak inadvertently occurred, peak lung capacity may steadily decline over time 4806. In one instance, at time t2 immediately after resection of the portion, a clinician may note the peak lung capacity has dropped from 6 L to 5 L, which is approximately aligned with the desired reduction in lung capacity. After resection of the portion, the surgical visualization system can monitor the patient's lung volume over time. If the surgical visualization system determines that there is a change in volume, the clinician can measure peak lung capacity again, such as at time $t_3$. At time $t_3$, the clinician may note that the peak lung capacity has dropped from 5 L to 4 L, which corroborates the data determined from the visualization system, which indicates that there may be an air leak in the right lung 4792.

In addition, the control circuit can be configured measure organ efficiency based on the visualization data and the non-visualization data. In one aspect, the organ efficiency can be determined by comparing visualization data to a difference in the non-visualization data before and after resection of the portion. In one example, the visualization system can generate the resection path to cause a 17% reduction in peak lung capacity. The ventilator can be configured to measure peak lung capacity before resection of the portion and after the resection of the portion. In the instance illustrated in FIG. 41C, there is approximately a 17% drop in peak lung capacity (6 L to 5 L). As there is a near 1:1 drop in actual lung capacity (17%) against desired lung capacity (17%), the clinician can determine that the lung is functionally efficient. In another example, the visualization system can generate the resection path to cause a 17% reduction in peak lung capacity. However, the ventilator may measure a drop in peak lung capacity that is greater than 17%, such as 25%, as an example. In this instance, the clinician can determine that the lung is not functionally efficient as resecting the portion of the lung resulted in a larger drop in peak lung capacity than would be expected.

FIG. 40 illustrates a logic flow diagram of a process 4760 for estimating a capacity reduction of an organ resulting from the removal of a selected portion of the organ, in accordance with at least one aspect of the present disclosure. The process 4760 is similar in many respects to the process 4750. Unlike the process 4750, however, the process 4760 relies on the clinician to select or propose a surgical resection path for removing a portion of an organ during a surgical procedure. The process 4760 includes receiving 4762 an input from a user indicative of a portion of an organ to resect. The process 4760 further includes estimating 4764 a capacity reduction of the organ that would result from removing the portion. In at least one example, the organ is a patient's lung, and the estimated 4762 capacity reduction is a reduction in the peak lung volume per breath of the patient's lung. Visualization data from a surgical visualization system (e.g. visualization system 100, 160, 500, 2108) can be employed to estimate the capacity reduction corresponding to removal of the portion. The process 4760 may further include determining 4766 a first value of a non-visualization parameter of the organ prior to resection of the portion and determining 4768 a second value of the non-visualization parameter of the organ after resection of the portion. Finally, the process 4760 may further include corroborating 4768 the estimated capacity reduction of the organ based on the first value of the non-visualization parameter and the second value of the non-visualization parameter.

One or more aspects of the process 4760 can be executed by one or more of the control circuits (e.g. control circuit 132, 400, 410, 420, 602, 622, 2108, 4620) described by the present disclosure. In at least one example, one or more aspects of the process 4760 are executed by a control circuit (e.g. control circuit 400 of FIG. 2A) that includes a processor and a memory storing a set of computer-executable instructions that, when executed by the processor, cause the processor to perform the one or more aspects of the process 4760. Additionally, or alternatively, one or more aspects of the process 4760 can be executed by a combinational logic circuit (e.g. control circuit 410 of FIG. 2B) and/or a sequential logic circuit (e.g. control circuit 420 of FIG. 2C). Furthermore, one or more aspects of the process 4760 can be executed by any suitable circuitry with any suitable hardware and/or software components that may be located in or associated with various suitable systems described by the present disclosure.

In various aspects, the process 4760 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4760 can be a component of a visualization system (e.g. visualization system 100, 160, 500, 2108).

In one instance, a clinician may provide an input to the surgical visualization system, such as surgical visualization system 2100, indicative of a portion of an organ to resect. In one instance, a clinician may draw a resection path on a virtual 3D construct of the organ, such as the virtual 3D construct generated 4104 during process 4100. In other instances, the visualization system can overlay a procedure layout plan, described in greater detail elsewhere herein, which can be in the form of a recommended treatment path. The recommended treatment path can based on a type of surgical procedure being performed. In one embodiment, the recommended treatment path can propose different starting points and propose different resection paths that the clinician can select between, similar to the resection paths 4146, 4147, 4148 described elsewhere herein. The proposed resection paths can be determined by the visualization system such that certain critical structures, such as arteries, are avoided. The clinician can select the proposed resection paths until a desired resection path to remove the portion of the organ is complete.

In one instance, the surgical visualization system can determine an estimated capacity reduction of the organ based on the selected resection path. After resecting the predetermined portion along the resection path, the clinician may desire to use non-visualization data to corroborate that the actual reduction in capacity corresponds to the estimated capacity reduction based on the visualization data. In one embodiment, this corroboration can be done using a similar procedure as described above in regard to process 4750 where the organ is a lung. The clinician can measure peak lung capacity before 4802 and after 4804 resection of the lung and compare the change in peak lung capacity to determine an actual drop in peak lung capacity. In one example, the surgical visualization system may estimate a 17% reduction in peak lung capacity based on the clinician's proposed resection path. Prior to resection, the clinician may note a peak lung capacity of 6 L (time $t_1$). After resection, the clinician may note a peak lung capacity of 5 L (time $t_2$), which is approximately a 17% drop in peak lung capacity. Using this non-visualization/ventilator data, the clinician has greater confidence that the actual reduction in capacity is aligned with the estimated reduction in capacity. In other instances, where there is a discrepancy between the non-visualization data and the visualization data, such as a larger drop in peak lung capacity than expected (too much lung resected) or a smaller drop in peak lung capacity than expected (not enough lung resected), the clinician can determine if appropriate action should be taken.

In addition, the control circuit can be configured to measure organ efficiency based on the visualization data and the non-visualization data. In one aspect, the organ efficiency can be determined by comparing visualization data to a difference in the non-visualization data before and after resection of the portion. In one example, the visualization system may estimate a 17% reduction in peak lung capacity based on the clinician's desired resection path. The ventilator can be configured to measure peak lung capacity before resection of the portion and after the resection of the portion. In the instance illustrated in FIG. 41C, there is approximately a 17% drop in peak lung capacity (6 L to 5 L). As there is a near 1:1 drop in actual lung capacity (17%) against the estimated lung capacity (17%), the clinician can determine that the lung is functionally efficient. In another example, the visualization system may estimate a 17% reduction in peak lung capacity based on the clinician's desired resection path. However, the ventilator may measure a drop in peak lung capacity that is greater than 17%, such as 25%, as an example. In this instance, the clinician can determine that the lung is not functionally efficient as resecting the portion of the lung resulted in a larger drop in peak lung capacity than would be expected.

As described above in regard to processes 4750, 4760, a clinician can corroborate visualization data with non-visualization data, such as by using a ventilator to measure peak lung volume before and after resection of a portion of the lung. Another example of corroborating visualization data with non-visualization data is through capnography.

FIG. 42 illustrates a graph 4810 measuring partial pressure of carbon dioxide ($PCO_2$) exhaled by a patient over time. In other instances, partial pressure of oxygen ($PO_2$) exhaled by a patient can be measured over time. The graph 4810 illustrates $PCO_2$ measured prior to resection 4812, immediately following resection 4814, and a minute after resection 4816. In FIG. 42, prior to resection 4812, $PCO_2$ is measured to be ~40 mmHg (at time t1). In the examples described above where the surgical procedure to be performed is an upper right lobectomy, a visualization system may desire or estimate a 17% decrease in lung capacity. The $PCO_2$ levels measured by the ventilator can be used to corroborate this desired or estimated reduction in capacity.

Utilizing the ventilator data, as shown in FIG. 42, the clinician can monitor the patient's $PCO_2$ over time, such as prior to section 4812 and immediately after resection 4814 of the portion of the lung 4790. At time $t_2$, the portion of the lung 4790 has been resected, and as a result, the $PCO_2$ measured by the ventilator can drop 4818. A clinician can corroborate with the ventilator data (pre-resection 4812 $PCO_2$ (at $t_1$) and post resection 4814 $PCO_2$ (at $t_2$)) to ensure that the actual reduction in capacity of the lung aligns with the estimated or desired reduction in capacity of the lungs. As shown in FIG. 42, immediately after resection 4814 of the portion 4790, the $PCO_2$ drops 4812, which can be measured as an approximate 17% drop in $PCO_2$ (~33.2 mmHg). Using this non-visualization/ventilator data, the clinician has greater confidence that the actual reduction in capacity of the lung aligns with the desired or estimated reduction in capacity of the lung.

In other instances, the clinician can utilize the non-visualization/$PCO_2$ data to determine discrepancies when compared to the visualization data. In one instance, immediately after resection 4814 of the portion 4790, at time t2, the $PCO_2$ may be measured at 4820, which is higher than the $PCO_2$ measured prior to resection 4812. The increase in $PCO_2$ may be the result of a bronchus being inadvertently occluded during the surgical procedure, causing $CO_2$ to build up within the patient. In another instance, immediately after resection 4814 of the portion 4790, at time t2, the $PCO_2$ may be measured at 4822, which is lower than the $PCO_2$ measured prior to resection 4812 and lower than expected. The decrease in $PCO_2$ may be a result of a vessel being inadvertently occluded during the surgical procedure, causing less $O_2$ being delivered to the body, and thus, less $CO_2$ being produced. In either case, the clinician can take appropriate action to remedy the situation.

The changes in $PCO_2$ can also be measured at a time other than immediately resection 4814, such as a minute after resection 4816 (such as at time $t_3$). At time $t_3$, other body functions (such as kidneys) compensate for the changes in $PCO_2$ as a result of the resection. In this situation, $PCO_2$ can be measured to be ~40 mmHg, or approximately the same that was measured prior to resection 4812. At time $t_3$, differences measured between the $PCO_2$ prior to resection 4812 can indicate the inadvertent occlusions discussed above. For example, at time $t_3$, $PCO_2$ may be measured 4824 as being higher than prior to resection 4812, indicating a possible inadvertently occluded bronchus, or $PCO_2$ may be measured 4826 as being lower than prior to resection 4812, indicating a possible inadvertently occluded vessel.

In addition, the control circuit can be configured measure organ efficiency based on the visualization data and the non-visualization data. In one aspect, the organ efficiency can be determined by comparing visualization data to a difference in the non-visualization data before and after resection of the portion. In one example, the visualization system may estimate a 17% reduction in capacity of the lung based on a clinician's desired resection path. The ventilator can be configured to measure $PCO_2$ before resection of the portion and after the resection of the portion. In the embodiment illustrated in FIG. 42, there is approximately a 17% drop in $PCO_2$ immediately after resection 4814. As there is a near 1:1 drop in $PCO_2$ (17%) against estimated reduction in capacity of the lung (17%), the clinician can determine that the lung is functionally efficient. In another example, the visualization system may estimate a 17% reduction in capacity of the lung based on the clinician's desired resection path. However, the ventilator may measure a drop in $PCO_2$ that is greater than 17%, such as 25%, as an example. In this instance, the clinician can determine that the lung is not functionally efficient as resecting the portion of the lung resulted in a larger drop in $PCO_2$ than would be expected.

In addition to peak lung volume and $PCO_2$ measurements described above, other non-visualization parameters that could be utilized including blood pressure or EKG data. EKG data would provide approximate frequency data on deformation of arteries. This frequency data with surface geometry changes within a similar frequency range could help identify critical vascular structures.

As described above, it may be desirable to utilize non-visualization data from non-visualization systems to corroborate visualization data derived from a surgical visualization system (e.g. visualization system 100, 160, 500, 2108). In the examples described above, the non-visualization data provides a means for corroborating visualization data after a portion of an organ has already been resected. In some instances, it may be desirable to supplement visualization data with non-visualization data prior to a portion of an organ being resected. In one example, non-visualization data could be used with visualization data to help determine characteristics of an organ that is going to be operated on. In one aspect, the characteristic could be an abnormality of the organ tissue that may not be suitable for cutting. The non-visualization data and the visualization data could help inform the surgical visualization system and the clinician about areas to avoid when planning out a resection path for the organ. This may be helpful in segmentectomy or complicated lobectomies without fissures.

FIG. 43 illustrates a logic flow diagram of a process 4850 for detecting a tissue abnormality based on visualization data and non-visualization data, in accordance with at least one aspect of the present disclosure. The process 4850 is generally executed during a surgical procedure. The process 4850 may include receiving 4852 first visualization data from the surgical visualization system in a first state of an organ and determining 4854 a first value of a non-visualization parameter of the organ in the first state. The process 4850 may further include receiving 4856 second visualization data from the surgical visualization system in a second state of the organ and determining 4858 a second value of the non-visualization parameter of the organ in the second state. The process may also include detecting 4860 a tissue abnormality based on the first visualization data, the second visualization data, the first value of a non-visualization parameter, and the second value of the non-visualization parameter.

One or more aspects of the process 4850 can be executed by one or more of the control circuits (e.g. control circuit 132, 400, 410, 420, 602, 622, 2108, 4620) described by the present disclosure. In at least one example, one or more aspects of the process 4850 are executed by a control circuit (e.g. control circuit 400 of FIG. 2A) that includes a processor and a memory storing a set of computer-executable instructions that, when executed by the processor, cause the processor to perform the one or more aspects of the process 4850. Additionally, or alternatively, one or more aspects of the process 4850 can be executed by a combinational logic circuit (e.g. control circuit 410 of FIG. 2B) and/or a sequential logic circuit (e.g. control circuit 420 of FIG. 2C). Furthermore, one or more aspects of the process 4850 can be executed by any suitable circuitry with any suitable hardware and/or software components that may be located in or associated with various suitable systems described by the present disclosure.

In various aspects, the process 4850 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4850 can be a component of a visualization system (e.g. visualization system 100, 160, 500, 2108).

FIG. 44A illustrates a right lung 4870 of a patient in a first state 4862. In one example, the first state 4862 could be a deflated state. In another example, the first state 4862 could be a collapsed state. An imaging device 4872 is shown inserted through a cavity 4874 in the patient's chest wall 4876. A clinician can utilize the imaging device 4872 to emit 4880 a pattern of light 4882 onto the surface of the right lung 4870, such as stripes, grid lines, and/or dots, to enable the determination of the topography or landscape of the surface of a patient's right lung 4870. The imaging device can be similar in various respects to imaging device 120 (FIG. 1). As described elsewhere herein, projected light arrays are employed to determine the shape defined by the surface of the patient's right lung 4870, and/or motion of the patient's right lung 4870 intraoperatively. In one embodiment, the imaging device 4782 can be coupled to the structured light source 152 of control system 133. In one embodiment, a surgical visualization system, such as surgical visualization system 100, could utilize the surface mapping logic 136 of control circuit 133, described elsewhere herein, to determine the topography or landscape of the surface of the patient's right lung 4786. In the first state 4862 of the right lung 4870, a ventilator can be used to measure parameters of the right lung 4870, such as a first state pressure ($P_1$ or positive end-expiratory pressure (PEEP)) or a first state volume ($V_1$).

FIG. 44B illustrates the right lung 4870 of the patient in a second state 4864. In one example, the second state 4864 could be a partially inflated state. In another example, the second state 4864 could be a completed inflated state. The imaging device 4872 can be configured to continue emitting 4880 the pattern of light 4882 onto the surface of the lung 4870 to enable the determination of the topography or landscape of the surface of the patient's right lung 4870 in the second state 4864. In the second state 4864 of the right lung 4870, the ventilator can be used to measure parameters of the right lung 4870, such as second state pressure ($P_2$) which is larger than the first state 4862 pressure $P_1$ and a second state volume ($V_2$) which is larger than the first state 4862 volume $V_1$.

Based on the surface topography determined from the surgical visualization system and imagine device 4872, along with the non-visualization data determined from the ventilator (pressure/volume), the surgical visualization system can be configured to determine abnormalities of the tissue of the right lung 4870. In one example, in the first state 4862, the imaging device 4872 can determine the first state 4662 topography of the right lung 4870 (shown in FIG. 44A and in greater detail in FIG. 44C) and the ventilator could determine a first state pressure/volume. In the second state 4864, the imaging device 4872 can determine the second state 4864 topography of the right lung 4870 (shown in FIG. 44B and in greater detail in FIG. 44D) and the ventilator could determine a second state pressure/volume, which are greater than the first state pressure/volume due to the lung being partially or completed inflated. Based on the known increase in pressure/volume, the visualization system can be configured to monitor changes in the topography of the right lung 4870 that are in accordance with the known increases in pressure/volume. In one aspect, this pressure/volume measurement from the ventilator can be correlated with surface deformation of the right lung 4870 to identify regions of disease within the lung to help inform stapler placement.

In one aspect, referring to FIGS. 44B and 44D, where pressure has increased from $P_1$ to $P_2$ (and volume has increased from $V_1$ to $V_2$), the surface topography determined from the structured light 4880 has changed compared to the first state 4862. In one example, the pattern of light 4882 can be dots and the dots have been spaced apart by distances from each other as the lung size increases. In another example, the pattern of light 4882 can be grid lines and the grid lines have been spaced apart or contoured as the lung size increases. Based on the known pressure increase, the imaging device can determine regions 4886 that did not change in accordance with the known pressure and volume increases. For example, where the imaging device 4872 emits a pattern 4882 of grid lines and dots onto the surface of the right lung 4870 (shown in FIGS. 6A-6D), the visualization system can be configured to monitor the contours of the grid lines and the positioning of the dots relative to one another for known pressure/volume increases. Where the visualization systems notices irregularities in the spacing of the dots or the positioning and curvature of the gridlines, the visualization system can determine that those regions correspond to potential abnormalities of the tissue, such as subsurface voids 4886 or regions where a critical structure 4884, such as a tumor, may be positioned. In one embodiment, referring to process 4100 where the process 4100 identifies 4105 anatomical structures of at least a portion of the anatomical organ, which are relevant to the surgical procedure, the process 4100 could identify abnormalities as described hereinabove and overlay these abnormalities onto the 3D construct.

In one example, a patient may have emphysema, which is a lung condition that causes shortness of breath. In people with emphysema, the air sacs in the lungs (alveoli) are damaged and, over time, the inner walls of the air sacs weaken and rupture, creating larger air spaces instead of many small ones. This reduces the internal surface area for of the lungs, used for $O_2/CO_2$ exchange, which therefore, reduces the amount of oxygen that reaches the bloodstream. In addition, the damaged alveoli do not function properly and old air becomes trapped, leaving no room for fresh, oxygen-rich air to enter. The voids within the lung in emphysema patients represent regions with less tissue thickness and can therefore influence stapling outcomes in the region. The tissue is also weakened, which results in the alveoli rupturing, and is less able to hold staples that pass through them.

As the lung with emphysema inflates and deflates, the regions with subsurface voids will have different amounts of deformation as the pressure changes compared to healthy tissue. Utilizing the above-described process 4850, these weak tissue regions with subsurface voids can be detected to inform the clinician that they should avoid stapling through these regions, which can decrease the likelihood of post-operative air leaks. The tissue deformation capabilities of this process 4850 would permit the detection of these differences allowing the surgeon to be guided in the placement of the stapler.

In a second example, a patient may have cancer. Prior to the procedure, the tumor may have been irradiated, which damages the tissue as well as the surrounding tissue. Irradiation changes the properties of the tissue, often making it much stiffer and less compressible. If the surgeon needs to staple across this tissue, the change in tissue stiffness should be considered when selecting a staple reload type (e.g. stiffer tissue will require a taller formed staple).

As the lung inflates and deflates, the regions with stiffer tissues will have different amounts of deformation compared to healthy tissue as the lung is less compliant in these regions. The tissue deformation capabilities of this process 4850 would permit the detection of these differences allowing the surgeon to be guided in the placement of the stapler, as well as and the selection of the cartridge/reload color.

In another aspect, a memory, such as memory 134, may be configured to store surface topographies of lungs for known pressures and volumes. In this instance, an imaging device, such as imaging device 4872, can emit a pattern of light to determine the topography of the surface of the patient's lung at a first known pressure or volume. The surgical system, such as surgical system 2100, can be configured to compare the first determined topography at the known first pressure or volume to topographies stored in the memory 134 for the given first pressure or volume. Based on the comparison, the visualization system can be configured to indicate potential abnormalities of the tissue in only a single state. The visualization system can note these potential areas of abnormalities and proceed with determining the topography of the surface of the patient's lung at a second known pressure or volume. The visualization system can compare the second determined surface topography to topographies stored in the memory for the second given pressure or volume, as well as the topography determined at the first known pressure or volume. If the visualization system determines potential areas of abnormalities that overlap with first determined potential areas of abnormalities, the visualization system can be configured to indicate the overlapping areas as potential abnormalities with greater confidence based on the comparisons at the first and second known pressure or volumes.

In addition to the above, a $PO_2$ measurement from a ventilator could be compared with the inflation lung volume, such as $V_2$ versus the deflated lung volume, such as $V_1$. The volume comparison could utilize EKG data to compare inhalation and exhalation that could be compared with blood oxygenation. This could also be compared with anesthesia gas exchange measurement to determine breathing volume versus oxygen intake versus sedation. In addition, EKG data could provide approximate frequency data on deformation of arteries. This frequency data with surface geometry changes within a similar frequency range could help identify critical vascular structures.

In another embodiment, current tracking/procedure information can be compared with a pre-surgical planning simulation. In challenging or high-risk procedures, the clinician can utilize pre-operative patient scans to simulate a surgical approach. This dataset could be compared in the display, such as display 146, against real time measurements to help enable a surgeon to follow a particular pre-surgical plan based on training runs. This would require the ability to match fiducial landmarks between pre-operative scans/simulations and current visualization. One method may simply use boundary tracking of an object. Insights into how current device-tissue interaction compares against previous interactions (per patient) or anticipated interaction (database or past patients) for tissue type discernment, relative tissue deformation assessment, or sub-surface structural differences can be stored in memory, such as memory 134.

In one embodiment, surface geometry could be a function of a tool position. A surface reference can be selected when no change in surface geometry is measured per change in tool position. As the tool interacts with tissue and deforms the surface geometry, the change in surface geometry as a function in tool position can be computed by the surgical system. For a given change in tool position upon contact with the tissue, the change in tissue geometry may be different in regions with sub-surface structures, such as critical structure 4884, than in regions without such structures, such as sub-surface voids 4886. In one example, such as thoracic procedures, this could be above an airway versus being in parenchyma only. A running average of the change in tool position versus change in surface geometry can be computed by the surgical system using the surgical visualization system for the given patient to given patient-specific differences, or the value can be compared to a second set of previously collected data.

Imaging System Utilizing Fusion Imagery

One issue inherent to surgical procedures where surgeons rely upon imaging systems 142 (FIG. 2) is obstructions to the camera 144 (FIG. 2) that impinge upon the imaging systems' 142 ability to visualize the surgical site and, thus, the surgeon's ability to perform the surgical tasks required for the procedure. Obstructions can include, for example, fluid (e.g., blood) on the lens of the camera 144, on the surface of the body cavity, or otherwise present at the surgical site; smoke generated by electrosurgical instruments or other aerosols present within the body cavity; and/or tissues or other structures overlaying the target tissues or structures. A surgical system could be configured to utilize various imaging techniques to compensate for obstructions including multispectral imaging of sub-regions of the FOV of the camera 144, interpolating sub-regions of prior image frames captured by the camera 144, comparative multispectral analysis of captured images, and so on.

In one general aspect, the present disclosure is directed to a surgical system configured to utilize segments of images captured at a sampling rate via an imaging system 142 a multispectral light source to minimize the impairment of visualization due to various obstructions (e.g., surgical smoke). In one aspect, the surgical system can be configure to combine hyperspectral imaging with visible light imaging to minimize image interference caused by obstructions. The surgical system can, for example, be configured to detect aspects of underlying or obstructed portions of surgical instruments, the surgical site, or the surroundings by utilizing a separate wavelength or range of wavelengths of EMR. For example, the surgical system can utilize a frame from a sequential scanning device to transmit separate wavelength(s) of EMR, include a hyperspectral imaging device configured to scan both within and outside of the visible light spectrum, or a second imaging system configured to emit EMR at a different length than the first or primary imaging system. Accordingly, the surgical system can be configured to identify obstructed portions of image frames at a particular wavelength or set of wavelengths and interpolate or substitute portions of the obstructed image portions with unobstructed image portions of image frames obtained at other EMR wavelengths in order to provide a fully visualized, unobstructed image of the surgical site for the users.

In aspects utilizing an imaging system including a hyperspectral imaging device, the hyperspectral imaging device could scan at a particular rate (e.g., 240 frames per second) that would allow a portion of the emitted scan to include EMR from a near IR or UV laser source. Since those EMR at those wavelengths are not affected in the same manner as visible light to obstructions such as surgical smoke, fluids, and so on, the hyperspectral imaging device could be utilized to obtain images of shapes, contours, or features that exist in both the hyperspectral image and the corresponding visible light image. A control system of the surgical system, such as the control system 133 illustrated in FIG. 2, could then be configured to substitute obstructed portions of the images obtained utilizing visible light with the corresponding detected hyperspectral feature(s) or image portion(s) to complete the visualization for the surgeon. As another example, the imaging system can include a tunable EMR source (e.g., the spectral light source 150) that is controllable by the control system 133 to emit EMR at a wavelength or set of wavelengths where absorption of the EMR by water is at a minimum (e.g., in the visible blue-green wavelength range) since obscuration by water or water-containing fluids is especially likely during a surgical procedure. As another example, the surgical system could further include a second imaging system in addition to the first primary imaging system (e.g., the imaging system 142 shown in FIG. 2). In this example, the first imaging system 142 could be configured for imaging of the visible or near visible EMR spectrums and the second imaging system could be configured for imaging of a different wavelength spectrum(s) (e.g., long-wave IR (LWIR)). Accordingly, the second imaging system could be activated or otherwise utilized by the surgical system as needed when the first imaging system is being obscured. In these various aspects, the surgical system would minimize the amount of cleaning required for the camera 144 (e.g., to remove obstructions from the image sensor 135 or other scanning array) and prevent temporary loss of sight of the surgical field due to obstructions between the camera 144 and the surgical field (e.g., surgical smoke or insufflation gasses).

In particular examples, the imaging or visualization systems are described as including a hyperspectral imaging device or as utilizing hyperspectral imaging techniques. However, it should be noted that hyperspectral imaging is one particular type of multispectral imaging. In hyperspectral imaging, the wavelength "bins" are continuous, so hyperspectral imaging techniques are utilizing the entire EMR spectrum. Conversely, multispectral can mean that the "bins" are separated. In other words, a multispectral imaging system may sense EMR within, for example, the visible, mid-wave IR (MWIR), and LWIR portions of the EMR spectrum (there can be gaps that a multispectral imaging system does not sense in, e.g., the near IR (NIR) portion of the EMR spectrum and/or between MWIR and LWIR portions). The imaging or visualization systems and methods described herein should not be construed to be limited to any particular example, including examples describing hyperspectral imaging. In fact, the imaging or visualization systems and methods can broadly utilize any multispectral imaging devices and techniques.

In order to assist in the understanding of the aforementioned systems and methods, various examples will be described within the context of a video-assisted thoracoscopic surgery (VATS) procedure. It should be understood that this is simply for illustrative purposes though and that the described systems and methods are applicable to other contexts and/or surgical procedures, however. A VATS procedure is a surgical procedure whereby one or more surgical instruments and one or more thoracoscopes (i.e., cameras) are inserted into the patient's chest cavity through slits positioned between the patient's ribs. The cameras are utilized to provide the surgeons with a view of the interior of the patient's chest cavity to allow the surgeon to properly position/move the surgical instrument(s) and manipulate tissue/structures within the chest cavity. Accordingly, FIG. 45 is a diagram of a surgical system 3000 during the performance of a surgical procedure on a lung 3010, in accordance with at least one aspect of the present disclosure. A surgical system 3000 for performing a video-assisted surgical procedure can include a variety of different surgical devices, including an imaging device 3002, a grasper 3004, an electrosurgical instrument 3006 or another surgical instrument, and a smoke evacuator 3008. Further, the surgical system 3000 can include or be coupled to a surgical hub 2106, 2236 (FIGS. 17-19), a visualization system 2108 (FIGS. 17-19) or an imaging system 142 (FIG. 2), a control system 133 (FIG. 2), a robotic system 2110 (FIGS. 17-19), and any other systems or devices described herein. The imaging device 3002 can include a camera 144 (FIG. 2), a spectral light source 150 (FIG. 2), a structured light source 152 (FIG. 2), any other imaging emitters or receivers described herein, or combinations thereof. The imaging device 3002 can be configured to capture and provide images or video of the surgical site within a FOV 3020 to a display screen (e.g., the display 146 as in FIG. 2) for viewing by a user (e.g., a surgeon). The imaging device 3002 can be configured to sense EMR within or outside of the visible light portion of the EMR spectrum and thereby visualize tissues and/or structures that are either visible or invisible to the naked eye. Based on the visualization provided by the imaging system 142 associated with the imaging device 3002, the surgeon can then control the surgical devices to manipulate the tissues and/or structures to perform the surgical procedure.

During a surgical procedure, various obscurants, such as surgical smoke clouds 3014 or other aerosols, fluids, gasses, tissues, structures, and so on, can move across the FOV 3020 of the imaging device(s) 3002 and thereby prevent the imaging system 132 from being able to fully visualize the surgical site, which can in turn negatively impact the surgeon's ability to perform the procedure. Many surgical systems 3000 include smoke evacuators 3008 to remove surgical smoke clouds 3014, other aerosols, and gasses from the body cavity being operated on. However, smoke evacuators 3008 may not be sufficient to remove all obscurants or there may be a delay associated with the removal of the obscurants during which the surgeon is unable to properly visualize the surgical site. Accordingly, systems and methods are needed to compensate for the presence of obscurants and allow for visualization of a surgical site through those obscurants.

In one aspect, an imaging system, such as the imaging system 142 illustrated in FIG. 2, can be configured to utilize hyperspectral imaging and image fusion techniques to allow for visualization through obscurants. For example, FIG. 46 is a diagram of an imaging device 3002 faced with multiple obscurants. In this example, the target of the surgical procedure is a subsurface tumor 3038. However, to actually visualize the tumor 3038, the imaging device 3002 would have to compensate for a number of different obscurants, including fluid 3030 present on the lens of the imaging device 3002, surgical smoke 3032 present within the body cavity, blood 3034 on the surface of the tissue 3036, the tissue 3036 itself, and structures 3040 located throughout the tissue 3036. In one aspect, the imaging device 3002 can be a hyperspectral imaging device that is configured to sense EMR across the wavelength spectrum. EMR interacts differently with various objects at different wavelengths. In particular, certain wavelengths of EMR may not be absorbed by particular obscurants at particular wavelengths or wavelength ranges. Therefore, by sensing EMR at multiple portions of the EMR spectrum, the imaging system 142 can visualize through obscurants by sensing EMR at wavelengths that are not absorbed by the obscurants. Further, the wavelengths sensed by the imaging device 3002 can be selected to sense at wavelengths that are non-interactive (or substantially non-interactive) with typical or expected obscurants. In the depicted example, the imaging device 3002 can be configured to sense EMR within the visible light, MWIR, and LWIR portions of the EMR spectrum.

In one aspect, a control system can be configured to utilize multispectral (e.g., hyperspectral) imaging to visualize a surgical site at multiple portions of the EMR spectrum and then provide a visualization to a user that is free from obscurants by replacing obscured portions of an image captured at one wavelength range with a corresponding portion of an image that is captured at another portion of the wavelength range that is not absorbed by the obscurant. One example of such an algorithm is shown in FIG. 47, which is a logic flow diagram of a process 3050 for generating fused images utilizing a multispectral EMR source. In the following description of the process 3050, reference should also be made to FIG. 2 and FIG. 46. The process 3050 can be embodied as, for example, instructions stored in a memory 134 coupled to a control circuit 132 that, when executed by the control circuit 132, cause the control circuit 132 to perform the enumerated steps of the process 3050. For brevity, the process 3050 is described as being executed by the control circuit 132; however, it should be understood that the process 3050 can be executed by other combinations of hardware, software, and/or firmware.

Accordingly, the control circuit 132 executing the process 3050 can cause the imaging system 142 to sense 3052 EMR (e.g., via the imaging device 3002) at a first wavelength range (e.g., visible light) from the surgical site and then generate 3054 a corresponding first image therefrom. Correspondingly, the control circuit 132 can cause the imaging system 142 to sense 3056 EMR (e.g., via the imaging device 3002) at a second wavelength range (e.g., MWIR or LWIR) from the surgical site and then generate 3058 a corresponding second image therefrom.

Accordingly, the control circuit 132 can determine 3060 whether the first image is at least partially obstructed. The control circuit 132 can be configured to make this determination by detecting obstructions utilizing object recognition and other computer vision techniques. If the first image is not at least partially obstructed, then the process 3050 proceeds along the NO branch and the control circuit 132 can continue sensing 3052, 3054 EMR and generating 3054, 3058 corresponding images, as described above. If the first image is at least partially obstructed (i.e., there is an obstruction present within the image), then the process 3050 proceeds along the YES branch and the control circuit 132 can generate 3062 a third image by replacing the obstructed portion of the first image with the corresponding portion of the second image. If the second wavelength range was selected such that it is not absorbed by the obscurant, then the corresponding portion of the second image should be unobstructed. Therefore, the third image should provide an unobstructed visualization of the surgical site for viewing by the surgeon.

For the brevity, the process 3050 is described in the context of generating and combining two images captured at two different wavelength ranges; however, the imaging system 142 can be configured to sense and generate images at any number of wavelength ranges. FIG. 46, for example, illustrates an implementation that combines image data from at least three different EMR wavelength ranges to generate the resulting image. Each of the depicted first image 3042a, second image 3042b, third image 3042c, and fourth image 3042d include an array of pixels 3043 that collectively visualize the surgical site at the corresponding EMR wavelength range. In this example, the first image 3042a was captured utilizing the visible light portion of the EMR spectrum and includes a first unobstructed portion 3044a, with the remaining portions of the image 3042a being obstructed; the second image 3042b was captured utilizing the MWIR portion of the EMR spectrum and includes a second unobstructed portion 3044b; and the third image 3042c was captured utilizing the LWIR portion of the EMR spectrum and includes a third unobstructed portion 3044c. The control system 133 can also be configured to perform various image processing techniques on the various generated images to improve the visualizations provided thereby. For example, the fourth image 3042d was also captured utilizing the visible light portion of the EMR spectrum and thus can correspond to the first image 3042a, but includes additional image processing to identify a fluid (water) obstructed portion 3044d. Accordingly, the corresponding portion of the first image 3042a could be filtered at a corresponding wavelength or wavelength range (e.g., the blue-green portion of the visible light spectrum) to remove the obstruction. Accordingly, a control circuit 132 executing the process 3050 can be configured to generate a combination or fused image 3070 from the aforementioned initial images 3042a, 3042b, 3042c, 3042d. The fused image 3070 can include a first portion 3072 corresponding to the unobstructed portion 3044a of the first image 3042a generated from the visible light portion of the EMR spectrum, a second portion 3074 corresponding to the unobstructed portion 3044b of the second image 3042b generated from the MWIR portion of the EMR spectrum, a third portion 3076 corresponding to the unobstructed portion 3044c of the third image 3042c generated from the LWIR portion of the EMR spectrum, and a fourth portion 3078 corresponding to the obstructed portion 3044d of an image generated from the visible light portion of the EMR spectrum, but post-processed to remove the blue-green portion of the visible light spectrum. Each of the aforementioned image portions 3072, 3074, 3076, 3078 can be fused together by the control system 133 to generate the fused image 3070 that provides for an unobstructed visualization of the tumor 3038 and any other relevant structures 3040.

Another technique that can be utilized to compensate for obscurants present at the surgical site is to image sub-region interpolation, whereby portions of an image that are obscured, damaged, or otherwise interfered with can be replaced by corresponding portions of images from a synchronized image set. For example, a surgical control system could utilize lucky-region fusion (LRF) techniques to enhance the quality of the visualization provided to users by using multiple image frames. In one aspect, a control system can be configured to provide a visualization to a user that is free from obscurants by replacing obscured portions of an image with an unobscured portion of a previously captured image. One example of such an algorithm is shown in FIG. 49, which is a logic flow diagram of a process 3100 for generating fused images utilizing multiple image frames. In the following description of the process 3100, reference should also be made to FIG. 2 and FIGS. 50-52. The process 3100 can be embodied as, for example, instructions stored in a memory 134 coupled to a control circuit 132 that, when executed by the control circuit 132, cause the control circuit 132 to perform the enumerated steps of the process 3100. For brevity, the process 3100 is described as being executed by the control circuit 132; however, it should be understood that the process 3100 can be executed by other combinations of hardware, software, and/or firmware.

Accordingly, the control circuit 132 executing the process 3100 can (e.g., via the imaging system 142) generate 3102 an image of the surgical site and then determine 3104 whether the image is at least partially obstructed, as described above. For example, FIG. 50 is a diagram of a series 3150 of n image frames 3160 captured by the imaging system 142. The nth image frame 3160 can be the most recently captured image frame 3160, the (n−1)th image frame 3160 can be the immediately previously captured image frame 3160, and so on. Each of the image frames 3160 comprises a number of pixels 3151, which may or may not correspond to the pixels or cells of an image sensor 135, for example. As can be seen in FIG. 50, the image frames 3160 can include unobstructed portions 3162 and obstructed portions 3164. In evaluating the nth image frame 3160 specifically, a control circuit 123 executing the process 3100 would determine that the nth image frame 3160 is at least partially obstructed because it includes an obstructed portion 3164 of pixels 3151.

If the control circuit 132 determines 3104 that the image is not at least partially obstructed, then the process 3100 proceeds along the NO branch and the control circuit 132 can cause the imaging system 142 to continue generating images (i.e., visualizing the surgical site) for visualization of the surgical site, as described above. If the control circuit 132 determines 3104 that the image is at least partially constructed (e.g., as shown in the nth image frame 3160), then the process proceeds along the YES branch and the control circuit 132 can retrieve 3106 a prior image from the image set 3150. In one aspect, the control circuit 132 can successively retrieve 3106 one or more prior images from the image set 3150 until the control circuit 132 has located corresponding unobstructed image portions with which they replace the obstructed portion(s) of the first image.

Accordingly, the control circuit 132 can generate 3108 an updated image from the original image and the one or more prior images retrieved from the image set 3150. For example, FIG. 51 and FIG. 52 illustrated an updated or fused image 3152 generated from multiple successive image frames 3160. In this particular example, n is equal to 60, although this is simply for illustrative purposes. In FIG. 51, the number indicated within each pixel 3151 corresponds to the image frame 3160 from which the particular pixel 3151 was extracted. As can be seen, the fused image 3152 is generated from a combination of pixels 3151 across a number of different image frames 3160. Specifically, image frames 3160 55 through 60, which in turn correspond to the (n−5)th through nth image frames 3160, respectively, as shown in FIG. 50. Accordingly, the control circuit 132 can be configured to repeatedly retrieve 3106 a preceding image from the image set 3150 captured by the imaging system 142 and extract the image portions, such as the pixels 3151, that are unobstructed in the retrieved image, but correspond to pixels 3151 that are obstructed in the successive image. The control circuit 132 can repeat this process until a completely or substantially unobstructed collection of image portions from the image set 3150 have been retrieved and then fuse the image portions together to generate 3108 an updated image. A resulting fused image 3152 generated using this technique is shown in FIG. 52, illustrating how a tumor 3038 and structures 3140, such as vessels, would be visualized for users from an initial partially obstructed image.

Another technique that can be utilized to compensate for obscurants present at the surgical site is to perform a comparative analysis of a set of synchronized imaging devices. A control system 133 could be configured to interlace multiple image portions generated by multiple synchronized imaging devices to generate a fused image. In particular, a portion of an image generated by a first or primary imaging system (e.g., the imaging system 142 shown in FIG. 2) could be substituted with a corresponding portion of an image generated by a secondary imaging system. In particular, a set of imaging systems could be configured to time index their scans. Obscured, corrupted, indistinct, or otherwise interfered with portions of a first scan generated by a first imaging system could be replaced with clearer and/or verified portions of a second scan (which is time indexed in accordance with the first scan) generated by a second imaging system. If image data is missing, corrupted, or obscured in the imaging of the primary dynamic data set generated by a first imaging system, a secondary scan from another imaging system (which could also be sensing in another wavelength or range of wavelengths) could be utilized by a control system 133 to sharpen, replace, or interpolate the primary image to improve the visualization of the surgical site for users.

Surgical System Control Based on Multiple Sensed Parameters

One issue that is inherent to any surgical procedures and surgical instruments is controlling the surgical instruments in an ideal manner for the given patient and/or tissue conditions. To that end, some surgical instruments include sensors for sensing various parameters associated with the surgical instruments and/or the tissues being manipulated by the surgical instruments. However, some sensed data can be indicative of different states or conditions of the tissue and can thus be inconclusive absent additional data. Accordingly, a surgical system could incorporate data from an imaging system with other sensed data to resolve ambiguities and control surgical instruments ideally according to the determined state/condition of the tissue.

In one general aspect, the present disclosure is directed to a control system configured to utilize of two sources of related, but not identical, data sources to differentiate between different states of a tissue being acted on by a surgical instrument. Such states that include, for example, fluid flow within the tissue and thermal impacts of energy directed by a surgical instrument on the tissue. The control system can be configured to control a surgical instrument, such as the surgical instrument 3290 described below.

FIG. 53 is a schematic diagram of a surgical instrument 3290 configured to control various functions, in accordance with at least one aspect of the present disclosure. In one aspect, the surgical instrument 3290 is programmed to control distal translation of a displacement member such as the closure member 3264. The surgical instrument 3290 comprises an end effector 3292 that may comprise a clamp arm 3266, a closure member 3264, and an ultrasonic blade 3268, which may be interchanged with or work in conjunction with one or more RF electrodes 3296 (shown in dashed line). The ultrasonic blade 3268 is coupled to an ultrasonic transducer 3269 driven by an ultrasonic generator 3271.

In one aspect, sensors 3288 may be implemented as a limit switch, electromechanical device, solid-state switches, Hall-effect devices, MR devices, GMR devices, magnetometers, among others. In other implementations, the sensors 3288 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 3288 may include electrical conductor-less switches, ultrasonic switches, accelerometers, and inertial sensors, among others.

In one aspect, the position sensor 3284 may be implemented as an absolute positioning system comprising a magnetic rotary absolute positioning system implemented as an AS5055EQFT single-chip magnetic rotary position sensor available from Austria Microsystems, AG. The position sensor 3284 may interface with the control circuit 3260 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 3284 may be omitted. Where the motor 3254 is a stepper motor, the control circuit 3260 may track the position of the closure member 3264 by aggregating the number and direction of steps that the motor has been instructed to execute. The position sensor 3284 may be located in the end effector 3292 or at any other portion of the instrument.

The control circuit 3260 may be in communication with one or more sensors 3288. The sensors 3288 may be positioned on the end effector 3292 and adapted to operate with the surgical instrument 3290 to measure the various derived parameters such as gap distance versus time, tissue compression versus time, and anvil strain versus time. The sensors 3288 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 3292. The sensors 3288 may include one or more sensors.

An RF energy source 3294 is coupled to the end effector 3292 and is applied to the RF electrode 3296 when the RF electrode 3296 is provided in the end effector 3292 in place of the ultrasonic blade 3268 or to work in conjunction with the ultrasonic blade 3268. For example, the ultrasonic blade is made of electrically conductive metal and may be employed as the return path for electrosurgical RF current. The control circuit 3260 controls the delivery of the RF energy to the RF electrode 3296.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

In various aspects, the sensors 3288 of the surgical instrument 3290 can include sensors configured to detect or take measurements of various electrical parameters associated with a tissue acted on by the surgical instrument 3290, such as the capacitance or impedance of the tissue. In various aspects, the sensors 3288 can also include sensors configured to detect or take measurements of various physical parameters associated with the tissue acted on by the surgical instrument 3290, such as the temperature, viscoelastic compression (e.g., the tissue creep, time to stability, or rate of initial loading), or thickness (e.g., which can be detected upon first contact of the jaws with the tissue). Further, the image sensor 135 of the control system 133 illustrated in FIG. 2 can be utilized to detect or take measurements of various tissue parameters based on the EMR emitted by the imaging system 142 using the various techniques described above. For example, the image sensor 135 can be configured to detect the refractivity of the tissue at various wavelengths, the polarization of EMR/light reflected by the tissue, passive IR emissions by the tissue, or Doppler wavelength shift associated with the tissue. Any of these imaging-based parameters can be utilized in conjunction with other sensed parameters (e.g., electrical or physical parameters) to ascertain the state or condition of the tissue that may not be directly ascertainable via the parameters individually.

In one aspect, a control system can be configured to control one or more operational parameters associated with the surgical system based on the state or condition of the tissue being acted on by a surgical instrument, which can be determined based on parameters sensed by the imaging system and other sensors. One example of such an algorithm is shown in FIG. 54, which is a logic flow diagram of a process 3300 for controlling a surgical system according to sensed parameters. In the following description of the process 3300, reference should also be made to FIG. 2 and FIG. 53. The process 3300 can be embodied as, for example, instructions stored in a memory 134 coupled to a control circuit 132 that, when executed by the control circuit 132, cause the control circuit 132 to perform the enumerated steps of the process 3300. For brevity, the process 3300 is described as being executed by the control circuit 132; however, it should be understood that the process 3300 can be executed by other combinations of hardware, software, and/or firmware.

Accordingly, a control circuit 132 executing the process 3300 can receive 3302 a measurement of a first tissue parameter via the imaging system 142. As noted previously, the first tissue parameter can include, for example, the refractivity of the tissue at various wavelengths, the polarization of light reflected by the tissue, passive IR emissions by the tissue, or Doppler wavelength shift associated with the tissue.

Accordingly, the control circuit 132 can receive 3304 a measurement of a second tissue parameter via the sensor(s) 788. As noted previously, the second tissue parameter can include, for example, various electrical and/or physical characteristics of the tissue, such as the temperature, viscoelastic compression, or thickness of the tissue.

Accordingly, the control circuit 132 can determine 3306 a state or condition of the tissue based on the combination of the measurements of the received 3302, 3304 tissue parameters and then control 3308 the surgical instrument 3290 accordingly. The same measurement value for various electrical and/or physical characteristics of the tissue can be indicative of different conditions of the tissue, which can in turn necessitate different control adjustments to be applied to the surgical instrument 3290. Absent additional or supplementary information, a control system 133 may not control the surgical instrument 3290 correctly for the given condition of the tissue in situations where the tissue condition is ambiguous based on the measurement value for various electrical and/or physical characteristics of the tissue. Therefore, the presently described control system supplements the electrical and/or physical characteristic(s) sensed by the sensor(s) 3288 with a tissue parameter(s) sensed via the imaging system 142 in order to accurately ascertain the state or condition of the tissue and then control the surgical instrument 3290 in an appropriate manner. For example, different manners of controlling a surgical instrument 3290 could be appropriate in response to detecting an increase in the tissue temperature (i.e., the second tissue parameter received 3304 during the process 3300) localized to the end effector 3292 of the surgical instrument 3290. If the control system 133 detects a corresponding change in the polarization or refractivity of the tissue (i.e., the first tissue parameter received 3302 during the process 3300), then the control circuit 132 can determine 3306 that the tissue is suffering from collateral thermal damage and control 3308 the surgical instrument 3290 to decrease the instrument power level or provide a suggestion to the user to decrease the instrument power level. Conversely, if no corresponding change in the polarization or refractivity of the tissue is detected, then the control circuit 132 can determine 3306 that the tissue is not suffering from collateral thermal damage and control 3308 the surgical instrument 3290 to maintain or increase the instrument power level or provide a suggestion to this effect. As another example, different manners of controlling a surgical instrument 3290 could be appropriate in response to detecting the tissue impedance (i.e., the second tissue parameter received 3304 during the process 3300) for the tissue grasped by the end effector 3292 of the surgical instrument 3290. If the control system 133 detects no change in the tissue impedance while the imaging system 142 visualizes movement, creep, or compression of the tissue (i.e., the first tissue parameter received 3302 during the process 3300), then the control circuit 132 can determine 3306 that there is a subsurface irregularity in the grasped tissue.

The control system 133 described herein can be, for example, implemented on or executed by surgical instrument 3290, a surgical hub 2236 (FIG. 21) to which a surgical instrument 3290 (e.g., an energy device 3241 as shown in FIG. 21) is communicably couplable, or a combination thereof (e.g., using a distributed processing protocol). When the control system is embodied as a component of a surgical instrument 3290, the imaging data can be received by either directly from the imaging system 142 or through a surgical hub 2106, 2236 (FIGS. 17-19), which is in turn coupled to an imaging system 142. When the control system 133 is embodied as a component of a surgical hub 2106, 2236, the imaging data can be received from an imaging system 142 coupled to the surgical hub 2106, 2236, the surgical instrument sensor data can be received from the surgical instrument 3290 coupled to the surgical hub 2106, 2236, and then the control system 133 of the surgical hub 2106, 2236 can determine the appropriate surgical instrument control adjustments and transmit them to the surgical instrument 3290 for execution thereby.

Adaptive Optics to Compensate for Imaging Artifacts

In one aspect, a control system, such as the control system 133 described in connection with FIG. 2, can be configured to compensate for imaging artifacts associated with the imaging system 142 coupled thereto. In one aspect, the control system 133 can be configured to adjust the optical signal received by the imaging system 142 across multiple light wavelengths in combination with selective imaging segment selection within a sample rate above 60 Hz to remove optical particulate obstructions from visualization. In one aspect, the control system 133 can be configured to emit a projected control beam (e.g., via the imaging system 142) and correspondingly monitor the return signal on an isolated frame of the scanning array (e.g., of the image sensor 135) to determine the distortion of the EMR/light by particulates within the gasses occupying the body cavity. The variance of the control projection from its source would give the control system 133 a baseline by which to adjust the scope visualization frames in a later portion of the scan.

Surgical System Control Based on Airborne Particulate Characteristics

One issue inherent to surgical procedures using electrosurgical instruments is the smoke generated by the instruments. Surgical smoke can include toxic gas and vapors; bioaerosols, including dead and living cell material, blood fragments, and viruses; and mutagenic and carcinogenic compounds. Therefore, it is highly desirable to remove these particulates from the surgical site and, accordingly, smoke evacuators are generally utilized in surgical procedures that result in the generation of surgical smoke. However, it would be desirable to control smoke evacuators and other surgical devices (including surgical instruments) according to the type(s) of particulates being generated because different particulate types may necessitate different types of control adjustments to precisely control and mitigate the generation of smoke during the surgical procedure. A surgical system could, e.g., change the surgical instrument energy profile to generate less smoke and/or automatically control the smoke evacuator according to the type of particulate being generated.

In one general aspect, the present disclosure is directed to a control system configured to detect the level of polarization of light emitted by an imaging system to determine a parameter of a particulate cloud and adjust the control parameters of a linked system or device accordingly. In one further aspect, the polarization of the EMR reflected from the detected particulates can be utilized in combination with the vectorization and quantity of the generated particulates to determine the source of the particulates, which can in turn be utilized to control the device(s) causing the generation of the particulates to improve visualization at the surgical site. In one further aspect, the polarization of the EMR reflected from the detected particulates could be utilized to determine whether adjusting the control parameters of an electrosurgical instrument or a smoke evacuator would be more effective at improving visualization at the surgical site.

FIG. 55 is a diagram of a polarizing EMR source 3500 for detecting different particulate types, in accordance with at least one aspect of the present disclosure. The polarizing EMR source 3500 can include an emitter 3502 configured to emit EMR 3506 and a polarizing filter 3504 configured to polarize the emitted EMR 3506. The polarizing filter 3504 can be removably affixable or integrally affixed to the emitter 3502. The polarizing EMR source 3500 can be embodied as a component of an imaging system, which can include the surgical visualization system 100 shown in FIG. 1, the imaging system 142 shown in FIG. 2, and/or the surgical visualization system 500 shown in FIG. 5, for example. Correspondingly, the emitter 3502 can include the emitter 106 shown in FIG. 1, the structured light source 152 shown in FIG. 2, the spectral light source 150 shown in FIG. 2, and so on. The imaging system can in turn be embodied as a component of a surgical system, such the robotic surgical system 110 shown in FIG. 1, which can further include a control system configured to control various aspects of the surgical system. The control system can include the control system 133 shown in FIG. 2 and/or the control system 600 shown in FIG. 11, for example.

During a surgical procedure, airborne particulates may be present at the surgical site. These particulates can include both naturally occurring particulates and non-natural or synthetic particulates. Naturally occurring particulates can be generated due to the interactions between the surgical instruments, such as an electrosurgical instrument, and the tissue being treated. Naturally occurring particulates can include, for example, dead and living cell material, blood fragments, and other biological material. Man-made or synthetic particulates can be introduced to the surgical site by surgical staff. These particulates can be embodied as smoke or aerosols present within or at the surgical site. Generally speaking, the presence of such particulates can be undesirable, so many surgical systems include a smoke evacuator to remove undesired smoke or aerosols from the surgical site. However, the imaging system can be configured to detect the particulates (i.e., smoke) generated at the surgical site and the control system can be configured to control various operational parameters of the surgical system or components thereof based on the characteristics or properties of the detected particulates. Some examples of such control algorithms are described herein.

Referring back to FIG. 55, as noted above, airborne particulates at a surgical site can include both naturally occurring particulates 3510 and man-made particulates 3512. It can be beneficial to be able to distinguish between the different types of particulates present at the surgical site because different actions may be needed to mitigate the presence of each of the different types of particulates. For example, if the detected particulate types are naturally occurring particulates 3510, which can be created from an electrosurgical instrument treating a tissue, then it may be desirable to control the electrosurgical instrument to mitigate the generation of the naturally occurring particulates 3510 (e.g., by decreasing the energy duty cycle or otherwise altering the energy delivery profile of the instrument). Conversely, if the detected particulate types are synthetic particulates 3512, then controlling the electrosurgical instrument would have no effect on the presence of the synthetic particulates 3512 since that particulate type is not generated by the action of the electrosurgical instrument. Instead, it may be desirable to increase the suction flow rate of a smoke evacuator to clear the synthetic particulates 3512 from the surgical site. Further, if a combination of different particulate types are detected at the surgical site, then it could be desirable to control the electrosurgical instrument and the smoke evacuator in combination with each other, with varying control adjustments for each device. Accordingly, a control system for a surgical system can be configured to detect the different types of airborne particulates present at the surgical site and control the various devices or components of the surgical system appropriately to mitigate or eliminate the particulates from the surgical site.

In one aspect, naturally occurring particulates 3510 and synthetic particulates 3512 can be distinguished from each other based upon the reflective characteristics of the airborne particulates 3510, 3512 when subject to polarized EMR 3506. For example, a control system 133 can be configured to cause the emitter 3502 to pulse coherent EMR, with and without polarization, at multiple different wavelength in order to determine the distance to the body that is subject to the surgical procedure and define a range gate so that the control system 133 is only taking depolarization measurements from EMR 3506 reflected from particulates within the air space between the emitter 3502 and the body cavity and not from the body cavity itself. In particular, the control system 133 can be configured to cause the emitter 3502 to pulse coherent EMR at a first wavelength and a second wavelength. The first wavelength can be selected such that the EMR at the first wavelength is substantially non-interactive with naturally occurring particulates 3510 and synthetic particulates 3512 and can therefore penetrate smoke and be reflected from the body cavity. The control system 133 can then determine the distance to the body cavity via, for example, a time-of-flight sensor system 1104, 1204, as described in connection with FIGS. 14-16, according to the difference in time between when the EMR is emitted and when the reflected EMR is detected. The second wavelength can be selected such that the EMR at the second wavelength is substantially interactive with naturally occurring particulates 3510 and synthetic particulates 3512 and can therefore be utilized to detect or measure characteristics associated with the different particulate types. Accordingly, the control system 133 can utilize the body cavity distance determined by pulsing EMR at the first wavelength to range gate the measurements received by the EMR at the second wavelength to ensure only that measurements are being taken of airborne particulates. The control system 133 can then determine whether the airborne particulates are naturally occurring particulates 3510 and/or synthetic particulates 3512 based on the reflective characteristics of the airborne particulates 3510, 3512 and control the other components of the surgical system accordingly.

In one aspect, a control system can be configured to control one or more operational parameters associated with the surgical system based on the type of airborne particulates detected at a surgical site. Example of such algorithms are shown in FIG. 56A, which is a logic flow diagram of a process 3600 for controlling a surgical system according to detected particulate types, and FIG. 56B, which is a logic flow diagram of a process 3650 for controlling a surgical system according to detected particulate types detected within a defined range gate. In the following description of the processes 3600, 3650, reference should also be made to FIG. 2. The processes 3600, 3650 can be embodied as, for example, instructions stored in a memory 134 coupled to a control circuit 132 that, when executed by the control circuit 132, cause the control circuit 132 to perform the enumerated steps of the processes 3600, 3650. For brevity, the processes 3600, 3650 are described as being executed by the control circuit 132; however, it should be understood that the processes 3600, 3650 can be executed by other combinations of hardware, software, and/or firmware.

Turning now specifically to FIG. 56A, the control circuit 132 executing the process 3600 can cause an imaging system 142 to emit 3602 polarized EMR directed at a surgical site via, for example, the polarizing EMR source 3500.

Accordingly, the control circuit 132 can receive 3604 the polarized EMR reflected from the airborne particulates at the surgical site (e.g., within the body cavity) and determine 3606 whether the detected particulate type is a naturally occurring particulate 3510 or a man-made particulate 3512. The control circuit 132 can differentiate between the different types of airborne particulates 3510, 3512 due to their different reflective characteristics when subject to polarized EMR. In particular, one of the types of the airborne particulates 3510, 3512 (e.g., man-made particulates 3512) could scatter polarized EMR at a higher rate than the other type (e.g., naturally occurring particulates 3510). This would decrease the degree of visualization of the scattering airborne particulate type or otherwise affect the manner in which the reflected EMR is received by the image sensor 135 of the imaging system 142. Therefore, this difference in visualization of the different types of airborne particulates 3510, 3512 can be characterized and utilized to identify the types of airborne particulates 3510, 3512 present at the surgical site (e.g., within the body cavity).

Accordingly, if the particulates are naturally occurring particulates 3510, then the process 3600 can proceed along the YES branch and the control circuit 132 can adjust 3608 a control parameter of the surgical system to a first state corresponding to naturally occurring particulates 3510. Conversely, if the particulates are man-made particulates 3512, then the process 3600 can proceed along the NO branch and the control circuit 132 can adjust 3610 the control parameter of the surgical system to a second state corresponding to man-made particulates 3512.

In another aspect, there could be various combinations of naturally occurring particulates 3510 and man-made particulates 3512 present within the body cavity. In such a case, the control circuit 132 could instead determine a relative ratio of the types of airborne particulates 3510, 3512 present within the body cavity (e.g., due to the relative degree by which visualization is reduced or impacted) and then control a surgical device or combination of surgical devices accordingly.

In yet another aspect, a control system can be configured to range gate the measurements and/or visualization based on the polarizing EMR source 3500. Such an aspect can be embodied by the process 3650 illustrated in FIG. 56B.

Accordingly, the control circuit 132 executing the process 3650 can cause the imaging system 142 to emit 3652 EMR at a first wavelength directed at a surgical site via, for example, a structured light source 152 and/or a spectral light source 150. In one aspect, the first wavelength can be a wavelength that is substantially non-interactive with the naturally occurring particulates 3510 and synthetic particulates 3512 that are to be imaged by the imaging system 142.

Accordingly, the control circuit 132 can, via the imaging system 142, receive 3654 the EMR reflected from the body cavity (i.e., surgical site) and define 3656 a range gate corresponding to the airspace between the emitter(s) of the imaging system 142 and the body cavity surface, as is described above.

Accordingly, the control circuit 132 can cause the imaging system 142 to emit 3658 polarized EMR at a second wavelength directed at a surgical site via, for example, a polarizing EMR source 3500. In one aspect, the second wavelength can be a wavelength that is substantially interactive with the naturally occurring particulates 3510 and synthetic particulates 3512 that are to be imaged by the imaging system 142.

Accordingly, the control circuit 132 can, via the imaging system 142, receive the polarized EMR reflected within the defined range gate, which could correspond to the airborne particulates 3510, 3512 located between the emitter(s) of the imaging system 142 and the body cavity surface. The control circuit 132 can then determine 3662 whether the detected particulate type is a naturally occurring particulate 3510 or a man-made particulate 3512 and adjust 3608, 3610 a control parameter of the surgical system to a first state or a second state, as is described above with respect to the process 3600 shown in FIG. 56A.

In another aspect, the surgical system can further be configured to track the movement of the airborne particulates throughout the course of a surgical procedure, which can in turn be utilized to characterize the movement and change in size or configuration of a cloud defined by the airborne particulates. By characterizing the movement of the airborne particulates over time, the surgical system can, for example, determine how well the smoke evacuation of the body cavity is performing and then adjust or provide recommendations to the user to adjust the location or magnitude of smoke evacuation or insufflation. For example, the surgical system could deactivating a first smoke evacuator or first insufflator and activate a second smoke evacuator or second insufflator to adjust the gaseous circulation currents within the body cavity and thereby mitigate any eddies within the body cavity (i.e., areas where the movement vectors of the particulates and/or gasses are zero or near zero) to improve smoke evacuation performance. As another example, the surgical system could adjust a motor or fan level of a smoke evacuator or insufflator to improve smoke evacuation performance.

In one aspect, the control system 133 can be configured to track and characterize the movement of airborne particulates by characterizing the detection of particulates across the cells or pixels of an image sensor 135. In particular, the control system 133 can determine at which pixels the image sensor 135 has detected particulates and then track the movement of the particulates over time across the pixel array of the image sensor 135. In one aspect, the control system 133 can be configured to divide an image obtained via an image sensor 135 into two or more pixel array sections, generate a movement vector corresponding to the generalized change in position by the detected airborne particulates from a first time instance to a second time instance, and then characterize the movement or change in configuration of the particulate cloud accordingly.

For example, FIGS. 57A-57C illustrate a pixel array 3700 of an image sensor 135 that consists of a number of pixels 3701. Further, FIGS. 57A-57C indicate the change in detected particulate position over time and a generalized particulate cloud movement vector calculated therefrom. It should be noted that although the pixel array 3700 is depicted as being a 5×5 array, this is simply for illustrative purposes and neither the image sensor 135 nor a selected subsection of the pixels thereof are restricted to being a 5×5 array. In the following description of FIGS. 57A-57C, reference should also be made to FIG. 2.

FIG. 57A illustrates the detection array 3700 at time t1, which indicates the detection of a first particulate 3702a, second particulate 3702b, third particulate 3702c, fourth particulate 3702d, and fifth particulate 3702e at the indicated pixels 3701 of the image sensor 135. FIG. 57B illustrates the detection array 3700 at time t2, which indicates that the first and fifth particulates 3702a, 3702e have not changed positions and the second, third, and fourth particulate 3702b, 3702c, 3702d have been detected at different pixels 3701 of the image sensor 135. Based on the detected movements of the particulates, the control circuit 132 can be configured to determine a vector representation of the movement of each of the pixels. The vector representations can include both a direction and a magnitude. Based on the directions and magnitudes of the movement vectors, the control circuit 132 can be further configured to calculate (e.g., using vector addition) a vector 3704 corresponding to the generalized movement of the cloud defined by the detected particulates. Accordingly, the control circuit 132 can track the change in a particulate cloud or aerosol from a first state 3710 (e.g., a first position or a first size) to a second state 3712 (e.g., a second position or a second size), as shown in FIG. 58, according to the vector 3704 calculated from the change in pixels of the image sensor 135 at which the particulates are detected.

In one aspect, a control circuit 132 coupled to the image sensor 135 can be configured to track the movements of detected airborne particulates, calculate a generalized movement vector corresponding to the changes in position of the detected airborne particulates within the pixel array 3700 (which can represent the entire pixel array of the image sensor 135 or a subsection thereof), and then control various connected surgical devices, such as insufflators, smoke evacuators, and/or surgical instruments accordingly. In one aspect, the control system 133 including the control circuit 132 can be embodied as a surgical hub 2106, 2236 as described above under the heading SURGICAL HUB SYSTEM. In this aspect, the surgical devices can be communicatively connected to (e.g., paired with) a surgical hub 2106, 2236 and controlled according to the described systems and processes.

In another aspect, the control system 133 can be configured to utilize Raman spectroscopy techniques to determine vibrational/rotational aspects of the airborne particulates using, for example, near IR, UV, or a combination of near IR and UV wavelengths. Data derived from such techniques could, for example, provide information on the gas phase species (e.g., benzenes vs. aldehydes), which in turn could give insights into the type of tissue from which the particulates were generated or to the efficiency of the energy being applied to the tissue. The control system 133 can include, for example, a filter (e.g., a bandpass or notch filter) coupled to the detector to filter out elastic scattering of the source EMR, since the desired information of the species is contained in the inelastic scattering of the EMR. The signals generated by the image sensor 135 or another such detector (e.g., a CCD detector) according to the Raman spectroscopy techniques can be based on the intrinsic structural properties of the detected molecules. In particular, Raman spectroscopy is based on the concept that, e.g., a photon emitted by an appropriate emitter excites a molecule to a higher energy state, which causes the scattered photon to change frequency as a result of conserving energy from the vibrational/rotational change in the molecule. This change in frequency of the scattered photon can be utilized to characterize the type of molecule with which the photon interacted with by comparing the detected signal with pre-characterized data for a given excitation frequency according to the particular type of monochromatic light source utilized. The determined molecule type of the particulates could be utilized for a number of different applications, including providing specific data on relative amounts of potentially hazardous molecules being generated at the surgical site for safety monitoring purposes. The determined molecule type of the particulates could also be utilized to assess the effectiveness and health of the smoke evacuator system or a filter thereof.

Surgical System Control Based on Smoke Cloud Characteristics

One issue inherent to surgical procedures using electrosurgical instruments is the smoke generated by the instruments. Surgical smoke can include toxic gas and vapors; bioaerosols, including dead and living cell material, blood fragments, and viruses; and mutagenic and carcinogenic compounds. Therefore, it is highly desirable to remove these particulates from the surgical site and, accordingly, smoke evacuators are generally utilized in surgical procedures that result in the generation of surgical smoke. However, it would be desirable to control smoke evacuators and other surgical devices (including surgical instruments) according to the amount of smoke at the surgical site, the variation in the smoke cloud over time (e.g., whether a smoke cloud is actively accumulating or diminishing), and other such smoke cloud characteristics in order to precisely control and mitigate the generation of smoke during the surgical procedure. A surgical system could, e.g., change the surgical instrument energy profile to generate less smoke and/or automatically control the smoke evacuator according to the amount of surgical smoke being generated.

In one general aspect, the present disclosure is directed to a surgical system configure to detect and characterize amorphous, three-dimensional particulate clouds generated during surgical procedures. The surgical system can be configured to detect the movements of the particulate cloud within the abdominal cavity and relative to the surgical site and then control various surgical devices, such as surgical instruments or a smoke evacuator, accordingly. In one general aspect, the present disclosure is directed to a control system configured to define a surface or boundary of a cloud or particulate cluster generated during a surgical procedure and analyze various characteristics of the defined cloud, such as the direction and rate-of-change of the boundary, to control various control parameters of a surgical system, such as the power level of a surgical instrument/generator or smoke evacuation motor control. In one further aspect, the control system can be configured to develop the boundary by defining a predefined density of the particulates based on the overall volume of the particulates or the size of the particulates. In another further aspect, the rate-of-change of the particulate cloud surface boundary can be utilized to directionally define the rate of change of the energy device or the smoke evacuation mechanism.

FIG. 59 is a diagram of a surgical system 3750 during the performance of a surgical procedure in which a particulate cloud 3752 is being generated, in accordance with at least one aspect of the present disclosure. The surgical system 3750 can be embodied as a robotic surgical system, such as the robotic surgical system 110 shown in FIG. 1, for example. The surgical system 3750 can include an electrosurgical instrument 3754, a smoke evacuator 3756, a grasper 3750, and any other surgical devices for treating, cutting, or otherwise manipulating a tissue 3760 for a surgical procedure. Although not shown in FIG. 59, the surgical system 3750 can further include an imaging system, which can include the surgical visualization system 100 shown in FIG. 1, the imaging system 142 shown in FIG. 2, and/or the surgical visualization system 500 shown in FIG. 5, for example. The surgical system 3750 can still further include a control system, which can include the control system 133 shown in FIG. 2 and/or the control system 600 shown in FIG. 11, for example.

During a surgical procedure, airborne particulates 3751 may be generated due to the interactions between the surgical instruments, such as an electrosurgical instrument 3754, and the tissue 3760 being treated. These particulates 3751 can be embodied as a cloud 3752 of smoke or an aerosol present within or at the surgical site. Generally speaking, the presence of such particulates 3751 can be undesirable, so many surgical systems 3750 include a smoke evacuator 3756 to remove the particulates 3751 from the surgical site. However, the imaging system can be configured to image the particulates 3751 and/or smoke generated at the surgical site and the control system can be configured to control various operational parameters of the surgical system 3750 or components thereof based on the characteristics or properties of the imaged smoke. Some examples of such control algorithms are described herein.

In one aspect, a control system can be configured to control one or more operational parameters associated with the surgical system 3750 based on one or more characteristics associated with a smoke cloud generated at a surgical site. One example of such an algorithm is shown in FIG. 60, which is a logic flow diagram of a process 3800 for controlling a surgical system according to particulate cloud characteristics. In the following description of the process 3800, reference should also be made to FIG. 2. The process 3800 can be embodied as, for example, instructions stored in a memory 134 coupled to a control circuit 132 that, when executed by the control circuit 132, cause the control circuit 132 to perform the enumerated steps of the process 3800. For brevity, the process 3800 is described as being executed by the control circuit 132; however, it should be understood that the process 3800 can be executed by other combinations of hardware, software, and/or firmware.

Accordingly, the control circuit 132 executing the process 3800 can detect 3802 the presence of airborne particulates within the FOV of the imaging system 142 using any of the techniques described above. In general, the image sensor 135 of the imaging system 142 can detect EMR emitted by a structured light source 152 and/or a spectral light source 150 and reflected by the airborne particulates to detect/image the particulates.

Accordingly, the control circuit 132 can characterize 3804 the particulate cloud defined by the detected particulates. In one aspect, the control circuit 132 can be configured to define a three-dimensional boundary of the particulate cloud to delineate an amorphous, three-dimensional construct whose density, volume, position, movement, and/or boundaries can be tracked over time. The boundary of the particulate cloud at the surgical site can be defined in a variety of different manners. For example, the particulate cloud boundary can be defined as the volume encompassing all of the airborne particulates detected within the FOV of the imaging system 142. As another example, the particulate cloud boundary can be defined as the volume having a threshold density of airborne particulates.

Accordingly, the control circuit 132 can determine 3806 whether one or more characteristics of the particulate cloud violate a threshold. Such tracked characteristics can include, for example, the density of the particulate cloud, volume of the particulate cloud, position of the particulate cloud and/or its boundary, movement of the particulate cloud and/or its boundary, and/or the rate of change or other derivative of any of the aforementioned characteristics. The threshold(s) for the tracked characteristics can be preprogrammed or dependent upon other parameters, such as the surgical context (e.g., the type of surgical procedure being performed). If a threshold is not violated, then the process 3800 can proceed along the NO branch and the control circuit 132 can continue as described above until, for example, a stopping criterion has been satisfied (e.g., the surgical procedure being completed). If a threshold is violated, then the process 3800 can proceed along the YES branch and the control circuit 132 can continue as described below.

Accordingly, the control circuit 132 can adjust 3808 one or more control parameters of the surgical system 3750. The control parameters that are adjustable by the control circuit 132 can include surgical instrument/generator energy level, smoke evacuator suction, visualization parameters, and so on. For example, FIG. 61 is a series of graphs 3850, 3852, 3854 illustrating the adjustment of control parameters based on particulate cloud characteristics by a control circuit 132 executing the process 3800. The first graph 3850 illustrates a first line 3860 indicating the change in smoke cloud density, represented by the vertical axis 3856, over time, represented by the horizontal axis 3858. The second graph 3852 illustrates a second line 3868 indicating the change in energy duty cycle of an electrosurgical instrument 3754 (or the generator driving the electrosurgical instrument 3754), represented by the vertical axis 3866, over time, represented by the horizontal axis 3858. The third graph 3854 illustrates a third line 3880 indicating the change in the smoke evacuation or suction flow rate of a smoke evacuator 3756, represented by the vertical axis 3878, over time, represented by the horizontal axis 3858. In combination, the graphs 3850, 3852, 3854 illustrate a representative, prophetic implementation of the process 3800 during a surgical procedure, wherein the process 3800 adjusts 3808 the electrosurgical instrument energy duty cycle and smoke evacuator suction flow rate control parameters according to the characterized smoke cloud density.

Initially, the electrosurgical instrument 3754 is not applying energy to the captured tissue 3760, as indicated by a first graphic 3890. Accordingly, the energy duty cycle of the electrosurgical instrument 3754 is zero, the smoke evacuator suction flow rate is at a base or default rate, and no smoke is being generated (because no energy is being applied to the tissue 3760). At time t1, the surgeon activates the electrosurgical instrument 3754 and begins applying energy to the tissue 3760, represented by the energy duty cycle increasing 3870 from zero to $E_3$. Due to the application of energy to the tissue 3760, smoke begins to be generated at the surgical site, represented by the smoke cloud density sharply increasing 3862 from zero a period of time after t1. Further, in response to the energy being activated, the smoke evacuator flow rate can be increased 3882 by the control circuit 132 from $Q_1$ to $Q_2$ as the smoke evacuator 3756 begins attempting to remove the generated smoke from the surgical site. At this stage, the control circuit 132 can begin detecting 3802 the airborne particulates generated by the application of energy and characterizing 3804 the corresponding smoke cloud defined by the airborne particulates.

At time $t_2$, the application of energy to the tissue 3760 has caused a smoke cloud 3752 to develop at the surgical site, as indicated by a second graphic 3892. The control circuit 132 can determine 3806 that the cloud density has exceeded a smoke cloud density threshold (e.g., as represented by $D_3$).

Accordingly, the control circuit 132 adjusts 3808 the electrosurgical instrument energy duty cycle control parameter by decreasing 3872 it from $E_3$ to $E_2$. The control circuit 132 can elect to make this adjustment because applying lower levels of energy to a tissue 3760 can result in less smoke being generated. In response, the smoke cloud density begins decreasing 3864 at time $t_1$.

At time $t_3$, the smoke cloud 3752 has decreased in size, but has not completely dissipated, as indicated by a third graphic 3894. The control circuit 132 can determine 3806 that the cloud density is not decreasing at a fast enough rate or that some other characteristic of the smoke cloud is violating some other threshold. Accordingly, the control circuit 132 again adjusts 3808 the electrosurgical instrument energy duty cycle control parameter by decreasing 3874 it from $E_2$ to $E_1$ in order mitigate further smoke generation.

At time $t_4$, the smoke cloud 3752 has nearly dissipated, as indicated by the fourth graphic 3896. The control circuit 132 can determine 3806 can determine 3806 that the smoke cloud has violated another threshold, such as the cloud density being above a particular level (e.g., as represented by $D_1$) for longer than a threshold period of time (e.g., as represented by $t_4$). Accordingly, the control circuit 132 adjusts the smoke evacuator suction flow rate control parameter by increasing 3884 it from $Q_2$ to $Q_3$ in order to fully remove the smoke particulates from the surgical site.

It should be noted that the implementation of the process 3800 embodied by FIG. 61 is provided for illustrative purposes and simply represents one possible implementation. In particular, different control parameters can be controlled by the process 3800, different thresholds can be utilized, different smoke cloud characteristics can be tracked, and so on. Therefore, FIG. 61 should not be construed to limit the process 3800 of FIG. 60 or any other described systems and methods in any way.

Resection Margin Determination and Adjustment

The aforementioned surgical visualization systems can be used to detect a critical structure to be removed, or a subject tissue (e.g. a tumor), from an anatomical structure (e.g. an organ). However, many surgical procedures also require the removal of a resection margin, or margin of unaffected tissue surrounding a subject tissue. The resection margin can be determined and/or adjusted based on a variety of characteristics of the anatomical structure, many of which are difficult to see via the "naked eye". Characteristics can include critical structures other than the subject tissue, but relevant to its excision. For example, a characteristic of the anatomical structure can include a secondary anatomical structure in proximity to the subject tissue (e.g. an artery or ureter), a foreign structure in proximity to the subject tissue (e.g. a surgical device, surgical fastener, or clip), a quality of the tissue surrounding the subject tissue (e.g. tissue damaged by emphysema), and/or a physical contour of the anatomical structure (e.g. a wall of the organ), among others. There is an increasing need for surgical visualization systems configured to detect such critical structures, synthesize data associated with the subject tissue, and communicate the synthesized data to the operating clinician(s) in the form of relevant information and/or instructions. For example, it would be desirable for a surgical visualization system to detect the location of a subject tissue associated with an anatomical structure, determine a resection margin about the subject tissue, and adjust that resection margin based on a detected characteristic of the anatomical structure. If the surgical visualization system were further configured to detect the position of a surgical instrument relative to the resection margin, it could notify the operating clinician(s) if the surgical instrument was improperly positioned prior to the commencement of the surgical operation. Accordingly, in various non-limiting aspects of the present disclosure, systems and methods are provided for determining, adjusting, and enforcing a resection margin about a subject tissue, based on the detection of various critical structures.

The foregoing principles are discussed in the context of a surgical stapler exclusively for the sake of demonstration. The present disclosure can be effectively implemented to a wide variety of surgical systems, including those using radio frequency (RF) energy. Accordingly, the examples herein are exemplary and not intended to limit the scope of the present disclosure.

For example, in the non-limiting aspect of FIG. 2, the control system 133 can be implemented in a surgical visualization system 100 and determine a resection margin based on a detected subject tissue associated with the anatomical structure. For example, the control circuit 132 can detect various critical structures based on a signal received from the image sensor 135. The signal can be associated with electromagnetic radiation emitted by the structured light source 152 and/or spectral light source 150, and reflected off various features of the anatomical structure. A critical structure detected by the control circuit 132 can be a subject tissue, and the control circuit 132 can further integrate data associated with the subject tissue into the three-dimensional digital representation, or model, of the anatomical structure. The control circuit 132 can determine a resection margin based on the data associated with the subject tissue relative to the model of the anatomical structure using the surface mapping logic 136, imaging logic 138, tissue identification logic 140, distance determining logic 141, and/or any combination of modules stored in the memory 134. However, alternate components and/or methods of determining the resection margin (e.g. a central processing unit, FPGA's) are contemplated by the present disclosure. Additionally and/or alternatively, a critical structure detected by the control circuit 132 can be a characteristic of the anatomical structure, and the control circuit 132 can further integrate data associated with the characteristic into the model of the anatomical structure. The control circuit 132 can further adjust the resection margin based on the data associated with the characteristic relative to the model of the anatomical structure. A display 146 of the control system 133 can depict real, virtual, and/or virtually-augmented images and/or information. For example, the display 146 can include one or more screens or monitors configured to convey information such as the model of the anatomical structure, the subject tissue, the resection margin, and/or the adjusted resection margin to the clinician(s).

Referring back to FIG. 13B, an example of a surgical visualization system configured to determine a resection margin 2330a and adjusted resection margin 2330b is depicted in accordance with at least one aspect of the present disclosure. The surgical visualization system of FIG. 13B includes a spectral imaging device 2320 configured to emit electromagnetic radiation onto an anatomical structure. The electromagnetic radiation can constitute a pattern of structured light and/or a spectral light including a plurality of wavelengths. In the non-limiting aspect of FIG. 13B, the spectral imaging device 2320 can emit both structured light and spectral light. For example, at least a portion of the electromagnetic radiation comprises a structured pattern that is emitted onto the anatomical structure, and at least a portion of the electromagnetic radiation comprises a plurality of wavelengths configured to penetrate obscuring tissue of the anatomical structure and reflect off critical structures 2332, 2338. The structured light and spectral light can be either visible or invisible. However, in other non-limiting aspects, the surgical visualization system can include separate spectral imaging devices 2320, wherein each emits either structured light or spectral light. Similarly, although the surgical visualization system of FIG. 13B is streamlined to minimize hardware, other aspects include separate, dedicated components configured to achieve the same affect.

In further reference to FIG. 13B, the spectral imaging device 2320 can further include an image sensor 135 (FIG. 2) configured to detect reflected electromagnetic radiation at various wavelengths. For example, the image sensor 135 can detect a structured pattern of electromagnetic radiation that has reflected off the anatomical structure. As previously described, the structured pattern (e.g. stripes or lines) of electromagnetic radiation is emitted by the spectral imaging device 2320 and projected onto a surface of the anatomical structure. The structured pattern of electromagnetic radiation can include wavelengths configured to reflect off the surface of the anatomical structure. Accordingly, the image sensor 135 can detect at least a portion of the structured pattern of electromagnetic radiation that has reflected off the surface of the anatomical structure. Although the image sensor 135 can include light-sensitive elements, such as pixels, and be configured as a CCD, and/or a CMOS, other suitable image sensors and configurations are contemplated by the present disclosure.

The image sensor 135 can include light-sensitive elements that can generate a signal associated with the reflected electromagnetic radiation via photoelectric effect. For example, a pixel of the image sensor 135 can convert a photo-generated charge into a voltage, and subsequently amplify and transmit the voltage to a control circuit 132 (FIG. 2) for further processing. After receiving the signal from the image sensor 135, the control circuit 132 (FIG. 2) can process the signal associated with the reflected electromagnetic radiation to determine a deformation of the structured pattern. The control circuit 132 (FIG. 2) can then assess a degree of deformation relative to the originally structured pattern of electromagnetic radiation, and generate a surface map of the anatomical structure based on the assessment. The surgical visualization system of FIG. 13B can further determine dimensions of the anatomical structure via distance determining logic 141 (FIG. 2) and contours of the anatomical structure via surface mapping logic 136 (FIG. 2), although other non-limiting aspects of the present disclosure utilize alternate methods of characterizing the anatomical structure. Accordingly, the surgical visualization system can generate a three-dimensional model of the anatomical structure that can be conveyed to the operating clinician(s) via a display 146 (FIG. 2). Although the surgical visualization system of FIG. 13B uses structured light to model the anatomical structure, other suitable methods mapping tissue are contemplated by the present disclosure, such as flash light detection and ranging (LIDAR) technologies.

Still referring to FIG. 13B, the image sensor 135 can further detect spectral light that has reflected off critical structures 2332, 2338 associated with the anatomical structure. For example, the image sensor 135 can detect wavelengths of electromagnetic radiation that have reflected off subject tissue 2332 and/or characteristics 2338 of the anatomical structure. As previously discussed, a spectral light portion of the emitted electromagnetic radiation comprises a plurality of wavelengths. Each wavelength of the plurality of wavelengths can be selected in consideration of an anticipated coefficient of absorption possessed by the various tissues constituting the anatomical structure. The coefficient of absorption affects the degree to which each wavelength of the plurality of wavelengths is reflected, refracted, and/or absorbed by various portions of the anatomical structure. This interaction between wavelength and tissue constitutes the "molecular response" discussed in reference to FIGS. 1 and 11. As such, the electromagnetic radiation can include a plurality of varying wavelengths, and each wavelength can react differently to different portions of the anatomical structure. Accordingly, the electromagnetic radiation can specifically target specific critical structures at specific locations within the anatomical structure.

The image sensor 135 can detect reflected spectral light in a manner similar to its detection of structured light. For example, the image sensor 135 can detect reflected spectral light using light-sensitive elements, which can generate signals via photoelectric effect. However, for spectral light, the image sensor 135 and/or the control circuit 132 (FIG. 2) can further compile signals generated by each reflected wavelength of the plurality of wavelengths into an image exclusively associated with that reflected wavelength. The image sensor 135 and/or the control circuit 132 can compile the images, each of which associated with signals generated by a particular reflected wavelength, into a three-dimensional spectral cube for further processing and analysis. For example, the spectral cube can include data associated with a first and second spatial dimension of the anatomical structure, and a third spectral dimension, associated with the range of wavelengths. The image sensor 135 and/or control circuit 132 can generate the spectral cube using a variety of spectral imaging techniques, including spatial scanning, spectral scanning, snapshot imaging, and/or spatial-spectral scanning, among others. Although the surgical visualization system of FIG. 13B utilizes an image sensor 135 to identify critical structures within an anatomical structure, the present disclosure contemplates other means of identification, such as ultra-sound and/or photoacoustic imaging.

The control circuit 132 (FIG. 2) can detect a location of a critical structure relative to the model of the anatomical structure based on the spectral cube. For example, the control circuit 132 can use a spectral cube generated by the image sensor 135 to identify a subject tissue 2332 (e.g. tumor) within the anatomical structure (e.g. organ). The control circuit 132 can integrate data from the spectral cube associated with the subject tissue 2332 into the model of the anatomical structure. The control circuit 132 can generate relational data, such as the position of the subject tissue 2332 relative to the anatomical structure. Accordingly, the control circuit 132 can determine a resection margin 2330*a* of unaffected tissue that surrounds the subject tissue 2332 based on the relational data. When determining the resection margin 2330*a*, the control circuit 132 can account for the geometrical contours of the anatomical structure based on the model. For example, if the control circuit 132 determines, based on the model, that the resection margin 2330*a* would otherwise intersect a boundary (e.g. wall) of the anatomical structure, the control circuit 132 can adjust the resection margin 2330*a* to the boundary of the anatomical structure. Likewise, the control circuit 132 can account for other geometric features of the anatomical structure when determining the resection margin 2330*a*. For example, if the control circuit 132 determines, based on the model, that the resection margin 2330*a* would otherwise traverse a geometric feature (e.g. fissure) of the anatomical structure, the control circuit 132 can adjust the resection margin 2330*a* to either circumvent or encompass the geometric feature.

The surgical visualization system of FIG. 13B can determine a resection margin 2330*a* based on relational data, such as the location of the subject tissue 2332 within the anatomical structure, as well as an instruction stored within the memory 134 (FIG. 2). For example, the instruction might include a predetermined dimension to be measured from the identified boundaries of the subject tissue 2332. In other non-limiting aspects, the instruction can include a predetermined, or safety, margin 5030 (FIG. 62) that the control circuit 132 can apply to the determined resection margin 2330*b* to enhance the isolation and removal of the subject tissue 2332. In still further non-limiting aspects, an instruction can be associated with various parameters of the surgical procedure. For example, if the operating clinician(s) inputs a parameter indicating that the anatomical structure is a lung, the control circuit 132 (FIG. 2) can automatically apply an instruction that adjusts the determined resection margin 2330*a* to preserve a residual volume of the anatomical structure (e.g. lung capacity) after the tumor is removed. Similar instructions associated with a variety of anatomical structures and/or subject tissues 2332 can be stored in the memory 134. For example, the control circuit 132 can adjust the resection margin 2330*a* based on instructions stored in the memory 134 and related to the size, geometry and type of subject tissue 2332 detected by the spectral imaging device 2320. The control circuit 132 can automatically apply instructions when determining the resection margin 2330*a*, or a list of instructions stored in the memory 134 can be presented to the operating clinician(s) for selection via a user interface of the surgical visualization system. The operating clinician(s) can also manage and/or modify instructions stored in the memory 134 via a user interface of the surgical visualization system. For example, the user interface can include a keyboard, mouse, touchscreen, wireless device, audible command, and/or any other suitable method for providing an instruction to the surgical visualization system.

In some aspects, the surgical visualization system can perform statistical analyses to characterize the anatomical structure. For example, the surgical visualization system can perform a Procrustes analysis to characterize the shape of the anatomical structure by comparing a three-dimensional scan of osseous features of the anatomical structure to establish relative dimensions and distances. Osseous features can include characteristics of the anatomical structure that will not undergo a material deformation as the anatomical structure is translated, rotated, and/or scaled. Physical indicia such as rigid fiducial markers can be used to establish geometric data points throughout the anatomical structure and assist to translate the three-dimensional coordinate system to the coordinate system of the surgical visualization system. A subsequent affine transformation can be performed to characterize lines, points, and planes of the anatomical structure, thereby accounting for the deformable, soft-tissue characteristics of the anatomical feature. The soft-tissue characteristics can be integrated into the Procrustes model, thereby completing the three-dimensional model of the anatomical structure.

The surgical visualization system of FIG. 13B can further depict the model of the anatomical structure, the subject tissue 2332, and the resection margin 2330*a* on a display 146 (FIG. 2) of the control system 133 (FIG. 2). Accordingly, the surgical visualization system can generate a model of the anatomical structure, detect a subject tissue 2332 within the anatomical structure, determine a resection margin 2330*a* around the subject tissue 2332, and communicate this information to the operating clinician(s) to enhance the isolation and removal of the subject tissue 2332 from the anatomical structure.

In further reference to FIG. 13B, the surgical visualization system can detect additional critical structures within the anatomical structure, and to determine an adjusted resection margin 2330b based on additional critical structures detected. The control circuit 132 (FIG. 2) can detect additional critical structures, such as characteristics of the anatomical structure, based on the image sensor 135 detecting reflected spectral light. The illustrated critical structures 2338, 2334 can include critical structures other than the subject tissue 2332, but relevant to its excision. For example, one such characteristic 2338 of the anatomical structure can include damaged tissue surrounding the subject tissue 2332. If tissue within the anatomical structure is damaged, it can have a higher coefficient of absorption and therefore, a reduced coefficient of refraction. Consequently, the image sensor 135 can detect less electromagnetic radiation reflecting off damaged tissue, and the control circuit 132 (FIG. 2) can identify the damaged tissue as a characteristic 2338 of the anatomical structure. The control circuit 132 (FIG. 2) can integrate the location of the detected characteristic 2338 into the model of the anatomical structure, and determine an adjusted resection margin 2330b based on the location of the characteristic 2338 relative to the subject tissue 2332. Although the aspect of FIG. 13B utilizes spectral light to detect additional critical structures, other non-limiting aspects can use of structured light to achieve the same affect. Structured light could be particular useful when detected critical structures are on, or closer to, the surface of the anatomical structured.

Although resection margin 2330a of FIG. 13B is initially determined by the control circuit 132 (FIG. 2) of the surgical visualization system, in other aspects of the present disclosure, resection margin 2330a can be determined by the operating clinician(s) and provided as an input via a user interface of the display 146 (FIG. 2) of the surgical visualization system.

Still referring to FIG. 13B, the originally determined resection margin 2330a surrounds the subject tissue 2332 (e.g. tumor) but traversed through the characteristic 2338 (e.g. damaged tissue) of the anatomical structure. Damaged tissue can include any tissue that is in a condition that could hinder the anatomical structure's ability to recover from the surgical procedure. For example, damaged tissue can include tissue that is diseased, tissue that is infected, tissue that contains adhesions, tissue that is affected by emphysema, and/or tissue that suffers from a reduced blood flow, among other conditions. Damaged tissue can be rigid and/or have poor integrity, thereby leaving the patient susceptible to post-operation complications. Therefore, the control circuit 132 (FIG. 2) can determine an adjusted resection margin 2330b to account for characteristics 2338 such as damaged tissue. For example, the adjusted resection margin 2330b can be broader than the original resection margin 2330a, encompassing not just the subject tissue 2332, but the characteristic 2338 as well. Thus, both the subject tissue 2332 (e.g. tumor) and characteristic 2338 (e.g. damaged tissue) can be removed from the anatomical structure (e.g. organ), thereby facilitating a more efficient recovery for the patient.

In other aspects, the surgical visualization system can include a laser emitter configured to emit a beam of photons at the blood cells of a tissue of the anatomical structure. The image sensor 135 can be further configured to detect a frequency-shift of photons that reflect off the blood cells of the tissue, and the control circuit 132 (FIG. 2) can be further configured to analyze the shift in frequency and determine a quality of the vascular flow through the tissue surrounding the subject tissue. Accordingly, the surgical visualization system can further assess the integrity of a tissue, and factor that into the determination of the adjusted resection margin 2330b. For example, if the vascular flow through a tissue is low, the tissue might be of low integrity, subject to tearing, and could cause post-operative complications. Thus, the surgical visualization system can determine an adjusted resection margin 2330b that encompasses tissue surrounding the subject tissue that has a low vascular flow.

In some aspects, the adjusted resection margin 2330b is determined based on an optimization of a residual quality of the anatomical structure, while fully removing the subject tissue 2332 as well as a characteristic 2338 of the anatomical structure. For example, if the anatomical structure includes a lung, the operating clinician(s) might want to remove a majority of tissue damaged by emphysema along with a targeted tumor, to reduce post-operative air leakage from the lung. However, if the operating clinician(s) remove too much tissue, they might not preserve a sufficient lung capacity, thereby increasing the risk of other post-operative complications. Accordingly, the surgical visualization system of FIG. 13B can assist in determining an optimal resection margin by characterizing the anatomical structure, the subject tissue 2332, and any characteristics 2338 of the anatomical structure, and applying any instructions stored in the memory 134 (FIG. 2) of the control system 133 (FIG. 2).

In some aspects, the surgical visualization system can depict the model of the anatomical structure, the subject tissue 2332, the resection margin 2330a, and/or the adjusted resection margin 2330b on a display 146 (FIG. 2) of the control system 133 (FIG. 2). As such, the surgical visualization system can determine an adjusted resection margin 2330b around the subject tissue 2332, and communicate this information to the operating clinician(s) to further enhance the isolation and removal of the subject tissue 2332 from the anatomical structure in consideration of other characteristics 2338 of the anatomical structure. If the resection margin 2330a was initially determined by the operating clinician(s) and provided as an input via a user interface of the display 146 (FIG. 2), the surgical visualization system can still determine and depict an adjusted resection margin 2330b, and allow the operating clinician(s) to either select it via the user interface, or preserve the originally determined resection margin 2330a.

Accordingly, the surgical visualization system of FIG. 13B can use electromagnetic radiation in the form of spectral and/or structured light to scan the anatomical structure, detect additional critical structures throughout the anatomical structure, and adjust the resection margin 2330a around a subject tissue 2332 in consideration of each additional critical structure detected. For example, the control circuit 132 (FIG. 2) can further detect a second characteristic 2334 of the anatomical structure that is relevant to the excision of the subject tissue 2332. Although the second characteristic can include another sample of damaged tissue, it can also include a feature of the anatomical structure or a second anatomical structure 2334 in proximity to the subject tissue 2332 and/or the anatomical structure. For example, the second characteristic 2334 can include a variety of critical structures, such as organs, veins, nerves, tissues, and/or vessels, among others. In the non-limiting aspect of FIG. 13B, the second characteristic 2334 can be an artery in proximity to the subject tissue 2332 of the anatomical structure. Once detected, the control circuit 132 (FIG. 2) can integrate the position of the second characteristic 2334 into the model of the anatomical structure, and determine a second adjusted resection margin 2330c based on the position of the second characteristic 2334 relative to the subject tissue 2332. Accordingly, the surgical visualization system can determine an adjusted resection margin 2330c that will ensure complete isolation and removal of the subject tissue 2332 (e.g. tumor).

Referring now to FIG. 62, a display 5020 of a surgical visualization system is shown in accordance with at least one aspect of the present disclosure. The display 5020 of FIG. 62 can depict an information index 5022 and a model of an anatomical structure 5024 generated by a control system 133 (FIG. 2) of the surgical visualization system. The anatomical structure 5024 includes unaffected tissue 5026 that is neither diseased, nor occupied by a critical structure. The model of the anatomical structure 5024 can depict detected and/or determined features, such as a subject tissue 5028, a predetermined margin 5030, a resection margin 5032, a first characteristic 5034 of the anatomical structure 5024, and an adjusted resection margin 5036. The control system 133 of the surgical visualization system has designated each of these detected features of the anatomical structure 5024 a specific color, and the display 5020 can depict each of the detected features in its specifically designated color, as is represented via the cross-hatching of FIG. 62. The information index 5022 can depict a correlation of each specific color with information that is relevant to its designated detected feature. For example, the information index 5022 of FIG. 62 correlates each specific color with a textual description of a corresponding feature of the anatomical structure 5024. In other aspects, the information index 5022 correlates each specific color with additional information that is relevant to a corresponding feature.

As depicted in FIG. 62, the surgical visualization system can detect a subject tissue 5028 within the anatomical structure 5024. The information index 5022 of the display 5020 can indicate that the detected subject tissue 5028 is a tumor. An instruction stored in the memory of a control system 133 (FIG. 2) of the surgical visualization system can instruct the control circuit 132 (FIG. 2) to apply a predetermined margin 5030 around the subject tissue 5028 based on detected qualities of the tumor, including its size, geometry, and/or type. Accordingly, the control system 133 can designate the resection margin 5030 a specific color, and the information index 5022 can correlate the specific color with additional information associated with the resection margin 5030. The control circuit of the surgical visualization system can determine a resection margin 5032 around the subject tissue 5028, in consideration of the detected subject tissue 5028 and predetermined margin 5030. In the display 5020 of FIG. 62, the resection margin 5032 is depicted in linear segments about the anatomical structure 5024, corresponding to the capabilities of an intended surgical instrument. For example, the surgical instrument can be a surgical stapler configured to staple tissue before cutting it via a linear stroke. However, the display 5020 can alternately depict the resection margin 5032 if other surgical instruments are implemented.

The display 5020 of FIG. 62 also depicts a characteristic 5034 of the anatomical structure 5024 detected by the surgical visualization system. The information index 5022 of the display 5020 of FIG. 62 indicates that the detected characteristic 5034 of the anatomical structure 5024 is tissue 5026 that has been damaged by emphysema. The initially determined resection margin 5032 of FIG. 62 traverses through the characteristic 5034 of the anatomical structure 5024 and thus, the control circuit of the surgical visualization system can determine an adjusted resection margin 5036 to encompasses the characteristic 5036, the subject tissue 5028, and the predetermined margin 5030. The display 5020 of FIG. 62, depicts the adjusted resection margin 5036 via dashed lines. In some aspects, the display 5020 can allow the operating clinician(s) to select either the initially determined resection margin 5032, or the adjusted resection margin 5036. In other aspects, the display 5020 will limit the operating clinician(s) to the adjusted resection margin 5036 based on an instruction stored in the memory of the control system.

Referring now to FIGS. 63A and 63B, various models of an anatomical structure generated by a surgical visualization system are depicted in accordance with at least one aspect of the present disclosure. The anatomical structure 5036 of FIG. 63A includes a subject tissue 5038 and a determined resection margin 5040 encompassing the subject tissue 5038. The anatomical structure 5036 further includes characteristics 5042 of the anatomical structure 5036 and an adjusted resection margin 5044 that encompasses the characteristics 5042 as well as the subject tissue 5038. For example, the subject tissue 5038 of FIG. 63A can be a tumor.

In FIG. 63B, the anatomical structure 5046 includes various resection margins 5048 encompassing various characteristics 5049 of the anatomical structure 5046. For example, the characteristics 5049 of the anatomical structure 5046 of FIG. 63B can be bronchial tubes of the anatomical structure. Additionally, the anatomical structure 5046 of FIG. 63B includes a plurality of indicators 5050, each of which is associated with an anticipated volume of the anatomical structure 5046 if a particular resection margin 5048 is selected by the operating clinician(s). For example, an operating clinician can select a resection margin 5048 based upon a desired post-operation lung capacity. In other aspects, a control system of the surgical visualization system can automatically determine a resection margin 5048 based on an instruction stored in a memory requiring a resulting volume of the anatomical structure 5046 to not fall below a predetermined threshold.

Referring now to FIG. 64A, another model 5052 of an anatomical structure generated by a surgical visualization system is depicted in accordance with at least one aspect of the present disclosure. FIG. 64A depicts a simplified model 5052 of the anatomical structure, including a subject tissue 5054 and a characteristic 5056 of the anatomical structure 5056 detected by the surgical visualization system. In the model 5052 of FIG. 64A, the subject tissue 5054 is a tumor and the detected characteristic 5056 includes tissue damaged by emphysema.

Referring now to FIG. 64B, a display 5058 of the model 5052 of FIG. 64A is depicted in accordance with at least one aspect of the present disclosure. The display 5058 of FIG. 64B can include a resection margin overlay with an information index 5060. The information index 5060 can include information that is relevant to the features depicted in the model 5052 of the anatomical structure, such as textual descriptions of the depicted features and/or recommended staple types and sizes for the determined margins. However, in other aspects, the information index 5060 can be configured to display any information that is relevant to the features depicted in the model 5052. The display 5058 of FIG. 64B also depicts a predetermined margin 5062 about the subject tissue 5054 and an originally determined resection margin 5064 encompassing the subject tissue 5062. The originally determined resection margin 5064 can be determined by the surgical visualization system or provided as an input by the operating clinician(s). In the aspect of FIG. 64B, the resection margin overlay can depict an adjusted resection margin 5066 based on the detected characteristic 5056, or emphysema, of the anatomical structure 5052. The adjusted resection margin 5066 can be determined based on an instruction stored in a memory of the surgical visualization system to accomplish a desired physiologic effect. For example, based on the characterization of the anatomical structure and/or critical structures detected therein, the surgical visualization system can determine an adjusted resection margin 5066 optimized to remove the subject tissue 5054, preserve a residual volume of the anatomical structure, and/or maintain a desired quality of the anatomical structure, such as minimal leakage of air. Accordingly, an operating clinician can select either the originally determined resection margin 5064 or the adjusted resection margin 5066, based on the information depicted by the information index 5060 of the resection margin overlay of the display 5058.

Referring now to FIG. 65, a three-dimensional model 5068 of an anatomical structure 5069 generated by a surgical visualization system 5067 is depicted in accordance with at least one aspect of the present disclosure. The surgical visualization system 5067 includes an imaging device 5070 with a distance sensor system 5071 having an emitter 5072 configured to emit electromagnetic radiation 5074 onto the anatomical structure 5069, and a receiver 5076 configured to detect reflected electromagnetic radiation 5074. The imaging device 5070 of FIG. 65 can utilize the aforementioned spectral light, structured light, and Laser Doppler techniques to identify critical structures, such as a tumor 5078, and generate a fully integrated model 5068 and detailed characterization of the anatomical structure 5069. For example, the three-dimensional model 5068 of FIG. 65 can depict the anatomical structure 5069 as the superior lobe of a right lung, and can depict various characteristics of the anatomical structure 5069 with specificity, such as an artery 5080, a vein 5082, a bronchus 5084, a superior lobar bronchus 5086, a right pulmonary artery 5090, and/or a main bronchus 5092. Although the anatomical structure 5069 of FIG. 65 is a lung, the surgical visualization system 5067 can model various anatomical structures depending on the intended implementation. Accordingly, the surgical visualization system 5067 can use spectral light, structured light, and/or Laser Doppler to characterize any anatomical structure and display detected characteristics in detail via a three-dimensional model.

The surgical visualization system 5067 of FIG. 65 can provide real-time, three-dimensional spatial tracking of the distal tip of a surgical instrument and can provide a proximity alert when the distal tip of a surgical instrument moves within a certain range of the critical structure 5078. For example, the distance sensor system 5071 of the imaging device 5070 can be positioned on the distal tip of a surgical instrument and configured according to the aspect previously described in reference to FIG. 5. Accordingly, the emitter 5072 can emit electromagnetic radiation 5074 onto the surface of the anatomical structure 5069 and the receiver 5076 can detect electromagnetic radiation 5074 that has reflected off the surface of the anatomical structure 5069. The surgical visualization system 5067 can determine a position of the emitter 5072 relative to the surface of the anatomical structure 5069 based on a time-of-flight of the electromagnetic radiation 5074, or the time between its emission from the emitter 5072 and its detection by the receiver 5076. Although the surgical visualization system 5067 of FIG. 65 uses a distance sensor system 5071 and time-of-flight technique to determine the position of a surgical instrument relative to the anatomical structure 5069, other suitable components and/or techniques can be employed to achieve the same effect and include the position of a surgical instrument in the three-dimensional model 5068 of the anatomical structure 5069.

Referring now to FIG. 66, a display 5093 of the three-dimensional model 5068 of FIG. 65 is depicted in accordance with at least one aspect of the present disclosure. The display 5093 of FIG. 66 can include a resection margin overlay configured to depict user selected transection path 5096 and a system proposed transection path 5104. For example, the resection margin overlay can further depict detected characteristics such as the artery 5080, vein 5082, and bronchus 5084, detected subject tissues such as a tumor 5094, and/or a predetermined margin 5095 based on an instruction stored in the memory 134 (FIG. 2). Having reviewed the display 5093, the operating clinician(s) can determine a user selected transection path 5096 to remove the tumor 5094 and predetermined margin 5095. For example, the operating clinician(s) can determine a user selected transection path 5096 that can optimize the residual volume of the anatomical structure 5069, such as lung volume. Accordingly, the operating clinician(s) can provide the user selected transection path 5096 to the surgical visualization system 5067 via a user interface.

The surgical visualization system 5067 of FIG. 65 can receive the user selected transection path 5096 via user interface and assess the user selected transection path 5096 relative to the position of any detected characteristics of the anatomical structure 5069. For example, as depicted in FIG. 66, the surgical visualization system can identify that the user selected transection path 5096 interferes with an artery 5080, vein 5082, and bronchus 5084 of the anatomical structure 5069. Accordingly, the display 5093 can depict the anticipated interference and issue a notification to the operating clinician(s). The notification can be visual, audible, haptic, and/or any combination thereof. The display 5093 can additionally highlight a characteristic or a portion of the anatomical structure 5069 affected by the user selected transection path 5096 and/or a portion of the anatomical structure 5069 that can be rendered non-viable by the user selected transection path 5096. For example, the display 5093 of FIG. 66 can highlight a transected portion 5098 of the artery 5080 to represent a blood supply 5100 that would be affected by the user selected transection path 5096. The display 5093 can also highlight a portion 5102 of the anatomical structure 5069 that can be rendered non-viable by the user selected transection path 5096 dude to a lack of blood or air.

Additionally and/or alternatively, the surgical visualization system 5067 of FIG. 66 can depict a system proposed transection path 5104 on the display 5093 that would optimize the residual volume of the anatomical structure 5069, remove the subject tissue 5094 and predetermined margin 5095, and minimize adverse impacts to the detected characteristics of the anatomical structure 5069. For example, although the system proposed transection path 5104 may preserve less residual volume of the anatomical structure 5069, it does not interfere with the artery 5080, vein 5082, and bronchus 5084 and will still remove the tumor 5094 and predetermined margin 5095 from the superior lobe of the lung. In some aspects, the surgical visualization system 5067 can allow the operating clinician(s) to choose either the user selected transection path 5096 or the system proposed transection path 5104. In other aspects, the surgical visualization system 5067 can allow the operating clinician(s) to decline the system proposed transection path 5104 and input a second user selected transection path based on the depicted information on the display 5093.

Referring now to FIG. 67, a display 5106 three-dimensional model 5108 of an anatomical structure 5110 generated by a surgical visualization system 5107 is depicted in accordance with at least one aspect of the present disclosure. The surgical visualization system 5107 can include a surgical instrument 5109 with a distance sensor system, a structured light system, a spectral light system, or any combination thereof. Having reviewed the display 5106, the operating clinician(s) can determine a user selected transection path 5112 to remove a subject tissue from the anatomical structure 5110. The surgical visualization system 5107 of FIG. 67 can receive the user selected transection path 5112 via user interface and assess the user selected transection path 5112 relative to the position of any detected characteristics of the anatomical structure 5110. For example, the surgical visualization system 5107 of FIG. 67 has identified that the user selected transection path 5112 can interfere with a portion 5114 of the anatomical structure 5110 that is underinflated. The underinflated portion 5114 of the anatomical structure 5110 can have an adverse effect on the excision of a subject tissue and can lead to post-operative complications, including a less than optimal residual volume of the anatomical structure 5110. Accordingly, the display 5106 can depict the anticipated problem and issue a notification to the operating clinician(s). The notification can be visual, audible, haptic, and/or any combination thereof.

Additionally and/or alternatively, the surgical visualization system 5107 of FIG. 67 can depict a system proposed transection path 5116 on the display 5106 that would optimize the residual volume of the anatomical structure 5110, remove the subject tissue and predetermined margin, and minimize adverse impacts caused by the detected characteristics of the anatomical structure 5110. For example, the transection of underinflated tissue 5114 could complicate the surgical procedure and introduce unnecessary risk. The system proposed transection path 5116 of FIG. 67 directs the operating clinician(s) to the fully inflated tissue of the anatomical structure 5110, thereby minimizes the risk. In some aspects, the surgical visualization system 5107 can allow the operating clinician(s) to choose either the user selected transection path 5112 or the system proposed transection path 5116. In other aspects, the surgical visualization system 5107 can allow the operating clinician(s) to decline the system proposed transection path 5116 and input a second user selected transection path based on the depicted information on the display 5106.

In any of the preceding aspects, a surgical instrument can be configured with a distance sensor system, or other means to enable the surgical visualization system to detect a position of the surgical instrument relative to the anatomical structure. The surgical visualization systems discussed herein can also issue notifications informing the operating clinician(s) if a detected position of the surgical instrument does not comply with the selected transection path. The surgical visualization systems can issue a visual, audible, and/or haptic notification to the operating clinician(s) indicating that the surgical instrument should be repositioned prior to commencing the surgical procedure. In some aspects, the surgical visualization system can prevent the operating clinician(s) from performing the surgical procedure until the surgical instrument is properly positioned in accordance with the selected transaction path depicted on the display.

Analyzing Surgical Procedure Trends And Surgical Actions

One issue inherent to surgical procedures is that they are performed by individuals who may utilize different techniques in performing any given surgical procedure. In some cases, the surgical outcome associated with any given decision point in a surgical procedure can be direct and easy to identify. For example, the amount of bleeding that occurs after making an incision is direct and easy to identify because one can generally visualize the blood, and it is highly time correlated with the act of making the incision. However, oftentimes the surgical outcome associated a surgical procedure decision point can be highly attenuated from the decision itself. For example, there can be a large time delay (e.g., years) in the readmission of patients who underwent surgical procedures performed by a given surgeon, and it is unlikely that it could be determined which particular action taken by the surgeon led to the readmission. This dynamic can create a substantial disconnect between identifying and correcting surgical techniques that are not ideal or are otherwise not associated with the most positive surgical outcomes. However, surgical systems can be configured to track perioperative surgical data, such as via surgical hubs 2106, 2236 as described above under the heading SURGICAL HUB SYSTEM, for analysis by computer systems (e.g., the cloud 2204 and/or remove servers 2213). Further, surgical systems can be configured to determine contextual information associated with surgical procedures, as described above under the heading SITUATIONAL AWARENESS. The ability to track perioperative surgical data, determine contextual information associated with the surgical procedures, and analyze all of this data across a network of surgical systems spread across a region or even the world can be leveraged to identify and track trends associated with the various decision points associated with a surgical procedure (e.g., what types of surgical devices to use in the procedure, where to make an incision, or how much tissue to remove) and then determine which actions are most highly correlated to surgical outcomes (e.g., the amount of bleeding at an incision, whether any intraoperative corrective actions were necessary, reoperation rates, postoperative bleeding rates, or readmission rates) that are positive in order to suggest particular actions at the various decisions points associated with a surgical procedure.

In various aspects, a surgical system can be configured to monitor the actions taken by users in performing a surgical procedure and then provide recommendations or alerts when the actions deviate from the baseline actions. The baseline actions can be determined by monitoring or recording the performance of surgical procedures, determining the surgical outcomes associated with the various surgical procedures, determining which particular surgical actions are most associated with positive surgical outcomes, and then establishing baselines for the various surgical actions in each surgical procedure type according to which actions are associated with positive surgical outcomes. For example, FIG. 68 is a diagram of a surgical system 7000 that could be configured to implement the aforementioned techniques. The surgical system 7000 includes a control system 7002 that is coupled to an imaging system 7004 and a back-end computer system 7010 via a data network (e.g., a LAN, a WAN, or the Internet). In one aspect, the control system 7002 can include the control system 133 described in connection with FIG. 2, a surgical hub 2106, 2236 as described in connection with FIGS. 17-19, and other such systems. The control system 7002 can include the imaging system 142 (FIG. 2) or any other such imaging or visualization systems described in connection with FIGS. 1-19, including imaging systems that are configured to utilize structure electromagnetic radiation (EMR) techniques and/or multispectral imaging techniques to characterize objects. The back-end computer system 7010 can include a cloud computing architecture or another computer system configured to store and execute various machine learning models or other algorithms.

At least in part by visualizing what is occurring in a surgical procedure via the imaging system 7004, the surgical system 7000 can monitor decision points within the procedure (e.g., device selection, stapler cartridge selection, or order of operating steps) and log these decisions. The surgical system 7000 can utilize the imaging system 7004 to monitor intraoperative decision points by visualizing objects that enter the field of view (FOV) of the imaging system 7004 and then performing (e.g., by the control system 7002) object recognition or other computer vision techniques to identify the surgical devices being utilized in the surgical procedure, the particular organ or tissue being operated on, and so on. The identified actions taken by the surgeon at the various decision points can then be utilized to inform algorithms that balance patient factors, surgeon factors, device utilization, and clinical outcome data to, for example, train machine learning models (e.g., an artificial neural network) using supervised or unsupervised machine learning techniques. Once trained, the machine learning models can offer suggestions to users when a statistically significant outcome could be influenced by a decision point during the surgical procedure. Further, these machine learning models or other algorithms could be utilized to postoperatively review actions taken by the surgical staff during a surgical procedure and flag actions for review by the surgical staff. The surgical staff could then be provided the opportunity to confirm or disagree with each flagged assessment to better inform and train both the surgical staff and the algorithm. In one aspect, the control system 7002 can be configured to collect perioperative data and then provide (e.g., intraoperatively or postoperatively) the data to a back-end computer system 7010 (e.g., a cloud computing system) via the data network 7008. The back-end computer system 7010 can then be configured to execute and train the machine learning models or other algorithms based on the data provided by the control system 7002 or network of control systems 7002 to which it is connected. In one aspect, the trained machine learning models can be executed by the back-end computer system 7010 and provide recommendations or analysis to the control system 7002 in real time, during the performance of a surgical procedure, based on intraoperative data provided by the control system 7002. In one aspect, the trained machine learning models can be provided to and executed by the control systems 7002 themselves.

In one aspect, the surgical system 7000 can be configured to analyze the various actions being taken during the surgical procedure, such as the type of surgical instrument selected to perform a given surgical procedure step or the position or orientation of the surgical instrument relative to the patient's tissues, via an imaging system 7004 that includes a structured light system (e.g., a structured light source 152) to identify objects within the FOV of the imaging system 7004 and thereby enable adaptive responses and comparisons between current actions with previous actions in similar surgical procedure types. In particular, the surgical system 7000 can be configured to compile perioperative data from multiple data sources to provide trends and references for structured light tracking of objects during a surgical procedure. The visualized surgical procedure data can be compared with clinical outcomes resulting during the performance of the procedure or after the procedure to determine trends in the techniques utilized for particular surgical procedure steps, the types of surgical instruments utilized, and other decision points with the clinical outcomes to provide future baselines. These baselines could thus define the best practices for performing a given surgical procedure.

In one implementation, the control system 7002 can be configured to execute various control algorithms, as described in connection with FIG. 2, including surface mapping logic 136, imaging logic 138, tissue identification logic 140, distance determining logic 141, targeting logic, and/or trajectory projecting logic. The control algorithms can be configured to control surgical instruments or other components of the surgical system 7000, display information to users, and/or control a robotic system 2110 (FIG. 17). The machine learning models or algorithms being trained on the perioperative surgical action data and the surgical outcome data can further be utilized to refine the various control algorithms executed by the control system 7002. In particular, targeting or trajectory projecting logic could be refined based on the visualization of tissue volumes and surfaces (e.g., as determined by a structured light system of the imaging system 7004) in combination with locally measured surgical instrument parameters. This intraoperative data can then be utilized in conjunction with the surgical outcome data, which could include data associated with interactions between the tissue and the surgical instrument, to improve control algorithms of the devices.

In another implementation, the control system 7002 can be configured to record the positions of the surgical devices utilized in a surgical procedure relative to the patient in a local or global coordinate system. A local coordinate system could be defined relative to, for example, the surgical devices themselves, particular tissues or organs, or virtual points of view, as described in U.S. patent application Ser. No. 16/729,803, titled ADAPTIVE VISUALIZATION BY A SURGICAL SYSTEM, filed Dec. 30, 2019, which is hereby incorporated by reference herein in its entirety. A global coordinate system could be defined relative to, for example, the patient or the operating theater. In combination with the recordation of the surgical devices' positions, the control system 7002 can be configured to record the functions performed by the surgical devices, such as whether a surgical instrument was fired, the power level of the surgical instrument, or tissue characteristics or other parameters sensed by the surgical instrument. Accordingly, the surgical devices' positions and functions can be utilized to inform/train the machine learning models or other algorithms, which can then correlate the relative positions and functions of the surgical devices to positive surgical outcomes to help surgeons improve technique or provide more precise information to study and improve surgical device functions. For example, an algorithm could be developed to change the function of the articulation buttons of a surgical instrument based on data that changing the function of the articulation buttons results in better surgical outcomes, possibly due to the articulation buttons being unintuitive when the surgical instrument is in a particular position and/or performing a particular function.

In another implementation, the control system 7002 can be configured to continuously monitor the movements of the surgeon in search of wasted steps, unnecessary tissue contact/manipulation, or actions/steps that were unexpected based on situational awareness. The control system 7002 could flag such identified events for postoperative review by the surgeon and provide the surgeon with the opportunity to confirm or disagree with each flagged assessment to better inform/train both the surgeon and the algorithm.

One example of an algorithm that can be utilized to perform the various techniques or implementations described above is shown in FIG. 69, which is a logic flow diagram of a process 7100 for providing dynamic surgical recommendations to users. In the following description of the process 7100, reference should also be made to FIG. 2, FIGS. 17-19, and FIG. 68. The process 7100 can be embodied as, for example, instructions stored in a memory 134 coupled to a control circuit 132 that, when executed by the control circuit 132, cause the control circuit 132 to perform the enumerated steps of the process 7100. It should be understood that the process 7100 can be executed by and/or between the control system 7002 (which can include a surgical hub 2106, 2236) and the back-end computer system 7010 (which can include the cloud 2204 or remote server 2213). Accordingly, the control circuit 132 can collectively refer to one or multiple control circuits associated with or distributed between the control system 7002 and the back-end computer system 7010. In other words, the control circuit 132 could include a control circuit of the control system 7002 and/or a control circuit of the back-end computer system 7010. For brevity, the process 7100 is described as being executed by the control system 7002 and the back-end computer system 7010; however, it should be understood that the process 7100 can be executed by other combinations of hardware, software, and/or firmware and that any particular step of the process 7100 can be executed by either the control system 7002 or the back-end computer system 7010.

Accordingly, the control system 7002 and/or the back-end computer system 7010 executing the process 7100 can receive 7102 images (e.g., captured via the imaging system 7004) of a surgical procedure being performed and perioperative data. The images can be associated with perioperative data, such as positions of surgical devices in local or global coordinate systems, sensor measurements, object recognition data, and so on. Further, the images can be generated at least in part based on a structured light system and can thus include three-dimensional (3D) volumetric data or surface mapping data. In one implementation, the control system 7002 can initially generate the images via the imaging system 7004 and then provide the image data to the back-end computer system 7010 for processing thereby. The back-end computer system 7010 can be communicatively connected to a number of different control systems 7002, which can in turn be located in or associated with a number of different facilities or hospital networks. Thus, the back-end computer system 7010 can receive the surgical image data across a number of different control systems 7002 to train the machine learning models or other algorithms.

Accordingly, the control system 7002 and/or the back-end computer system 7010 can determine 7104 surgical outcomes associated with the surgical procedures for which the perioperative data was received. In one aspect, the control system 7002 could determine a surgical outcome by, for example, visualizing the surgical outcome (e.g., bleeding along an incision line) via the imaging system 7004. In another aspect, the back-end computer system 7010 could determine a surgical outcome by, for example, storing a database of surgical outcomes associated with a given surgical procedure. The database could be updated as additional information related to the patient is received by the back-end computer system 7010, or the back-end computer system 7010 could allow users to update the database as surgical outcomes are identified. For example, users (e.g., medical facility personnel) could update the database when a patient returns for a reoperation procedure or reports undue amounts of pain or other negative outcomes associated with the surgical procedure.

Accordingly, the control system 7002 and/or the back-end computer system 7010 can determine 7106 a baseline surgical action corresponding to the images and the outcome data. In one aspect, the back-end computer system 7010 can be programmed to execute and train a machine learning model to correlate the received images and other perioperative data with the determined outcomes to establish the surgical action at each defined decision point in the surgical procedure that is most correlated (or correlated at least above a threshold) to desired or positive surgical outcomes. Such surgical actions can thus be defined as the baseline or recommended surgical actions to be performed at each decision point associated with each surgical procedure type. Once trained, the machine learning model can then be utilized to provide preoperative, intraoperative, or postoperative recommendations to users according to the defined baseline.

Accordingly, the control system 7002 can generate 7108 an image of the surgical site during a surgical procedure via, for example, the imaging system 7004. The image can be generated 7108 using structured EMR, multispectral imaging, or any other imaging techniques described above. Further, the image can be associated with a variety of perioperative data, including, for example, surface mapping or 3D geometry determined via structured EMR, subsurface or tissue characteristic data determined via multispectral imaging techniques, object recognition data, positional data relative to global and/or local coordinates systems, and/or contextual data determined via a situational awareness system.

Accordingly, the control system 7002 and/or back-end computer system 7010 can determine 7110 a surgical action that is being performed at a given decision point in the surgical procedure. In one aspect, the control system 7002 and/or back-end computer system 7010 can make this determination via a situational awareness system. For example, the control system 7002 could determine that the surgeon is dissecting to mobilize a lung, ligating vessels, or transecting parenchyma based upon generator data and surgical instrument data (including the relative activations of the surgical devices), as described above in connection with FIG. 21. In this example, the decision points for the surgical actions would include what devices are being utilized for the particular step of the surgical procedure (e.g., ultrasonic instrument or electrosurgical instrument, size and type of staple cartridge, or brand of surgical instrument), where or what the surgeon is transecting or ligating, and so on. As another example, the control system 7002 and/or back-end computer system 7010 could determine what preoperative mix of surgical devices are planned for the surgical procedure by visualizing the prep table in the operating theater. In this example, the decision point for the surgical action would thus be the selected surgical devices for the procedure.

Accordingly, the control system 7002 and/or back-end computer system 7010 can compare 7112 the current surgical action to the baseline surgical action for the given decision point of the surgical procedure that was determined using the techniques described above. Accordingly, the control system 7002 and/or back-end computer system 7010 can provide 7114 a recommendation based on the comparison between the surgical action and the baseline. In various aspects, the recommendation can be provided preoperatively (e.g., recommending a different mix of surgical devices to perform the procedure), intraoperatively (e.g., recommending a different position for the end effector of the surgical instrument), or postoperatively (e.g., recommending different surgical actions at flagged points in the procedure via a report to be reviewed by the surgeon). In one aspect, the recommendation can only be provided if the surgical action deviates from the baseline by at least a threshold amount. The recommendation can take the form of an audible alert, textual or graphical feedback, haptic feedback, and so on. As one example shown in FIG. 70, a display 7006 coupled to the control system 7002 can display a video feed 7200 of the surgical site 7014 as provided by the imaging system 7004. The video feed 7200 can show the position of the surgical instrument 7210 and visualizations of other tissues and/or structures, which in this specific example include a tumor 7016 and various vessels 7018. In this example, the control system 7002 and/or back-end computer system 7010 has determined that the position of the surgical instrument 7210 has deviated from the baseline position for the given step of the surgical procedure. Accordingly, the control system 7002 has caused the display 7006 to provide 7114 a recommendation in the form of a graphical overlay 7212 that shows the recommended or baseline position for the surgical instrument 7210 for the given surgical procedure step.

These systems and methods allow surgeons to visualize what the recommended course of action for any given decision point in the surgical procedure would be and then act accordingly. Surgeons could therefore learn and further develop based on feedback derived from large amounts of data collected from any number of surgical procedures performed by any number of individuals throughout the world. This would allow surgeons to further hone their intraoperative techniques or other decisions associated with the performance of surgical procedures to improve patient outcomes. Further, such systems could be integrated into robotic surgical systems to leverage the vast amount of available surgical data to improve their control algorithms and thereby control the performance of the robotic surgical systems over time.

In one aspect, surgical systems could also be configured to predict and project an effect of an action that could be taken during a surgical procedure for users. In particular, 3D surface and volume visualizations of tissues and/or structures could be combined with a computational analysis and modeling data set derived from a data source to record the effects of various surgical devices on the tissues and/or structures. For example, a surgical system 7000 could, via an imaging system 7004, visualize the surgical site 7014 (including any tissues and/or structures located there) and then record the effects on the various tissues and/or structures in response to various treatments, such as firing a surgical stapler or firing an electrosurgical instrument. The effects on the tissues and/or structures could then be recorded and modeled for any given type(s), size(s), and configuration(s) of the tissues and/or structures. Further, a computational analysis could then be executed (e.g., by the control system 7002) to predict an aspect of the treatment projection from the surgical device being utilized in the surgical procedure. For example, a treatment projection could include the application of thermal or electrical energy to a tissue and the extent to which the application of energy would penetrate into the 3D scanned volume of the tissue. This treatment projection could be provided to the user as a graphical overlay on the video feed 7200 shown on the display 7006, for example.

In one aspect, the projection from the model could be determined separately from and compared against predictions developed by other models or surgical devices. For example, the imaging system 7004 could include a secondary sensing array (e.g., an IR CMOS array) configured to sense tissues characteristics and project the application of energy to the tissue to compare the projections with projections forecast from other models or surgical devices (e.g., an electrosurgical generator). Further, the forecast from the other data source could be adjusted based on the comparative accuracy of the projection modeled by the control system 7002 relative to the forecast from the other data source, as determined according to historical surgical procedure data. For example, a power level of an electrosurgical instrument or ultrasonic surgical instrument and the visualization of the tissue-to-instrument jaw interaction could be utilized to provide the algorithm (which could be based on finite element analysis, for example) and the boundary conditions of the forecast (e.g., by the generator).

In one aspect, when the prediction from the computational analysis of the imaging system 7004 and the prediction from the algorithm executed by the other data (e.g., surgical generator) differ by at least a threshold, the control system 7002 could take a variety of different actions. For example, the control system 7002 could provide a user alert (e.g., emit a different tone than normal) prior to the user opening the jaws to inspect the tissue, notify the user after completion of the surgical step (e.g., emit a different tone at the end of the energy delivery by the surgical instrument), soft lockout the jaws of the surgical instrument (e.g., until overridden by the user), or adjust the generator control algorithm to adjust the delivery of energy to the tissue (e.g., extend the delivery of energy to ensure a safe outcome at the cost of additional time).

These systems and methods allow surgeons to visualize what a predicted course of action for any given decision point in the surgical procedure would be and then act accordingly. Surgeons could therefore make more informed intraoperative decisions based on feedback derived from large amounts of data collected from any number of surgical procedures performed by any number of individuals throughout the world. This would allow surgeons to further hone their intraoperative techniques to improve patient outcomes. Further, such systems could be integrated into robotic surgical systems to leverage the vast amount of available surgical data to improve their control algorithms and thereby control the performance of the robotic surgical systems over time.

Visualization with Structured Light to Extrapolate Metadata from Imaged Tissue

Surface irregularities (e.g. deformations and/or discontinuities) on tissue can be difficult to capture and portray in a visualization system. Additionally, tissue often moves and/or changes during a surgical procedure. In other words, the tissue is dynamic. For example, the tissue may be distorted, stressed, or become otherwise deformed by a surgical fastening operation. The tissue may also be transected and/or certain portions and/or layers of tissue may be removed. Underlying tissue and/or structures may become exposed during the surgical procedure. As the tissue moves, embedded structures underlying the visible tissue and/or hidden tissue margins within an anatomical structure may also move. For example, a resection margin may be concentrically positioned around a tumor prior to tissue deformation; however, as the anatomical structure is deformed during a surgical procedure, the resection margin may also become deformed. In certain instances, adjacent portions of tissue can shift, including those portions with previously-identified physical characteristics or properties. Generating three-dimensional digital representations or models of the tissue as it is deformed, transected, moved, or otherwise changed during a surgical procedure presents various challenges; however, such dynamic visualization imaging may be helpful to a clinician in certain instances.

In various aspects of the present disclosure, a visualization system can include a plurality of light sources in combination with structured light patterns to extrapolate additional tissue characteristics or metadata related to the imaged tissue. For example, surface irregularities of tissue can be identified with the combination of structured light and multiple coherent light sources. Additionally or alternatively, the surface irregularities can be identified with the combination of structured light and non-coherent or diffuse light and stereoscopic image sensors. In one instance, the plurality of light sources can emit patterns of structured light at different wavelengths. The different wavelengths can reach different surfaces of an anatomical structure, such as an outer surface and an underlying subsurface. An image sensor of the visualization system can receive imaging data from the image sensor indicative of the different surfaces of the anatomical structure. The visualization system can then generate a three-dimensional digital representation of the anatomical structure based on the structured light patterns on the different surfaces of the anatomical structure imaged by the image sensor. In certain instances, subsurface contours can be utilized to fill-in gaps in a visualization of the surface due to tissue irregularities thereon. Additionally or alternatively, subsurface contours can be analyzed to determine and track movement of embedded structures and/or tissue layers.

As the tissue moves during a surgical procedure, it may be useful in certain circumstances to update information in a visualization display. For example, it can be helpful to show tissue velocity, tissue distortion, tissue irregularities, tissue vascularization, and/or updated identification of one or more embedded structures. By comparing imaging frames of the tissue at different points in time, a control circuit of the surgical system can analyze the additional tissue characteristics or metadata and provide updated visualization images to the clinician to communicate the same.

In various instances, a situational awareness module can inform the identification of tissue irregularities based on expectations at the surgical site. For example, the situational awareness module may expect to identify a row of staples or a scar at a particular location based on the type of surgical procedure, the step in the surgical procedure, the type(s) of tissue, and/or various tissue characteristics, for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

Imaging by a visualization system can be converted into measurable data and information for the clinician(s) and/or surgical hub(s). For example, visualization can be utilized to analyze surgical device usage and to provide opportunities for improvement or device optimization in certain instances. In various instances, situational awareness can inform the visualization system. For example, a surgical system including a situational awareness module communicatively coupled to a visualization system, as described herein, can be configured to provide updated information, such as updated tissue characteristics and/or metadata, for example, to a clinician via a display during a surgical procedure. Updated visualization imaging or other data can be provided automatically based on input from the situational awareness module and/or can be suggested by the situational awareness module based on an awareness of the surgical procedure, patient, and/or tissue. Such a visualization system is adaptive to the surgical scenario.

More specifically, the visualization images can be updated in accordance with input from the situational awareness module. For example, the situational awareness module can determine the type of surgical procedure, the step in the surgical procedure, the type(s) of tissue, and/or various tissue characteristics, as further described herein. Updates to the visualization images can be automated and/or recommended to a clinician based on inputs from the situational awareness module. For example, if the situational awareness module becomes aware that a staple line has been fired into tissue, the situational awareness module can order or suggest updating the visualization imaging to show the tissue compression along the staple line. As another example, if the situational awareness module becomes aware that visible tissue has shifted during a surgical procedure, the situational awareness module can order or suggest updating the visualization imaging to show the updated configuration of a resection margin. Additional surgical scenarios are contemplated and various examples are provided throughout the present disclosure.

Referring now to FIG. 71, portions of a computer-implemented interactive surgical system are shown. The computer-implemented interactive surgical system includes a cloud-based system 6004 and at least one surgical hub 6006 in communication with the cloud-based system 6004. Various elements of the computer-implemented interactive surgical system can be identical to those of the computer-implemented interactive surgical system 2100 (FIG. 17). For example, the surgical hub 6006 can be identical to the surgical hub 2106 and the cloud-based system 6004 can be identical to the cloud-based system 2104. The computer-implemented interactive surgical system in FIG. 71 also includes a visualization system 6008 having a control circuit 6032, which is configured to communicate with the hub 6006 and/or a situational awareness module such as the situational awareness module 6007 of the hub 6006, for example.

The visualization system 6008 can be similar in many respects to the visualization system 100 (FIG. 1) and the visualization system 2108 (FIG. 17). For example, the visualization system 6008 includes a memory 6034 communicatively coupled to the control circuit 6032. The visualization system 6008 also includes multiple light sources 6050, an imaging system 6042 having a camera 6044, a display 6046, and controls 6048. The camera 6044 includes at least one image sensor 6035. In other instances, the adaptive visualization system 6008 can include multiple cameras, for example.

The visualization system 6008 is configured to adapt in response to input from the hub 6006. In such instances, the visualization system 6008 is an adaptive visualization system. For example, the hub 6006 includes the situational awareness module 6007, which is configured to synthesize data from multiple sources to determine an appropriate response to a surgical event. For example, the situational awareness module 6007 can determine the type of surgical procedure, step in the surgical procedure, type of tissue, and/or tissue characteristics, as further described herein. Moreover, such a situational awareness module 6007 can recommend a particular course of action or possible choices to a system based on the synthesized data. In various instances, a sensor system encompassing a plurality of sensors distributed throughout a surgical system can provide data, images, and/or other information to the situational awareness module 6007. Such a situational awareness module 6007 can be incorporated into a control unit of the surgical hub 6006, for example. In various instances, the visualization system 6008 is configured to update or otherwise modify the visualization(s) provided to the clinician(s) based on the input from the situational awareness module 6007.

The light sources 6050 can include at least one structured light source for determining the surface geometry and contours of an anatomical structure. 3DIntegrated, Inc. (3Di) of Copenhagen, Denmark, provides a platform based on structured light, deep learning, and structure from motion principles to obtain three-dimensional data in real-time. For example, in certain instances, 3Di software can be utilized to determine the three-dimensional position of surgical tools, generate the three-dimensional reconstruction of surgical surfaces, and obtain coordinates for computer-driven surgery, for example. In various instances, a structured light pattern utilizing a single imaging array can be utilized to determine surface contouring, for example. Reliance on a single structured light pattern can provide an incomplete digital model. Certain portions of a surface can be obstructed if there are surface irregularities, for example. In certain instances, as further described herein, multiple structured light arrays can be employed, such as multiple arrays on the same laparoscopy camera, for example, to generate a more complete digital model.

The visualization system 6008, for example, can include multiple light sources in combination with structured light patterns to extrapolate additional aspects, characterizations, or metadata of the imaged tissue. As further described herein, the additional aspects can be tissue velocity, tissue distortion, tissue irregularity, tissue vascularization, and identification of an embedded structure within the anatomical structure, for example. Vascularization can be analyzed by tracking the underlying moving particles, for example. In one aspect, Doppler imaging may be used to determine the velocity flow of particles such as blood cells flowing within a blood vessel such as a vein, capillary, or artery. Doppler imaging may provide a direction and velocity of cell flow through the blood vessel. Additionally or alternatively, infrared (IR) absorption may identify the red blood cells as being oxygen-rich—thereby identifying the blood vessel as an artery—or oxygen-depleted—thereby identifying the blood vessel as a vein. Tissue characterization is further described in U.S. patent application Ser. No. 15/940,722, titled CHARACTERIZATION OF TISSUE IRREGULARITIES THROUGH THE USE OF MONO-CHROMATIC LIGHT REFRACTIVITY and U.S. patent application Ser. No. 15/940,704, titled USE OF LASER LIGHT AND RED-GREEN-BLUE COLORATION TO DETERMINE PROPERTIES OF BACK SCATTERED LIGHT, both filed Mar. 29, 2018, which are incorporated by reference herein in their respective entireties.

In certain aspects of the present disclosure, certain portions of the imaging frames with structured light can be utilized to add three-dimensional tissue variances. These portions can provide additional tissue characteristics and/or metadata of the imaged tissue. In various instances, the structured light source can include a multi-source structured light. For example, the light sources 6050 (FIG. 71) can be multiple coherent light sources or lasers. The use of coherent light can enable the differentiation and separation of the surface refractivity from the three-dimensional distortion of the structured light pattern. Additionally or alternatively, phase shift data from the multiple coherent light sources can be utilized to characterize tissue properties.

In one example, coherent light can be projected onto visible tissue in a predefined two-dimensional structured light pattern (i.e., a spatial intensity pattern such as a series of lines or a grid). The structured light pattern of coherent light can be cycled. In one aspect, the coherent light patterns may be cycled among a variety of grids having different line spacings or orientations. In another aspect, the coherent light patterns may be cycled among a variety of parallel lines at a variety of line spacings. In yet another aspect, the light patterns may be cycled among a variety of light wavelengths. For example, at 480 frames-per-second (FPS), sixty frames can be used for each of eight different color segments or wavelengths. In some aspects, multiple sequential frames may be taken at the same light wavelength. Alternatively, sequential frames may be taken using alternating light wavelengths for each frame. A portion of the frames can be digitally removed from the three-dimensional surface mapping visualization. For example, ten frames for each of the sixty frames of each wavelength can be digitally removed. If the visualized tissue remains stationary throughout a group of frames, the digitally removed frames may be used to produce an averaged image. Though the digitally-removed frames may not be utilized for three-dimensional surface mapping, the surface refractivity (or other properties) of those portions can be utilized to determine additional tissue characteristics and/or metadata. Examples of such tissue characteristics may include, without limitation, a tissue composition and/or a tissue sub-structure orientation (for example, the underlying orientation of collagen or elastin fibers). Tissue characterization is further described in U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

In various instances, the light source 6050 can includes red, green, blue, infrared, and ultraviolet lasers. Multiple wavelengths can be utilized for certain light, such as infrared and/or ultraviolet, for example. In some aspects, multiple infrared light sources within the range of about 700 nm to about 1400 nm may be used. In some examples, the infrared light may have a wavelength of about 705 nm, about 730 nm, about 761 nm, about 780 nm, about 785 nm, about 800 nm, about 830 nm, 850 nm, 940 nm, 980 nm, 1064 nm, or 1370 nm. In some aspects, multiple ultraviolet light sources within the range of about 200 nm to about 400 nm may be used. In some examples, the ultraviolet light may have a wavelength of about 211 nm, about 236 nm, about 263 nm, about 266 nm, about 351 nm, or about 351 nm. In certain instances, nine sources can be utilized. For example, the infrared and ultraviolet frame sets can be alternated as they are displayed in a 60 Hz visualization portion in real time and the metadata obtained from these frame sets can be superimposed on the image as needed.

In various instances, the light sources 6050 can include non-coherent or broad spectrum sources, which can be imaged with stereoscopic imaging sensors. Stereoscopic imaging of structured light can provide a three-dimensional image of the distorted structured light pattern. A three-dimensional image of the distorted pattern can lessen the need for a calculative adjustment of the two-dimensional image, for example. However, the distorted pattern can still be compared with the surface refractivity to determine if the surface of the anatomical structure, or the tissue just under the surface, contains a three-dimensional irregularity.

In certain aspects of the present disclosure, multiple CMOS arrays and FPGA conversion circuits can be incorporated into the visualization system to acquire time-synced interrelated metadata about the imaged tissue. For example, the resolution of an image obtained by a CMOS sensor can be enhanced by combining a multi-color structured light image received by the CMOS sensor with an image obtained by a higher resolution grey scale imaging sensor to enable the micronization of the specific array such that more than one array can be positioned on the same laparoscopy camera. The multiple arrays enable stereoscopic replication of the same image as well as independent FPGAs or independent sensors to monitor different aspects of the image or related metadata in real-time. Multi-array imaging is further described in U.S. patent application Ser. No. 15/940,742, titled DUAL CMOS ARRAY IMAGING, filed Mar. 29, 2018, which is incorporated by reference herein in its entirety.

Referring now to FIG. 72, portions of a visualization system 6108 are shown. The visualization system 6108 is similar in many respects to the visualization system 6008 in FIG. 71. For example, the visualization system 6108 includes a structured light projector 6150 for projecting structured light patterns onto tissue T at a plurality of different wavelengths and a camera 6144 having at least one image sensor. The structured light projector 6150 and the camera 6144 are communicatively coupled to a control circuit, such as the control circuit 6032 (FIG. 71). The camera 6144 is configured to detect imaging data from the structured light projector 6150 and convey the imaging data to the control circuit for processing.

In various instances, surface irregularities of the tissue T can be identified with the imaging data obtained by the camera 6144 and sent to the control circuit. For example, the structured light pattern reflected from the surface of the tissue T may provide an incomplete picture of the surgical site due to irregularities along the surface of the tissue T in certain instances. When the surface has one or more irregularities such as a tear, cut, and/or deformation that interferes with the structured light pattern, the entire structured light pattern may not be reflected by the surface and, thus, may not be detected by the image sensor of the camera 6144. For example, a surface deformation can cast a shadow that obstructs a portion of the structured light pattern. In such instances, structured light patterns penetrating the surface of the tissue and reflected from a sub-surface thereof can be utilized to fill gaps in the three-dimensional digital rendering. For example, one or more wavelengths of coherent light that penetrate the surface of the tissue can be utilized to determine the contours of the subsurface. As further described herein, the structured light pattern or patterns can be emitted at different wavelengths and captured by the image sensor. Certain subsurface light patterns may be digitally removed from the three-dimensional digital rendering; however, such patterns can be used to extrapolate the contours of the tissue surface. More specifically, the geometry of the tissue surface can be extrapolated from the curvature of one or more tissue sub-surfaces.

Referring again to FIG. 72, the visualization system 6108 can be configured to identify the surface geometry of an organ 6160, such as a stomach, for example, as further described herein. However, irregularities 6164 on the surface of the organ 6160 can inhibit the generation of a complete three-dimensional model of the organ 6160. For example, the irregularity 6164, which may be a scar or other tissue malformation, can block the structured light pattern emitted by the structured light projector 6150 from reaching portions of the tissue T surface. However, a pattern of structured light at a tissue-penetrating wavelength can be configured to penetrate the irregularity 6164 and can be detected at a sub-surface layer by the image sensor of the camera 6144. The tissue-penetrating structured light pattern can be utilized by the control circuit to determine a curvature of the underlying tissue surface and, thus, extrapolate the surface of the organ 6160 including the irregularity 6164 thereof.

In certain instances, a tissue-penetrating structured light pattern can be utilized to determine compression of tissue. For example, tissue can be compressed along a staple line. In various instances, uniform tissue compression is desired to obtain a reliable tissue seal. The tissue-penetrating structured light patterns can be utilized by the control circuit to generate a subsurface three-dimensional visualization of tissue compression along an embedded staple line. More specifically, the movement of tissue layers, include one or more subsurface layers, can be monitored and tracked to analyze the compression thereof along a staple line.

Additionally or alternatively, the refractivity R of the structured light pattern, as detected by the image sensor of the camera 6144, can provide supplemental information and/or metadata regarding the tissue characteristics of the imaged tissue in certain instances. Also, in certain instances, phase shift data for multiple coherent lights from the structured light projector 6150 can provide supplemental information and/or metadata regarding the imaged tissue. For example, irregularities 6164 can be identified based on refractivity and/or phase shift data. In certain instances, an irregularity 6164 can include one or more key anatomical structures 6162, which can be tracked by the structured light pattern reflected thereon and mapped to the digital model thereof.

Another visualization system 6208 is shown in FIG. 73. The visualization system 6208 can be similar to the visualization system 6108 (FIG. 72) and can be configured to visualize the organ 6160, including irregularities 6164 along the surface and/or key anatomical structures 6162 thereof. The visualization system 6208 comprises a single surgical device including both a structured light source 6250 and a camera 6244. In various instances, the structured light source 6250 can be configured to emit coherent light and the camera 6244 can be configured to detect the phase shift of the coherent light reflected back from the surface of the tissue T. The tissue can be characterized by the phase shift data. For example, the phase shift data can be a supplementary source of information regarding the visualized tissue. Different degrees of phase shift can correspond to different physical properties. In some aspects, a phase shift of the reflected light may indicate motion of the surface or sub-surface structures. In other aspects, a phase shift of the reflected light may indicate subsurface layers.

Referring now to FIG. 89, a logic flow diagram of a process 6800 of conveying a three dimensional model to a clinician is shown. In the following description of the process 6800, reference should be made to the control circuit 132 (FIG. 2) and/or the visualization system 6008 (FIG. 71). In one aspect, the process 6800 can be embodied as a set of computer-executable instructions embodied as software (e.g., as stored in the memory 134) or hardware that are executed by the control circuit 132 of the control system 133 and/or the control circuit 6032.

The visualization system 6008 executing the process 6800 can obtain, at block 6802, first imaging data from an image sensor, such as the image sensor 6035, for example. The first imaging data can be indicative of an outer surface contour of an anatomical structure from a first pattern of structured light detected by the image sensor 6035. At block 6804, the visualization system 6008 can obtain second imaging data from the image sensor 6035. The second imaging data can be indicative of a subsurface contour of the anatomical structure from a second pattern of structured light. The second pattern of structured light can comprise a different wavelength than the first pattern of structured light. The first imaging data and the second imaging data can be transmitted to the control circuit 6032, for example, at blocks 6806 and 6808, respectively. The control circuit 6032 can generate a three-dimensional digital representation of the anatomical structure at block 6812. The digital representation or model can include the outer surface contour and the subsurface contour. In various instances, additional layers of tissue can be imaged with the process 6800. Upon completing the three-dimensional model, the control circuit 6032 can transmit, at block 6814, the three-dimensional model to a display 6046, for example.

In one aspect, the control circuit 6032 is also configured to receive a signal from the situational awareness module 6007 of the surgical hub 6006 and, in response to the signal from the situational awareness module 6007, update the three-dimensional model of the anatomical structure. In various aspects, the control circuit 6032 is further configured to obtain metadata from at least one of the first imaging data and the second imaging data at the processing block 6810. The control circuit 6032 can be configured to overlay the metadata with the three-dimensional model at block 6812 and transmit the additional information to the clinician at block 6814. The metadata can correspond to at least one of tissue velocity, tissue distortion, tissue irregularity, tissue vascularization, or identification of an embedded structure within the anatomical structure, as further described herein. In one aspect, the metadata can be indicative of tissue compression, such as embedded tissue along a staple line, for example. The situational awareness module 6007 can dictate or suggest when metadata is processed and conveyed to the clinicians based on a detected surgical scenario and corresponding information that may be helpful to the clinician in each surgical scenario.

In various instances, an adaptive visualization system can provide visualization of motion at the surgical site. Structured light can be used with stereoscopic imaging sensors and multi-source coherent light to map light pattern distortions from one time frame to another time frame. The mapping of light pattern distortions across frames can be used to visualize and analyze anatomic distortion. Moreover, as the three-dimensional digital representations or models are deformed, any superimposed three-dimensional imaging-such as embedded structures, tissue irregularities, and/or hidden boundaries and/or tissue margins—can be proportionately deformed with the three-dimensional model. In such instances, the visualization system can convey movement of the superimposed three-dimensional imaging to a clinician as the tissue is manipulated, e.g. dissected and/or retracted.

In various aspects of the present disclosure, an adaptive visualization system can obtain baseline visualization data based on situational awareness (e.g. input from the situational awareness module 6007). For example, a baseline visualization of an anatomical structure and/or surgical site can be obtained before initiation of a surgical procedure-such as before the manipulation and dissection of tissue at the surgical site. The baseline visualization image of the anatomical geometry can include a visualization of the surface of the anatomical structure and its boundaries. Such a baseline visualization image can be used to preserve overall orientation of the surgical site and anatomic structure even as local regions within the anatomic structure are progressively disrupted, altered, or otherwise manipulated during the surgical procedure. Maintaining the baseline visualization image can allow the disrupted regions to be ignored when mapping other imaging irregularities. For example, when mapping or overlaying structures and/or features obtained by other imaging sources, the baseline visualization image can be used and the distorted regions ignored to appropriately position the additional structures and/or features in the updated visualization image.

Situational awareness can be used to instruct and/or recommend an update to a baseline visualization image. For example, referring again to FIG. 71, the situational awareness module 6007 can instruct the control circuit 6032 to update the baseline visualization image upon identifying a particular type of surgical procedure, step in the surgical procedure, type of tissue, and/or one or more specific tissue characteristics. In one example, an updated baseline visualization image can be helpful after a transection or after the application of one or more rows of staples. In certain instances, distorted sub-regions within an original anatomical structure can separately create a new baseline visualization image or update an existing baseline visualization image for the distorted sub-region(s) to properly inform image overlays. For example, a key region of a patient's anatomy can be updated after removal of a tumor or growth therein.

In various instances, a frame-to-frame comparison can be used to calculate the deformation of the tissue. For example, surface features can be tracked and compared against subsequent frames with a reference frame set by the user or by an external data source. For example, the pattern of structured light on the surface can deflect and move as the tissue surface moves. Stereoscopic image sensors can detect the deflection of the structured light patterns. A user can set the reference frame with a manual timestamp, for example. A ventilator (i.e. external data source) can set the reference frame in other instances. For example, the ventilator timestamp can correspond to the expiratory pressure to denote an expired lung. Non-rigid iterative closest point algorithms can be used to compute correspondences between the frames. In one aspect, an initial image frame may be taken as a baseline image and subsequent image frames may be geometrically transformed so that the subsequent images are referenced to the baseline image. From this comparison, deformation between the frames can be computed. Such a technique can become more robust with increased strain rates, for example.

In various instances, the model can be analyzed to compute estimated changes in deformation for a proposed resection. For example, before a clinician resects a portion of tissue, the proposed resection line(s) can be added to the digital model, which can be updated to show the anatomical structure with the hypothetical resection. Referring again to FIG. 13B, in one example, a clinician may intend to remove a wedge-shaped portion from the tissue at the surgical site 2325 to remove the tumor 2332 along with the tissue abnormalities 2338. In such instances, the model can be updated to show the organ with the wedge-shaped portion removed therefrom. The updated model can depict the deformation of the tissue, as well as the computed stress and/or strain in the tissue based on the known tissue mechanical properties and the deformation induced by the surgery. For example, the tissue can be shaded or otherwise layered with the stress and/or strain data so that the clinician is informed regarding how a particular resection may impact strain on the tissue. In some aspects, the stress/strain data may be overlaid on the image as a set of vector lines indicating stress/strain direction and line type or color to indicate the value of the stress/strain. Based on the computed stresses and strains, a clinician may modify the proposed resection and consider an alternative strategy to reduce and/or better distribute the stresses and strains within the tissue. For example, the angles of the resections can be modified. In certain instances, the clinician can reorient a staple line with a preferred strain direction.

In various instances, the deformation data can be used to effect resection margins. For example, a resection margin can be distorted in the same distortion pattern as the tissue boundary. Referring again to FIG. 13B, after a first transection to remove a portion of the tissue at the surgical site 2325, the digital model can be updated by comparing the frames and computing the deformation of the tissue. As the tissue visualized with the structured light moves, the underlying resection margins 2330a, 2330b, 2330c can also shift and/or move. In various instances, the digital model can be updated to show the surgical site 2325 including the computed updated position of the resection margins 2330a, 2330b, 2330c, which can be modeled with the same distortion pattern as the visible tissue at the surgical site 2325. It can be assumed the resection margins 2330a, 2330b, 2330c deform along with the visible tissue, for example. Additionally, with the use of tissue penetrating laser light, the structure or orientation of the underlying tissue components, such as collagen or elastin fibers, may be determined. Such fiber orientation may provide additional information regarding the stress and/or strain applied to the tissue.

The projected distorted resection margins, i.e. distortions based on frame-to-frame comparisons of structured light patterns on a tissue surface, may be modified as new underlying layers of tissue are exposed and the refractivity of the newly exposed tissue is also checked for refractivity changes. The newly-identified tissue characteristics can be indicated to the user in real-time during tissue dissections and/or as the clinician approaches the margin boundaries. For example, referring to FIGS. 74A and 74B, a surgical site 6325 includes tissue T and a surgical device includes a structured light source 6350 and image sensor 6344, similar to the surgical device in FIG. 73. A first refractivity R can be expected (FIG. 74B); however, the actual deflected reflected light R' (FIG. 74B) can be different as new layers of tissue are exposed. The different refractivity can be indicative of different tissue characteristics. For example, upon complete removal of a tumor 2332 and/or tissue abnormalities 2338, the refractivity can indicate different, i.e. healthy, tissue properties. In various instances, refractivity within a boundary 6330 of an irregularity can be different than the refractivity outside the boundary 6330 of the irregularity.

Adjustment of Surgical Instrument Controls According to POV Coordinate System

In one general aspect, a surgical system can be configured to communicate a locally displayed coordinate system from an imaging system to a surgical instrument or other medical device to enable the instrument/device controls to be adapted to control motion relative to a local visualization coordinate system. In particular, at least one measurement derived from the imaging system can be utilized to define the local coordinate system. Further, the surgical instrument or other medical device can be provided a transfer function from the visualization system 2108 and/or the surgical hub 2106 (e.g., as described in connection with FIGS. 17-19) coupled to the visualization system 2108 to enable the surgical instrument or other medical device to orient the user controls relative to the local coordinate system, rather than a standard global coordinate system or another coordinate system.

As an example, handheld surgical instruments that have a rotatable shaft and/or an articulatable end effector require the user to understand how the shaft and the end effector are oriented relative to the patient when deciding which articulation control (e.g., left or right articulation controls) will articulate the end effector in the desired direction with respect to the patient. Accordingly, the surgical instrument or a control system coupled to the surgical instrument can be configured to automatically reorient the function of the articulation controls based on the shaft and the end effector's position relative to the handle. However, linking the reorientation of the controls directly to a change in the orientation of the surgical instrument handle assembly or rotation of the surgical instrument shaft can be undesirable in certain instances because the particular orientation of the handle assembly, shaft, and/or other surgical instrument components relative to the user may not necessarily correspond to how those components are oriented on a display screen in a video-assisted surgical procedure, such as a VATS procedure. Surgeons utilize display screens or video monitors as their sole POV for controlling the surgical instrument(s) during a video-assisted surgical procedure. Causing the surgical instrument controls to automatically change in response to reorientation or rotation of the surgical instrument could cause the functions of the controls to change unpredictably for users and would not necessarily correspond to the POV provided on the display for the surgeon.

To address this issue, the orientation of the surgical instrument (i.e., the shaft and/or end effector of the surgical instrument) currently displayed to the surgeon by the imaging system on a display screen could be utilized as a reference relative to a global coordinate system associated with the patient. Accordingly, the displayed orientation of the surgical instrument relative to the global coordinate system could be utilized to adjust the function of the controls on the surgical instrument, which would in turn cause the controls to correspond to the orientation displayed on the display screen. Having the surgical instrument's controls be automatically adjusted so that they correspond to how the surgical instrument is shown on the display screen would improve the ease of using the surgical instruments and reduce user confusion and disorientation by obviating the need for surgeons to be constantly aware of how the handle, shaft, and/or end effector of the surgical instrument is oriented relative to the patient before controlling the articulation or movement of the surgical instrument. Further, for surgical instruments that have built-in display screens, the orientation of the display screens could likewise be controlled in the same manner as the controls of the surgical instrument. In sum, the functions of the controls, such as the left/right articulation controls and/or display screen of a surgical instrument, could be adjusted according to, or to coincide with, the locally displayed coordinate system.

In one aspect, the present disclosure is directed to a control system for a surgical instrument that includes a user control. The control system can include an imaging system and a control circuit connected to the imaging system and connectable to the surgical instrument (e.g., via wired or wireless connections). The imaging system can be configured to visualize a surgical site, as described above. The control circuit can be configured to generate an image of the surgical site utilizing the imaging system, define a first coordinate system with respect to the surgical site according to the image thereof, receive a second coordinate system defined by the surgical instrument, determine a transfer function to translate a coordinate in the second coordinate system to the first coordinate system, and provide the transfer function to the surgical instrument to cause the surgical instrument to adjust the user control according to the transfer function. In another aspect, the present disclosure is directed to a surgical instrument operably in signal communication with the control system, including the imaging system that is configured to generate an image of the surgical site based on the electromagnetic radiation (EMR) reflected therefrom and define a first coordinate system with respect to the surgical site according to the image thereof. The surgical instrument can include a user control configured to control a function of the surgical instrument and/or a display screen. The surgical instrument can further include a control circuit coupled to the user control and/or the display screen. The control circuit can be configured to determine a second coordinate system with respect to the surgical instrument that can be provided to the control system, receive the transfer function to translate a coordinate in the second coordinate system to the first coordinate system from the control system, and adjust the user control and/or the display screen according to the transfer function.

In order to assist in the understanding of the aforementioned systems and methods, various examples will be described within the context of a VATS procedure. It should be understood that this is simply for illustrative purposes. The described systems and methods are applicable to other contexts and/or surgical procedures, however. A VATS procedure is a surgical procedure whereby one or more surgical instruments and one or more thoracoscopes (i.e., cameras) are inserted into the patient's chest cavity through slits positioned between the patient's ribs. The cameras are utilized to provide the surgeons with a view of the interior of the patient's chest cavity to allow the surgeon to properly position/move the surgical instrument(s) and manipulate tissue/structures within the chest cavity. Because the surgeon controls the surgical instrument(s) based on what is displayed by the imaging system via the camera(s) and because the surgical instrument(s) may not be aligned with the viewing perspective of the camera(s), the spatial relationship between the surgical instrument and the POV displayed by the imaging system can be potentially disorienting, especially for imaging systems that allow users to pan, manipulate, and reorient the displayed visualization, as described below under the headings "Fusion of Images from Different Sources to Expand Visualization Field Scope" and "Fusion of Overlapping Images to Expand Visualization Field Scope", for example. Accordingly, the present disclosure is directed to surgical instruments and control systems associated therewith that are configured to intelligently adapt the surgical instrument controls so that they correspond to the POV displayed to the surgeon.

To illustrate further, FIGS. 75 and 76 are diagrams of aspects of a VATS procedure. In this particular VATS procedure, the surgeon is seeking to remove a tumor 6506 located within the apical segment of the superior lobe of a lung 6508. In this particular illustrative procedure, the surgeon has placed a port 6502 between the second rib 6501 and the third rib 6503 to provide an access path 6504 for a surgical instrument 6510 (e.g., a surgical stapler) insertable through the port 6502 to access the tumor 6506 and/or the surrounding area within the chest cavity. Once the location of the access for the surgical instrument 6510 has been selected, the surgeon can place one or more cameras 6520a, 6520b through other ports 6502 that are positioned to allow the camera(s) 6520a, 6520b to visualize the interior of the patent chest cavity in the vicinity of the surgical site. Visualizing the surgical site in this manner allows the surgeon to position and orient an end effector 6514 of the surgical instrument 6510 to manipulate the tissue as needed (e.g., excise a portion of the lung 6508 around the tumor 6506). In the particular illustrated example, two cameras 6520a, 6520b are utilized, although a different number of cameras can be utilized and/or one or more of the cameras 6520a, 6520b can be oriented in a different manner depending upon the particular type of surgical procedure that is being performed and/or the region within the body of the patient 6500 that needs to be visualized.

As shown in FIG. 76 and set forth below in TABLE 1, a variety of different coordinate systems can be defined with respect to the differing POVs of the patient, devices, or device components. Further, for imaging systems that allow users to manipulate the displayed visualization, as described below under the headings "Fusion of Images from Different Sources to Expand Visualization Field Scope" and "Fusion of Overlapping Images to Expand Visualization Field Scope", for example, "virtual" POVs can be defined that correspond to the virtual or predicted visualization being displayed to the surgeon and coordinate systems can also be defined according to these POVs. The generation and control of such visualizations are further described herein.

TABLE 1

| Coordinate System | Description |
|---|---|
| $x_p, y_p, z_p$ | Patient anatomical plane POV |
| $x_d, y_d, z_d$ | Handle assembly POV |
| $x_j, y_j, z_j$ | End effector/cartridge POV |
| $x_{c1}, y_{c1}, z_{c1}$ | Camera #1 POV |
| $x_{c2}, y_{c2}, z_{c2}$ | Camera #2 POV |
| $x_{L1}, y_{L1}, z_{L1}$ | Virtual local POV #1 |
| $x_{L2}, y_{L2}, z_{L2}$ | Virtual local POV #2 |
| $x_{L3}, y_{L3}, z_{L3}$ | Virtual local POV #3 |

In one aspect, the coordinate systems can be defined based upon sensor measurements and/or measurements by the imaging system 142 (FIG. 2). For example, a coordinate system with respect to a surgical instrument handle assembly 6512, a shaft 6513, or the end effector 6514 could be defined according to measurements by an accelerometer or another such sensor associated with the respective components. As another example, any of the aforementioned coordinate systems could be defined based upon measurements of the relative distances and/or positions of objects with respect to each other or a global coordinate system as determined by imaging the objects via the imaging system 142.

Referring now to FIG. 78, a logic flow diagram of a process 6550 of adjusting a display screen 6516 and/or user control 6518 (e.g., articulation control 6519a, 6519b) of a surgical instrument 6510 according to a displayed coordinate system is shown. In the following description of the process 6550, reference should also be made to the control circuit 132 in FIG. 2. In one aspect, the process 6550 can be embodied as a set of computer-executable instructions embodied as software (e.g., as stored in the memory 134) or hardware that are executed by the control circuit 132 of the control system 133. In the following description of the process, reference should also be made to the exemplary procedure of FIGS. 75-77.

The control circuit 132 executing the process 6550 can generate, at block 6552, an image of the surgical site utilizing the imaging system 142. As noted above, the imaging system 142 can be configured to generate images (including of both visible and nonvisible structures) and take measurements of or characterize imaged objects by emitting structured or non-structured EMR, emitting EMR in both the visible and nonvisible spectrums, and so on. The generated image can include an image directly captured by an image sensor 135 representing the POV of one of the cameras 6520a, 6520b, as shown in FIG. 79, for example. Alternatively, the generated image can include a virtual image, as are shown in FIGS. 82 and 83, for example.

The control circuit 132 can define, at block 6554, a local or POV coordinate system based on the imaging system 142 for the generated image. The local coordinate system can be defined based on sensor measurements, imaging system measurements, tracking movement relative to an established coordinate system (e.g., a camera coordinate system $x_c$, $y_c$, $z_c$ as shown in FIG. 81), and so on.

The control circuit 132 can receive, at block 6556, a coordinate system from the surgical instrument 6510. In one aspect, the control circuit 132 is operably in signal communication with the surgical instrument 6510 via a wireless connection (e.g., a Bluetooth connection), for example. In one aspect, the control circuit 132 can be embodied as a control circuit of a surgical hub 2106, 2236 (FIGS. 17-19) and the surgical instrument 6510 can be paired with the surgical hub 2106, 2236 to transmit data therebetween.

The control circuit 132 can determine, at block 6558, a transfer function to translate a coordinate in one of the surgical instrument coordinate system or the local coordinate system to the other coordinate system. For example, the transfer function can be configured to translate. The transfer function can be embodied as an algorithm, an equation, a lookup table, and so on.

The control circuit 132 can provide, at block 6560, the transfer function to the surgical instrument 6510. As noted above, the control circuit 132 can be communicatively coupled to the surgical instrument 6510 via a wireless connection, for example, for transferring data therebetween. Once received by the surgical instrument 6510, the surgical instrument 6510 can utilize the transfer function to translate the coordinates in its coordinate system to the displayed coordinate system and determine whether to adjust its controls 6518 and/or display screen 6516 based upon the updated coordinates, which indicate how the surgical instrument 6510 or components thereof are being visualized by the surgeon.

In the example shown in FIG. 77, the surgical instrument 6510 has utilized the provided transfer function to determine that the controls 6518 and display screen 6516 should be adjusted based on the updated coordinates. In various instances, situational awareness, as further described herein, can inform when the controls 6518 and/or the display screen 6516 are updated. The display screen 6516 can display a GUI 6517 that is adjusted from a first orientation, shown on the left side of FIG. 77, to a second orientation, shown on the right side of FIG. 77, to ensure that the GUI 6517 is oriented properly for the surgeon controlling the surgical instrument 6510. In one aspect, the GUI 6517 can further include a GUI element 6524 (e.g., an icon) indicating the POV or coordinate system being utilized by the surgical instrument 6510. In this example, the GUI element 6524 shifts to indicate that the POV displayed by the visualization system 2108 has changed from the device coordinate system ("DVC") to the local coordinate system ("Local") associated with the image/video displayed by the visualization system 2108.

As an example, the surgical instrument controls 6518 adjusted according to the updated coordinates can include articulation controls. The articulation controls can include a first control 6519a configured to cause the surgical instrument 6510 to articulate in a first direction and a second control 6519b configured to cause the surgical instrument 6510 to articulate in a second direction, for example. The articulation controls 6519a, 6519b can be embodied as a rocker, toggle, or separate actuators and/or buttons, for example. In this example, the surgical instrument 6510 has caused the first articulation control 6519a and the second articulation control 6519b to swap functions in response to the change in orientation of the surgical instrument 6510. In other words, actuating the first articulation control 6519a would instead cause the surgical instrument 6510 to articulate in the second direction, and actuating the second articulation control 6519b would cause the surgical instrument 6510 to articulate in the first direction. Accordingly, the functions of the articulation controls 6519a, 6519b can be set according to the orientation of the surgical instrument 6510 or a component thereof (e.g., the end effector 6514) as displayed to the user, such as shown in FIGS. 79 and 81-83.

Additionally or alternatively, in certain instances, the GUI 6517 on the display screen 6516 can be adjusted. For example, the GUI 6517 can be inverted when the handle assembly 6512 is inverted. In certain instances, the GUI 6517 can include a touch screen such that the surgeon can switch between coordinate systems by interacting with the GUI 6517. For example, the surgeon can toggle between a device POV, local POV, and/or one or more other POVs by interacting with the GUI 6517.

Fusion of Images from Different Sources to Expand Visualization Field Scope

One issue that can arise during video-assisted surgical procedures is that the field of view (FOV) offered by the visualization system can be inadequate in certain circumstances because the cameras are necessarily limited in number and fixed in position due the surgical constraints of the procedure. In particular, the POV offered by the cameras could be non-ideal for performing particular steps of the surgical procedure (e.g., dissecting a vessel), hiding particular tissues and/or structures from view, and so on. In one general aspect, a surgical system comprising an imaging system can be configured to create 3D representations of objects within the visualization field of the imaging system and characterize the 3D shapes to allow users to alter the displayed visualization with respect to the established coordinate system to better visualize the surgical site. The 3D representations can be generated from images generated from real-time sources (e.g., the imaging system 142) or non-real-time sources (e.g., CT scans or MRIs). In one aspect, the imaging system 142 can be configured to project structured light, or structured EMR, to create structured 3D shapes that can be tracked in real time. These 3D shapes could be generated in such a manner as to allow the POV displayed by the imaging system 142 to be moved or rotated away from the scanning source's local coordinate system to improve the perspective view of the user through the display.

Various aspects of the present disclosure can address the various technical problems described above. In one aspect, the present disclosure is directed to a control system, including an imaging system, a display screen, and a control circuit coupled to the imaging system and the display screen. The imaging system can be configured to image tissues, structures, and objects at the surgical site using a variety of different imaging techniques, including structured EMR. Further, the control circuit can be configured to generate a first image of the surgical site based on the structured EMR reflected therefrom received by the image sensor, receive a second image of the surgical site, generate a 3D representation of the surgical site based on the first image and the second image as aligned, display the 3D representation on the display screen, receive a user selection to manipulate the 3D representation, and update the 3D representation as displayed on the display screen from a first state to a second state according to the user selection.

Various examples will be described herein within the context of a VATS procedure; however, alternative surgical procedures are also contemplated. In particular, FIG. 79 illustrates a FOV 6570 of a camera 6520 (FIG. 81) during a VATS procedure. The target of this particular illustrative procedure is a tumor 6506 located within the apical segment of the superior lobe 6580 of a lung 6508. A number of biological structures are identifiable within this FOV 6570, including the thoracic wall 6509, veins 6574, arteries 6576, bronchi 6578, the fissure 6582 delineating the superior lobe 6580, a pulmonary artery 6584, and a pulmonary vein 6586. Non-biological objects are also viewable within the FOV 6570, including the end effector 6514 and the shaft 6513 of the surgical instrument 6510 being controlled by the surgeon. In a conventional imaging system, such a view, in combination with any corresponding views from any additional camera(s) 6520 being utilized, would be the sole view(s) available to surgeons performing a video-assisted procedure. Although the cameras are placed with the intent to provide the surgeon with an adequate visualization field scope for performing the surgical procedure, the visualization field scope provided by the camera(s) 6520 may ultimately not provide the ideal FOV 6570 for performing each step or task in the surgical procedure, or unexpected obstructions may be present at the surgical site that impede the surgeon's view. Further, intraoperatively repositioning or reorienting the camera(s) 6520 can be impractical or undesirable in certain instances due to the surgical constraints of the procedure.

In one aspect, a surgical system can be configured to expand the visualization field scope provided by the camera(s) 6520 by combining multiple images of the surgical site, including preoperative images and intraoperative images, to generate 3D representations of the surgical site or tissues and/or structures located at the surgical site. During the surgical procedure, the user can then manipulate the 3D representations displayed by the imaging system 142 to visualize the surgical site from orientations that are outside the scope of the FOV 6570 of the camera(s) 6520 being utilized in the procedure. Such reoriented views can be referred to as "virtual POVs," as noted above. Accordingly, the surgical system can supplement the FOV 6570 provided by the camera(s) 6520 and allow surgeons to dynamically adjust the displayed visualization of the surgical site during the surgical procedure to find ideal viewing POVs for performing one or more of the surgical tasks.

FIG. 80 is a diagram of image sources from which a 3D representation of a surgical site can be generated. In order to generate the 3D representations and thereby allow users to manipulate the visualization field scope to POVs extending beyond the FOV 6570 of the camera(s) 6520, the patient cavity would need to be viewed from multiple reference points (e.g., camera positions). These different reference points or perspectives can in turn be utilized to construct the 3D representations that can be intraoperatively manipulated by the surgeon to extend the visualization field scope beyond the fixed perspectives of the camera(s) 6520. In one aspect, at least some of the images can be captured utilizing structured EMR to map the surface of the tissues and/or structures located at the surgical site for generating the 3D representations. In one aspect, intraoperative images 6600 can be utilized in constructing the 3D representations. For example, as a camera 6520 is initially placed, the user may be prompted by the surgical system to pan the camera 6520 around the patient cavity to observe all of the anatomy and thereby establish a baseline set of images that can be fused together to form a 3D representation of the surgical site. This baseline can be updated automatically throughout the procedure as tissues are manipulated, the patient is moved, and so on. Alternatively, the baseline can be generated automatically as the camera 6520 is panned and/or reoriented during the surgical procedure and updated as more regions of the patient anatomy are exposed to the FOV 6570 of the camera 6520. In certain instances, situational awareness, as further described herein, can provide update instructions and/or suggestions to the surgeon based on the detected surgical scenario. In another aspect, preoperative images, such as CT scans 6602 and MRIs 6604 can be utilized in constructing the 3D representations. For example, images from non-real-time sources (e.g., CT scans 6602 and MRIs 6604) can be incorporated into the real-time mapping of the surgical site in its baseline coordinate system. The corresponding fused images provided by the non-real-time image sources can then be utilized to generate the 3D representation and manipulated in a similar fashion as described above.

The 3D representations can be generated from any combination of preoperative and intraoperative image sources. In one aspect, the 3D representations can be generated by aligning two-dimensional images and then constructing the 3D representation using photogrammetry techniques and/or 3D scanning software. Further, some captured images can include or indicate a 3D topography of the tissues and/or structures that can aid in constructing the 3D representations, such as images captured via structured EMR. Further details regarding the generation of 3D representations of tissues and/or structures can be found in U.S. patent application Ser. No. 16/128,195, titled INTEGRATION OF IMAGING DATA, filed on Sep. 11, 2018, which is hereby incorporated by reference herein in its entirety.

In various aspects, the imaging system 142 can display the 3D representations generated from the fused images and provide users with controls (e.g., a GUI) for manipulating the displayed visualization POV. As one example, FIG. 81 is a visualization display 6620 and GUI 6622 of the surgical procedure of FIG. 76 provided by an imaging system 142. The visualization display 6620 and GUI 6622 can be displayed on a display 146 (FIG. 2), for example. The visualization display 6620 can include a real-time video feed from the camera(s) 6520 supplemented with the generated 3D representation of the surgical site, for example. The video feed provided by the camera(s) 6520 can be overlaid on or otherwise displayed in conjunction with the generated 3D representations on the visualization display 6620. The visualization display 6620 can be configured to display the video feed and transition to the 3D representations when the user causes the visualization display 6620 to display a POV that differs from the real-time video feed POV provided by the camera(s) 6520. In this particular example, the visualization display 6620 displays 3D representations of a lung 6508, a tumor 6506, and various structures 6610 (e.g., vessels). The 3D representations can be generated from non-real-time image sources and real-time images 6600 captured via the camera 6520, for example. The 3D representations can include portions that lie at least partially outside of the FOV of the camera 6520 and that can be displayed on the visualization display 6620 when desired by the user, as shown in FIG. 81.

In one aspect, the display 146 can include an interactive control, such as a GUI 6622, which allows the user to select portions of the visualization display 6620, particular camera POVs, or underlying 3D structures and then highlight, zoom in or out, rotate, or otherwise manipulate the visualization display 6620 to visualize the surgical site from a different perspective or approach than the view provided by the camera(s) 6520. The GUI 6622 can be configured to allow the user to select a surface, point, coordinate system, instrument, or superimposed scanned image and then adjust the visualization display 6620 with respect to that selection resulting in a view or visualization that is not directly aligned with the real-time image/video being provided by the camera(s) 6520 coupled to the imaging system 142.

For example, FIG. 82 illustrates the visualization display 6620 as shifted by a user to a first updated perspective 6530 corresponding to a first virtual POV $x_{L1}$, $y_{L1}$, $z_{L1}$ to view 3D representations of the lung 6508, the tumor 6506, and/or the end effector 6514 of the surgical instrument 6510 from a different, "local" perspective that may be more beneficial for the particular surgical procedure step. As indicated in FIG. 82, the first virtual POV $x_{L1}$, $y_{L1}$, $z_{L1}$ is shifted relative to the camera POV $x_c$, $y_c$, $z_c$ (e.g., as shown in FIG. 79) and the user is thus viewing, at least partially, 3D representations of the corresponding tissues, structures, and/or objects as displayed. As another example, FIG. 83 illustrates the visualization display 6620 as shifted by a user to a second updated perspective 6632 corresponding to a second virtual POV $x_{L2}$, $y_{L2}$, $z_{L2}$ to view the lung 6508, the tumor 6506, and/or the end effector 6514 of the surgical instrument 6510 from yet a different "local" perspective that is likewise shifted relative to the camera POV $x_c$, $y_c$, $z_c$ (e.g., as shown in FIG. 79). In one aspect, the GUI 6622 can include a perspective control widget 6628 that can be actuated by the user to shift, pan, or otherwise manipulate the perspective being shown on the visualization display 6620. Further, the GUI 6622 can include a coordinate GUI element 6626 that can indicate the shift in the displayed perspective relative to a reference perspective (e.g., the camera POV $x_c$, $y_c$, $z_c$). The GUI 6622 can also include various other controls for controlling the visualization display 6620, such as a zoom widget 6625 configured to cause the visualization display 6620 to zoom in our out on a particular point, structure, or object within the visualization display 6620.

In one aspect, the imaging system 142 can be configured to display the 3D representation in a different color than the real-time video feed, highlight the structure of the 3D representation, or otherwise indicate that the user is no longer viewing the real-time video feed when the user shifts the displayed POV of the visualization display 6620 away from the real-time video feed POV provided by the camera(s) 6520. Further, the imaging system 142 can be configured to allow users to shift back to the real-time video feed POV provided by the camera(s) 6520. In one aspect, the GUI 6622 includes a POV selection widget 6624 that allows the user to shift between various POVs, including camera POVs ("CAMERA"), device POVs ("DEVICE 1" and "DEVICE 2"), and virtual POVs defined by the user ("LOCAL"). In various instances, by selecting one of the POVs from the POV selection widget 6624, the visualization image can snap to the selected POV.

The visualization display 6620 can be further configured to calculate and/or display various measurements or parameters associated with the displayed tissues, structures, and objects. In one aspect, the surgical system can be configured to determine and display a tumor margin 6572 about the tumor 6506. The tumor margin 6572 can define the minimum volume of tissue that should be excised by the surgeon to ensure complete removal of the tumor 6506. The tumor margin 6572 can be calculated as a set distance extending about the tumor 6506 in three dimensions or can vary according to the size, geometry, location, and other such factors associated with the tumor 6506. In one aspect, the surgical system can be configured to determine and display relative distances between tissues, structures, and objects within the visualization display 6620. In the illustrated example, the visualization display 6620 includes the distance $d_1$ between the surgical instrument 6510 and the tumor margin 6572 and the distance $d_2$ between the surgical instrument 6510 and the surface of the tissue over which the surgical instrument end effector 6514 is located (which, in the illustrated example, is a lung 6508). In another aspect, the GUI 6622 can include a distance GUI element 6627 indicating the calculated distances between the various tissues, structures, and/or objects being visualized, i.e. between the corresponding elements in column A and column B. The aforementioned measurements are provided for illustrative purposes and the surgical system can calculate and display a variety of other measurements or parameters.

Referring now to FIG. 84, a logic flow diagram of a process 6650 of controlling a visualization display 6620 is shown. In the following description of the process 6650, reference should also be made to the control circuit 132 in FIG. 2. In one aspect, the process 6650 can be embodied as a set of computer-executable instructions embodied as software (e.g., as stored in the memory 134) or hardware that are executed by the control circuit 132 of the control system 133. In the following description of the process, reference should also be made to FIGS. 79-83.

The control circuit 132 executing the process 6650 can generate, at block 6652, a first image of the surgical site. The first image can be generated via the imaging system 142 utilizing structured or non-structured EMR to generate a 3D surface map of the imaged region, multispectral imaging techniques to identify and characterize nonvisible tissues and/or structures, and any other visualization techniques described above. Further, the first image can be generated as a series of images obtained by panning a camera about a surgical site to generate a 3D representation of the surgical site, as shown in FIG. 80, for example.

The control circuit 132 can receive, at block 6654, a second image of the surgical site. The second image can be a non-real-time image, such as a CT scan 6602 or MRI 6604, as shown in FIG. 80, for example.

The control circuit 132 can generate, at block 6656, a 3D representation of the surgical site from the first image, the second image, and any other images obtained from various image sources and then display, at block 6658, the 3D representation on a display screen coupled to the imaging system, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Once the 3D representation is displayed (either alone or in conjunction with a video feed from the cameras 6520), the control circuit 132 can update, at block 6660, the POV or state of the 3D representation according to a user selection. For example, the user could update the visualization display 6620 from the camera POV shown in FIG. 79 to a first virtual POV shown in FIG. 82 or a second virtual POV shown in FIG. 83. The user can provide the input to update the visualization display 6620 via a perspective control widget 6628 provided via a GUI 6622 associated with the visualization display 6620, for example.

Fusion of Overlapping Images to Expand Visualization Field Scope

As noted above, one issue that can arise during video-assisted surgical procedures is that the FOV offered by the visualization system can be inadequate in certain circumstances because the cameras are necessarily limited in number and fixed in position due the surgical constraints of the procedure. Systems and methods for addressing this and other technical problems can include, in one aspect, the use of two independent image scanning sources and sensors (e.g., cameras) having scanned regions that at least partially overlap or intersect. This enables the surgical system to generate 3D surfaces and volumes that have aspects that are not fully captured by only one of the fixed image scanning sources. Accordingly, the surgical system can create a virtual display visualization POV that can be moved relative to the surgical site, allowing the user to see around structures, tissues, or objects (e.g., surgical instruments) at the surgical site that may be obstructing one of the imaging devices.

Various aspects of the present disclosure can address the various technical problems described above. In one aspect, the present disclosure is directed to a control system, including an imaging system, a display screen, and a control circuit coupled to the imaging system and the display screen. The imaging system can include a first image sensor having a first FOV and a second image sensor having a second FOV that at least partially overlaps with the first FOV. The imaging system can be configured to image tissues, structures, and objects at the surgical site using a variety of different imaging techniques, including structured EMR. The control circuit can be configured to generate a first image of the surgical site based on the first image sensor, generate a second image of the surgical site based on the second image sensor, align the first image and the second image according to overlapping portions thereof, generate a 3D representation of a structure based on the first image and the second image as aligned, cause the display screen to display the 3D representation, and cause the display screen to adjust a displayed portion of the 3D representation according to a user selection.

In one aspect, a computational image generator could also be used to select clear image frames between the imaging devices and to display only the clear image frames in the areas where the FOVs of the imaging devices overlap. In another aspect, the surgical system can be configured to remove obstructions from the visualization display or render the obstructions semi-transparent in the areas where the FOVs of the imaging devices overlap. A visualization display 6620 (FIG. 87) and/or a GUI 6622 (FIG. 87) associated therewith can be configured to indicate to the user when the advanced visualization features are active to make the user aware that portions of the visualization display 6620 are simulated or have been adjusted from the "real" video feed provided by the cameras 6520a, 6520b (FIG. 87).

In one aspect, one of the cameras 6520a, 6520b can be designated as the default or primary camera, and images generated therefrom can likewise be considered to be the default or primary images displayed via the visualization display 6620. In this aspect, the images or other sensed information (e.g., multispectral tissue data) from the primary imaging device can be compared against that of the secondary imaging device to confirm the consistency of the images generated by the first imaging device. Further, differences between the two sets of images that are within a certain magnitude can be interpolated by the surgical system. Still further, differences between the two sets of images above a threshold can prevent calculated information from being displayed to the user (e.g., due to concerns of the accuracy of the calculated information caused by the lack of consistency between the images within the primary image set). In certain instances, situational awareness, as further described herein, can determine a suitable accuracy range or tolerance based on the detected surgical scenario, for example.

In one aspect, the surgical site surface information obtained by the imaging devices can be used to inform the superposition of underlying structures (e.g., a tumor) imaged via another imaging source (e.g., a CT scan). The superposition of the underlying structures can be adjusted to account for tissue deformation in the computational image against the data from the alternative or secondary imaging source in order to confirm the projected location of the underlying structures with respect to the imaged surface.

Referring now to FIGS. 85-87, various diagrams and a visualization display 6620 of a VATS procedure being performed utilizing two cameras 6520a, 6520b that have overlapping FOVs are shown. In particular, the first camera 6520a can have a first FOV 6700 and the second camera 6520b can have a second FOV 6702. The FOVs 6700, 6702 can further define an overlapping portion 6704 therebetween. Due to the overlapping portion 6704 of the images generated by the cameras 6520a, 6520b, the images can be aligned and then utilized to generate a 3D representation of the surgical site using the various techniques described above. Further, the control system 133 (FIG. 2) can be configured to remove an obstruction or correct an imaging artifact present within the overlapping portion 6704 of one of the generated images and replace the offending image portion with an interpolation of the corresponding unobstructed or correct portion of the other image. In this way, the control system 133 can dynamically update and maximize the visualization scope provided by the visualization display 6620. For example, the control system 133 can be configured to remove objects laying within the FOV of one or both of visualization FOVs 6700, 6702, such as the cameras 6520a, 6520b as shown in FIG. 87 or other surgical devices present at the surgical site, from the visualization display 6620.

Referring now to FIG. 88, a logic flow diagram of a process 6750 of controlling a visualization display 6620 (FIG. 87) is shown. In the following description of the process 6750, reference should also be made to the control circuit 132 in FIG. 2. In one aspect, the process 6750 can be embodied as a set of computer-executable instructions embodied as software (e.g., as stored in the memory 134) or hardware that are executed by the control circuit 132 of the control system 133. In the following description of the process, reference should also be made to FIGS. 85-87.

The control circuit 132 executing the process 6750 can generate, at block 6752, a first image of the surgical site and can generate, at block 6754, a second image of the surgical site. The images can be generated via the imaging system 142 utilizing structured or non-structured EMR to generate a 3D surface map of the imaged region, multispectral imaging techniques to identify and characterize nonvisible tissues and/or structures, and any other visualization techniques described above. Further, the first and second images can be generated by respective cameras 6520a, 6520b having overlapping FOVs. Therefore, the first and second images can correspondingly overlap with each other.

The control circuit 132 can generate, at block 6756, a 3D representation of the surgical site from the first image, the second image, and any other images obtained from various image sources and then display, at block 6758, the 3D representation on a display screen coupled to the imaging system, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Once the 3D representation is displayed (either alone or in conjunction with a video feed from at least one of the cameras 6520*a*, 6520*b*), the control circuit 132 can update, at block 6760, the POV or state of the 3D representation according to a user selection. The user can provide the input to update the visualization display 6620 via a perspective control widget 6628 provided via a GUI 6622 associated with the visualization display 6620, for example.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

EXAMPLES

Various aspects of the subject matter described herein are set out in the following numbered examples:

Example 1—A method for generating and updating a three-dimensional representation of a surgical site based on imaging data from an imaging system. The method comprises the steps of generating a first image of the surgical site based on structured electromagnetic radiation (EMR) emitted from the imaging system, receiving a second image of the surgical site, aligning the first image and the second image, generating a three-dimensional representation of the surgical site based on the first image and the second image as aligned, displaying the three-dimensional representation on a display screen, receiving a user selection to manipulate the three-dimensional representation, and updating the three-dimensional representation as displayed on the display screen from a first state to a second state according to the received user selection.

Example 2—The method of Example 1, wherein the second image is received from a non-real-time image source.

Example 3—The method of Example 2, wherein the non-real-time image source comprises at least one of a computed tomography scan or a magnetic resonance imaging scan.

Example 4—A method for generating a three-dimensional representation of a surgical site. The method comprises the steps of detecting a first pattern of structured light on an anatomical surface contour of the surgical site via an image sensor, detecting a second pattern of structured light on a subsurface contour of the surgical site via the image sensor, transmitting first imaging data indicative of the first pattern of structured light to a control circuit, transmitting second imaging data indicative of the second pattern of structured light to the control circuit, processing the first imaging data and the second imaging data via the control circuit, generating a three-dimensional digital representation of an anatomical structure including the anatomical surface contour and the subsurface contour, and transmitting the three-dimensional digital representation of the anatomical structure to a display.

Example 5—The method of Example 4, further comprising the steps of updating the three-dimensional digital representation of the anatomical structure in real time in response to changes to the first pattern of structured light and changes to the second pattern of structured light detected by the image sensor, and transmitting the updated three-dimensional digital representation of the anatomical structure in real time to the display.

Example 6—The method of Example 4 or 5, further comprising the steps of obtaining metadata from the first imaging data and the second imaging data and overlaying the metadata with the three-dimensional digital representation.

Example 7—The method of Example 6, wherein the metadata comprises at least one of tissue velocity, tissue distortion, tissue irregularity, tissue vascularization, or identification of an embedded structure within the anatomical structure.

Example 8—The method of Example 6 or 7, wherein the metadata is indicative of tissue compression along a staple line.

Example 9—A method for determining a surgical scenario based on input signals from multiple surgical devices. The method comprises detecting imaging data from a plurality of light sources via an image sensor. The plurality of light sources are configured to emit a pattern of structured light onto an anatomical structure. The method further comprises receiving the imaging data from the image sensor, generating a three-dimensional digital representation of the anatomical structure from the pattern of structured light detected by the imaging data, obtaining metadata from the imaging data, overlaying the metadata on the three-dimensional digital representation, receiving updated imaging data from the image sensor, generating an updated three-dimensional digital representation of the anatomical structure based on the updated imaging data, and updating the overlaid metadata on the updated three-dimensional digital representation of the anatomical structure in response to a surgical scenario determined by a situational awareness module.

Example 10—The method of Example 9, wherein the plurality of light sources comprises a plurality of coherent light sources.

Example 11—The method of Example 10, wherein the metadata comprises phase shift data for the plurality of coherent light sources.

Example 12—The method of Example 10 or 11, wherein the plurality of coherent light sources are configured to emit the pattern of structured light.

Example 13—The method of Example 12, wherein the pattern of structured light is emitted from the coherent light sources at a plurality of different wavelengths having different tissue penetration depths.

Example 14—The method of Example 9, 10, 11, 12, or 13, wherein the image sensor is configured to capture the pattern of structured light at the different tissue penetration depths.

Example 15—The method of Example 9, 10, 11, 12, 13, 14, wherein the three-dimensional digital representation is generated from a surface pattern of structured light and a sub-surface pattern of structured light.

Example 16—The method of Example 9, 10, 11, 12, 13, 14, or 15, wherein the overlaid metadata is indicative of a tissue irregularity.

Example 17—The method of Example 16, wherein the tissue irregularity comprises a sub-surface irregularity.

Example 18—The method of Example 9, 10, 11, 12, 13, 14, 15, 16, or 17, wherein the overlaid metadata is indicative of tissue compression along a staple line.

Example 19—The method of Example 9, 10, 11, 12, 13, 14, 15, 16, 17, or 18, wherein the overlaid metadata is indicative of a margin around an embedded structure.

Example 20—The method of Example 9, 10, 11, 12, 13, 14, 15, 16, 17, 18, or 19, wherein the overlaid metadata comprises at least one of tissue velocity, tissue distortion, tissue irregularity, tissue vascularization, and identification of an embedded structure within the anatomical structure.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical hub for use with a surgical system in a surgical procedure performed in an operating room, the surgical hub comprising:
a control circuit configured to:
receive real-time visualization data from a camera;
determine an estimated parameter change based on the visualization data and surgical procedure;
receive pre-operative non-visualization data, wherein the pre-operative non-visualization data is received before the surgical procedure is performed;
determine a tissue parameter based on the real-time visualization data;
adjust an operational parameter of a surgical device used to perform the surgical procedure based on the tissue parameter, wherein the surgical device is communicably coupled to the surgical hub;
receive post-operative non-visualization data, wherein the post-operative non-visualization data is received after the surgical procedure is performed;
determine a difference between the pre-operative non-visualization data and the post-operative non-visualization data; and
assess an output of the surgical procedure based on a comparison of the difference and the estimated parameter change,
wherein the pre-operative non-visualization data comprises pre-operative partial pressure of carbon dioxide of a patient, and the post-operative non-visualization data comprises post-operative partial pressure of carbon dioxide of the patient,
wherein the difference comprises a difference between the pre-operative partial pressure of carbon dioxide and the post-operative partial pressure of carbon dioxide,
wherein assessing the output of the surgical procedure based on the comparison of the difference and the estimated parameter change comprises comparing the comparison of the difference between the pre-operative partial pressure of carbon dioxide and the post-operative partial pressure of carbon dioxide with the estimated parameter change.

2. The surgical hub of claim 1, wherein the control circuit is further configured to provide recommendations for the surgical procedure based on the pre-operative non-visualization data and the real-time visualization data.

3. The surgical hub of claim 1, wherein the control circuit is further configured to:
receive surgical procedure parameters from a user; and
provide recommendations for the surgical procedure based on the surgical procedure parameters and the real-time visualization data.

4. The surgical hub of claim 1, wherein the pre-operative non-visualization data and the post-operative non-visualization data are received from another surgical device coupled to the surgical hub.

5. The surgical hub of claim 1, wherein the control circuit is further configured to:
receive pre-operative visualization scans simulating a surgical approach; and
display the pre-operative visualization scans against the real-time visualization data during the surgical procedure.

6. The surgical hub of claim 1, wherein the surgical procedure comprises an organ being resected.

7. The surgical hub of claim 1, wherein the tissue parameter comprises tissue density.

8. A surgical hub for use with a surgical system in a surgical procedure performed in an operating room, the surgical hub comprising:
a control circuit configured to:
receive real-time visualization data from a camera;
determine an estimated parameter change based on the visualization data and surgical procedure;
receive pre-operative data, wherein the pre-operative data is received before the surgical procedure is performed;
determine a tissue parameter based on the real-time visualization data;
adjust an operational parameter of a surgical device used to perform the surgical procedure based on the tissue parameter, wherein the surgical device is communicably coupled to the surgical hub;
receive post-operative data, wherein the post-operative data is received after the surgical procedure is performed;
determine a difference between the pre-operative data and post-operative data; and
assess an output of the surgical procedure based on the difference and the estimated parameter change,
wherein the pre-operative data comprises pre-operative partial pressure of carbon dioxide of a patient, and the post-operative data comprises post-operative partial pressure of carbon dioxide of the patient,
wherein the difference comprises a difference between the pre-operative partial pressure of carbon dioxide and the post-operative partial pressure of carbon dioxide,
wherein assessing the output of the surgical procedure based on the difference and the estimated parameter change comprises comparing the difference between the pre-operative partial pressure of carbon dioxide and the post-operative partial pressure of carbon dioxide with the estimated parameter change.

9. The surgical hub of claim 8, wherein the control circuit is further configured to provide recommendations for the surgical procedure based on the pre-operative data and the real-time visualization data.

10. The surgical hub of claim 9, wherein the pre-operative data comprises visualization data and non-visualization data.

11. The surgical hub of claim 8, wherein the control circuit is further configured to:
receive surgical procedure parameters from a user; and
provide recommendations for the surgical procedure based on the surgical procedure parameters and the real-time visualization data.

12. The surgical hub of claim 8, wherein the pre-operative data and the post-operative data are received from another surgical device coupled to the surgical hub.

13. The surgical hub of claim 8, wherein the pre-operative data comprises pre-operative visualization scans simulating a surgical approach, and wherein the control circuit is further configured to display the pre-operative visualization scans against the real-time visualization data during the surgical procedure.

14. The surgical hub of claim 8, wherein the surgical procedure comprises an organ being resected.

15. The surgical hub of claim 14, wherein assess an output comprises determining an efficiency of the organ.

16. A surgical hub for use with a surgical system in a surgical procedure performed in an operating room, the surgical hub comprising:
 a control circuit configured to:
  receive real-time visualization data from a camera;
  determine an estimated parameter change based on the visualization data and surgical procedure;
  receive pre-operative non-visualization data from a surgical device, wherein the pre-operative non-visualization data is received before the surgical procedure is performed;
  determine a first value of a non-visualization parameter based on the pre-operative non-visualization data;
  determine a tissue parameter based on the real-time visualization data;
  adjust an operational parameter of a surgical device used to perform the surgical procedure based on the tissue parameter, wherein the surgical device is communicably coupled to the surgical hub;
  receive post-operative non-visualization data from the surgical device, wherein the post-operative non-visualization data is received after the surgical procedure is performed;
  determine a second value of the non-visualization parameter based on the post-operative non-visualization data; and
  assess an output of the surgical procedure based on at least the estimated parameter change, the first value, and the second value,
 wherein the first value of the non-visualization parameter comprises a pre-operative partial pressure value of carbon dioxide of a patient, and the second value of the non-visualization parameter comprises a post-operative partial pressure value of carbon dioxide of the patient,
 wherein assessing the output of the surgical procedure based on at least the estimated parameter change, the first value, and the second value comprises comparing a difference between the pre-operative partial pressure value of carbon dioxide and the post-operative partial pressure value of carbon dioxide with the estimated parameter change.

17. The surgical hub of claim 16, wherein the control circuit is further configured to provide recommendations for the surgical procedure based on the pre-operative non-visualization data and the real-time visualization data.

18. The surgical hub of claim 16, wherein the control circuit is further configured to:
 receive surgical procedure parameters from a user; and
 provide recommendations for the surgical procedure based on the surgical procedure parameters and the real-time visualization data.

19. The surgical hub of claim 16, wherein the surgical procedure comprises an organ being resected.

20. The surgical hub of claim 16, wherein the control circuit is further configured to:
 receive pre-operative visualization scans simulating a surgical approach; and
 display the pre-operative visualization scans against the real-time visualization data during the surgical procedure.

* * * * *